United States Patent
Alphandéry et al.

(10) Patent No.: US 12,150,689 B2
(45) Date of Patent: *Nov. 26, 2024

(54) CRYOSYSTEM COMPRISING NANOPARTICLES FOR TREATING A BODY PART OF AN INDIVIDUAL BY CRYOTHERAPY

(71) Applicant: NANOBACTERIE, Paris (FR)

(72) Inventors: Edouard Alphandéry, Paris (FR); Sha Li-Soulisse, Antony (FR)

(73) Assignee: NANOBACTERIE, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 18/298,801

(22) Filed: Apr. 11, 2023

(65) Prior Publication Data

US 2023/0240738 A1    Aug. 3, 2023

Related U.S. Application Data

(63) Continuation of application No. 16/887,179, filed on May 29, 2020, now Pat. No. 11,744,629.

(30) Foreign Application Priority Data

Jun. 3, 2019    (EP) .................................... 19020359
Jun. 3, 2019    (EP) .................................... 19020360
Mar. 24, 2020  (EP) .................................... 20020134

(51) Int. Cl.
  *A61B 18/02*    (2006.01)
  *A61F 7/12*     (2006.01)
  (Continued)

(52) U.S. Cl.
  CPC .............. *A61B 18/02* (2013.01); *A61F 7/12* (2013.01); *A61B 2018/00095* (2013.01);
  (Continued)

(58) Field of Classification Search
  CPC ................ A61B 18/02; A61B 18/0218; A61B 2018/00005; A61B 2018/00041;
  (Continued)

(56) References Cited

U.S. PATENT DOCUMENTS

2008/0027419 A1    1/2008  Hamel et al.
2009/0011032 A1    1/2009  Patrick et al.
(Continued)

FOREIGN PATENT DOCUMENTS

EP    3363496 A1    8/2018
EP    3492102 A1    6/2019
(Continued)

OTHER PUBLICATIONS

European Search Report issued on Dec. 20, 2019 in corresponding Application No. European 19 02 0359; 8 pages.
(Continued)

*Primary Examiner* — Ankit D Tejani
(74) *Attorney, Agent, or Firm* — Maier & Maier, PLLC

(57) ABSTRACT

A cryo-system for treating a body part of an individual by cryotherapy, which includes two parts. The first part is either i) a cryo-probe suitable for internal cooling, which includes a penetrating segment in communication with a cryogen source and is at least smaller than $\frac{1}{10}$th of the body part's biggest volume and/or at least one dimension smaller than 1 cm or ii) a cryo-probe suitable for external cooling, which includes a non-penetrating segment in communication with a cryogen source. The second part is either i) an assembly of at least two nanoparticles bound to each other or associated with each other via binding or associating material or ii) at least one nanoparticle, which includes iron and at least one other metal than iron. The assembly of at least two nanoparticles or the at least one nanoparticle may be cooled by the cryo-probe or by switching on the cryo-probe.

29 Claims, 15 Drawing Sheets

(51) Int. Cl.
*A61B 18/00* (2006.01)
*A61F 7/00* (2006.01)

(52) U.S. Cl.
CPC ............... *A61B 2018/00577* (2013.01); *A61B 2018/00791* (2013.01); *A61F 2007/0057* (2013.01); *A61F 2007/0096* (2013.01); *A61F 2007/126* (2013.01)

(58) Field of Classification Search
CPC ........... A61B 2018/00095; A61B 2018/00577; A61B 2018/00714; A61B 2018/00791; A61B 2018/0212; A61B 2018/0262; A61B 2018/0293; A61F 2007/0057; A61F 2007/0096; A61F 2007/126; A61F 7/12; A61K 33/26; A61K 41/0052; A61K 9/51; A61K 9/5161; A61N 5/0625; A61N 5/067; A61P 31/00; A61P 35/00; B82Y 5/00

See application file for complete search history.

(56) References Cited

U.S. PATENT DOCUMENTS

| | | |
|---|---|---|
| 2010/0221351 A1 | 9/2010 | He |
| 2018/0310979 A1 | 11/2018 | Peled et al. |
| 2019/0192871 A1 | 6/2019 | Alphandery |
| 2019/0350871 A1 | 11/2019 | Steinmetz et al. |
| 2020/0297403 A1 | 9/2020 | Kochavi |

FOREIGN PATENT DOCUMENTS

| | | |
|---|---|---|
| EP | 3492103 A1 | 6/2019 |
| EP | 3569247 A1 | 11/2019 |
| JP | 2018526179 A | 9/2018 |
| JP | 2019514616 A | 6/2019 |
| WO | 2012166796 A1 | 12/2012 |
| WO | 2016203121 A1 | 12/2016 |
| WO | 2018142411 A1 | 8/2018 |

OTHER PUBLICATIONS

Yiu et al, "Cryosurgery: A review", Int J Angiol, 2007, pp. 1-6, vol. 16 No. 1; 6 pages.
European Search Report issued on Oct. 15, 2020, in corresponding EP Application No. 20020253.9; 11 pp.
Kim et al., "Thermally responsive nanocapsules with independent dual drug release profiles for combined cryotherapy of osteoarthritis", Osteoarthritis and Cartilage, vol. 24, 2016, pp. 5390-5391.
Bhargava et al., "Study of bioheat transfer phase change during cryosurgery for an irregular tumor tissue using EFGM", arxiv.org, Cornell University Library, 2017, pp. 1-16.
Zhang et al., "Synthesis and Characterization of Thermally Responsive Pluronic F127-Chitosan Nanocapsules for Controlled Release and Intracellular Delivery of Small Molecules", ACS Nano, vol. 4, No. 11, 2010, pp. 6747-6759.
Di et al., "A new nano-cryosurgical modality for tumor treatment using biodegradable MgO nanoparticles", Nanomedicine, Nanotechnology, Biology and Medicine, vol. 8, No. 8, 2012, pp. 1233-1241.
Yan et al., "Nanocryosugery and its mechanisms for enhancing freezing efficiency of tumor tissues", Nanomedicine, Nanotechnology, Biology and Medicine, vol. 4, No. 1, 2008, pp. 79-87.
Rao et al., "11. Effective destruction of cancer stem cells by combing freezing and anticancer drug encapsulated in nanoparticles", Cryobiology, vol. 66, No. 3, 2013, p. 345.
Zhang et al., "Two-phase flow and heat transfer in a self-developed MRI compatible LN2 cryoprobe and its experimental evaluation", International Journal of Heat and Mass Transfer, vol. 136, 2019, pp. 709-718.
European Search Report issued on Feb. 1, 2021, in connection with corresponding European Application No. 20020253.9; 18 pp.
Office Action issued on Jul. 11, 2023, in corresponding Japanese Application No. 2020-095137, 31 pages.
Yuan et al., "Enhanced killing of HepG2 during cryosurgery with Fe3O4-nanoparticle improved intracellular ice formation and cell dehydration", Oncotarget, 2017, vol. 8, No. 54, pp. 92561-92577.

[Fig. 1]
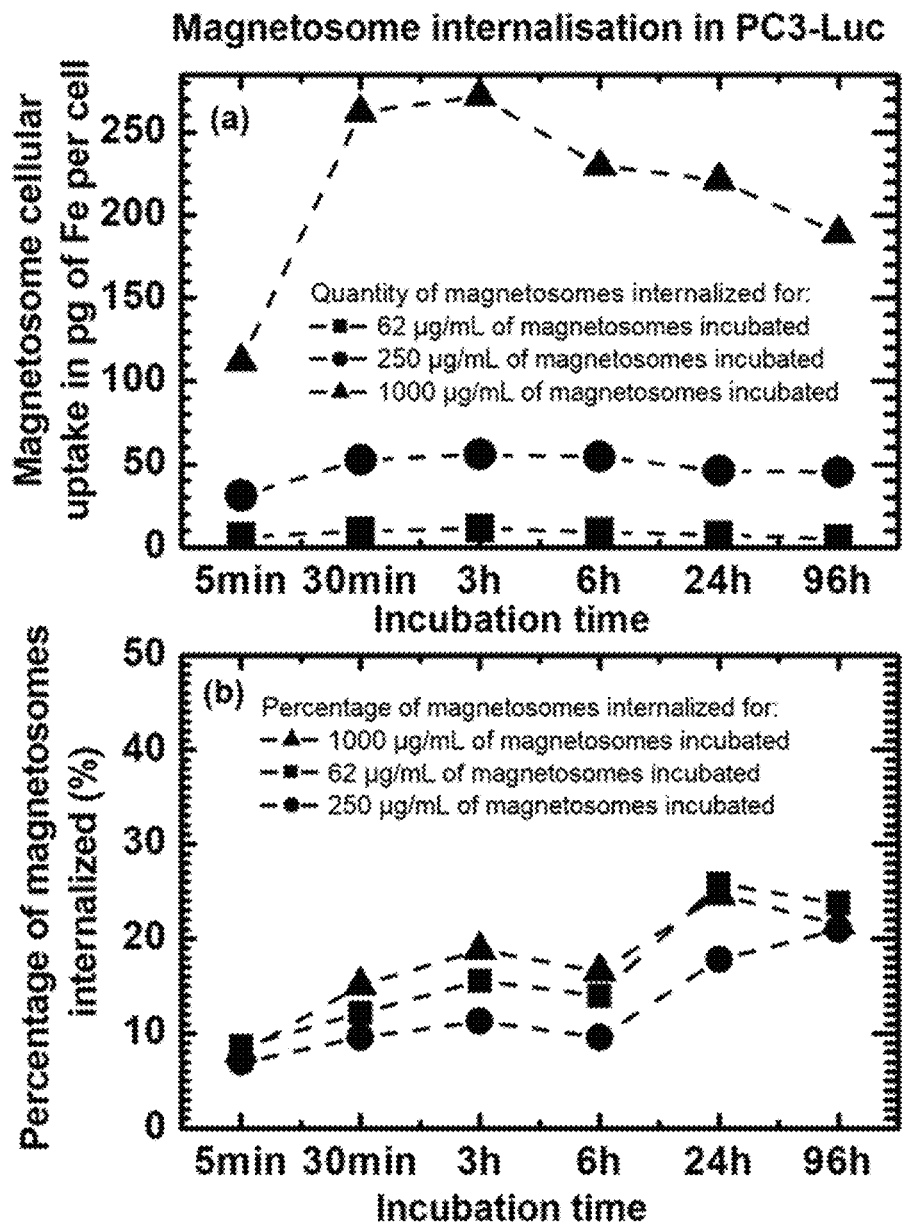

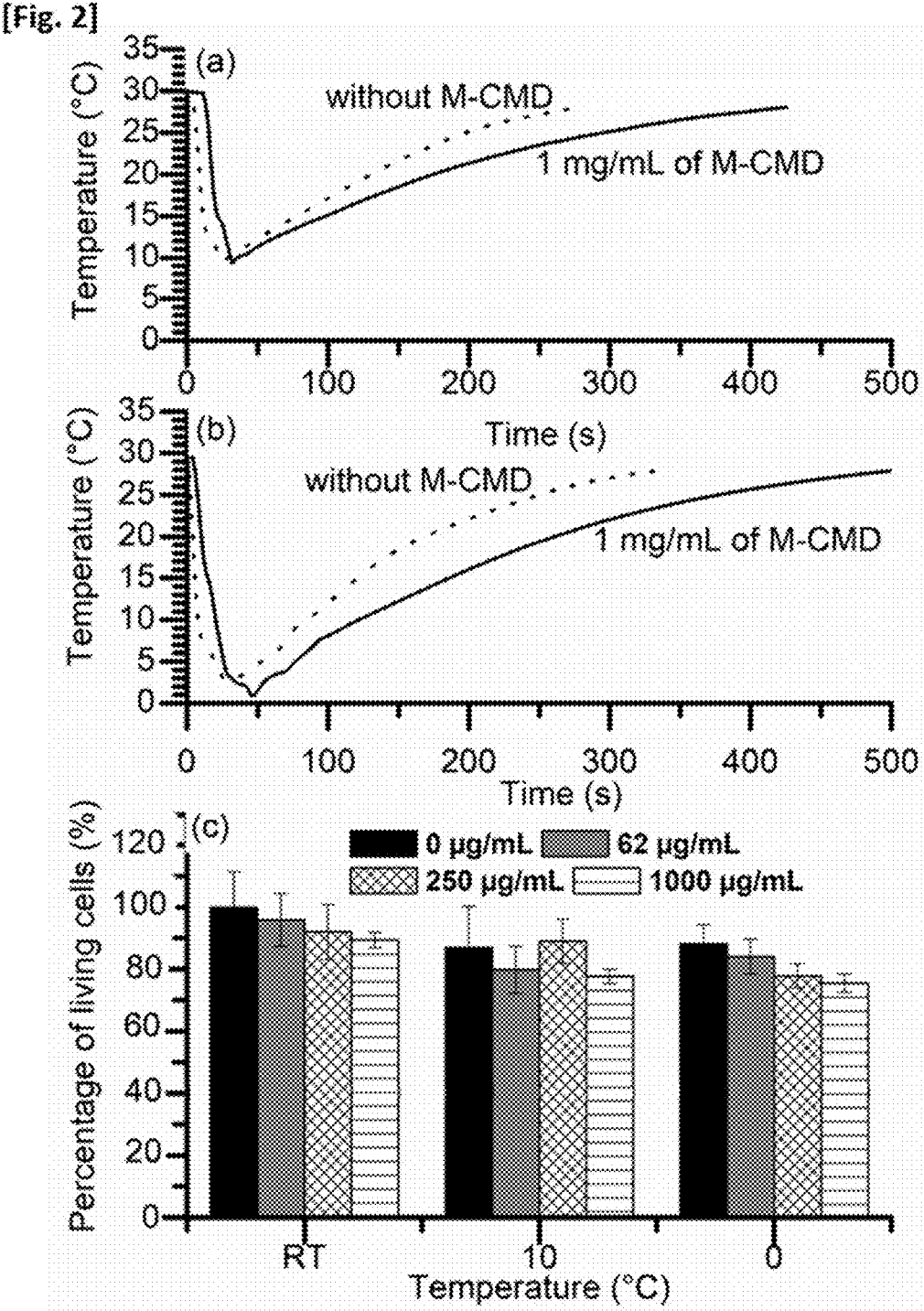

[Fig. 3]
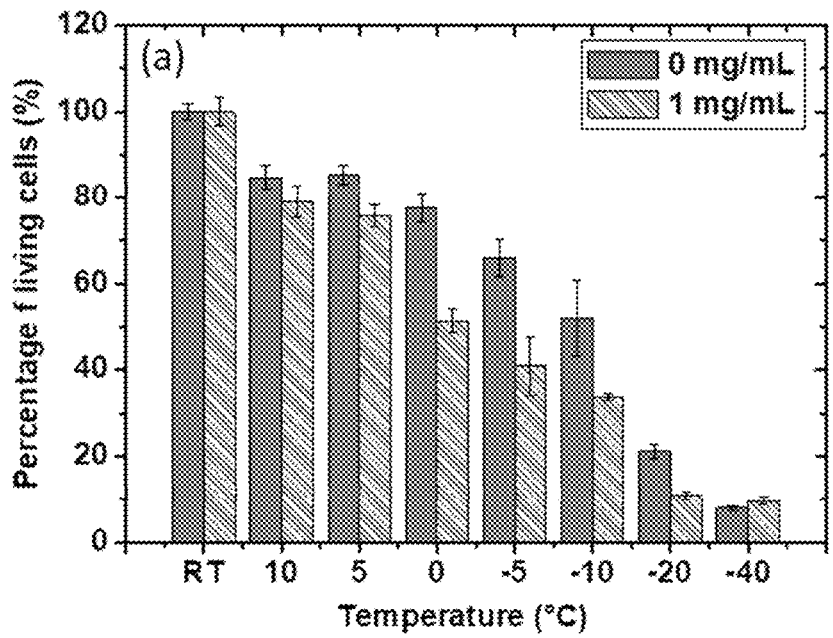
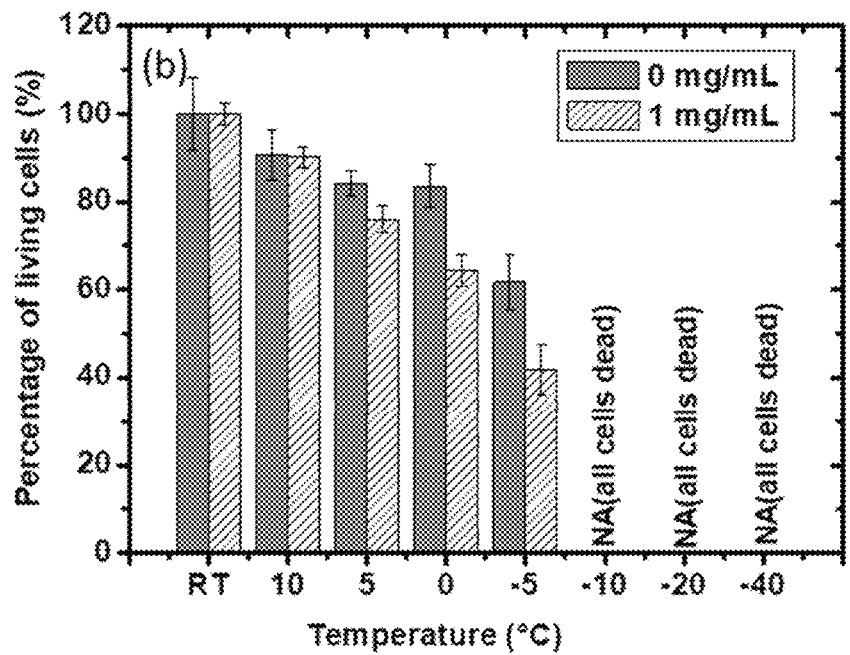

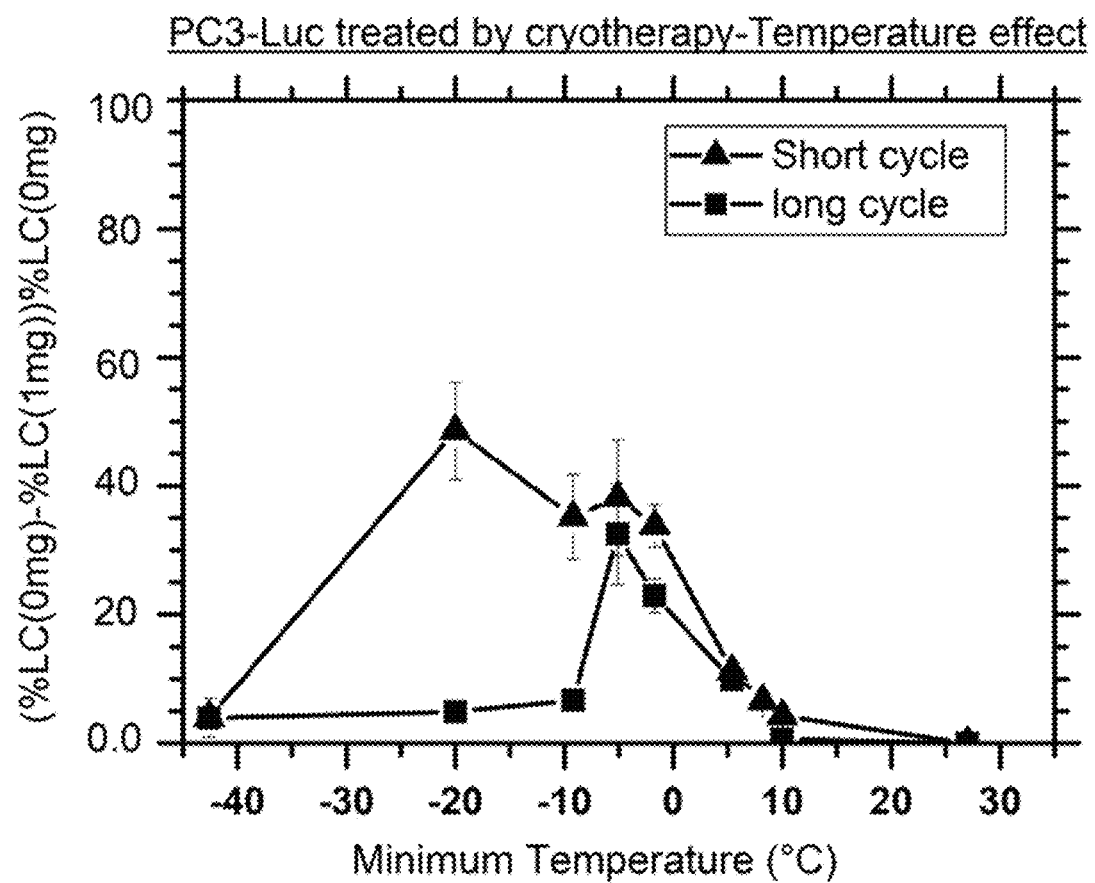
[Fig. 4]

[Fig. 5]
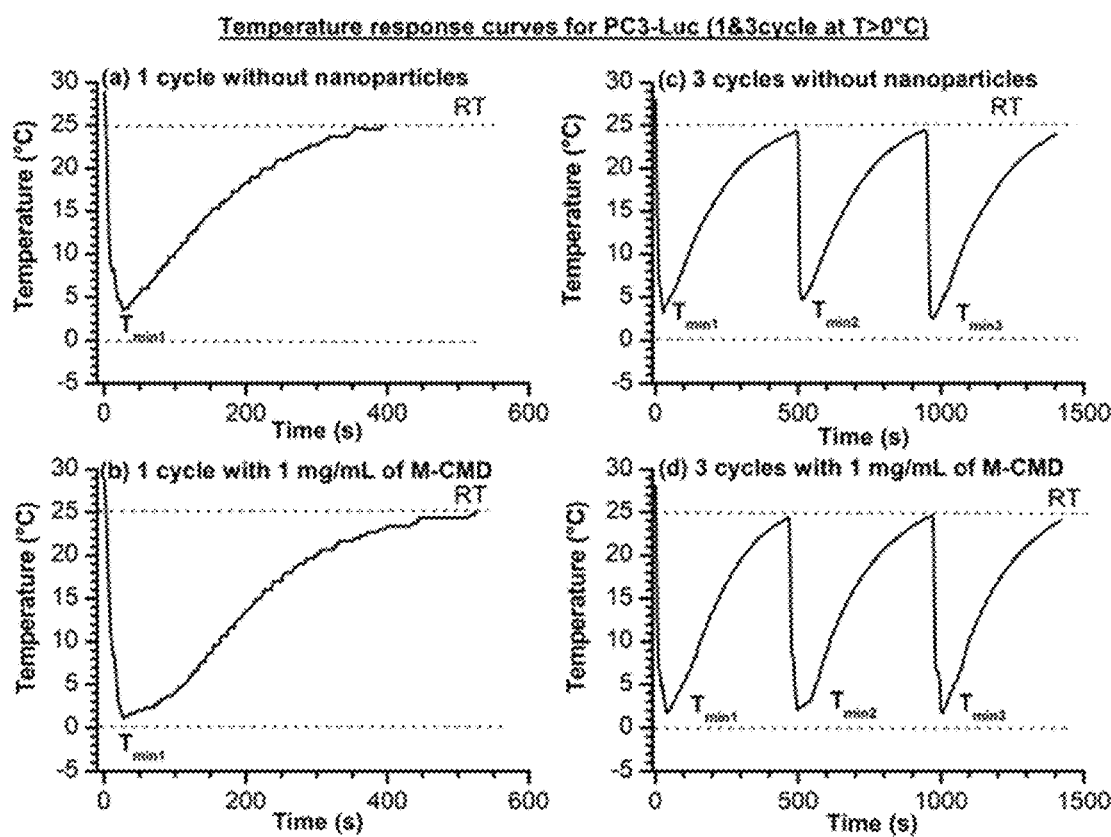

[Fig. 6]
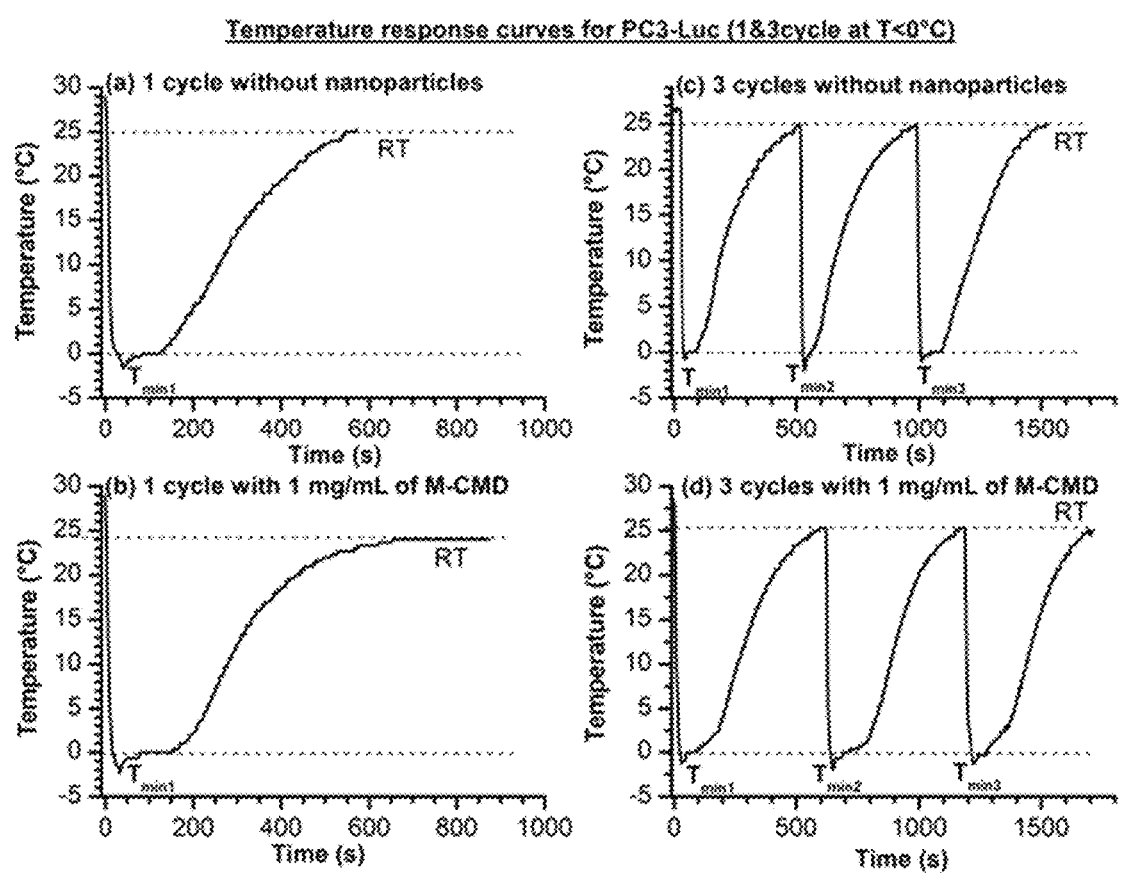

[Fig. 7]
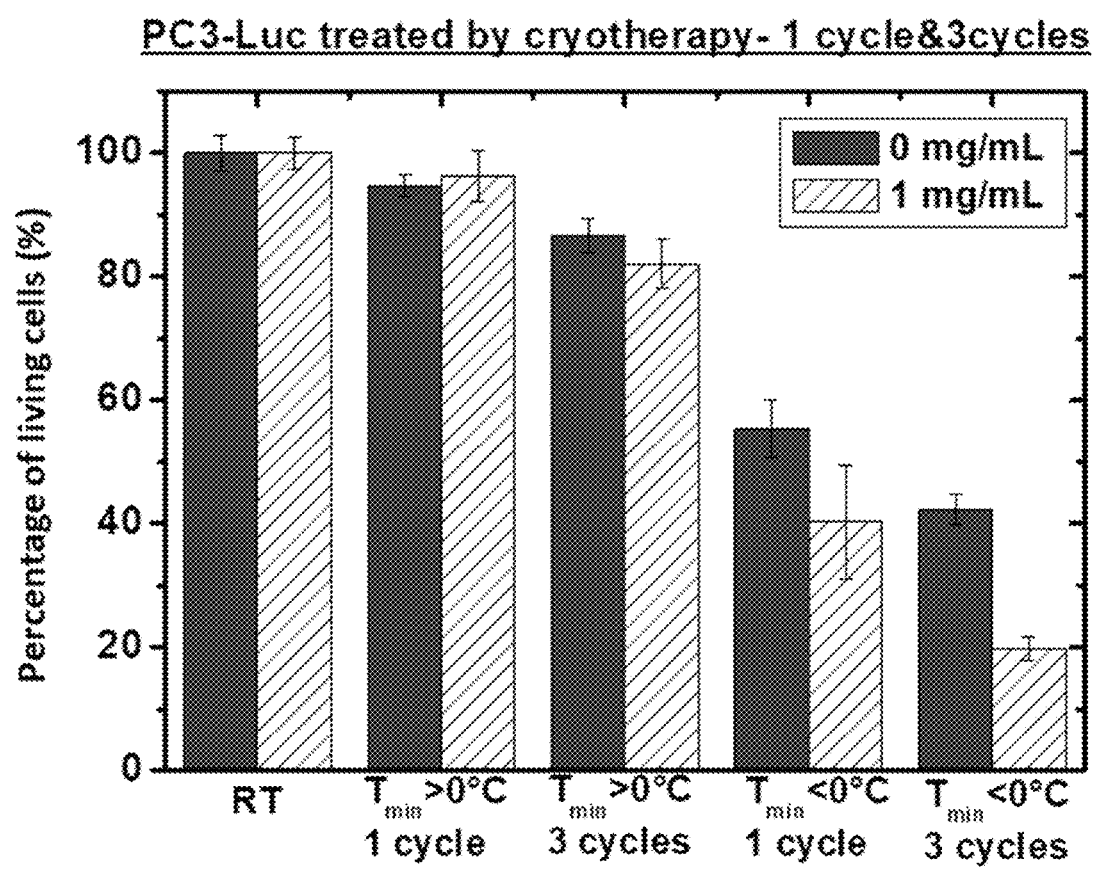

[Fig. 8]
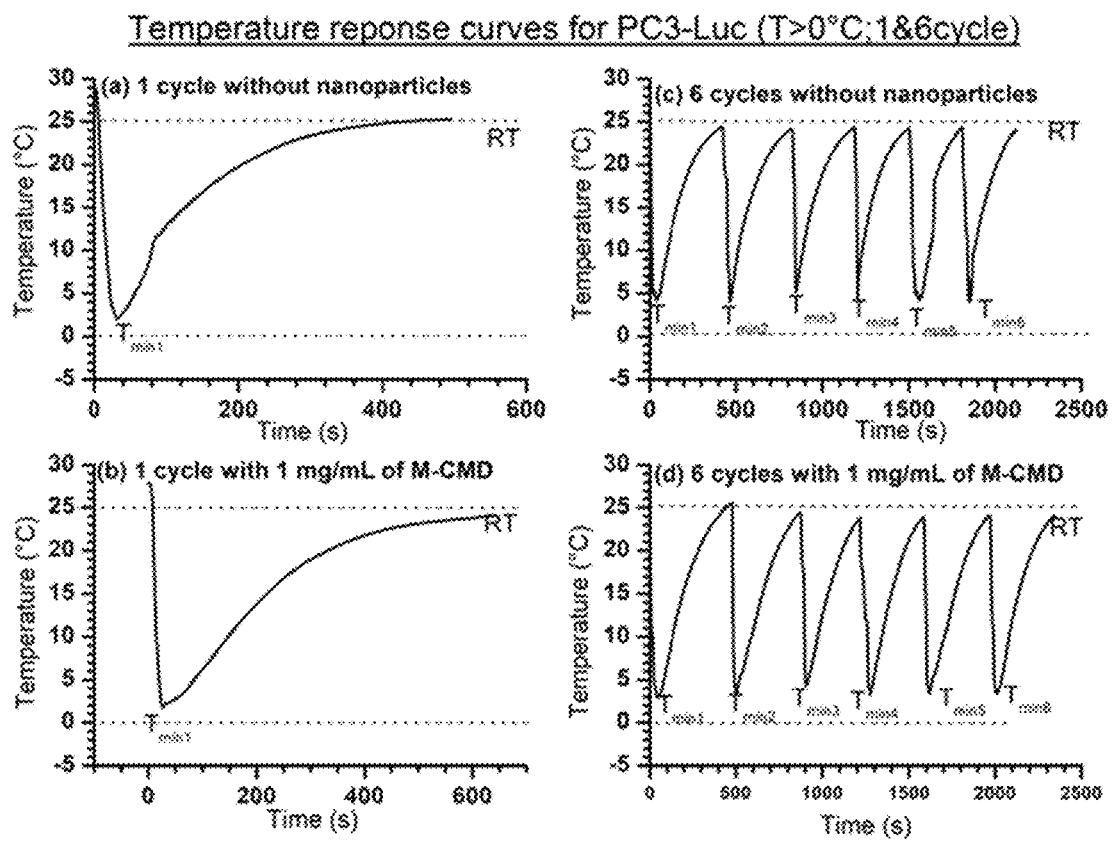

[Fig. 9]
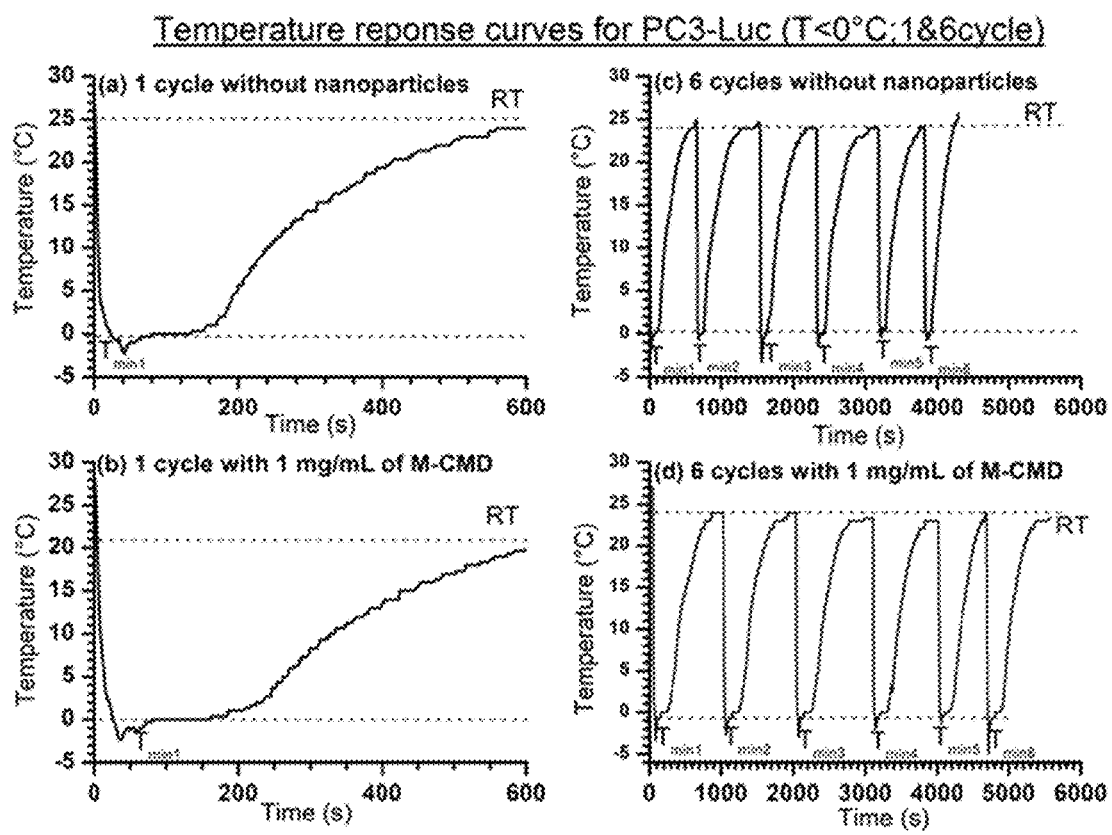

[Fig. 10]
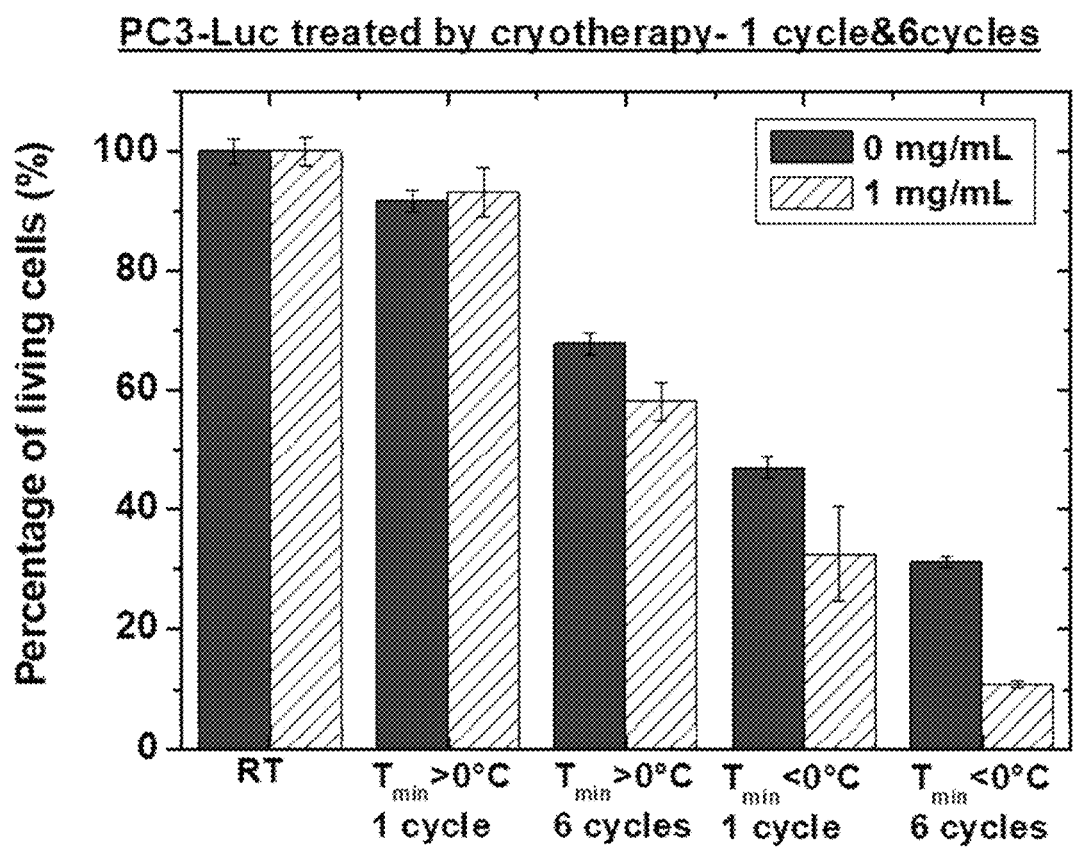

[Fig. 11]
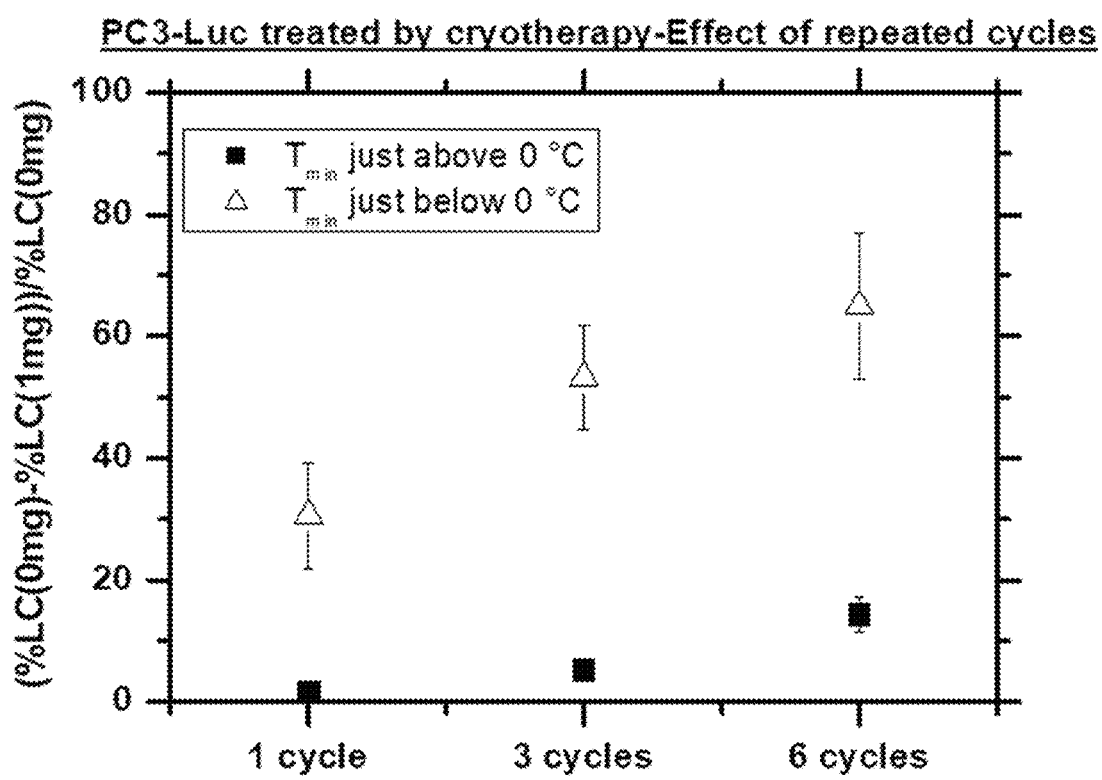

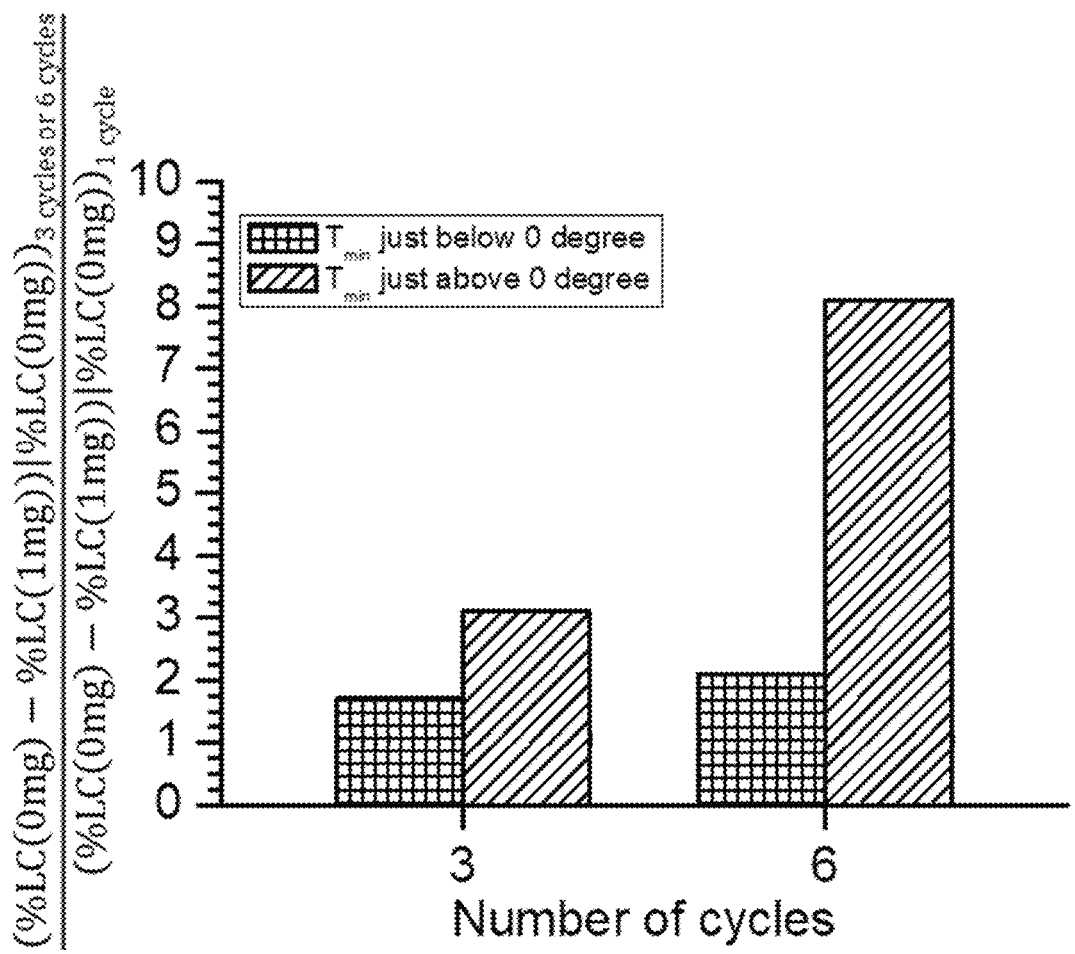
[Fig. 12]

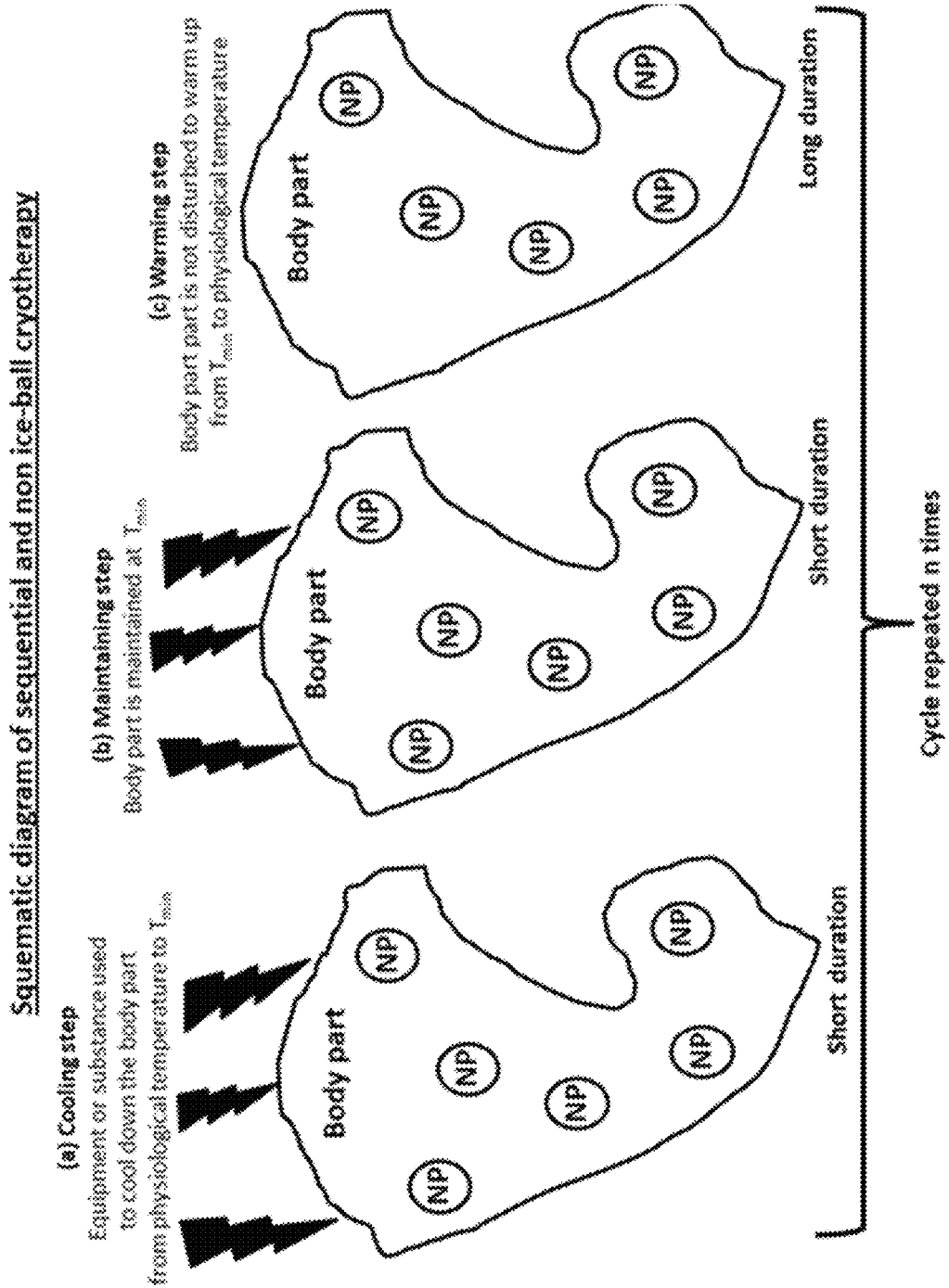
[Fig. 13]

[Fig. 14]
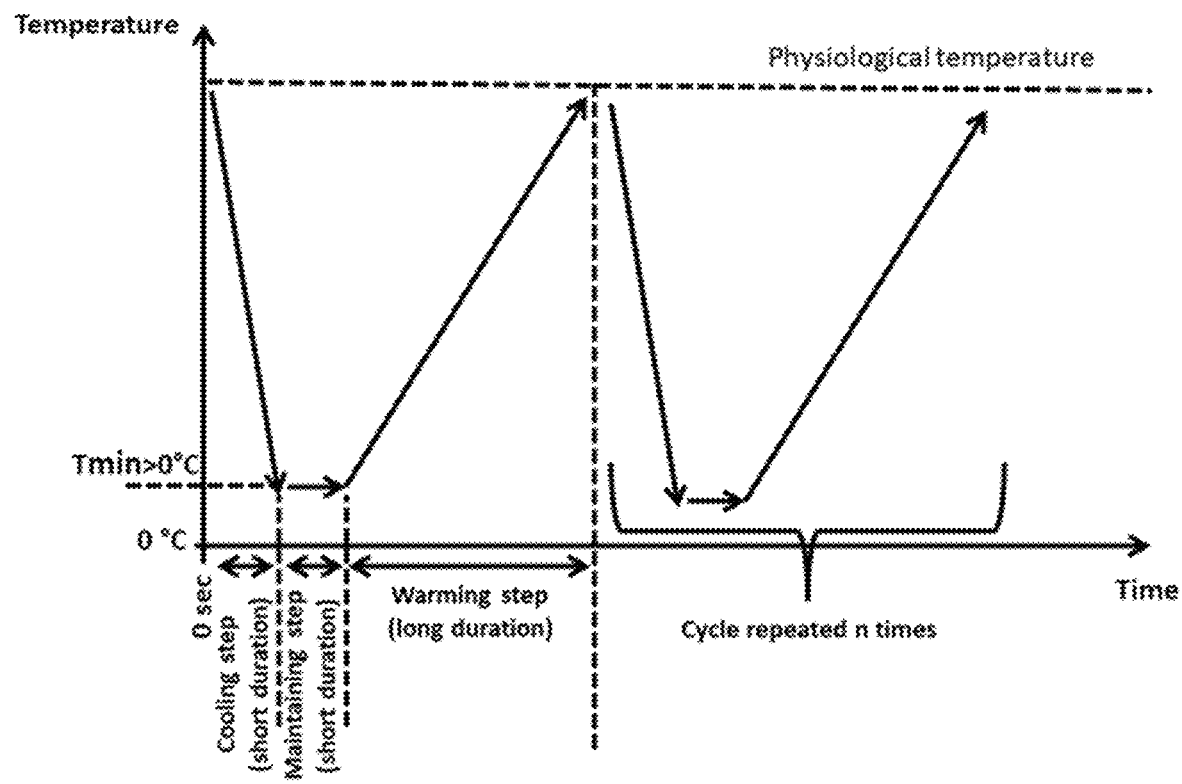

[Fig. 15]
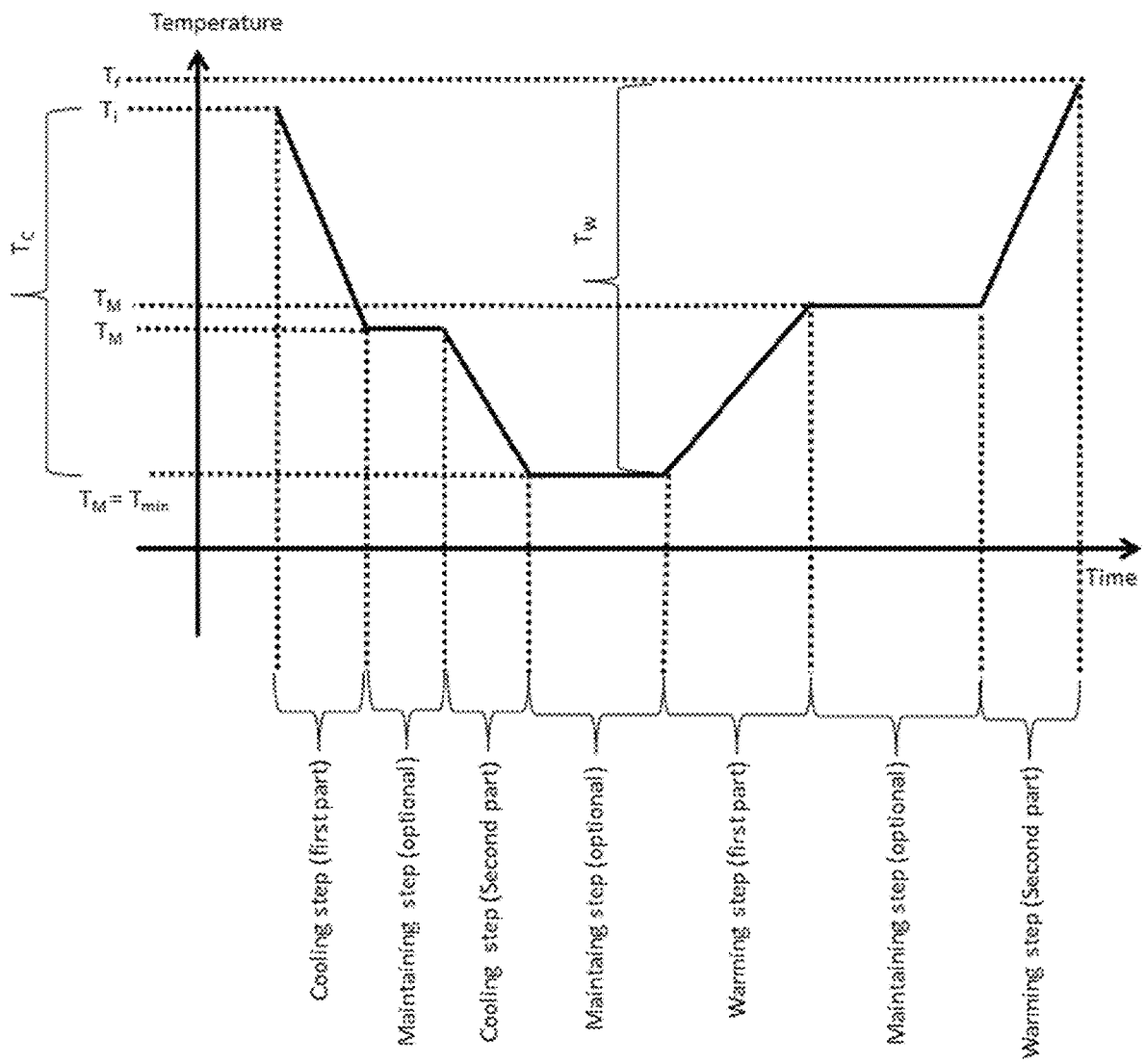

CRYOSYSTEM COMPRISING NANOPARTICLES FOR TREATING A BODY PART OF AN INDIVIDUAL BY CRYOTHERAPY

CROSS-REFERENCE TO RELATED APPLICATIONS

This application is a continuation of U.S. application Ser. No. 16/887,179, filed on May 29, 2020, which claims priority to European Application No. 20020134.1, filed on Mar. 24, 2020, European Application No. 19020359.6, filed on Jun. 3, 2019, European Application No. 19020360.4, filed on Jun. 3, 2019, the entire contents of which are incorporated herein by reference.

FIELD

The field of the invention is that of a cryo-system comprising a cryo-probe and at least one nanoparticle for treating the body part of an individual by cryotherapy.

BACKGROUND

The use of cryotherapy has been proposed for a number of medical applications (Yiu et al, *Int. J. Angiol.*, 16, 1, 2007). It usually works by cooling down the body part of an organism in the absence of nanoparticles. Here, we introduce a cryo-system that comprises a cryo-probe and at least one nanoparticle comprising iron and at least one other metal than iron to improve the efficacy of cryo-therapy. In addition, we present two methods of cryotherapy that either work in the absence of ice formation or sequentially, bringing some improvement in the efficacy of cryotherapy compared with currently used cryotherapy methods.

SUMMARY

The invention relates to a cryo-system for treating a body part of an individual by a treatment, preferentially cryotherapy, comprising two parts:
a) a first part, which is a cryo-probe wherein:
  i) the cryo-probe is suitable for an internal cooling action as it comprises a penetrating segment which is in communication with a cryogen source and which is at least smaller than $\frac{1}{10}^{th}$ of the biggest volume or volume of said body part and/or has at least one dimension smaller than 1 cm;
  or
  ii) the cryo-probe is suitable for an external cooling action as it comprises a non-penetrating segment in communication with a cryogen source, and
b) a second part, which is either:
  i) an assembly of at least two nanoparticles characterized in that this assembly comprises at least two nanoparticles bound to each other or associated with each other via binding or associating material, or
  ii) at least one nanoparticle characterized in that it comprises: a) iron and at least
  one other metal than iron and/or 1) more than 50% in mass of iron or iron oxide, wherein the assembly of at least two nanoparticles or the at least one nanoparticle is preferentially meant to be cooled down by: a) the cryo-probe or (3) switching on or activating the cryo-probe.

The assembly of at least two nanoparticles or the at least one nanoparticle is preferentially meant to warm up by: a) not using the cryo-probe or (3) switching off or not activating the cryo-probe.

The cryo-system preferentially does not involve the application of a magnetic field or a source of ice-destruction.

In some cases, the cryo-system can have at least one property in common with the nanoparticle(s) and/or cryo-probe.

In some other cases, the nanoparticle(s) and/or cryo-probe can have at least one property in common with the cryo-system.

In some cases, the cryo-system can have at least one property that differs from that of the nanoparticle(s) and/or cryo-probe.

In some other cases, the nanoparticle(s) and/or cryo-probe can have at least one property that differs from that of the cryo-system.

In some cases, the cryo-system can be inside or outside a body part.

In some other cases, the cryo-system can be the cryo-system during at least one step of the method according to the invention also designated as the cryo-system of at least one step of the method.

In some other cases, the cryo-system can be a cryo-system selected from the group consisting of: i) the cryo-system before its administration or location in the body part also designated as cryo-system before administration or location, ii) the cryo-system during its administration or location in the body part also designated as cryo-system during administration or location, iii) the cryo-system after its administration or location in the body part also designated as cryo-system after administration or location, iv) the cryo-system before at least one step of the method or treatment also designated as the pre-cryo-system or non-operating cryo-system, v) the cryo-system during at least one step of the method or treatment also designated as the operating cryo-system, and vi) the cryo-system after at least one step of the method or treatment also designated as post-cryo-system or non-operating cryo-system.

In one embodiment of the invention, the nanoparticle(s) has/have at least one the following property: i) they capture or store the cold locally, ii) they enable increasing the volume that is cooled down by the cryo-system compared with the volume that is cooled down by the cryo-probe in the absence of nanoparticles, iii) they enable reducing the temperature gradient within the body part or between the position of the cryo-probe and a location at some distance from this position, iv) they enable cryo-therapy to work at a temperature or minimum or cooling temperature that is larger than when the cryo-probe is used alone in the absence of nanoparticles, v) they enable the formation of a plateau or temperature maintenance or a slow-down of the warming up of the body preferentially compared with the situation where the cryo-system is used alone, where at least one of these properties preferentially increases the efficacy or reduces the toxicity of the cryotherapy.

In one embodiment, an internal cooling action is a cooling action or cooling that occurs in the body part or originates from equipment or the segment, preferentially the penetrating segment, located inside the body part or at a distance from the body part of less than 1, 10, $10^3$, $10^6$ or $10^9$ nm.

In another embodiment, an external cooling action is a cooling action or cooling that occurs outside of the body part or originates from equipment or the segment, preferentially the non-penetrating segment, located outside the boy part or at a distance from the body part of more than 1, 10, $10^3$, $10^6$ or $10^9$ nm.

In one embodiment, cooling or the cooling action, also designated as cryo in some cases, is the decrease or action of decreasing the temperature, preferentially of the body part, in some cases by more than 0, 1, 5, 10, 50, 100 or $10^{3\circ}$ C., in some other cases by less than $10^{10}$, $10^3$, 100, 5, 2 or 1° C., preferentially starting from an initial temperature, preferentially ending at a final temperature.

In some cases, the cryo-probe can comprise a segment that cools down the body part and a cryo-source that cools down the segment, where the segment can be in communication with the cryo-source, preferentially to have the cold diffuse or transported from the cryo-source to the segment, preferentially to result in the segment being at a similar temperature as the cryo-source or at a temperature that is less than $10^3$, 100, 50, 20, 10, 5, 2 or 1° C. above the temperature of the cryo-source.

In some cases, when the cryo-probe is activated or switched on, the segment is at a temperature that is below 100, 50, 10, 5, 2, 0, −5, −20, −40, −100, −200 or −250° C. In some other cases, when the cryo-probe is activated or switched on, the segment is at a temperature that is above −200, −150, −100, −50, −40, −20, −10, −5, −1, 0, 2, 5 or 10° C.

In some other cases, when the cryo-probe is de-activated or switched off, the segment is at physiological temperature or a temperature that is not cooled or lower preferentially by more than 10 or 100° C. preferentially compared with the temperature of the room or environment in which it is comprised.

In some other cases, when the cryo-probe is activated or switched on, the segment is at temperature that is at least 0, 1, 5, 10, 20, 50, 100 or 200° C. lower than when the cryo-probe is de-activated or switched off. This can occur when the cryo-probe is switched on and there has been a sufficiently long time for the cryo-source to cool down the segment.

In some cases, the segment can be at the same temperature when the cryo-probe is activated or switched on than when the cryo-probe is de-activated or switched off. This can occur when the cryo-probe is switched on and there has not been a sufficiently large time for the cryo-source to cool down the segment.

In some cases, the body part can be at the same temperature as the segment or nanoparticle(s), or at a temperature than differs by less than $10^5$, $10^3$, $10^2$, 50, 20, 10, 5, 2, 1 or 0.1° C. from the temperature of the segment or nanoparticle(s). This can be the case for part of the body part close to the segment or nanoparticle(s), or located at a distance of less than $10^9$, $10^6$, $10^3$, 10 or 1 nm from the segment or nanoparticle(s).

In some other cases, the body part can be at a different temperature from the temperature of the segment or nanoparticle(s), or at a temperature than differs by more than $10^{-5}$, $10^{-3}$, $10^{-2}$, 0.1, 0, 1, 10 or 100° C. from the temperature of the segment or nanoparticle(s). This can be the case for part of the body part far from the segment or nanoparticle(s), or located at a distance of more than 0.1, 1, 10, $10^3$, $10^6$ or $10^9$ nm from the segment or nanoparticle(s).

BRIEF DESCRIPTION OF THE FIGURES

FIG. 1: (a), Quantity of N-CMD (magnetosome minerals coated with CMD) inside PC3-Luc cells, estimated in pg of Fe per cell, when various quantity of N-CMD (62 µg/mL, 250 µg/mL, or 1000 µg/mL of magnetosomes) are brought into contact with PC3-Luc cells during incubation times of 5 minutes, 30 minutes, 3 hours, 6 hours, 24 hours, and 96 hours. (b), Percentage of N-MCD internalized in cells when various quantity of N-CMD (62 µg/mL, 250 µg/mL, or 1000 µg/mL of magnetosomes) are brought into contact with PC3-Luc cells during incubation times of 5 minutes, 30 minutes, 3 hours, 6 hours, 24 hours, and 96 hours. This percentage is the ratio between the quantity of N-CMD in iron inside cell and the quantity of N-CMD in iron that is incubated with cells.

FIG. 2: (a) Temperature variation of PC3-Luc cells without N-CMD or PC3-Luc cells incubated with 1 mg/mL of N-CMD during 3 hours that are cooled down from room temperature (RT) to $T_{min}$ of 10° C. and then let warming up from $T_{min}$ to room temperature. (b), Temperature variation of PC3-Luc cells without N-CMD or PC3-Luc cells incubated with 1 mg/mL of N-CMD during 3 hours that are cooled down from RT to $T_{min}$ of 0° C. and then let warming up from $T_{min}$ to room temperature. (c) Percentages of living cells when PC3-Luc cells are incubated during 3 hours with only the growth medium (0 mg/mL) or with 62 µg/mL, 250 µg/mL, or 1000 µg/mL of N-CMD and are either maintained to RT (RT), cooled down from RT to $T_{min}$ of 10° C. and let warming up from $T_{min}$ to RT (10° C.), cooled down from RT to $T_{min}$ of 0° C. and let warming up from $T_{min}$ to RT (0° C.).

FIG. 3: (a) Percentages of living cells when PC3-Luc cells are incubated during 3 hours with only the growth medium (0 mg/mL) or with 1 mg/mL of N-CMD (1 mg/mL) and are either maintained to RT (RT), cooled down from RT to $T_{min}$ of 10° C. and let warming up from $T_{min}$ to RT, cooled down from RT to $T_{min}$ of 5° C. and let warming up from $T_{min}$ to RT, cooled down from RT to $T_{min}$ of 0° C. and let warming up from $T_{min}$ to RT, cooled down from RT to $T_{min}$ of −5° C. and let warming up from $T_{min}$ to RT, cooled down from RT to $T_{min}$ of −10° C. and let warming up from $T_{min}$ to RT, cooled down from RT to $T_{min}$ of −20° C. and let warming up from $T_{min}$ to RT, cooled down from RT to $T_{min}$ of −40° C. and let warming up from $T_{min}$ to RT. In (a), the cycles are short. This means that the temperature is maintained at $T_{min}$ for less than 10 seconds. (b) Percentages of living cells when PC3-Luc cells are incubated during 3 hours with only the growth medium (0 mg/mL) or with 1 mg/mL of N-CMD (1 mg/mL) and are either maintained to RT (RT), cooled down from RT to $T_{min}$ of 10° C. and let warming up from $T_{min}$ to RT, cooled down from RT to $T_{min}$ of 5° C. and let warming up from $T_{min}$ to RT, cooled down from RT to $T_{min}$ of 0° C. and let warming up from $T_{min}$ to RT, cooled down from RT to $T_{min}$ of −5° C. and let warming up from $T_{min}$ to RT, cooled down from RT to $T_{min}$ of −10° C. and let warming up from $T_{min}$ to RT, cooled down from RT to $T_{min}$ of −20° C. and let warming up from $T_{min}$ to RT, cooled down from RT to $T_{min}$ of −40° C. and let warming up from $T_{min}$ to RT. In (b), the cycles are long. This means that the temperature is maintained at $T_{min}$ for more than 1 minute.

FIG. 4: Value of [% LC(0 mg)−% LC(1 mg)]/% LC(0 mg) as a function of minimal temperatures reached during the various treatments (RT, 10° C., 5° C., 0° C., −5° C., −10° C., −20° C., −40° C.), where % LC(0 mg) and % LC(1 mg) are the percentages of living cells obtained when PC3-Luc cells are incubated only with the cellular growth medium during 3 hours (0 mg) and PC3-Luc cells are incubated with 1 mg/mL of N-CMD during 3 hours (1 mg).

FIG. 5: (a) Temperature variation of PC3-Luc cells incubated without N-CMD during 3 hours, cooled down from room temperature (RT) to $T_{min}$ of 3° C. and then let warming up from $T_{min}$ to room temperature. (b) Temperature variation of PC3-Luc cells incubated with 1 mg/mL of N-CMD during 3 hours, cooled down from room temperature (RT) to $T_{min}$ of 1° C., and then let warming up from $T_{min}$ to room temperature. (c), Temperature variation of PC3-Luc cells incubated with growth medium without N-CMD during 3 hours, cooled down from RT to $T_{min1}$ of 0.2° C. and then let warm up from $T_{min1}$ of 0.2° C. to room temperature (first cycle), cooled down from RT to $T_{min2}$ of 2° C. and then let warming up from $T_{min2}$ of 2° C. to RT (second cycle), cooled down from RT to $T_{min3}$ of 1° C. and then let warming up from $T_{min3}$ to RT (third cycle). (d) Temperature variation of PC3-Luc cells incubated during 3 hours with 1 mg/mL of N-CMD, cooled down from RT to $T_{min1}$ of 2° C. and let warming up from $T_{min1}$ of 2° C. to RT (first cycle), cooled down from RT to $T_{min2}$ of 1° C. and let warming up from $T_{min2}$ of 1° C. to RT (second cycle), cooled down from RT to $T_{min3}$ of 2° C. and let warming up from $T_{min3}$ of 2° C. to RT (third cycle).

FIG. 6: (a) Temperature variation of PC3-Luc cells incubated without N-CMD during 3 hours, cooled down from room temperature (RT) to $T_{min}$ of −2° C. and then let warming up from $T_{min}$ of −2° C. to room temperature. (b) Temperature variation of PC3-Luc cells incubated with 1 mg/mL of N-CMD during 3 hours, cooled down from room temperature (RT) to $T_{min}$ of −2° C., and then let warming up from $T_{min}$ of −2° C. to room temperature. (c), Temperature variation of PC3-Luc cells incubated with growth medium without N-CMD during 3 hours, cooled down from RT to $T_{min1}$ of −1° C. and then let warming up from $T_{min1}$ to room temperature (first cycle), cooled down from RT to $T_{min2}$ of −2° C. and then let warming up from $T_{min2}$ of −2° C. to RT (second cycle), cooled down from RT to $T_{min3}$ of −1° C. and then let warming up from $T_{min3}$ of −1° C. to RT (third cycle). (d) Temperature variation of PC3-Luc cells incubated during 3 hours with 1 mg/mL of N-CMD, cooled down from RT to $T_{min1}$ of −1° C. and let warming up from $T_{min1}$ of −1° C. to RT (first cycle), cooled down from RT to $T_{min2}$ of −2° C. and let warming up from $T_{min2}$ of −2° C. to RT (second cycle), cooled down from RT to $T_{min3}$ of −1° C. and let warming up from $T_{min3}$ of −1° C. to RT (third cycle).

FIG. 7: Percentages of living cells resulting from the treatment where PC3-Luc cells are incubated during 3 hours with growth medium without N-CMD (0 mg/mL) or with 1 mg/mL of N-CMD (1 mg/mL), and treated by 1 or 3 cycles at $T_{min}>0°$ C. (minimum temperatures just above 0° C.) or at $T_{min}<0°$ C. (minimum temperatures just below 0° C.), where the temperature variations of the different cycles are shown in FIGS. 5 and 6.

FIG. 8: (a) Temperature variation of PC3-Luc cells incubated without N-CMD during 3 hours, cooled down from room temperature (RT) to $T_{min}$ of 2° C. and then let warming up from $T_{min}$ of 2° C. to room temperature. (b) Temperature variation of PC3-Luc cells incubated with 1 mg/mL of N-CMD during 3 hours, cooled down from room temperature (RT) to $T_{min}$ of 2° C., and then let warming up from $T_{min}$ of 2° C. to room temperature. (c), Temperature variation of PC3-Luc cells incubated with growth medium without N-CMD during 3 hours, cooled down from RT to $T_{min1}$ of 4° C. and then let warming up from $T_{min1}$ of 4° C. to room temperature (first cycle), cooled down from RT to $T_{min2}$ of 4° C. and then let warming up from $T_{min2}$ of 4° C. to RT, cooled down to $T_{min3}$ of 4° C. and then let warming up from $T_{min3}$ of 4° C. to RT (third cycle), cooled down from RT to $T_{min4}$ of 5° C. and then let warming up from $T_{min4}$ of 5° C. to room temperature (fourth cycle), cooled down from RT to $T_{min5}$ of 5° C. and then let warming up from $T_{min5}$ of 5° C. to RT, cooled down to $T_{min6}$ of 5° C. and then let warming up from $T_{min6}$ of 5° C. to RT (sixth cycle). (d) Temperature variation of PC3-Luc cells incubated during 3 hours with 1 mg/mL of N-CMD, cooled down from RT to $T_{min1}$ of 3° C. and then let warming up from $T_{min1}$ of 3° C. to room temperature (first cycle), cooled down from RT to $T_{min2}$ of 3° C. and then let warming up from $T_{min2}$ of 3° C. to RT, cooled down to $T_{min3}$ of 4° C. and then let warming up from $T_{min3}$ of 4° C. to RT (third cycle), cooled down from RT to $T_{min4}$ of 3° C. and then let warming up from $T_{min4}$ of 3° C. to room temperature (fourth cycle), cooled down from RT to $T_{min5}$ of 3° C. and then let warming up from $T_{min5}$ of 3° C. to RT, cooled down to $T_{min6}$ of 3° C. and then let warming up from $T_{min6}$ of 3° C. to RT (sixth cycle).

FIG. 9: (a) Temperature variation of PC3-Luc cells incubated without N-CMD during 3 hours, cooled down from room temperature (RT) to $T_{min}$ of −2° C. and then let warming up from $T_{min}$ of −2° C. to room temperature. (b) Temperature variation of PC3-Luc cells incubated with 1 mg/mL of N-CMD during 3 hours, cooled down from room temperature (RT) to $T_{min}$ of −2° C., and then let warming up from $T_{min}$ of −2° C. to room temperature. (c), Temperature variation of PC3-Luc cells incubated with growth medium without N-CMD during 3 hours, cooled down from RT to $T_{min1}$ of −2° C. and then let warming up from $T_{min1}$ of −2° C. to room temperature (first cycle), cooled down from RT to $T_{min2}$ of −1° C. and then let warming up from $T_{min2}$ of −1° C. to RT, cooled down to $T_{min3}$ of −3° C. and then let warming up from $T_{min3}$ of −3° C. to RT (third cycle), cooled down from RT to $T_{min4}$ of −1° C. and then let warming up from $T_{min4}$ of −1° C. to room temperature (fourth cycle), cooled down from RT to $T_{min5}$ of 0° C. and then let warming up from $T_{min5}$ of 0° C. to RT, cooled down from RT to $T_{min6}$ of −1° C. and then let warming up from $T_{min6}$ of −1° C. to RT (sixth cycle). (d) Temperature variation of PC3-Luc cells incubated during 3 hours with 1 mg/mL of N-CMD, cooled down from RT to $T_{min1}$ of −3° C. and then let warming up from $T_{min1}$ of −3° C. to room temperature (first cycle), cooled down from RT to $T_{min2}$ of −3° C. and then let warming up from $T_{min2}$ of −3° C. to RT, cooled down from RT to $T_{min3}$ of −3° C. and then let warming up from $T_{min3}$ of −3° C. to RT (third cycle), cooled down from RT to $T_{min4}$ of −2° C. and then let warming up from $T_{min4}$ of −2° C. to room temperature (fourth cycle), cooled down from RT to $T_{min5}$ of −1° C. and then let warming up from $T_{min5}$ of −1° C. to RT, cooled down from RT to $T_{min6}$ of −5° C. and then let warming up from $T_{min6}$ of −5° C. to RT (sixth cycle).

FIG. 10: Percentages of living cells resulting from the treatment where PC3-Luc cells are incubated during 3 hours with growth medium without N-CMD (0 mg/mL) or with 1 mg/mL of N-CMD (1 mg/mL), and treated by 1 or 6 cycles at $T_{min>0° C.}$ (minimum temperatures just above 0° C.) or at $T_{min<0° C.}$ (minimum temperatures just below 0° C.), where the temperature variations of the different cycles are shown in FIGS. 8 and 9.

FIG. 11: Values of [% LC(0 mg)−% LC(1 mg)]/% LC(0 mg) as a function of the number cycles for $T_{min>0° C.}$ (minimum temperatures above 0° C.) and $T_{min<0° C.}$ (minimum temperatures below 0° C.), where % LC(0 mg) and % LC(1 mg) are the percentages of living cells obtained when PC3-Luc cells are incubated only with the cellular growth medium during 3 hours (0 mg) and PC3-Luc cells are incubated with 1 mg/mL of N-CMD during 3 hours (1 mg) and the cells with/without nanoparticles are exposed to 1 cycle, 3 cycles, or 6 cycles.

FIG. 12: Value of:

[[% LC(0 mg)–% LC(1 mg)]/% LC(0 mg)]$_{3cycle}$/
  [[% LC(0 mg)–% LC(1 mg)]/% LC(0 mg)]$_{1cycle}$
  (increase of [% LC(0 mg)–% LC(1 mg)]/%
  LC(0 mg)] between 1 and 3 cycles)

and

[[% LC(0 mg)–% LC(1 mg)]/% LC(0 mg)]$_{6cycle}$/[[%
  LC(0 mg)–% LC(1 mg)]/% LC(0 mg)]$_{1cycle}$ (increase of [[% LC(0 mg)–% LC(1 mg)]/% LC(0 mg)] between 1 and 6 cycles) estimated for $T_{min>0}$° C. (minimum temperatures above 0° C.) and $T_{min<0}$° C. (minimum temperatures below 0° C.), where % LC(0 mg) and % LC(1 mg) are the percentages of living cells obtained when PC3-Luc cells are incubated only with the cellular growth medium during 3 hours (0 mg) and PC3-Luc cells are incubated with 1 mg/mL of N-CMD during 3 hours (1 mg) and the cells with/without nanoparticles are exposed to 1 cycle (% LC(0 mg)$_{1cycle}$ and % LC(1 mg)$_{1cycle}$), 3 cycles (% LC(0 mg)$_{3cycle}$ and % LC(1 mg)$_{3cycle}$), or 6 cycles (% LC(0 mg)$_{6cycle}$ and % LC(1 mg)$_{6cycle}$).

FIG. 13: Schematic diagram illustrating how the method according to the invention can be implemented. A cycle is divided in three steps. The body part comprising the nanoparticles is first cooled down from an initial temperature to $T_{min}$, which is preferentially above 0° C., during the cooling step, preferentially of short duration, using an equipment or substance (temperature adjuster or cryo-probe) that cools down the body part to $T_{min}$. The temperature of the body part comprising the nanoparticles is optionally maintained at $T_{min}$ during the maintaining step, preferentially of short duration. The temperature of the body part comprising the nanoparticles is then increased during the warming step, preferentially of long duration, from $T_{min}$ preferentially above 0° C., to the final temperature. A cycle can be repeated n times, preferentially until the desired medical, therapeutic or medical or cosmetic or therapeutic or diagnostic activity of the treatment is reached. The body part is indicated by the large truncated cylinder. Nanoparticles are indicated by circles inside which NP is inserted. The use of temperature adjuster or cryo-probe during the cooling and maintaining steps is indicated by thunder signs.

FIG. 14: Schematic diagram illustrating how the temperature can vary as a function of time during the different steps of two cycles and one session of the method according to the invention. The different steps of the method are described in the legend of FIG. 13.

FIG. 15: Schematic diagram representing a possible variation of temperature as a function of time during the treatment steps (cooling step, maintaining step, warming step). $T_c$, $T_m$, $T_i$, $T_f$, $T_{mm}$, $T_W$, are the cooling temperature, maintaining temperature, initial temperature, final temperature, warming temperature, respectively.

DETAILED DESCRIPTION

Cryo-Probe

In one embodiment of the invention, the cryo-probe comprises: a) a segment, penetrating or non-penetrating in a body part, b) a cryogen source, and/or c) a system that brings into contact or communication the cryogen source with the segment.

In some cases, the segment or cryo-probe can be or be designated as instrument, equipment, apparatus, piece, part, section, chunk, division, portion, slice, fragment, component, wedge, lump, slab, hunk, parcel, tranche, wodge, subdivision, fraction, constituent, element, unit, module, ingredient, department, compartment, sector, branch, and/or wing, preferentially cryo-instrument, cryo-equipment, cryo-apparatus, cryo-piece, cryo-part, cryo-section, cryo-chunk, cryo-division, cryo-portion, cryo-slice, cryo-fragment, cryo-component, cryo-wedge, cryo-lump, cryo-slab, cryo-hunk, cryo-parcel, cryo-tranche, cryo-wodge, cryo-subdivision, cryo-fraction, cryo-constituent, cryo-element, cryo-unit, cryo-module, cryo-ingredient, cryo-department, cryo-compartment, cryo-sector, cryo-branch, and/or cryo-wing.

Preferentially, the segment belongs to the cryo-probe for example when it has not detached from the cryo-probe, for example when it is not fully or partly degraded in the body part or remains in contact with the cryo-probe.

In some cases, the segment doesn't belong to the cryo-probe, for example when it has detached from the cryo-probe, for example when it is biodegradable and is degraded in the organism.

In some cases, the nanoparticles are separated from the segment by a body part not comprising nanoparticle(s).

In one embodiment of the invention, the cryo-probe is an instrument or equipment or apparatus or temperature adjuster or piece of instrument, equipment or apparatus or temperature adjuster, which is preferentially used to apply cold to tissue. It is preferentially a medical or surgical instrument or a medical device. It is preferentially inserted or positioned in a body part of an individual, but can also in some cases be positioned outside of the body part of an individual.

In another embodiment of the invention, the cryo-probe is suitable for an internal cooling action, preferentially a cooling action of a body part, and preferentially comprises a segment and/or a cryogen source, wherein the segment is preferentially cooled down by the cryogen source.

In some cases, the cryo-probe comprises a segment that penetrates inside the body part, preferentially designated as penetrating segment of the cryo-probe. Preferentially, the penetrating segment of the cryo-probe has at least one of its surface or part of its surface, preferentially external surface, which is in contact with the body part.

In some other cases, the cryo-probe comprises a segment that does not penetrate inside the body part or is located outside the body part, preferentially designated as the non-penetrating segment of the cryo-probe. Preferentially, the non-penetrating segment of the cryo-probe is different from the penetrating segment of the body part and does not have at least one of its surface or part of its surface, preferentially external surface, which is in contact with the body part.

In some cases, the segment has a volume $V_S$ or length $L_S$ or dimension $D_S$ or diameter $d_S$ that is smaller than the biggest volume of the body part, $V_{BP}$, or biggest length of the body part, $L_{BP}$, or biggest dimension of the body part, $D_{BP}$, or biggest diameter of the body part, $d_{BP}$. The ratio $V_S/V_{BP}$ or $L_S/L_{BP}$ or $D_S/D_{BP}$ or $d_S/d_{BP}$ can be smaller than 1, 0.8, 0.5, 0.2, $10^{-1}$, $10^{-3}$, $10^{-5}$ or $10^{-10}$.

In some cases, the biggest volume, dimension, length, diameter of the body part can be: i) the biggest volume, dimension, length, diameter of the body part that is cooled down or that is pathogenic or tumoral or that swells or ii) the volume, dimension, length, diameter of the body part that is unhealthy or tumoral or comprises at least one pathological cell or is an unhealthy site.

In some cases, the frontier between the biggest volume, dimension, length, diameter of the body part and another body part of an individual is the frontier between a healthy site and a unhealthy site of an individual such as the border or margin of a tumor or unhealthy site, which can in some cases be identified by microscopy or histology or surgical resection.

In some other cases, the segment has a volume $V_S$ or length $L_S$ or dimension $D_S$ or diameter $d_S$ that is larger than the biggest volume of the body part, $V_{BP}$, or biggest length of the body part, $L_{BP}$, or biggest dimension of the body part, $D_{BP}$, or biggest diameter of the body part, $d_{BP}$. The ration $V_S/V_{BP}$ or $L_S/L_{BP}$ or $D_S/D_{BP}$ or $d_S/d_{BP}$ can be larger than 1, 2, 5, 10, $10^3$ or $10^5$.

In still some other cases, the ratio $V_S/V_{BP}$ or $L_S/L_{BP}$ or $D_S/D_{BP}$ or $d_S/d_{BP}$ is between $10^{-10}$ and $10^{10}$, $10^{-5}$ and $10^5$, $10^{-5}$ and 1, or $10^{-3}$ and 1.

In one embodiment of the invention, the segment has at least one dimension or length or diameter or surface or volume smaller than $10^{10}$, $10^5$, $10^3$, 200, 100, 50, 20, 10, 5, 2, 1, 0.5, $10^{-1}$, $10^{-3}$, $10^{-5}$, $10^{-7}$ or $10^{-10}$ cm or cm$^2$ or cm$^3$.

In one aspect, the present invention allows the cryo-probe, preferentially the segment, most preferentially the penetrating segment to have a size that is smaller when it is used in the presence than in the absence of the nanoparticles. In some cases, such size can be decreased by a factor of at least 0, 0.5, 1, 1.1, 2, 3, 5, 10 or 100 when the cryo-probe is used with the nanoparticle(s) than when the cryo-probe is used without the nanoparticle(s).

In one embodiment of the invention, the cryo-probe comprises a non-penetrating segment, which is a segment not penetrating inside the body part.

Preferentially, the segment, penetrating or not, is in communication with a cryogen source that preferentially cools down the segment.

In some cases, the segment is cooled down below the physiological temperature or below 100, 50, 37, 20, 10, 5, 1, 0, −2, −5, −10, −20, −50, −100, −150, −200, or −250° C. Low cooling temperatures can be desired, for example when ice-ball formation is searched for.

In some other cases, the segment is cooled down above −250, −200, −150, −100, −50, −40, −20, −10, −5, −2, −1, 0, 2, 5, 10 or 20° C. Too low cooling temperatures can be avoided, for example to prevent the formation of ice-balls.

Preferentially, the penetrating or non-penetrating segment, preferentially the non-penetrating segment, cools down the body part, preferentially by expelling or diffusing or carrying a gas or a liquid, preferentially a cryogenic gas or liquid, which preferentially originates from the cryogen source, and preferentially diffuses from the segment to the body part, preferentially without a contact or direct or solid contact between the segment and the body part.

Preferentially, the penetrating or non-penetrating segment, preferentially the penetrating segment, cools down the body part, preferentially by having its surface or part of its surface in contact, preferentially in direct or solid contact with the body part.

In one embodiment of the invention, the cryo-probe, preferentially the segment, most preferentially the penetrating segment cools down a volume preferentially comprised in the body part or medium that is larger, preferentially by a factor of at least 0, 0.5, 1, 2, 5, 10, $10^3$ or $10^5$ when the cryo-probe is used with the nanoparticle(s) than when the cryo-probe is used without the nanoparticle(s).

In another embodiment of the invention, the cryo-probe, preferentially the segment, most preferentially the penetrating segment, cools down the body part at a cooling or minimum temperature, which is larger in the presence than in the absence of nanoparticle(s) preferentially by at least 0.1, 1, 5, 10, 20 or 50° C., preferentially to reach a similar activity such as the destruction of the body part or tumor.

In some cases, the minimum temperature of at least one step of the treatment can be designated as $T_{min}$.

In another embodiment of the invention, the cryo-probe, preferentially the segment, most preferentially the penetrating segment, cools down the body part with a spatial temperature distribution within the body part or spatial temperature gradient within the body part, which is lower in the presence than in the absence of nanoparticle(s) preferentially by at least 0.1, 1, 5, 10, 20 or 50° C., preferentially to reach a similar activity such as the destruction of the body part or tumor.

In another embodiment of the invention, the cryo-probe enables the realization of at least one cycle comprising at least one cooling step and at least one warming step, wherein the cooling step is accelerated or produced or initiated by the cryo-probe or by the activation of the cryo-probe and the warming step is slowed down by the nanoparticle(s).

In another embodiment of the invention, the body part or tumor is more efficiently destroyed and/or with less side effects using the cryo-system than using the cryo-probe without nanoparticles. This can be due to at least one of the properties of the cryo-system selected in the group consisting of: i) smaller cryo-probe size with than without nanoparticles, ii) increased volume of body part that is cooled down with than without nanoparticles, iii) reduced temperature gradient with than without nanoparticles, iv) increased cooling or minimum temperature with than without nanoparticles, and, v) slower warming step with than without nanoparticle(s).

Associating or Binding Material

In one aspect of the invention, the cryo-system comprises a second part, which is, in one embodiment of the invention, an assembly of at least two nanoparticles characterized in that this assembly comprises at least two nanoparticles bound to each other or associated with each other via binding or associating material.

In one embodiment of the invention, the associating or binding material is a junction or material of junction between at least two nanoparticles.

In some cases, the associating or binding material separates the at least two nanoparticles by more than $10^{-3}$, $10^{-1}$, 0, 1, 5, 10, $10^2$ or $10^3$ nm.

In some other cases, the associating or binding material separates the at least two nanoparticles by less than $10^5$, $10^3$, 100, 70, 50, 20, 10, 5, 2 or 1 nm.

In still some other cases, the distance separating the at least two nanoparticle(s) is larger in the presence than in the absence of associating or binding material, preferentially by a factor of at least 0, 1, 1.1, 2, 5, 10 or $10^3$.

In still some other cases, the associating or binding material can form or be or transform into ice or ice-ball and preferentially can't form or be or transform into nanoparticle-ice-ball, preferentially when its temperature is decreased below 10, 5, 2, 1, 0, −2, −5 or −10° C.

In still some other cases, in the presence of associating or binding material the nanoparticles are preferentially well-distributed, not aggregated, well dispersed, homogenously distributed, while in the absence of associating or binding material the nanoparticles are preferentially aggregated, stuck together, or in-homogeneously distributed.

In some cases, the binding or associating material is a material that embeds or surrounds or coats at least two nanoparticles, preferentially in such a way that the two nanoparticles are linked or bound to each other through this material.

In some cases, the associating or binding material can be destroyed during cryotherapy.

In some other cases, the associating or binding material can be preserved during cryotherapy.

In some cases, the associating or binding material can be the coating of the nanoparticle(s).

In some cases, the cooling temperature can designate a temperature selected in the group consisting of: i) at least one temperature between the initial and minimum temperature, ii) at least one temperature of the cooling step, iii) the minimum temperature, and iv) the maintaining temperature, also preferentially designated as at least one temperature of the maintaining step.

In some cases, the minimum temperature is the minimum temperature of the whole treatment or of at least one step of the treatment.

In one embodiment, the associating or binding material contains less than 50%, 25%, 10%, or 1% preferentially in mass of non-denatured organic material, preferentially coming from magnetotactic bacteria, e.g. lipids, endotoxins and/or non-denatured proteins preferentially coming from magnetotactic bacteria.

In one embodiment, the associating or binding material comprises at least one compound able to establish interactions or bonds with metallic ions, $Fe^{2+}$ or $Fe^{3+}$ ions, hydroxyls $OH^-$, oxides $O^{2-}$, crystalline defects or impurities of the nanoparticle(s), which may be in or at the surface of the nanoparticles.

In one embodiment, the associating or binding material comprises at least one compound, atom, ion, or chemical function such as an acid, carboxylic acid, phosphoric acid, or sulfonic acid function, wherein the compound, atom or ion embedded in the associating or binding material is able to establish interactions or bonds with the nanoparticle(s), a chemical function of the nanoparticle(s), an ion of the nanoparticle(s) such as e metallic ion, $Fe^{2+}$, $Fe^{3+}$, Hydroxyl $OH^-$, oxide $O^{2-}$ or a crystalline defect of the nanoparticle(s).

The atom, the chemical function or the ion of the nanoparticle(s) may be in or at the surface of the nanoparticle(s).

In one embodiment, the associating or binding material is chosen from substances which yield better cooling properties of the nanoparticle(s). It is thus preferred that the associating or binding material comprises substances, which are good thermal conductors.

In one embodiment, the associating or binding material is chosen from compounds which produce among nanoparticle(s) an organization or assembly properties, which favor the effects of the treatment or cryotherapy on the nanoparticle(s).

In some cases, the effect of the treatment or cryotherapy may in particular be production of ice and/or movements, vibrations, rotations, translations of these nanoparticles.

In one embodiment, the associating or binding material has a thickness which is less than the average diameter of the nanoparticle(s), less than half, a quarter of that diameter, less than 10.5, 2.5 or 1 μm, 500, 400, 300, 200, 100, 90, 80, 70, 60, 50, 40, 30, 20, 10, 5, 4, 3, 2, 1 or 0.5 nm. Such a thickness may in particular enable to limit the toxicity.

In one embodiment, the associating or binding material has a thickness typically larger than the average diameter of the nanoparticle(s), larger than one-half one-fourth of this diameter, larger than 0.1, 0.5, 1, 2, 4, 8, 10, 15, 20 or 25 nm. Such a thickness may in particular enable to bind the nanoparticle(s) together or enable to prevent the formation of aggregates. Advantageously, the presence of a sufficiently thick coating enables to prevent the nanoparticle(s) from sticking together, in particular under the effect of the magnetic forces which they exert on each other and whose intensity increases when these nanoparticles become closer to each other.

In one embodiment, the associating or binding material has a metallic or iron content or percentage in mass lower by factor of at least 1, 2, 5, 10, $10^2$, $10^3$, $10^4$, $10^5$ or $10^6$ than the nanoparticles.

In another embodiment, the associating or binding material has a content or percentage in mass in at least one atom other than iron and oxygen which is larger than or equal to 1, 2, 5, 10, $10^2$, $10^3$, $10^4$, $10^5$ or $10^6$ times that of the central part of synthetic nanoparticles.

In one embodiment, the associating or binding material comprises carbon compounds.

In one embodiment, the associating or binding material comprises at least one compound selected from the group consisting of: a chelator, an amphipathic molecule, a polarized or charged polymer, a metal or silicon oxide, a metal or silicon hydroxide, an acid, an acidic, basic, oxidized, reduced, neutral, positively charged, negatively charged, derivative of these compounds, and a combination of several of these compounds or derivatives.

In one embodiment, the associating or binding material comprises at least one compound selected from the group consisting of: a polysaccharide, a fatty acid, a phospholipid, a polymer of amino acids, polymeric or non-polymeric silica, and an aliphatic amine polymer, of an acidic, basic, oxidized, reduced, neutral, positively charged, negatively charged derivative of these compounds, and a combination of several of these compounds or derivatives.

In one embodiment, the associating or binding material does not include phospholipids or proteins or RNA or DNA or compounds of bacterial, cellular or biological origin or compound derived from a magnetotactic bacterium.

In one embodiment, the associating or binding material comprises at least one function selected from the group consisting of phosphoric acids, carboxylic acids, sulfonic acids, esters, amides, ketones, alcohols, phenols, thiols, amines, ethers, sulfides, acid anhydrides, acyl halides, amidines, nitriles, hydroperoxides, imines, aldehydes, peroxides, of an acidic, basic, oxidized, reduced, neutral, positively charged, negatively charged derivative of these compounds, and a combination of several of these compounds or their derivatives.

In one embodiment, the associating or binding material according to the invention is chosen from sterilizable, preferably by autoclaving, biocompatible, and/or biodegradable substances, which preferentially do not induce metabolic, immunological, cytotoxic, and/or pharmacological effect, which preferentially can be administered by an intravenous, intra-arterial route and/or intra. Such a substance may be povidone, PEG 400, poloxamer 188, dextran, phosphatidylcholine, dipalmitoyl-sn-glycero-3-phosphatidylcholine, or a derivative of these substances.

In some cases, the type of associating or binding material can be selected according to the following parameters:
  (i) Administration route of synthetic nanoparticles: for example, for an intravenous administration, a coating that enables to prevent macrophages from capturing synthetic nanoparticles, such as PEG or dextran can eventually be chosen,
  (ii) Cellular internalization: to support it, a coating with a positive charge such as poly-L-lysine can "eventually" be chosen.

In one embodiment, the associating or binding material and/or nanoparticle(s) according to the invention can be used as drug or as diagnostic agent, in particular in the context of the treatment of a tumor, for example using cryotherapy.

In one embodiment, the associating or binding material is selected in the group consisting of compounds being or comprising: citric acid, oleic acid, polymethacrylic acid, poly(ethyleneoxide)-b-poly(methacrylic acid) acid, polyacrylic acid (PAA), polylactic acid, poly(ethylene oxide)-blockpoly(glutamic acid) acid, phosphonic acid, albumin, alendronate, alginate, gold, Au, $Al_2O_3$, Alginate, Aluminium hydroxide, Arabinogalactan, Bentonite, Carboxymethylcellulose, Cellulose, Chitosan, Cholseterol, Citrate, Dextran, Dimercaptosuccinic acid, Dopamine, DOPC, DTAP, DVB, Ethylcellulose, Erythrocyte, Ferrite, Folic acid, Gelatin, Human serum albumin, Liposome, MIPS, MnO, $Mn_3O_4$, Oleic acid, PEI, PEG, PEO-PGA, PLA, PLGA, a polymer, Phosphatidylcholine, Phosphorylcholine, Pluronic, Polyacrylamide, Polyacrylic acid PAA, Polyaniline, Polyethylene glycol with terminal carboxyl groups, Polypeptides, Poly(ethylene oxide), Poly(vinyl alcohol), Ploy(N-isopropylacrylamide), Poly(vinylpyrrolidone), Poly(oligoethylene oxide), Poly(N,N-dimethyl ethylamino acrylate), Poly(imine), Poly(acrylic acid), Poly-D-L lactide, Polyalkylcyanoacrylate, Polymer (PAMAM, PDMAEMA, PPEGMA), PolyNIPAAM, Polyacrylic acid, Polydipyrrole/dicarbazole, Poly-L-lysine, Polymethylmethaacrylate, Polymersomes, Polysaccharide such as Agarose, alginate, carregeenan, chitosan, dextran, haparin, Gum Arabic, Pullulan and/or Starch, Polystyrene, PVA, PVP, Silica preferentially amorphous or mesoporous, Silane, SiO2, Sodium Oleate, Starch, Styrenedivinylbenzene, TaOx, ZrO2, and a derivative or combination of these compounds.

In one embodiment, the associating or binding material is not at least one compound listed in the previous embodiment.

In one embodiment, the associating or binding material is selected in the group consisting of: i) Polysaccharides such as Agarose, alginate, carregeenan, chitosan, dextran, haparin, Gum Arabic, Pullulan and/or Starch, ii) Acids such as acid citric, acid oleic, polymethacrylic acid, poly(ethyleneoxide)-b-poly(methacrylic acid), polyacrylic (PAA) acid, polylactic acid, poly(ethylene oxide)-blockpoly(glutamic acid) acid, Phosphonic acid, Dimercaptosuccinic acid, Fatty acids, folic acid, PLA (poly(lactide acid) Polyacrylic acid PAA, compounds comprising at least one carboxylic acid function, iii) Polymers such as Dextran, Poly(ethylene oxide), Poly(vinyl alcohol), Ploy(N-isopropylacrylamide), Poly(vinylpyrrolidone), Poly(oligoethylene oxide), Poly(N, N-dimethyl ethylamino acrylate), Poly(imine), Poly(acrylic acid), iv) Carboxylates, v) Inorganic compounds such as $SiO_2$, $Al_2O_3$, $ZrO_2$, ferrites, MnO, $Mn_3O_4$, Au, Bentonite, Carbon such as activated or graphitized carbon, vi) Metallic compounds, vii) Organic compounds such as MIPs, Cellulose, DVB, Ppy, Chitosan, Polyacrylamide, alginate, PEI, surfactants, viii) compounds comprising Phosphate, ix) compounds comprising Silica, x) compounds comprising Gold, xi) compounds comprising Dextran, xii) compounds comprising PEG, xiii) and a combination or derivative of these compounds.

Nanoparticles

In one embodiment of the invention, the at least one nanoparticle is characterized in that it comprises or comprises:
α) iron and/or at least 1, 2, 3, 5 or 10 other metal(s) or metalloid(s) than iron, where this(these) other metal(s) or metalloid(s) is/are preferentially comprised in or at the surface of the nanoparticle(s) at a concentration preferentially larger than 0, $10^{-10}$, $10^{-5}$, $10^{-1}$, 1, 5, 10, 50, 100, 200, 500, $10^3$ or $10^5$ µg of metal(s) or metalloid(s) per gram of nanoparticle(s), and/or β) more than 0, 1, 5, 10, 20, 50, 70, 90, 99 or 99% in mass of iron or iron oxide, where this percentage in mass is preferentially equal to $M_I/M_{allmetals}$, $M_{IO}/M_{allmetals}$, $M_I/M_{Nano}$ or $M_{IO}/M_{Nano}$, where $M_I$, $M_{IO}$, $M_{allmetals}$, are the masses of iron, iron oxide, and all metals comprised in and at the surface of the nanoparticles respectively, and $M_{Nano}$ is the mass of the nanoparticle(s).

In another embodiment of the invention, the at least one nanoparticle is characterized in that it comprises or comprises:
α) a first metal or metalloid and either 0 other metal or metalloid or at least 1, 2, 3, 5 or 10 other metal(s) or metalloid(s) than the first metal or metalloid, where this(these) metal(s) or metalloid(s) is/are preferentially comprised in or at the surface of the nanoparticle(s) at a concentration preferentially larger than 0, $10^{-10}$, $10^{-5}$, $10^{-1}$, 1, 5, 10, 50, 100, 200, 500, $10^3$ or $10^5$ µg of metal(s) or metalloid(s) per gram of nanoparticle(s), and/or β) more than 0, 1, 5, 10, 20, 50, 70, 90, 99 or 99% in mass of a first metal or first metalloid, where this percentage in mass is preferentially equal to $M_{FM}/M_{allmetals}$ or $M_{FM}/M_{Nano}$, where $M_{FM}$ and $M_{allmetals}$ are the masses of the first metal/metalloid and of all metals comprised in and/or at the surface of the nanoparticles respectively, and $M_{Nano}$ is the mass of the nanoparticle(s).

In some other cases, the at least one nanoparticle can comprise:
α) iron and less than 100, 50, 20, 10, 5, 2 or 1 other metal(s) or metalloid(s) than iron, where this(these) other metal(s) or metalloid(s) is/are preferentially comprised in or at the surface of the nanoparticle(s) at a concentration preferentially smaller than $10^{10}$, $10^5$, $10^3$, 100, 50, 20, 10, 5, 2 or 1 0 µg of metal(s) or metalloid(s) per gram of nanoparticle(s), and/or β) less than 100, 90, 70, 50, 20, 5, 2 or 1% in mass of iron or iron oxide, where this percentage in mass is preferentially equal to $M_I/M_{allmetals}$, $M_{IO}/M_{allmetals}$, $M_I/M_{Nano}$ or $M_{IO}/M_{Nano}$, where $M_I$, $M_{IO}$, $M_{allmetals}$, are the masses of iron, iron oxide, and all metals comprised in and at the surface of the nanoparticles respectively, and $M_{Nano}$ is the mass of the nanoparticle(s).

In some other cases, the at least one nanoparticle can comprise:
α) a first metal or a first metalloid and less than 100, 50, 20, 10, 5, 2 or 1 other metal(s) or metalloid(s) than the first metal or first metalloid, where this(these) metal(s) or metalloid(s) is/are preferentially comprised in or at the surface of the nanoparticle(s) at a concentration preferentially smaller than $10^{10}$, $10^5$, $10^3$, 100, 50, 20, 10, 5, 2 or 1 0 µg of metal(s) or metalloid(s) per gram of nanoparticle(s), and/or β) less than 100, 90, 70, 50, 20, 5, 2 or 1% in mass of the first metal or first metalloid, where this percentage in mass is preferentially equal to $M_{FM}/M_{allmetals}$ and $M_{FM}/M_{Nano}$, where $M_{FM}$ and $M_{allmetals}$ are the masses of the first metal/metalloid comprised in and/or at the surface of the nanoparticles respectively, and $M_{Nano}$ is the mass of the nanoparticle(s).

In some cases, the metal or metalloid can designate or be designated as first metal or metalloid.

In some other cases, the metal or metalloid can designate or be designated as the other metal or metalloid.

In one embodiment of the invention, the cryo-system comprises a second part, which is at least one nanoparticle, preferentially a magnetic or metallic nanoparticle.

As used herein, the term "nanoparticle" is meant to include any nano-sized material with at least one dimension such as length, width, surface, volume, or thickness, within the size range of 0.1-1000 nm, preferentially within the size range of 1-100 nm.

As used herein, the term "magnetic nanoparticle" is meant to include any nanoparticle which gives rise to a response when it is subjected to a magnetic field, where the response can be: i), a non-zero magnetization or coercivity, ii) a coercivity or magnetization that increases in strength with increasing magnetic field strength, iii) a nanoparticle magnetic moment that gets coupled with the magnetic field, and/or iv) a nanoparticle movement, preferentially induced when the magnetic field is non-uniform spatially. This term is meant to also include ferromagnetic, ferrimagnetic, paramagnetic, superparamagnetic and diamagnetic materials. Non-limiting suitable examples can include: i) $Fe_2O_3$, $Fe_3O_4$, $Fe_2O_4$, $Fe_xPt_y$, $Co_xPt_y$, $MnFe_xO_y$, $CoFe_xO_y$, $NiFe_xO_y$, $CuFe_xO_y$, $ZaFe_xO_y$, and $CdFe_xO_y$, wherein x and y are preferentially between 1 and 6, depending on the method of synthesis known in the art, and/or ii) nanoparticles comprising a magnetic material, preferentially predominantly, such as Fe, Pt, Au, Ag, Mg, Zn, Ni, or Si. A distinction can be made between nanoparticles that are magnetic in the absence of application of an external magnetic field or in the presence of a magnetic field of strength lower than 1 mT, such as those composed of iron or iron oxide, and nanoparticles that are magnetic in the presence of an external strength of strength preferentially higher than $10^{-5}$, $10^{-3}$, 1 or 10 mT, such as those composed of gold or silver.

As used herein, the term "metallic nanoparticle" is meant to include any nano sized metal with at least one dimension such as length, width, surface, volume, or thickness, within the size range of 0.1-1000 nm, preferentially within the size range of 1-100 nm. In some embodiment, the term "metallic nanoparticle" excludes some metallic nanoparticles such as gold or silver nanoparticles. In some embodiment, the term "metallic nanoparticle" only includes iron or iron oxide nanoparticles.

In one embodiment, the nanoparticle is not a thermosensitive nanoparticle or thermosensitive nano-capsule or thermos-capsule or thermosensitive polymer or thermosensitive vesicle or thermosensitive hollow nanoparticle or is not a nanoparticle or nano-capsule or polymer or hollow nanoparticle or vesicle that releases a drug when it is cooled down or warmed up.

In some cases, the drug according to the invention can be an active principle that is different from or not comprised in the nanoparticle core.

In some cases, a hollow nanoparticle is a nanoparticle that is not filled, preferentially with at least one metal or metal atom.

In one aspect, the invention relates to nanoparticle or cryo-system for use according to the invention or to the method according to the invention, wherein the nanoparticles have at least one property selected from the group consisting of: i) a size in the range from 1 to $10^3$ nm, ii) a metallic, magnetic, and/or crystallized structure, iii) a thermal conductivity in the range from $10^{-5}$ to $10^5$ W/mK, and iv) a concentration in the range from $10^{-5}$ to $10^5$ mg of nanoparticles per $cm^3$ of suspension or mg of nanoparticles per $cm^3$ of body part.

In one embodiment of this invention, the nanoparticle is selected from the group consisting of: a nanosphere, a nanocapsule, a dendrimer, a carbon nanotube, a lipid/solid nanoparticle, a lipid or protein or DNA or RNA based nanoparticle, a nanoparticle with an inner aqueous environment surrounded by a layer, preferentially a stabilizing layer, most preferentially a phospholipid layer, a multilayer nanoparticle, a polymeric nanoparticle, a quantum dot, a metallic nanoparticle, a polymeric micelle or nanoparticle, a carbon based nano-structure, a nanobubble, a nanosome, a pharmacyte, a niosome, a nanopore, a microbivore, a liposome, a virus, preferentially recombinant, a herbal nanoparticle, an antibody, and a vesicle.

In some cases, the nanoparticles do not comprise cytotoxins.

In another embodiment of this invention, the nanoparticle is not: a nanosphere, a nanocapsule, a dendrimer, a carbon nanotube, a lipid/solid nanoparticle, a lipid or protein or DNA or RNA based nanoparticle, a nanoparticle with an inner aqueous environment surrounded by a layer, preferentially a stabilizing layer, most preferentially a phospholipid layer, a multilayer nanoparticle, a polymeric nanoparticle, a quantum dot, a metallic nanoparticle, a polymeric micelle or nanoparticle, a carbon based nano-structure, a nanobubble, a nanosome, a pharmacyte, a niosome, a nanopore, a microbivore, a liposome, a virus, preferentially recombinant, a herbal nanoparticle, an antibody, and/or a vesicle.

In some embodiment, the nanoparticle can be comprised in a liquid, gaseous, or solid environment, preferentially before, during or after its presence or administration in the body part.

In still some other cases, the nanoparticles can be comprised in a ferrofluid, a chemical or biological ferrofluid, wherein chemical and biological ferrofluids are fluids containing iron, preferentially forming nanoparticles, which are fabricated through a chemical or biological synthesis, respectively.

In still some other cases, the ferrofluid or nanoparticle assembly can comprise the nanoparticles and an excipient, a solvent, a matrix, a gel, which preferentially enables the administration of the nanoparticles to the individual or body part.

In still some other cases, the nanoparticle comprises synthetic material and/or biological material and/or inorganic material and/or organic material.

In one embodiment of the invention, (the) nanoparticle(s) has/have at least one property in common with: i) a suspension of nanoparticles, ii) a composition comprising nanoparticles, iii) an assembly of nanoparticles, iv) the mineral part of the nanoparticle, vi) the organic part of the nanoparticle, vii) the inorganic part of the nanoparticle, viii) the coating of the nanoparticle, ix) the binding/associating material or x) the compound.

In one embodiment of the invention, nanoparticles are assemblies of more than 1, 10, $10^2$, $10^3$, $10^5$, $10^{10}$ or $10^{50}$ nanoparticle(s) or nanoparticle(s) per $cm^3$ of body part.

In another embodiment of the invention, nanoparticles are assemblies of less than $10^{50}$, $10^{10}$, $10^5$, $10^3$, $10^2$, 10, 5 or 2 nanoparticle(s) or nanoparticle(s) per $cm^3$ of body part.

In one embodiment of the invention, the nanoparticle(s) represent(s) or is or are an assembly or suspension or composition of more or comprising more than $10^{-100}$, $10^{-50}$, $10^{-10}$, $10^{-5}$, $10^{-1}$, 1, 10, $10^2$, $10^3$, $10^5$, $10^{10}$, $10^{20}$ or $10^{50}$ nanoparticle(s) or mg of nanoparticle(s) or mg of iron or metal comprised in nanoparticle(s) or mg of nanoparticle(s) per $cm^3$ or mg of nanoparticle(s) per $cm^3$ of body part or mg of iron comprised in nanoparticle(s) per $cm^3$ or mg of iron comprised in nanoparticle(s) per $cm^3$ of body part.

In some embodiment, an assembly or suspension or composition comprising at least one nanoparticle or a large number of nanoparticles can be used to induce or produce a temperature increase, radical or reactive species, or the dissociation of a compound from the nanoparticles.

In another embodiment of the invention, nanoparticle(s) represent(s) or is or are an assembly or suspension or composition of less or comprising less than $10^{100}$, $10^{50}$, $10^{20}$, $10^{10}$, $10^5$, $10^2$, 10, 1, 5, 2, 1, $10^{-1}$, $10^{-5}$, $10^{-10}$ or $10^{-50}$ nanoparticle(s) or mg of nanoparticle(s) or mg of iron or metal comprised in nanoparticle(s) or mg of nanoparticle(s) per $cm^3$ or mg of nanoparticle(s) per $cm^3$ of body part or mg of iron comprised in nanoparticle(s) per $cm^3$ or mg of iron comprised in nanoparticle(s) per $cm^3$ of body part. In some embodiment, an assembly or suspension or composition of nanoparticles comprising a low number of nanoparticle(s) can be used to prevent toxicity.

The invention also relates to nanoparticles or cryo-system for use according to the invention, wherein the nanoparticles are crystallized, metallic, or magnetic.

In some other cases, the nanoparticle can be amorphous.

In an embodiment of the invention, the nanoparticles are crystallized. In this case, they preferentially possess more than or at least 1, 2, 10, $10^2$, $10^3$, $10^6$ or $10^9$ crystallographic plane(s) or regular atomic arrangement(s), preferentially observable by electron microscopy.

In one embodiment of the invention, the nanoparticles are metallic. In this case, they contain at least 1, 10, $10^3$, $10^5$ or $10^9$ metallic atom(s) or contain at least 1, 10, 50, 75 or 90% of metallic atoms, where this percentage can be the ratio between the number or mass of metallic atoms in the nanoparticle divided by the total number or mass of all atoms in the nanoparticle. The nanoparticles, preferentially metal oxide nanoparticles, can also contain at least 1, 10, $10^3$, $10^5$ or $10^9$ oxygen atom(s), or contain at least 1, 10, 50, 75 or 90% of oxygen atoms, where this percentage can be the ratio between the number or mass of oxygen atoms in the nanoparticles divided by the total number or mass of all atoms in the nanoparticles.

In some cases, the nanoparticle(s) comprise(s) or is/are composed of iron and at least one metal or metalloid different from iron. In some cases, the metal or metalloid different from iron is selected in the group consisting of: Sodium, Magnesium, Aluminum, Potassium, Calcium, Scandium, Titanium, Chromium, Manganese, Zinc, Gallium, Strontium, Yttrium, Zirconium, Niobium, Molybdenum, Technetium, Indium, Cesium, Barium, Lanthanum, Cerium, Praseodymium, Neodymium, Samarium, Europium, Gadolinium, Terbium, Dysprosium, Holmium, Erbium, Thulium, Lutetium, Hafnium, Rhenium, and Tungstate.

In some cases, the at least one nanoparticle comprises or is composed of iron or iron oxide, partly or predominantly or fully. The iron oxide can have at least one of the following properties: i), it comprises at least one atom of iron and one atom of oxygen, ii), it forms a crystallized or mineral structure, iii), it can have the chemical formula $FeO$, $FeO_2$, $Fe_3O_4$, $Fe_4O_5$, $Fe_5O_6$, $Fe_5O_7$, $Fe_{25}O_{32}$, $Fe_{13}O_{19}$, $\alpha$-$Fe_2O_3$, $\beta$-$Fe_2O_3$, $\gamma$-$Fe_2O_3$, $\epsilon$-$Fe_2O_3$, iv), it can be composed of wüstite, iron dioxide, magnetite, hematite, maghemite, v), it can be in the epsilon phase, alpha phase, beta phase, gamma phase, vi), it can be in various levels of oxidations, vii), it has the formula $Fe_\alpha O_\beta D_\gamma$, where $\alpha$, $\beta$ and/or $\gamma$ is/are coefficients, preferentially stoichiometric coefficients. In some cases, $\alpha$, $\beta$ and/or $\gamma$ is/are equal to 0, 1, 2, 3, 4, 5, 6, 7, 8, 9, 10, 11, 12, 13, 14, 15, 16, 18, 19 or 20. In some other cases, $\alpha$, $\beta$ and/or $\gamma$ is/are larger than 0, 1, 2, 3, 4, 5, 6, 7, 8, 9, 10, 11, 12, 13, 14, 15, 16, 18, 19 or 20. In still some other cases, $\alpha$, $\beta$ and/or $\gamma$ is/are smaller than 0, 1, 2, 3, 4, 5, 6, 7, 8, 9, 10, 11, 12, 13, 14, 15, 16, 18, 19 or 20. In some other cases, D is the doping material of the nanoparticles. In some cases, the doping material can be a metal or metalloid, preferentially different from iron, or can be selected from the group consisting of: Aluminum, antimonite, barium, chrome, copper, gold, manganese, silver, tin, titanium, and zinc.

In one embodiment of the invention, the iron oxide comprised in the nanoparticles is the predominant chemical element of the nanoparticle. In some cases, the high purity iron oxide nanoparticles can comprise a large quantity of iron oxide. In some cases, the percentage, preferentially in mass, of iron oxide comprised in the nanoparticle(s), is larger than $10^{-40}$, $10^{-20}$, $10^{-10}$, $10^{-5}$, $10^{-2}$, $10^{-1}$, 1, 5, 10, 25, 50, 75, 80, 90, 99 or 99.9%. According to the invention, this percentage of iron oxide can in some cases be defined as the ratio between the number of atoms, quantity, mass, or volume of iron oxide in the nanoparticle(s) divided by the total number of atoms, quantity, mass, or volume of all chemical element(s) comprised in the nanoparticle(s). In still some other cases, the concentration of iron oxide, comprised in the nanoparticle(s) is larger than $10^{-100}$, $10^{-50}$, $10^{-20}$, $10^{-10}$, $10^{-5}$, $10^{-3}$, $10^{-2}$, $10^{-1}$, 1, 10, 50, 100, $10^3$, $10^5$ or $10^{10}$ μg of iron oxide, per gram of nanoparticle(s).

In one embodiment of the invention, the nanoparticle(s) comprise(s) a low quantity of iron oxide, for example when the nanoparticle(s) are dissolved by the body part. In some cases, the percentage, preferentially in mass, of iron oxide, comprised inside or at the surface of the nanoparticle(s), is lower than 100, 90, 80, 70, 50, 30, 10, 5, 1, 0.1 or 0.001%. In some other cases, the concentration of iron oxide, comprised in the nanoparticle(s) can be lower than $10^{50}$, $10^{30}$, $10^{10}$, $10^5$, $10^3$, 500, 100, 50, 10, 1, $10^{-1}$, $10^{-3}$, $10^{-5}$, $10^{-10}$ or $10^{-50}$ μg of iron oxide per gram of nanoparticle(s).

In another embodiment of the invention, the percentage, concentration, number of atoms, quantity, mass, or volume of iron oxide comprised in the nanoparticle(s) is larger, preferentially by a factor of 1.00001, 1.001, 1.1, 2, 5, 10, 50, $10^2$, $10^3$, $10^5$, $10^{10}$, $10^{20}$ or $10^{50}$, than the percentage, concentration, number of atoms, quantity, mass, or volume of impurity(ies) comprised in the nanoparticle(s).

In some cases, the at least one nanoparticle is a composition.

In some cases, the at least one nanoparticle comprises more than 0, 1, 5, 10, 25, 50, 70, 80, 90, 99 or 99.9% in mass of: i) metal, ii) metalloid, iii) metallic element, iv) magnetic element, v) iron, or vi) iron oxide. This percentage in mass can correspond to the percentage in mass of the metallic or magnetic part of the nanoparticle or of the core of the nanoparticles or can exclude or not take into consideration the coating or associating or binding material. It can be beneficial to use nanoparticles with a metallic composition since such composition can help to keep the cold within the nanoparticles.

In some cases, the at least one nanoparticle comprises more than 0, 1, 5, 10, 25, 50, 70, 80, 90, 99 or 99.9% of:
i) iron, preferentially based on a ratio of $M_{FeN}/M_{MN}$, where $M_{FeN}$ is the mass of iron in the at least one nanoparticle and $M_{MN}$ is mass of iron and metals or metalloids other the than iron in the at least one nanoparticle, ii) iron and at least one other metal than iron selected in the group 1 consisting of: Sodium, Magnesium, Aluminum, Potassium, Calcium, Scandium, Titanium, Chromium, Manganese, Zinc, Gallium, Strontium, Yttrium, Zirconium, Niobium, Molybdenum, Technetium, Indium, Cesium, Barium, Lanthanum, Cerium, Praseodymium, Neodymium, Samarium, Europium, Gadolinium, Terbium, Dysprosium, Holmium, Erbium, Thulium, Lutetium, Hafnium, Rhenium, and Tungstate, preferentially based on a ratio of $M_1/M_2$, where $M_1$ is the mass of iron and of at least one other metal selected in the above group 1 in the at least one nanoparticle, and $M_2$ is the mass of all metals or of more than 5 or 10 different metals or metalloids comprised in the at least one nanoparticle, and/or iii) iron and at least one other non-metal selected in the group 2 consisting of: Hydrogen, Carbon, Nitrogen, Phosphorus, Sulfur, Fluorine, Chlorine, Bromine, Iodine, Helium, Neon, Argon, Krypton, Xenon, Radon, and Oxygen, preferentially based on a ratio $M_3/M_4$, where $M_3$ is the mass in the at least one nanoparticle of iron and of at least one other non-metal selected in the above group 2 and $M_4$ is the mass of all non-metallic elements or of more than 5 or 10 different non-metallic elements comprised in the at least one nanoparticle.

In some cases, the at least one nanoparticle comprises less than 100, 99.9, 99, 80, 75, 60, 50, 30, 20, 10 or 5% in mass of: i) metal, ii) metalloid, iii) metallic element, iv) magnetic element, v) iron, or vi) iron oxide. This percentage in mass can correspond to the percentage in mass of the metallic or magnetic part of the nanoparticle or of the core of the nanoparticles or can exclude or not take into consideration the coating or associating/binding material. It can be beneficial to use nanoparticles with a composition that does not only comprise metals such as iron, for example to reduce toxicity, or to improve the capacity of the nanoparticle(s) to keep the cold.

In some cases, the at least one nanoparticle comprises less than 100, 99.9, 99, 90, 80, 70, 50, 25, 10, 5, 2 or 1% in mass of: i) metal, ii) metalloid, iii) metallic element, iv) magnetic element, v) iron, or vi) iron oxide. This percentage in mass can correspond to the percentage in mass of the metallic or magnetic part of the nanoparticle or of the core of the nanoparticles or can exclude or not take into consideration the coating or associating/binding material. It can be beneficial to use nanoparticles with a non-fully metallic or iron composition since such composition can help to keep the cold within the nanoparticles or prevent toxicity or improve the efficacy of the cryotherapy.

In some cases, the at least one nanoparticle comprises less than 100, 99, 90, 80, 70, 50, 20, 10, 5, 2 or 1% of:

i) iron, preferentially based on a ratio of $M_{FeN}/M_{MN}$, where M is the mass of iron in the at least one nanoparticle and $M_{MN}$ is mass of iron and metals or metalloids other than iron in the at least one nanoparticle, ii) iron and at least one other metal than iron selected in the group 1 consisting of: Sodium, Magnesium, Aluminum, Potassium, Calcium, Scandium, Titanium, Chromium, Manganese, Zinc, Gallium, Strontium, Yttrium, Zirconium, Niobium, Molybdenum, Technetium, Indium, Cesium, Barium, Lanthanum, Cerium, Praseodymium, Neodymium, Samarium, Europium, Gadolinium, Terbium, Dysprosium, Holmium, Erbium, Thulium, Lutetium, Hafnium, Rhenium, and Tungstate, preferentially based on a ratio of $M_1/M_2$, where $M_1$ is the mass of iron and of at least one other metal selected in the above group 1 in the at least one nanoparticle, and $M_2$ is the mass of all metals or of more than 5 or 10 different metals or metalloids comprised in the at least one nanoparticle, and/or iii) iron and at least one other non-metal selected in the group 2 consisting of: Hydrogen, Carbon, Nitrogen, Phosphorus, Sulfur, Fluorine, Chlorine, Bromine, Iodine, Helium, Neon, Argon, Krypton, Xenon, Radon, and Oxygen, preferentially based on a ratio $M_3/M_4$, where $M_3$ is the mass in the at least one nanoparticle of iron and of at least one other non-metal selected in the above group 2 and $M_4$ is the mass of all non-metallic elements or of more than 5 or 10 different non-metallic elements comprised in the at least one nanoparticle.

In one embodiment of the invention, the at least one nanoparticle according to the invention is or comprises an assembly of more than 1, 2, 5, 10, $10^3$, $10^5$, $10^{10}$, $10^{20}$, $10^{50}$ or $10^{100}$ nanoparticle(s), nanoparticles per $cm^3$ of body part.

In one embodiment of the invention, the at least one nanoparticle comprises: i) at least one impurity, ii) at least one chemical element, and/or iii) iron oxide, partly or fully.

In some cases, iron oxide represents or is an assembly of more than 1, 10, $10^3$, $10^5$, $10^{10}$, $10^{20}$, $10^{50}$ or $10^{100}$ atom(s) of iron and/or more than 1, 10, $10^3$, $10^5$, $10^{10}$, $10^{20}$, $10^{50}$ or $10^{100}$ atom(s) of oxygen.

In some other cases, the chemical element(s), and/or impurity(ies) comprised in the at least one nanoparticle, are/is or represent(s) more than 1, 10, $10^3$, $10^5$, $10^{10}$, $10^{20}$, $10^{50}$ or $10^{100}$ chemical element(s), and/or impurity(ies) comprised in the at least one nanoparticle.

In another embodiment of the invention, the at least one nanoparticle according to the invention is or comprises an assembly of less than $10^{100}$, $10^{50}$, $10^{20}$, $10^{10}$, $10^5$, $10^3$, 100, 50, 10, 5 or 2 nanoparticles, or nanoparticles per $cm^3$ of body part.

In some cases, iron oxide represents or is an assembly of less than 1, 10, $10^3$, $10^5$, $10^{10}$, $10^{20}$, $10^{50}$ or $10^{100}$ atom(s) of iron and/or less than 1, 10, $10^3$, $10^5$, $10^{10}$, $10^{20}$, $10^{50}$ or $10^{100}$ atom(s) of oxygen.

In still some other cases, the chemical element(s) and/or impurity(ies) comprised in the at least one nanoparticle is or represents less than $10^{100}$, $10^{50}$, $10^{20}$, $10^{10}$, $10^5$, $10^3$, 100, 50, 10, 5 or 2 chemical elements, and/or impurity(ies) comprised in the nanoparticles.

In one embodiment, the at least one nanoparticle comprises a low quantity of impurity(ies), preferentially to enable the cryotherapy to work. In some cases, the nanoparticle(s) does/do not comprise at least one impurity or comprise(s) or comprise(s) less than $10^{50}$, $10^{20}$, $10^{10}$, $10^5$, $10^2$, 10, 5, 2, 5, 1, $10^{-2}$, $10^{-10}$, $10^{-20}$ or $10^{-50}$ impurity(ies) or impurity(ies) per gram of nanoparticles or gram of impurity (ies) per gram of nanoparticles. In some other cases, the percentage, preferentially in mass, of impurity(ies) comprised inside or at the surface of the nanoparticle(s) is lower than 100, 90, 80, 70, 60, 50, 30, 20, 10, 5, 1, 0.1 or 0.001%. According to the invention, this percentage of impurity(ies) can in some cases be defined as the ratio between the number of atoms, quantity, mass, or volume of impurity(ies) comprised in the nanoparticle(s) divided by the total number of atoms, quantity, mass, or volume of all chemical element(s) comprised in the nanoparticle(s). In some cases, all chemical element(s) comprised in the nanoparticle(s) can be the sum of the iron oxide, doping material, and impurity(ies), comprised in the nanoparticle(s). In still some other cases, the concentration of the impurity(ies) comprised inside or at the surface of the nanoparticle(s) is lower than $10^{50}$, $10^{30}$, $10^{10}$, $10^5$, $10^3$, 500, 100, 50, 10, 1, $10^{-1}$, $10^{-3}$, $10^{-5}$, $10^{-10}$ or $10^{-50}$ µg of impurity(ies) per gram of nanoparticle(s).

In another embodiment of the invention, the high purity iron oxide nanoparticles comprise a large or significant quantity of impurity(ies), for example when the impurity (ies) is/are useful to the cryotherapy for example to make it non-toxic or to improve its efficacy. In some cases, the nanoparticles comprise more than $10^{-50}$, $10^{-20}$, $10^{-10}$, $10^{-5}$, $10^{-2}$, 1, 2, 5, 10, $10^3$, $10^5$, $10^{10}$, $10^{20}$ or $10^{50}$ impurity(ies) or impurities per gram of nanoparticles or gram of impurity per gram of nanoparticles. In some cases, the nanoparticles comprise a large quantity of impurity(ies). In some cases, the percentage, preferentially in mass, of the impurity(ies) comprised inside or at the surface of the nanoparticle(s) is larger than $10^{40}$, $10^{-20}$, $10^{-10}$, $10^{-5}$, $10^{-2}$, $10^{-1}$, 1, 5, 10, 25, 50, 75, 80 or 90%. In still some other cases, the concentration of impurity(ies) comprised inside or at the surface of the nanoparticle(s) is larger than $10^{-100}$, $10^{-50}$, $10^{-20}$, $10^{-10}$, $10^{-5}$, $10^{-3}$, $10^{-2}$, $10^{-1}$, 1, 10, 50, 100, $10^3$, $10^5$ or $10^{10}$ µg of impurity(ies) per gram of nanoparticle(s).

In some cases, the impurities can be the same impurities, i.e. preferentially impurities comprising the same chemical elements.

In some other cases, the impurities can be different impurities, i.e. preferentially impurities comprising at least one different chemical element.

In one embodiment of the invention, the chemical element(s) is selected from the group consisting of: actinide, actinium, aluminum, americium, antimony, argon, arsenic, astatine, barium, berkelium, beryllium, bismuth, bohrium, boron, bromine, caesium, calcium, californium, carbon, cerium, chlorine, chromium, cobalt, copernicium, cadmium, copper, curium, darmstadtium, dubnium, dysprosium, einsteinium, erbium, europium, fermium, flerovium, fluorine, francium, gadolinium, gallium, germanium, gold, hafnium, helium, hassium, holmium, hydrogen, indium, iodine, iridium, iron, krypton, lanthanide, lanthanum, lawrencium, lead, lithium, livermorium, lutetium, magnesium, manganese, meitnerium, mendelevium, mercury, molybdenum, neodymium, neon, neptunium, nickel, niobium, nitrogen, nobelium, osmium, oxygen, palladium, phosphorus, platinum, plutonium, polonium, potassium, praseodymium, protactinium, promethium, radium, radon, rhenium, rhodium, roentgenium, rubidium, ruthenium, rutherfordium, samarium, selenium, silicon, silver, sodium, strontium, Sulphur, scandium, seaborgium, tellurium, terbium, thorium, thulium, tin, tantalum, technetium, thallium, titanium, tungsten, ununoctium, ununpentium, ununseptium, ununtrium, uranium, vanadium, xenon, ytterbium, yttrium, zinc, zirconium, and a combination of several of these chemical element(s).

The invention also relates to the cryo-system according to the invention, wherein the impurity(ies) comprised in the nanoparticles is/are at least one chemical element different from iron, oxygen, and/or iron oxide.

In some cases, the impurity(ies) can be carbon or carbonaceous material.

In one embodiment of the invention, the carbonaceous material comprises at least one carbon atom, preferentially but not necessarily mixed or assembled with other chemical element(s) than carbon.

In still another embodiment of the invention, the carbon or carbonaceous material originates from, is produced by, or comes from cell(s) that produce(s) the at least one nanoparticle, also designated as nanoparticle-producing cell(s).

In one embodiment of the invention, the iron and/or iron oxide and/or impurity(ies) and/or doping material and/or chemical element is/are comprised or inserted: i) inside the nanoparticle(s), ii) at the surface of the nanoparticle(s), iii) outside of the nanoparticle(s), iv) in the crystalline or amorphous structure of the nanoparticle(s), v) in a defect of the nanoparticle(s), and/or vi) in a vacancy of the nanoparticle(s).

In one embodiment of the invention, the iron and/or iron oxide and/or impurity(ies) and/or doping material and/or chemical element is/are in interaction, such as electrostatic, strong, weak, nuclear, metallic, Van der Waals, Debye, London, or hydrogen interactions with the nanoparticle(s).

In one embodiment of the invention, the iron and/or iron oxide and/or impurity(ies) and/or doping material and/or chemical element is/are located at a distance from the nanoparticle(s), preferentially from the center or surface of the nanoparticle(s), which is lower than $10^{50}$, $10^{20}$, $10^{10}$, $10^5$, $10^3$, 100, 10, 5 or 1 nm. In some cases, the center of the nanoparticles is the region or volume or location or assembly of chemical elements that is at the middle of the largest, lowest, and/or average dimension of the nanoparticle such as half of the diameter of a spherical nanoparticle or half of the largest, lowest, and/or average length of a nanoparticle. In some other cases, the surface of the nanoparticles is the region or location or assembly of chemical elements that is at the largest distance from the center of the nanoparticle while remaining in the nanoparticle.

In still another embodiment of the invention, the iron and/or iron oxide and/or impurity(ies) and/or doping material and/or chemical element is/are located at a distance from nanoparticle(s), preferentially from the center or surface of the nanoparticle(s), which is larger than 0.001, 0.01, 0.1, 1, 10, 100, $10^3$, $10^5$, $10^{10}$, $10^{20}$ or $10^{50}$ nm.

In another embodiment of the invention, the metal or metal atom is selected in the list consisting of: Lithium, Beryllium, Sodium, Magnesium, Aluminum, Potassium, Calcium, Scandium, Titanium, Vanadium, Chromium, Manganese, Iron, Cobalt, Nickel, Copper, Zinc, Gallium, Rubidium, Strontium, Yttrium, Zirconium, Niobium, Molybdenum, Technetium, Ruthenium, Rhodium, Palladium, Silver, Cadmium, Indium, Tin, Cesium, Barium, Lanthanum, Cerium, Praseodymium, Neodymium, Promethium, Samarium, Europium, Gadolinium, Terbium, Dysprosium, Holmium, Erbium, Thulium, Ytterbium, Lutetium, Hafnium, Tantalum, Tungsten, Rhenium, Osmium, Iridium, Platinum, Gold, Mercury, Thallium, Lead, Bismuth, Polonium, Francium, Radium, Actinium, Thorium, Protactinium, Uranium, Neptunium, Plutonium, Americium, Curium, Berkelium, Californium, Einsteinium, Fermium, Mendelevium, Nobelium, Lawrencium, Rutherfordium, Dubnium, Seaborgium, Bohrium, Hassium, Meitnerium, Darmstadtium, Roentgenium, Copernicium, Nihonium, Flerovium, Moscovium, and Livermorium or Livermorium atom.

In another embodiment of the invention, the nanoparticle contains less than 1, 10, $10^3$, $10^5$ or $10^9$ metallic atom(s) or contains less than 1, 10, 50, 75 or 90% of metallic atoms, where this percentage can be the ratio between the number or mass of metallic atoms in the nanoparticle divided by the total number or mass of all atoms in the nanoparticle. It can also contain less than 1, 10, $10^3$, $10^5$ or $10^9$ oxygen atom(s), or contain less than 1, 10, 50, 75 or 90% of oxygen atoms, where this percentage can be the ratio between the number or mass of oxygen atoms in the nanoparticle divided by the total number or mass of all atoms in the nanoparticle.

In one embodiment of the invention, the nanoparticle is magnetic when it has a magnetic behavior or property, where the magnetic behavior or property is preferentially selected from the group consisting of a diamagnetic, superparamagnetic, paramagnetic, ferromagnetic, and ferrimagnetic behavior or property.

In some embodiment, the magnetic behavior or property exists at a temperature, which is lower than: i) $10^5$, $10^3$, 500, 350, 200, 100, 50, 20, 10, 1, 0.5 or 1 K (Kelvin), ii) the Curie temperature, or iii) the blocking temperature.

In some other embodiment, the magnetic behavior or property exists at a temperature, which is larger than: i) 0.5, 1, 10, 20, 50, 100, 200, 350, 500, $10^3$ or $10^5$ K, ii) the Curie temperature, or iii) the blocking temperature, i.e. the temperature where there is a transition between a superparamagnetic behavior and a ferromagnetic or ferrimagnetic behavior.

In still some other embodiment, the magnetic behavior or property exists at a temperature, which is between $10^{-20}$ and $10^{20}$ K, or between 0.1 and 1000 K.

In one embodiment of the invention, the nanoparticles have or are characterized by at least one of the following properties: i) the presence of a core, preferentially magnetic, preferentially mineral, preferentially composed of a metallic oxide such as iron oxide, most preferentially maghemite or magnetite, or an intermediate composition between maghemite and magnetite, ii) the presence of a coating that surrounds the core and preferentially prevents nanoparticle aggregation, preferentially enabling nanoparticle administration in an organism or in the body part or stabilizing the nanoparticle core, where coating thickness may preferably lie between 0.1 nm and 10 μm, between 0.1 nm and 1 μm, between 0.1 nm and 100 nm, between 0.1 nm and 10 nm, or between 1 nm and 5 nm, iii) magnetic properties leading to diamagnetic, paramagnetic, superparamagnetic, ferromagnetic, or ferrimagnetic behavior, iv) a coercivity larger than 0.01, 0.1, 1, 10, 100, $10^3$, $10^4$, $10^5$, $10^9$ or $10^{20}$ Oe, v) a ratio between remnant and saturating magnetization larger than 0.01, 0.1, 0.2, 0.3, 0.4, 0.5, 0.75, 0.9 or 0.99, vi) a saturating magnetization larger than 0.1, 1, 5, 10 or 50 emu/g, vii) magnetic properties such as coercivity, remnant and saturating magnetization, preferentially measured or observed at a temperature larger than 0.1 K, 1 K, 10 K, 20 K, 50 K, 100 K, 200 K, 300 K, 350 K or 3000 K, viii) a crystallinity, i.e. nanoparticles preferentially possessing at least 1, 2, 5, 10 or 100 crystalline plane(s), preferentially observable or measured by electron microscopy, ix) the presence of a single domain, x) a size that is larger than 0.1, 0.5, 1.5, 10, 15, 20, 25, 30, 50, 60, 70, 80, 100, 120, 150 or 200 nm, xi) a size lying between 0.1 nm and 10 μm, between 0.1 nm and 1 μm, between 0.1 nm and 100 nm, between 1 nm and 100 nm, or between 5 nm and 80 nm, xii) a non-pyrogenicity or apyrogenicity, which preferentially means that nanoparticles possess an endotoxin concentration lower than $10^{20}$, 10000, 1000, 100, 50, 10, 5, 2 or 1 EU (endotoxin unit) per mg of nanoparticle or per mg of iron comprised in nanoparticles, or which means that nanoparticles do not trigger fever or an increase in whole body temperature larger than 100, 50, 6.6, 5, 3, 2 or 1° C. following their administration to a living organism or body part, xiii) a synthesis by a synthetizing living organism, preferentially by bacteria, xiv) a chemical synthesis, xv) the presence of less than 50, 25, 15, 10, 5, 2 or 1% of organic or carbon material originating from the synthetizing living organism, xv), the presence of more than 99, 95, 80, 70, 60, 50 or 25% of mineral material originating from the synthetizing living organism or nanoparticle producing cells, or xvi) a specific absorption rate (SAR) that is larger than 1, 10, 1000 or $10^4$ Watt per gram of nanoparticle, preferentially measured under the application of an alternating magnetic field of strength preferentially larger than 0.1, 1, 10 or 100 mT, and/or frequency larger than 1, 10, 100 or 1000 KHz, alternatively preferentially measured under the application of the acoustic wave, alternatively under the application of a radiation such as an electromagnetic, acoustic, or light radiation.

In another embodiment of the invention, the nanoparticles have or are characterized by at least one of the following properties: i) a coercivity lower than 0.01, 0.1, 1, 10, 100, $10^3$, $10^4$, $10^5$, $10^9$ or $10^{20}$ Oe, ii) a ratio between remnant and saturating magnetization lower than 0.01, 0.1, 0.2, 0.3, 0.4, 0.5, 0.75, 0.9 or 0.99, iii) a saturating magnetization lower than 0.1, 1, 5, 10, 50, 200, 1000 or 5000 emu/g, iv) magnetic properties preferentially measured or observed at a temperature lower than 0.1 K, 1 K, 10 K, 20 K, 50 K, 100 K, 200 K, 300 K, 350 K or 3000 K, v) a size that is lower than 0.1, 0.5, 1.5, 10, 15, 20, 25, 30, 50, 60, 70, 80, 100, 120, 150 or 200 nm, vi) the presence of more than 50, 25, 15, 10, 5, 2 or 1% of organic or carbon or carbonaceous material originating from the synthetizing living organism, vii) the presence of less than 99, 95, 80, 70, 60, 50 or 25% of mineral material originating from the synthetizing living organism, or xi), a specific absorption rate (SAR) that is lower than 1, 10, 1000 or $10^4$ Watt per gram of nanoparticle, preferentially measured under the application of an alternating magnetic field of strength preferentially lower than 0.1, 1, 10, or 100, 200, 500, $10^3$ or $10^5$ mT, and/or of frequency preferentially lower than 1, 10, 100, $10^3$, $10^5$ or $10^9$ KHz, alternatively preferentially measured under the application of the acoustic wave, alternatively under the application of a radiation such as an electromagnetic acoustic, or light radiation.

In some cases, the synthetizing living organism is the nanoparticle producing cells.

In some embodiment, the mineral can be the part of the nanoparticle or magnetosome that does not comprise organic material or comprises a low percentage in mass of organic material, preferentially less than 100, 99, 50, 20, 10, 5, 1, $10^{-1}$ or $10^{-2}$ percent or percent in mass of organic material. The mineral is preferentially the core of the nanoparticle.

In some other embodiment, the mineral can comprise a percentage in mass of organic material larger than 0, $10^{-50}$, $10^{-10}$, $10^{-2}$, $10^{-1}$ or 1 percent or percent in in mass of organic material. This can be the case when the purification step unsuccessfully removes the organic material or when organic material is added to the mineral after the purification step.

In some embodiment, the nanoparticles can be surrounded by a coating. The coating can be made of a synthetic, organic, or inorganic material or of a substance comprising a function selected in the group consisting of carboxylic acids, phosphoric acids, sulfonic acids, esters, amides, ketones, alcohols, phenols, thiols, amines, ether, sulfides, acid anhydrides, acyl halides, amidines, amides, nitriles, hydroperoxides, imines, aldehydes, and peroxides. In some cases, the coating can be made of carboxy-methyl-dextran, citric acid, phosphatidylcholine (DOPC), or oleic acid. In some cases, the coating can enable the dispersion of the nanoparticles in a matrix or solvent such as water, preferentially without aggregation or sedimentation of the nanoparticles. In some cases, the coating can enable internalization of the nanoparticles in cells. In some other cases, the coating can enable: i) to bind two or more nanoparticle(s) together preferentially in a chain, ii) to prevent nanoparticle aggregation and/or, iii) to obtain uniform nanoparticle distribution.

In some cases, the coating can be the association/binding material.

In one embodiment of the invention, the nanoparticles are non-pyrogenic. Non-pyrogenic nanoparticles preferentially: i) comprise less than $10^{100}$, $10^{50}$, $10^{20}$, $10^8$, $10^5$, $10^3$, or 10 EU (endotoxin unit) or EU per cm$^3$ of body part or EU per mg of nanoparticle or EU per cm$^3$ of body part per mg of nanoparticle, or ii) induce a temperature increase of the individual or body part of less than $10^5$, $10^3$, $10^2$, 50, 10, 5, 4, 3, 2 or 1° C., preferentially above physiological temperature, preferentially before, after or without the application of the acoustic wave or radiation on the nanoparticle.

In one embodiment of this invention, the nanoparticle is composed of or comprises a chemical element of the families selected from the group consisting of: metals (alkali metal, alkaline earth metal, transition metals), semimetal, non-metal (halogens element, noble gas), chalcogen elements, lanthanide, and actinide.

In another embodiment of the invention, the nanoparticle is composed of or comprises a chemical element selected from the group consisting of: hydrogen, lithium, sodium, potassium, rubidium, caesium, francium, beryllium, magnesium, calcium, strontium, barium, radium, scandium, yttrium, lanthanide, actinide, titanium, zirconium, hafnium, rutherfordium, vanadium, niobium, tantalum, dubnium, chromium, molybdenum, tungsten, seaborgium, manganese, technetium, rhenium, bohrium, iron, ruthenium, osmium, hassium, cobalt, rhodium, iridium, meitnerium, nickel, palladium, platinum, darmstadtium, copper, silver, gold, roentgenium, zinc, cadmium, mercury, copernicium, boron, aluminum, gallium, indium, thallium, ununtrium, carbon, silicon, germanium, tin, lead, flerovium, nitrogen, phosphorus, arsenic, antimony, bismuth, ununpentium, oxygen, Sulphur, selenium, tellurium, polonium, livermorium, fluorine, chlorine, bromine, iodine, astatine, ununseptium, helium, neon, argon, krypton, xenon, radon, ununoctium, lanthanum, cerium, praseodymium, neodymium, promethium, samarium, europium, gadolinium, terbium, dysprosium, holmium, erbium, thulium, ytterbium, lutetium, actinium, thorium, protactinium, uranium, neptunium, plutonium, americium, curium, berkelium, californium, einsteinium, fermium, mendelevium, nobelium, and lawrencium.

In some embodiment, the nanoparticle can also be composed of or comprise an alloy, a mixture, or an oxide of this(these) chemical element(s).

In some embodiment, the nanoparticle can be composed of more than $10^{-50}$, $10^{-20}$, $10^{-10}$, $10^{-5}$, $10^{-2}$, 1, 5, 10, 50, 75, 80, 90, 95 or 99% of one or several of this(these) element(s), where this percentage can represent the mass or number of this(these) chemical elements comprised in the nanoparticle divided by the total number or total mass of all chemical elements comprised in the nanoparticle or by the total mass of the nanoparticle or compound.

In some other cases, the nanoparticle can be composed of or comprise less than $10^{-50}$, $10^{-20}$, $10^{-10}$, $10^{-5}$, $10^{-2}$, 1, 5, 10, 50, 75, 80, 90, 95 or 99% of one or several of this(these) chemical element(s).

In still some other embodiment, this(these) chemical element(s) is(are) comprised inside the nanoparticle or compound, or at the surface of the nanoparticle or compound, or in the mineral or central part of the nanoparticle or compound, or in the coating of the nanoparticle or compound.

In one embodiment of the invention, the nanoparticle has a size in one dimension, which is larger than $10^{-1}$, 1, 2, 5, 10, 20, 50, 70, 100, 200 or 500 nm. A nanoparticle with a large size can have a larger coercivity and/or a larger remnant magnetization and/or can more strongly or more efficiently absorb the energy or power of the acoustic wave or radiation than a nanoparticle with a small size. In some cases, the amount of energy or power absorbed by a nanoparticle is increased by a factor of more than 1.001, 1.01, 1.1, 1.2, 1.5, 2, 5, 10, $10^3$, $10^5$ or $10^7$ by increasing the size of the nanoparticle by a factor of more than 1.001, 1.01, 1.1, 1.2, 1.5, 2, 5, 10, $10^3$, $10^5$ or $10^7$.

In another embodiment of the invention, the nanoparticle is defined as a particle with a size in one dimension, which is lower than $10^4$, $10^3$, $10^2$, 10, 1 or $10^{-1}$ nm. A nanoparticle with a small size can more easily be administered, for example intravenously, or can enable the avoidance of some toxicity effects, such as embolism.

In still another embodiment of the invention, the nanoparticle size is between $10^{-2}$ and $10^{20}$ nm, $10^{-2}$ and $10^4$ nm, between $10^{-1}$ and $10^3$ nm, or between 1 and $10^2$ nm. This can be the case when the nanoparticle or nanoparticle assembly possesses a well-defined, preferentially narrow, distribution in sizes.

In still another embodiment of the invention, the nanoparticle size distribution is lower than 1000, 100, 75, 50, 25, 10, 5, 2 or 1 nm. A narrow nanoparticle size distribution may be desired to prevent aggregation, or to favor an organization in chains of the nanoparticles.

In still another embodiment of the invention, the nanoparticle size distribution is larger than 1000, 100, 75, 50, 25, 10, 5, 2 or 1 nm. A large nanoparticle size distribution may in some cases enable nanoparticles to be eliminated more rapidly.

In another embodiment of the invention, the nanoparticle has a surface charge, which is higher than −200, −100, −50, −10, −5, 0.1, 1, 2, 5, 10, 50 or 100 mV, preferentially at a pH lower than 0.1, 1, 2, 3, 4, 5, 6, 7, 8, 9, 10, 11, 12, 13 or 14. Preferentially, a nanoparticle can have a high surface charge at low pH when it is surrounded by a coating that enables to reach such charge without being destroyed.

In another embodiment of the invention, the nanoparticle has a surface charge, which is lower than −200, −100, −50, −10, −5, 0.1, 1, 2, 5, 10, 50 or 100 mV, preferentially at a pH larger than 0.1, 1, 2, 3, 4, 5, 6, 7, 8, 9, 10, 11, 12, 13 or 14. A nanoparticle can have a low surface charge at high pH when it is surrounded by a coating that enables to reach such charge without being destroyed.

In still another embodiment of the invention, the nanoparticle has a surface charge comprised between +200 and −200 mV, +100 and −100 mV, +50 and −50 mV, +40 et-40 mV, +20 and −20, +10 and −10 mV, or between +5 and −5 mV, preferentially at a pH lower than 0.1, 1, 2, 3, 4, 5, 6, 7, 8, 9, 10, 11, 12, 13 or 14.

In still another embodiment of the invention, the nanoparticle has a surface charge comprised between +200 and −200 mV, +100 and −100 mV, +50 and −50 mV, +40 et-40 mV, +20 and −20, +10 and −10 mV, or between +5 and −5 mV, preferentially at a pH larger than 0.1, 1, 2, 3, 4, 5, 6, 7, 8, 9, 10, 11, 12, 13 or 14.

In another embodiment of the invention, the nanoparticle has a weight or a mass, preferentially expressed in unit such as gram (g), kilogram (kg), or milligram (mg). A gram of nanoparticle can be a gram of metal such as iron comprised in the nanoparticle. The mass or weight of the nanoparticle can correspond to the mass or weight of one nanoparticle or to the mass or weight of an assembly of nanoparticles.

In an embodiment, the mass of the one or at least one nanoparticle is larger than $10^{-20}$, $10^{-10}$, $10^{-5}$, $10^{-2}$, 1, 10, $10^3$, $10^9$ or $10^{20}$ gram. In some cases, a large nanoparticle mass may be desired to increase the quantity of acoustic wave energy absorbed by the nanoparticle.

In an embodiment, the mass of the one or at least one nanoparticle is lower than $10^{-20}$, $10^{-10}$, $10^{-5}$, $10^{-2}$, 1, 10, $10^3$, $10^9$ or $10^{20}$ gram. In some cases, a low nanoparticle mass may be desired to prevent or minimize nanoparticle toxicity.

In one embodiment of the invention, the nanoparticle, the suspension, composition, or assembly of nanoparticle is stable, preferentially during a lapse of time, preferentially being its stability duration, which is larger than $10^{-10}$, 5, 10, $10^{50}$ or $10^{100}$ minute(s). In some cases, the nanoparticle, the suspension, composition, or assembly of nanoparticle can be stable at a concentration of nanoparticles larger than 1, 5, 10, 50, 100, 200, 500 or 1000 mg of nanoparticles per mL of solvent, matrix, or body part surrounding or comprising the nanoparticle(s). In some cases, the nanoparticle(s), the suspension, composition, or assembly of nanoparticle(s) can be stable when: i) the nanoparticle is not degraded or does not lose partly or fully its coating or can be administered to the body part, or ii) the optical density of the nanoparticle(s), the suspension, composition, or assembly of nanoparticle(s), preferentially measured at 480 nm or at another fixed wavelength, does not decrease, preferentially by more than 1, 5, 10, 50, 75 or 90% or preferentially by more than $10^{-10}$, $10^{-3}$, $10^{-1}$, 0.5 or 0.7, preferentially within 1, 5, 10, $10^3$, $10^7$ or $10^{20}$ second(s) following homogenization or mixing or optical density measurement or absorption measurement of this suspension or composition of nanoparticle(s). This percentage can be equal to $(OD_B-OD_A)/OD_B$ or $OD_A/OD_B$, where $OD_B$ is the optical density of the nanoparticle, the suspension, composition, or assembly of nanoparticle measured just after, or less than 1 second or 1 minute after the homogenization or mixing or optical density measurement or absorption measurement of the nanoparticle(s), the suspension, composition, or assembly of nanoparticle(s) and $OD_A$ is the optical density of the nanoparticle(s), the suspension, composition, or assembly of nanoparticle(s), measured sometime after, or more than 1 second or 1 minute after the homogenization or mixing or optical density measurement or absorption measurement of the nanoparticle(s), the suspension, composition, or assembly of nanoparticle(s).

In some cases, the nanoparticle(s) can be suspended in a liquid or dispersed in a matrix or body part to yield a homogenous nanoparticle dispersion or a highly stable nanoparticle composition or suspension.

In one embodiment of the invention, the nanoparticle(s) are arranged in chains comprising more than 1, 2, 3, 4, 5, 6, 7, 8, 9, 10, 15, 20, 25, 30, 35 or 40 nanoparticles.

In another embodiment of the invention, the nanoparticles are arranged in chains, which have: i) a length smaller than $2 \cdot 10^{10}$, $2 \cdot 10^5$, $2 \cdot 10^3$ or $2 \cdot 10^2$ nm, or ii) a number of nanoparticles in each chain smaller than 2, 5, 10, $10^2$ or $10^3$. In some cases, short chains of nanoparticles may be desired or obtained, for example to favor nanoparticle internalization in cells or after partial or total destruction of long chains.

In another embodiment of the invention, the nanoparticles are arranged in chains, which have: i) a length longer than $10^{-1}$, 1, 5, 10, $2 \cdot 10^2$, $2 \cdot 10^3$ or $2 \cdot 10^5$ nm, or ii) a number of nanoparticles in each chain larger than 2, 5, 10, $10^2$ or $10^3$. In some cases, long chains of nanoparticles may be desired or obtained to increase the quantity of heat or compounds dissociated from the nanoparticles under the application of an acoustic wave or radiation or to prevent nanoparticle aggregation or enable uniform nanoparticle distribution.

In still another embodiment of the invention, the nanoparticles are arranged in chains, which have: i) a length between $10^{-1}$ and $10^{10}$ nm, or between 1 and $10^5$ nm, or ii) a number of nanoparticles in each chain between 2 and $10^5$, 2 and $10^3$, 2 and $10^2$, or between 2 and 50.

In still another embodiment of the invention, the nanoparticles are arranged in chains when they are bound or linked to each other or when the crystallographic directions of two adjacent nanoparticles in the chain are aligned, wherein such alignment is preferentially characterized by an angle between two crystallographic directions belonging to two adjacent nanoparticles in the chains of less than 90, 80, 70, 60, 50, 20, 10, 3, or 2° C. (degree).

Preferentially, when the nanoparticles are biologically synthesized, the nanoparticles can be arranged in chains: i) inside the organism that synthesizes them, also designated as synthetizing living organism, or ii) outside this organism. Preferentially, nanoparticles are arranged in chains after or before their extraction or isolation from this organism.

In one embodiment of the invention, the nanoparticles are not arranged in chains.

In another embodiment of the invention, the nanoparticles are synthesized chemically or are not synthesized by a living organism when less than 1, 2, 5, 10 or 100 step(s) of their production, such as crystallization of iron oxide, stabilization of the iron oxide mineral, organization of the nanoparticles, involves or is due to a living organism. In some cases, a chemical synthesis can be defined as a synthesis involving a majority of steps, or more than 1, 2, 5 or 10 steps, or more than 1, 2, 5, 25, 50, 75 or 90% of steps, which involve chemical reactions occurring without the involvement of living organisms, or parts of living organisms such as DNA, RNA, proteins, enzymes, lipids.

In another embodiment of the invention, a chemical synthesis is used to produce a chemical substance that mimics, copies, or reproduces the compartment, organelle, or other biological material, wherein this chemical synthesis or chemical substance can be used or can result in the production of the nanoparticles. In some cases, the compartment, organelle, or other biological material, can be a lysosome, an endosome, a vesicle, preferentially biological material that has the capacity or the function either to dissolve or transform crystallized iron into free iron or to transform free iron into crystalized iron. In some cases, this transformation is partial and preferentially results in the destruction or formation of partly crystallized assembly of iron atoms or ions, or preferentially results in a mixture of crystallized iron and non-crystallized iron. In some cases, crystallized iron can be defined as an assembly of iron atoms or ions that leads to the presence of crystallographic planes, preferentially observable using a technique such as transmission or scanning electron microscopy as a characterization method, and free iron can preferentially be defined as one of several iron atoms or ions that do not lead to the presence of crystallographic planes, preferentially highlighted by the absence of diffraction patterns, using for example transmission or scanning electron microscopy as a characterization method.

In one embodiment of the invention, the nanoparticles are synthesized biologically or by a living organism, designated as synthetizing living organism or nanoparticle producing cells, which preferentially consist(s) or comprise(s) at least 1, 2, 5, 10, $10^3$, $10^6$ or $10^9$ eukaryotic cell(s), prokaryotic cell(s), or part of these cells. In some cases, part of eukaryotic or prokaryotic cell(s) can be biological material originating or produced by these cells such as RNA, DNA, organelle, nucleolus, nucleus, ribosome, vesicle, rough endoplasmic reticulum, Golgi apparatus, cytoskeleton, smooth endoplasmic reticulum, mitochondrion, vacuole, cytosol, lysosome, centrosome, cell membrane. In some cases, a biological synthesis can be defined as a synthesis involving a majority of steps, or more than 1, 2, 5 or 10 steps, or more than 1, 2, 5, 25, 50, 75 or 90% of steps, which involve chemical reactions occurring with the involvement of at least 1, 2, 10, $10^3$, $10^6$ or $10^9$ living organisms, or parts of living organisms such as DNA, RNA, proteins, enzymes, lipids.

In some embodiment, the synthetizing living organisms are magnetotactic bacteria, other types bacteria than magnetotactic bacteria or enzymes of certain bacteria, preferentially synthetizing nanoparticles extra-cellularly, such as *Mycobacterium paratuberculosis, Shewanella oneidensi, Geothrix fermentans*, ants, fungi, or various plants.

In still another embodiment of the invention, the nanoparticles are synthesized or produced or crystallized or assembled or transformed into a nanoparticle by a compartment, organelle, or other biological material, such as protein, lipid, enzyme, DNA, or RNA, which is preferentially produced by or originates from an eukaryotic or prokaryotic cell.

In another embodiment of the invention, the nanoparticles are synthesized by or in at least one eukaryotic cell, prokaryotic cell, or part of this cell.

In another embodiment of the invention, the nanoparticles are synthesized by or in: i) the matrix or medium or environment located outside of at least one eukaryotic cell, prokaryotic cell, or part of this cell, or ii) the extracellular matrix.

In one embodiment of the invention, the nanoparticles are synthesized by a living organism when at least 1, 2, 5, 10 or 100 step(s) of their production, such as crystallization of iron oxide, stabilization of the iron oxide mineral, organization of the nanoparticles, for example in chains or aggregates, involves or is due to a living organism.

In another embodiment of the invention, the nanoparticle(s) according the invention comprise(s) a core and/or a coating, which preferentially surrounds the core of the nanoparticle(s).

In another embodiment of the invention, the nanoparticle(s) according to the invention comprise(s) metallic atom(s) and carbonaceous material, wherein the carbonaceous material either surrounds the metallic atom(s) or is mixed with or inserted in the metallic atom(s).

In one embodiment of the invention, the core and/or coating of the nanoparticles possess at least one property in common with the nanoparticles such as the concentration in iron and/or iron oxide and/or impurity(ies) and/or doping material and/or chemical element.

In one embodiment of the invention, the nanoparticle(s), the core and/or coating of the nanoparticle(s), has/have at least one of the following properties (a) to (p):

(a) magnetic, diamagnetic, superparamagnetic, ferromagnetic, ferrimagnetic, and/or paramagnetic behavior(s) or property(ies), preferentially observed or measured under the application of magnetic field of strength preferentially larger than $10^{-50}$, $10^{-40}$, $10^{-20}$, $10^{-10}$, $10^{-5}$, $10^{-2}$ or $10^{-1}$ T, preferentially observed or measured at temperatures lower than $10^{10}$, $10^5$, $10^3$, $10^2$, 10 or 1 K. In some cases, the core can have different magnetic property(ies) from the coating. For example, the core can be ferromagnetic or superparamagnetic while the coating can be diamagnetic or paramagnetic.

(b) a crystalline part or structure, preferentially comprising at least 1, 2, 5, 10, 50, 100, $10^3$, $10^5$, $10^7$, $10^9$, $10^{20}$ or $10^{50}$ crystalline plane(s) or crystalline ordered structures, which can preferentially be observed or measured under electron microscopy. In some cases, the core can have a different crystalline structure from the coating. For example, the core can comprise more than 1, 5, 10, $10^3$ or $10^5$ crystalline plane(s) or crystalline ordered structure(s) while the coating can have less than $10^5$, $10^3$, 10, 5 or 2 crystalline planes or crystalline ordered structures.

(c) a composition made of metal(s) or metal oxide(s), preferentially iron oxide, most preferentially maghemite and/or magnetite. In some cases, the core comprises a different composition from the coating. For example, the core comprises more than 1, 5, 10, 25, 50, 75, 90, 95 or 99 percent or percent in mass of iron oxide while the coating comprises less than 99, 95, 90, 75, 50, 10, 5 or 1 percent or percent in mass of iron oxide. This percentage can be the ratio between the quantity, volume, number of atoms, mass of iron oxide comprised in the core and/or coating divided by the total quantity, total volume, total number of atoms, total mass, of all chemical element(s) comprised in the core and/or coating.

(d) single domain, or be magnetically mono-domain, (e) a magnetic microstructure, which can be characterized by the presence of magnetic field lines, which can be oriented in a preferential direction such as an axis of easy magnetization or a crystallographic direction of the core of the nanoparticle(s) such as [111], where such a magnetic microstructure can under certain conditions be observable, in particular by electronic holography, (f) a size comprised between 1 nm and $10^5$ nm, 1 nm and $10^3$ nm, or between 1 nm and 100 nm, (g) a size in some cases larger than 0.1, 1, 2, 5, 10, 15, 20, 25, 30, 35 or 40 nm, (h) a size in some other cases lower than $10^{10}$, $10^5$, $10^4$, 2000, 1000, 500, 400, 300, 200, 150, 120, 100, 95, 90, 80, 75, 70, 65, 60, 55, 50, 45, 40, 35, 30, 25, 20, 15, 10 or 5 nm, (i) a zeta potential, charge, or surface charge comprised between $-10^{10}$ mV and $10^{10}$ mV, $-10^5$ mV and $10^5$ mV, $-10^4$ mV and $10^4$ mV, $-10^2$ mV and $10^2$ mV, $-10$ and 10 mV, preferentially at pH comprised between 0 and 14, 1 and 13, 2 and 12, 3 and 11, 4 and 10, 5 and 9, or between 6 and 8.

(j) a zeta potential, charge, or surface charge, which is in some cases larger than $-10^{50}$, $-10^{20}$, $-10^{10}$, $-10^5$, $-10^3$, $-10$, $-5$, $-1$, 0, 5, 10, 20, 50, or 100 mV, preferentially at pH larger than 0, 1, 2, 3, 4, 5, 6, 7, 8, 9, 10, 11, 12 or 13.

(k) a zeta potential, charge, or surface charge, which is in some other cases larger than $-10^{50}$, $-10^{20}$, $-10^{10}$, $-10^5$, $-10^3$, $-10$, $-5$, $-1$, 0, 5, 10, 20, 50, or 100 mV, preferentially at pH lower than 14, 13, 12, 11, 10, 9, 8, 7, 6, 5, 4, 3, 2, 1 or 0.

(l) a zeta potential, charge, or surface charge, which is in some other cases lower than $10^{50}$, $10^{20}$, $10^{10}$, $10^5$, $10^3$, 10, 5, 1, 0, $-5$, $-10$, $-20$, $-50$, or $-100$ mV, preferentially at pH larger than 0, 1, 2, 3, 4, 5, 6, 7, 8, 9, 10, 11, 12 or 13.

(m) a zeta potential, charge, or surface charge, which is in some other cases lower than $10^{50}$, $10^{20}$, $10^{10}$, $10^5$, $10^3$, 10, 5, 1, 0, $-5$, $-10$, $-20$, $-50$, or $-100$ mV, preferentially at pH lower than 14, 13, 12, 11, 10, 9, 8, 7, 6, 5, 4, 3, 2, 1 or 0.

(n) an isoelectric point comprised between 0 and 14, 1 and 13, 2 and 12, 3 and 11, 4 and 10, 5 and 9, or between 6 and 8, (o) in some cases, an isoelectric point in some cases larger than 0, 1, 2, 3, 4, 5, 6, 7, 8, 9, 10, 11, 12 or 13, and/or (p) in some other cases, an isoelectric point in some other cases lower than 14, 13, 12, 11, 10, 9, 8, 7, 6, 5, 4, 3, 2, 1 or 0.

In one embodiment of the invention, the core and/or coating is/are synthesized by the nanoparticle-producing cell(s).

In another embodiment of the invention, the core and/or coating is/are not synthesized by the nanoparticle-producing cell(s).

In one embodiment of the invention, the nanoparticle-producing cell(s) are eukaryotic or prokaryotic cell(s).

In one embodiment of the invention, the nanoparticle-producing cell(s) are whole cell(s).

In still another embodiment of the invention, the nanoparticle-producing cell(s) are parts of the cell(s) such as cell membrane(s), vesicle(s), enzyme(s), protein(s), lipid(s), DNA, RNA, organelle(s), compartment(s), cytoplasm, virus(es), comprised in, originating from, replicating in, or produced by the nanoparticle-producing cell(s).

In one embodiment of the invention, the nanoparticle-producing cell(s) is/are the cell(s) synthetizing the nanoparticles.

In one embodiment of the invention, the nanoparticle-producing cell(s) synthesize(s) the nanoparticle(s) inside the cell(s). Preferentially nanoparticle(s) is/are synthesized inside cell(s) when they are synthesized, assembled, crystallized, partly or fully: i), by or in or near or inside part of the cell such as an organelle, Golgi vesicle or apparatus, endosome, exosome, ribosome, endoplasmic reticulum, actin filament, nucleus, peroxisome, microtubule, lysosome, mitochondrion, filament, centrosome, flagellum, or the cell membrane, ii) in a region that is located inside the cell(s), or iii) in a region located at a distance from part of the cell(s) that is lower than $10^5$, $10^3$, 100, 10 or 1 nm.

In another embodiment of the invention, the nanoparticle-producing cell(s) synthesize(s) the nanoparticle(s) outside the cell(s). Preferentially nanoparticle(s) is/are synthesized outside the cell(s) when it/they is/are synthesized, assembled, crystallized, partly or fully: i) in a region that is located outside the cell(s), or ii) in a region located at a distance from part of the cell(s) that is larger 1, 10, 100, $10^3$ or $10^5$ nm.

In some cases, the cell(s) is/are assemblies of more than 1, 10, $10^3$, $10^5$, $10^{10}$, $10^{20}$, $10^{50}$ or $10^{100}$ cell(s). In some other cases, the cell(s) is/are assemblies of less than $10^{100}$, $10^{50}$, $10^{20}$, $10^{10}$, $10^5$, $10^3$, 100, 50, 10, 5 or 2 cell(s).

In one embodiment of the invention, the nanoparticle-producing cell(s) is/are eukaryotic cell(s), preferentially belonging to humans, animals, plants, trees, flours, branches, mushrooms, fungi, archaea, birds, fishes, pigeons, trout, mammals, ants, bees, or insects.

In one embodiment of the invention, the nanoparticle-producing cell(s) is/are prokaryotic cell(s) or bacteria.

In some cases, the nanoparticle-producing cells can be *Mycobacterium*, preferentially *Mycobacterium paratuberculosis*, *Shewanella*, preferentially *Shewanella oneidensi*, *Geothrix*, preferentially *Geothrix fermentans*. These bacteria preferentially synthesize nanoparticle(s) outside the cells.

In some other cases, the nanoparticle-producing cells can be magnetotactic bacteria, such as *Magnetospirillum magneticum* strain AMB-1, magnetotactic coccus strain MC-1, three facultative anaerobic vibrios strains MV-1, MV-2 and MV-4, the *Magnetospirillum magnetotacticum* strain MS-1, the *Magnetospirillum gryphiswaldense* strain MSR-1, a facultative anaerobic magnetotactic spirillum, *Magnetospirillum magneticum* strain MGT-1, and an obligate anaerobe, *Desulfovibrio magneticus* RS-1. These bacteria preferentially synthesize nanoparticle(s) inside the cell(s).

Body Part

In some cases, the body part can be designated as the body part of an individual or the boy part of the individual.

Preferably, the individual is a living organism, most preferably a metazoan, most preferably an animal, even more preferably a mammal, most preferably a human, in particular an adult, an adolescent, or a child.

In one embodiment of the invention, the individual is a mammal, a bird, a fish, a human, a plant, a fungus, or an archaea.

In some cases, the body part can be the body part comprising the nanoparticle(s) or a certain amount of nanoparticle(s), preferentially more than 1, 2, 5, 10, $10^3$, $10^5$, $10^{10}$, $10^{50}$ or $10^{100}$ nanoparticle(s), for example after nanoparticle administration to the body part.

In some other cases, the body part can be the body part comprising the cryo-probe(s) or a certain amount of cryo-probe(s), preferentially more than 1, 2, 5, 10, $10^3$, $10^5$, $10^{10}$, $10^{50}$ or $10^{100}$ cryo-probe(s), for example after insertion of the cryo-probe to the body part.

In still some other cases, the body part can be the body part comprising the cryo-system(s) or a certain amount of cryo-system(s), preferentially more than 1, 2, 5, 10, $10^3$, $10^5$, $10^{10}$, $10^{50}$ or $10^{100}$ cryo-system(s), for example after administration/insertion of the cryo-system to the body part.

In some cases, the body part can be the body part not comprising the nanoparticle(s) or a certain amount of nanoparticle(s), preferentially less than $10^{100}$, $10^{50}$, $10^{10}$, $10^5$, $10^3$, 10, 5, 2 or 1 nanoparticle(s), for example before administration of the nanoparticle(s) to the body part.

In some other cases, the body part can be the body part not comprising the cryo-probe(s) or a certain amount of cryo-probe(s), preferentially less than $10^{100}$, $10^{50}$, $10^{10}$, $10^5$, $10^3$, 10, 5, 2 or 1 cryo-probe(s), for example before administration of the cryo-probe(s) to the body part.

In still some other cases, the body part can be the body part not comprising the cryo-system(s) or a certain amount of cryo-system(s), preferentially less than $10^{100}$, $10^{50}$, $10^{10}$, $10^5$, $10^3$, 10, 5, 2 or 1 cryo-system(s), preferentially before administration of the cryo-system(s) to the body part.

In some cases, the amount of nanoparticle(s), cryo-probe(s), cryo-system(s) is preferentially measured or estimated per unit volume such as $cm^3$ of body part.

In another embodiment of the invention, the body part comprises between or is an assembly of between 1 and $10^{100}$, 1 and $10^{10}$, or 1 and $10^3$ nanoparticle(s), cryo-probe(s), cryo-system(s), cell(s), apparatus, tissue(s), organ(s), biomolecule(s), molecule(s), atom(s), entities(s), or biological material(s), preferentially as measured per $cm^3$ of body part.

In some embodiment, the apparatus, the nanoparticle(s), cryo-probe(s), cryo-system(s), tissue(s), organ(s), biomolecule(s), molecule(s), atom(s), entities(s), and/or biological material(s) is/are the same or belong to an assembly comprising the same nanoparticle(s), cryo-probe(s), cryo-system(s), tissue(s), organ(s), biomolecule(s), molecule(s), atom(s), entities(s), or biological material(s).

In some other embodiment, the apparatus, the nanoparticle(s), cryo-probe(s), cryo-system(s), tissue(s), organ(s), biomolecule(s), molecule(s), atom(s), entities(s), or biological material(s) is different or belongs to an assembly comprising different nanoparticle(s), cryo-probe(s), cryo-system(s), tissue(s), organ(s), biomolecule(s), molecule(s), atom(s), entities(s), or biological material(s).

In still some other embodiment, the nanoparticle(s), cryo-probe(s), cryo-system(s), apparatus, the tissue(s), organ(s), biomolecule(s), molecule(s), atom(s), entities(s), and/or biological material(s) belong(s) to, originate(s) from, is/are produced by a living organism.

In still some other embodiment, the nanoparticle(s), cryo-probe(s), cryo-system(s), apparatus, the tissue(s), organ(s), biomolecule(s), molecule(s), atom(s), entities(s), and/or biological material(s) doesn't/don't belong to or originate from a loving organism, and/or is/are not produced by a living organism.

In still some other embodiment, the body part is a whole or part of a living organism.

In one embodiment of the invention, the living organism or body part is or comprises at least 1, 10, $10^3$, $10^5$, $10^{10}$ or $10^{100}$ eukaryotic or prokaryotic cell(s), DNA, RNA, protein, lipid, biological material, cell organelle, cell nucleus, cell nucleolus, ribosome, endoplasmic reticulum, Golgi apparatus, chloroplast, or mitochondria.

In some embodiment, the body part is all or part of the head, neck, shoulder, arm, leg, knee, foot, hand, ankle, elbow, trunk, inferior members, or superior members. In some other cases, the body part can be or belong to an organ, the musculoskeletal, muscular, digestive, respiratory, urinary, female reproductive, male reproductive, circulatory, cardiovascular, endocrine, circulatory, lymphatic, nervous (peripheral or not), ventricular, enteric nervous, sensory, or integumentary system, reproductive organ (internal or external), sensory organ, endocrine glands. The organ or body part can be human skeleton, joints, ligaments, tendons, mouth, teeth, tongue, salivary glands, parotid glands, submandibular glands, sublingual glands, pharynx, esophagus, stomach, small intestine, duodenum, jejunum, ileum, large intestine, liver, gallbladder, mesentery, pancreas, nasal cavity, pharynx, larynx, trachea, bronchi, lungs, diaphragm, kidneys, ureters, bladder, urethra, ovaries, fallopian tubes, uterus, vagina, vulva, clitoris, placenta, testes, epididymis, vas deferens, seminal vesicles, prostate, bulbourethral glands, penis, scrotum, pituitary gland, pineal gland, thyroid gland, parathyroid glands, adrenal glands, pancreas, heart, arteries, veins, capillaries, lymphatic vessel, lymph node, bone marrow, thymus, spleen, gut-associated lymphoid tissue, tonsils, brain, cerebrum, cerebral hemispheres, diencephalon, brainstem, midbrain, pons, medulla, oblongata, cerebellum, spinal cord, choroid plexus, nerves, cranial nerves, spinal nerves, ganglia, eye, cornea, iris, ciliary body, lens, retina, ear, outer ear, earlobe, eardrum, middle ear, ossicles, inner ear, cochlea, vestibule of the ear, semicircular canals, olfactory epithelium, tongue, taste buds, mammary glands, or skin. The body part or organ can belong to the blood circulation or circulatory system.

In some embodiment, the body part comprises or is at least one tumor, cancer, virus, bacterium, or cell, preferentially a living cell, preferentially a pathological cell. In some cases, the body part can comprise healthy cells. In some other cases, the body part does not comprise healthy cells.

In one embodiment of the invention, the body part comprises water, an excipient, a solution, a suspension, at least one chemical element, organic material, or gel. In some embodiment, the body part can be synthetic, i.e. preferentially be produced with chemicals to mimic the body part of a living organism. In some other embodiment, the body part can be produced by a living organism.

In an embodiment of the invention, the body part comprises a pathological site, a healthy site, and/or a nanoparticle region.

In one embodiment of the invention, the body part is or comprises a pathological site or pathological cell(s) or virus(es).

In some embodiment, the pathological site is an unhealthy site, or a site that is in a different condition from a site of a healthy individual, or the site of an unhealthy individual. It can comprise pathological cells, such as tumor cells, bacteria, eukaryotic or prokaryotic cells, as well as viruses or other pathological material. Pathological cells can be cells that are: i) not arranged or working as they usual do in a healthy individual, ii) dividing more quickly than healthy cells, iii) healthy cells having undergone a transformation or modification, iv) dead, sometimes due to the presence of a virus or to other organisms, or v), in contact, in interaction, with foreign material not belonging to the individual, such as viruses, where viruses can possibly penetrate, colonize, or replicate in these cells. In some cases, pathological cells can be assimilated to or comprise or produce or amplify viruses or to other organisms or entities that colonize cells or target cells or destroy cells or use cells or enter in interaction with cells, preferentially to enable their own reproduction, multiplication, survival, or death. In some cases, a pathological site can comprise healthy cells, preferentially with a lower number, activity or proliferation, than that of pathological cells.

In one embodiment, the virus belongs to at least one virus family selected in the group consisting of: Abyssoviridae, Ackermannviridae, Adenoviridae, Alloherpesviridae, Alphaflexiviridae, Alphasatellitidae, Alphatetraviridae, Alvernaviridae, Amalgaviridae, Amnoonviridae, Ampullaviridae, Anelloviridae, Arenaviridae, Arteriviridae, Artoviridae, Ascoviridae, Asfarviridae, Aspiviridae, Astroviridae, Avsunviroidae, Bacilladnaviridae, Baculoviridae, Barnaviridae, Belpaoviridae, Benyviridae, Betaflexiviridae, Bicaudaviridae, Bidnaviridae, Birnaviridae, Bornaviridae, Botourmiaviridae, Bromoviridae, Caliciviridae, Carmotetraviridae, Caulimoviridae, Chrysoviridae, Chuviridae, Circoviridae, Clavaviridae, Closteroviridae, Coronaviridae, Corticoviridae, Cruliviridae, Cystoviridae, Deltaflexiviridae, Dicistroviridae, Endornaviridae, Euronivirida, Filoviridae, Fimoviridae, Flaviviridae, Fuselloviridae, Gammaflexiviridae, Geminiviridae, Genomoviridae, Globuloviridae, Guttaviridae, Hantaviridae, Hepadnaviridae, Hepeviridae, Herelleviridae, Herpesviridae, Hypoviridae, Hytrosaviridae, Iflaviridae, Inoviridae, Iridoviridae, Kitaviridae, Lavidaviridae, Leishbuviridae, Leviviridae, Lipothrixviridae, Lispiviridae, Luteoviridae, Malacoherpesviridae, Marnaviridae, Marseilleviridae, Matonaviridae, Medioniviridae, Megabirnaviridae, Mesoniviridae, Metaviridae, Microviridae, Mimiviridae, Mononiviridae, Mymonaviridae, Myoviridae, Mypoviridae, Nairoviridae, Nanoviridae, Narnaviridae, Nimaviridae, Nodaviridae, Nudiviridae, Nyamiviridae, Orthomyxoviridae, Ovaliviridae, Papillomaviridae, Paramyxoviridae, Partitiviridae, Parvoviridae, Peribunyaviridae, Permutotetraviridae, Phasmaviridae, Phenuiviridae, Phycodnaviridae, Picobirnaviridae, Picornaviridae, Plasmaviridae, Pleolipoviridae, Pneumoviridae, Podoviridae, Polycipiviridae, Polydnaviridae, Polyomaviridae, Portogloboviridae, Pospiviroidae, Potyviridae, Poxviridae, Pseudoviridae, Qinviridae, Quadriviridae, Reoviridae, Retroviridae, Rhabdoviridae, Roniviridae, Rudiviridae, Sarthroviridae, Secoviridae, Siphoviridae, Smacoviridae, Solemoviridae, Solinviviridae, Sphaerolipoviridae, Spiraviridae, Sunviridae, Tectiviridae, Tobaniviridae, Togaviridae, Tolecusatellitidae, Tombusviridae, Tospoviridae, Totiviridae, Tristromaviridae, Turriviridae, Tymoviridae, Virgaviridae, Wupedeviridae, Xinmoviridae, and Yueviridae.

In one embodiment of the invention, the body part is or comprises a healthy site or healthy cells. In some cases, the healthy site can be defined as a site or region that comprises healthy cell(s), where a healthy cell can be defined as a cell that belongs to a healthy individual or to the body part of a healthy individual or a cell that is not a pathological cell or a cell that divides at a normal rate or speed or at a lower rate or speed than a pathological cell or a cell that does not form a tumor or metastasis.

In some embodiment, the healthy site surrounds the pathological site preferentially when it is located at a distance of less than 1, $10^{-1}$, $10^{-3}$, $10^{-6}$ or $10^{-9}$ m from the pathological site.

In some embodiment, the number of pathological or healthy cells, preferentially comprised in the body part or volume exposed to the treatment as defined in the invention, is lower than $10^{100}$, $10^{50}$, $10^{20}$, $10^{10}$, $10^5$, 10, 5, 2 or 1 cell(s) preferentially per $cm^3$ of body part. In some other embodiment, the number of pathological or healthy cells, preferentially comprised in the body part or volume exposed to the treatment as defined in the invention, can be larger than 1, 10, $10^3$, $10^5$, $10^7$, $10^9$, $10^{20}$, $10^{50}$ or $10^{100}$ cell(s) preferentially per $cm^3$ of body part.

In still some other embodiment, the ratio between the number of pathological cells and the number of healthy cells, preferentially comprised in the body part or volume exposed to the treatment according to the invention, is lower than $10^{100}$, $10^{50}$, $10^{20}$, $10^{10}$, $10^5$, $10^3$, $10^2$, 10, 5, 2 or 1.

In still some other embodiment, the ratio between the number of pathological cells and the number of healthy cells, preferentially comprised in the body part or volume exposed to the treatment according to the invention, is larger than 1, 2, 5, 10, $10^3$, $10^5$, $10^{20}$ or $10^{100}$.

In another embodiment of the invention, the body part, healthy or pathological site, or nanoparticle region, has a length, surface area, or volume, which is larger than $10^{-50}$, $10^{-10}$, $10^{-5}$, $10^{-3}$, $10^{-1}$, 1, 5, 10 or $10^3$ m (for length), $m^2$ (for surface) or $m^3$ (for volume).

In another embodiment of the invention, the body part, healthy or pathological site, or nanoparticle region, has a length, surface area, or volume, which is lower than $10^{50}$, $10^{10}$, $10^3$, 1, $10^{-1}$, $10^{-2}$, $10^{-3}$, $10^{-4}$, $10^{-5}$, $10^{-6}$, $10^{-7}$, $10^{-8}$ or $10^{-9}$ m (for length), $m^2$ (for surface) or $m^3$ (for volume).

In one embodiment of the invention, an amount of nanoparticle that enables to induce cellular toxicity by the method or cryo-system according to the invention is 100 µg of nanoparticles per 250 000 cells (0.5 ng of nanoparticle per cell or 0.01 ng per µm of body part). In some embodiment, a lower quantity of nanoparticle, preferentially by a factor of at least 2, 5, 10, $10^3$ or $10^5$, can be efficient in destroying cells by the method, for example if the temperature is decreased below 0° C. during the method and/or if the method involves an important number of cycles. In some other embodiment, a larger quantity of nanoparticles, preferentially by a factor of at least 2, 5, 10, $10^3$ or $10^5$, can be efficient in destroying cells by the method, for example if the temperature is decreased above 0° C. during the method and/or if the method involves a limited number of cycles.

In another embodiment of the invention, the nanoparticles remain in the body part during the treatment according to the invention, preferentially during more than 1, 2, 5, 10, 20, 50, 100, $10^3$ or $10^4$ step(s) or cycle(s) of the treatment, according to the invention, preferentially during more than 1, 2, 5, 10, 50, 100 or $10^3$ second(s), hour(s), day(s), month(s) or year(s).

In some other embodiment, the nanoparticles remain in the body part during the treatment according to the invention without decreasing in size by more than $10^{-4}$, $10^{-1}$, 1, 10, 20, 50, 70, 99, 100, 500, $10^3$ or $10^4$% between before and after nanoparticle administration in/to the body part, where this percentage can be the ratio between the size of the nanoparticle after administration of the nanoparticles in the body part and the size of the nanoparticle before administration of the nanoparticles in the body part.

In some other embodiment, the at least one nanoparticle is or remains in the body part during the treatment according to the invention.

In some cases, the nanoparticle(s) preferentially decrease(s) in size by more than $10^{-4}$, $10^{-1}$, 1, 10, 20, 50, 100, 500, $10^3$ or $10^4$% between before and after nanoparticle administration in/to the body part.

In some other embodiment, more than 1, 5, 10, 50, 90 or 99% of body part, preferentially by mass or volume, is/are destroyed or is/are treated by the treatment according to the invention, preferentially when more than $10^{-10}$, $10^{-5}$, $10^{-1}$, 1, 5, 10, $10^3$, $10^6$ or $10^{10}$ nanoparticle(s) or mg of nanoparticle(s) per $cm^3$ or mg of body part are comprised in the body part, In still some other embodiment, less than 100, 99, 90, 50, 10, 5 or 1% of body part, preferentially by mass or volume, is/are destroyed, preferentially when less than $10^{10}$, $10^6$, $10^3$, 10, 5, 1, $10^{-1}$ or $10^{-3}$ nanoparticle(s) or mg of nanoparticle(s) per mg or $cm^3$ of body part are comprised in the body part.

Treatment

In one embodiment of the invention, the treatment is selected in the group consisting of: i) cryo-therapy or the therapy of a disease such as cancer following at least one step of the method according to the invention, ii) a diagnosis, preferentially cryo-diagnosis or the diagnosis of a disease such as cancer following at least one step of the method according to the invention, iii) a cosmetic treatment, preferentially cryo-cosmetic or the cosmetic treatment of an indication such as a skin disease, malformation, aging, riddles, or condition, following at least one step of the method according to the invention, and iv) the mixing or administration of nanoparticles with or to a medium or body part followed by at least one step of the method according to the invention.

In one embodiment of the invention, cryotherapy, the treatment, the method, one step of the method, the nanoparticle, or the cryo-system according to the invention, does not or does not result in or is not associated with the presence or release or activation of a drug or doxorubicin or a chemotherapeutic drug or a pharmaceutical product, which is preferentially different or a different entity from the nanoparticle or cryo-system according to the invention.

In another embodiment of the invention, cryotherapy, the treatment, the method, one step of the method, the nanoparticle, or the cryo-system according to the invention, is or results in or is associated with the presence or release or activation of a drug or doxorubicin or a chemotherapeutic drug or a pharmaceutical product, which is preferentially different or a different entity from the nanoparticle or cryo-system according to the invention.

In still some other embodiment, the treatment, preferentially the warming step, induces or is characterized by or has a temperature increase of the body part or at least one temperature of the warming step also designated as warming temperature, which is preferentially larger, by a factor of at least 1.001, 1.1, 1.2, 1.5, 2, 5, 10 or $10^3$, when the body part comprises at least one nanoparticle than when the body part does not comprise at least one nanoparticle.

In some cases, at least one property of the treatment or body part with at least one nanoparticle is compared with at least one property of the treatment or body part without at least one nanoparticle under conditions, preferentially of measurements, that are similar or the same or as close as possible except the presence (or not) of nanoparticles.

In some cases, the treatment or at least one step of the method is carried out in the presence of radiation.

In some other cases, the treatment or at least one step of the method is carried out in the absence of radiation.

In some other cases, the treatment or at least one step of the method is not carried out in the presence of a multi-frequency magnetic field or of a magnetic field oscillating at more than one frequency or of a magnetic field having at least one property on common with the magnetic field described in patent EP3363496/PCT-IB2018000218/WO2018150266 incorporated by reference.

In some other cases, the treatment or at least one step of the method is not carried out in the presence of a magnetic field oscillating at a high frequency and at a medium and/or low frequency, wherein the high frequency is 1 MHz at the most, the medium frequency is lower than the high frequency, and the low frequency is lower than the high frequency and lower than the medium frequency when it is present,
- wherein optionally the ratio $f_h/f_l$ between the high frequency, $f_h$, and the low frequency, $f_l$, is larger than 1.01, and/or the ratio $f_m/f_l$ between the medium frequency, $f_m$, and the low frequency, $f_l$, is larger than 1.01,
- wherein optionally the ratio between the maximum magnetic field, $H_{max}$, and the average magnetic field, $H_{av}$, is larger than 1.00001, wherein $H_{max}$ is the maximum magnetic field amplitude estimated among the different values of local maximum magnetic field amplitude of each high frequency oscillation, designated as $H_{max,i}$, and $H_{av}$ is defined as the average value of the different values of $H_{max,i}$,
- wherein optionally the magnetic field oscillating at the high, medium and low frequency comprises: at least one sequence during which the magnetic field strength or amplitude, or the maximum or average magnetic field, is first constant at a value $A_7$ during a time $t_7$, or increases to a value $A_7$ during a time $t_7$, and at least another sequence, during which the magnetic field strength or amplitude, or the maximum or average magnetic field, is constant at another value $A_8$ during a time $t_8$, or decreases down to $A_8$ during a time $t_8$, where $A_8$ is lower than $A_7$,
- wherein optionally these at least two different sequences are repeated more than 1 time,
- wherein optionally the magnetic field oscillating at the high and low frequency comprises: at least one sequence during which the magnetic field strength or amplitude, or the maximum or average magnetic field, is first constant at a value $A_9$ during a time $t_9$, or increases to a value $A_9$ during a time $t_9$, and at least another sequence, during which the magnetic field strength or amplitude, or the maximum or average magnetic field, is constant at another value $A_{10}$ during a time $t_{10}$, or decreases down to $A_{10}$ during a time $t_{10}$, where $A_{10}$ is lower than $A_9$,
- wherein optionally these at least two different sequences are repeated more than 1 time.

In some cases, the radiation can be a radiation that is intentionally applied by a human and preferentially differs from a natural radiation such as the radiation due to the earth magnetic field, preferentially differs from a radiation of strength or power larger than: i) 1 µT or 1 mT or ii) $10^{-9}$, $10^{-6}$, $10^{-3}$ Watt or Watt per cm or $cm^2$ or $cm^3$ of body part.

In still some other embodiment, the treatment, preferentially the warming step, induces or is characterized by or has a temperature increase of the body part or at least one temperature of the warming step also designated as warming temperature, which is preferentially smaller, by a factor of at least 1.001, 1.1, 1.2, 1.5, 2, 5, 10 or $10^3$, when the body part comprises at least one nanoparticles than when the body part does not comprise at least one nanoparticle.

In still some other embodiment, the treatment, in particular with a temperature adjuster or cryo-probe, preferentially the cooling step, induces or is characterized by or has a temperature decrease of the body part or cooling temperature or minimum temperature, which is preferentially larger, by a factor of at least 1.001, 1.1, 1.2, 1.5, 2, 5, 10 or $10^3$, when the body part comprises nanoparticles than when the body part does not comprise nanoparticles.

In some cases, the temperature adjuster is the cryo-probe.

In still some other embodiment, the treatment, in particular with a temperature adjuster, preferentially the cooling step, induces or is characterized by a temperature decrease of the body part, which is preferentially smaller, by a factor of at least 1.001, 1.1, 1.2, 1.5, 2, 5, 10 or $10^3$, when the body part comprises nanoparticles than when the body part does not comprise nanoparticles.

In an embodiment of the invention, the treatment is characterized by the production of radical or reactive species such as radical or reactive oxygen species (ROS) or radical or reactive nitrogen species (RNS). In some embodiment, ROS can be, originate from, or produce peroxides, superoxide, hydroxyl radical, singlet oxygen, and alpha-oxygen. In some other embodiment, RNS is/are, originate from, or produce nitric oxide, superoxide, peroxynitrite, peroxynitrous acid, nitrogen dioxide, hydroxyl radical, carbon dioxide, nitrosoperoxycarbonate, nitrogen dioxide, carbonate radical, dinitrogen trioxide.

In another embodiment of the invention, the treatment is characterized by the absence of production of radical or reactive species.

In some cases, the concentration of radical or reactive species produced during the treatment or at least one step of the method or treatment can be lower than $10^{50}$, $10^{10}$, $10^5$, $10^3$, $10^2$, 10, 5, 2, 1, $10^{-1}$, $10^{-5}$, or $10^{-10}$ µM of radical or reactive species, preferentially comprised in the body part, preferentially per $cm^3$ of body part.

In still another embodiment of the invention, radical or reactive species are produced during the treatment or at least one step of the method or treatment according to the invention.

In some other embodiment, radical or reactive species are produced by the nanoparticles or body part under a variation in temperature, a temperature increase, or a temperature decrease, preferentially of the body part or nanoparticles, preferentially larger than $10^{10}$, $10^{-5}$, $10^{-1}$, 1, 5, 10 or $10^{3\circ}$ C., preferentially per second or minute, preferentially per $cm^3$ of body part.

In some other embodiment, radical or reactive species are produced by the nanoparticles or body part under: i) no temperature increase, or no temperature decrease, preferentially of the body part or nanoparticles or ii) a variation in temperature, a temperature increase, or a temperature decrease, preferentially of the body part or nanoparticles, preferentially lower than $10^{10}$, $10^5$, $10^3$, $10^2$, 50, 10, 5, 2, 1, $10^{-1}$ or $10^{-5}$° C.

In some other embodiment, the concentration of radical or reactive species produced during the treatment or at least one step of the method or treatment is larger than $10^{40}$, $10^{-5}$, $10^{-1}$, 1, 5, 10, $10^3$, $10^5$, $10^{10}$ or $10^{50}$ μM of radical or reactive species, preferentially comprised in the body part, preferentially per $cm^3$ of body part.

In still another embodiment of the invention, the production of radical or reactive species, the temperature increase, and/or the temperature decrease, is responsible for the efficacy of the treatment according to the invention, for the destruction or damage of at least one cell, preferentially pathological cell, or body part, partly or fully.

In one embodiment of the invention, the treatment according to the invention leads to or is associated with: i), the destruction or damage of at least 1, 10, $10^3$, $10^{10}$ or $10^{50}$ pathological cell(s), of a portion of the body part, or of the whole body part, or ii), the cure or healing of the body part.

In some embodiment, the treatment or method according to the invention is or is combined with a heat therapy, such as hyperthermia or thermo-ablation, or with another treatment such as radiotherapy, chemotherapy, surgery, or immunotherapy.

In some cases, the treatment or method can be cryo-ablation, optionally when the cooling temperature is smaller than 0, −10, −20, −40, −50, −100 or −200° C. and/or the treatment and/or method result(s) in or is associated with the formation of at least one ice-ball and/or the ablation of the body part.

In some other cases, the treatment or method is not cryo-ablation, optionally when the cooling temperature is larger than −250, −200, −150, −100, −50, −40, −30, −20, −10, −5, −2, −1, or 0° C., and/or the treatment and/or method do(does) not result in or is/are not associated with the formation of at least one ice-ball and/or the ablation of the body part.

In some embodiment, the treatment or method according to the invention is not or is not combined with cryo-ablation, a heat therapy, such as hyperthermia or thermo-ablation, or with another treatment such as radiotherapy, chemotherapy, surgery, or immunotherapy.

In one embodiment of the invention, the destruction or damage of the body part is or is associated with: i), variations in sizes, thickness, or morphology of the body part, ii), conformation change such as a change from a three or two dimensional conformation to a two or one conformation or geometry change or denaturation of protein, lipid, DNA, RNA or biological material comprised in the body part.

In some embodiment, the destruction or damage or healing or detection of the body part is partial.

In some cases, the destruction or damage or healing or detection of the body part can occur for or within less than 99, 90, 80, 70, 50, 20, 10 or 5% in mass or volume of the body part.

In some other embodiment, the destruction or damage or healing or detection of the body part is total.

It some other cases, the destruction or damage or healing or detection of the body part can occur for or within more than $10^{-10}$, $10^{-5}$, $10^{-1}$, 1, 5, 10, 50, 70, 90 or 99% in mass or volume of the body part.

In one embodiment of the invention, the treatment, also preferentially designated as the treatment of the body part, is the repair of the body part, the destruction or detection or healing or cure of the body part, pathological site or of pathological cells such as tumor cells, preferentially comprised in the body part.

In one embodiment of the invention, the treatment according to the invention is carried out by cryotherapy, where cryotherapy preferentially consists in cooling the body part, where cooling can be the temperature decrease of the body part between the beginning and the end of the treatment by cryotherapy or during the treatment by cryotherapy. In some cases, cryotherapy can involve a moderate decrease in temperature of the body part, preferentially above −100, −40, −20° C. in at least one part of the body part, and preferentially differ from cryo-ablation preferentially by not inducing immediate or direct destruction or destruction within one or two cooling application(s)/cycle(s) of the body part. In some cases, cryo-therapy differs from current tumor cryo-ablation methods that destroy tumors under two cooling cycles at temperatures below −100° C. in at least one part of the body part.

In one embodiment of the invention, the treatment according to the invention is carried out by cryosurgery, where cryosurgery is preferentially a treatment by cryotherapy comprising a step of introducing a substance or equipment in the body part or a step of removing a substance or equipment from the body part, where this equipment or substance is preferentially the first part and/or second part of the cryo-system.

In one embodiment of the invention, the treatment by cryosurgery comprises, preferentially before, during or after step(s) a) to d) of the method according to the invention, the introduction/administration to/in the body part and/or the removal from the body part of: i) the nanoparticle(s), ii) the cryo-probe, iii) the sensor as defined in the invention, iv) the temperature adjuster, v) an equipment or substance used to warm up the body part, preferentially during the warming step, and/or vi) part of the body part.

In some cases, the sensor, the temperature adjuster, and/or the equipment or substance used to warm up the body part can be comprised in the cryo-probe.

In one embodiment of the invention, cryosurgery is carried out with the help of a catheter, syringe, utensil, substance, cryo-probe, also designated as cryosurgery equipment, enabling the insertion/introduction/administration of an equipment or substance or nanoparticle or cryo-probe to or in the body part or the removal of the equipment or substance or nanoparticle or cryo-probe from the body part.

In some embodiment, the cryosurgery equipment is located in the body part or is in contact with the body part, or is located at a distance from the body part that is lower than $10^3$, $10^2$, 10, 1, $10^{-1}$, $10^{-3}$, $10^{-6}$ or $10^{-9}$ m (meter). This can be the case when the cryosurgery equipment is directly introduced in the body part.

In some other embodiment, the cryosurgery equipment is located outside of the body part or is not in contact with the body part or is located at a distance from the body part of more than $10^{-5}$°, $10^{-10}$, $10^{-9}$, $10^{-5}$, $10^{-3}$, $10^{-1}$ or 1 m. This can be the case when the cryosurgery equipment is an imaging equipment or an equipment of electromagnetic radiation located at some distance from the body part.

In another embodiment of the invention, cryosurgery or cryotherapy is nano-cryosurgery or nano-cryotherapy, where nano-cryosurgery and nano-cryotherapy are types of cryosurgery and cryotherapy, respectively, in or during which nanoparticles are used, preferentially administered to/in the body part.

In some embodiment, nano-cryosurgery or nano-cryotherapy enables to reach efficient treatment at a larger minimum temperature or with less side effects compared with cryosurgery or cryotherapy that does not use nanoparticles.

In one embodiment of the invention, the method or treatment or the treatment of the body part according to the invention is or corresponds to a cryotherapy, cryosurgery, nano-cryotherapy, or nano-cryosurgery treatment.

In still another embodiment of the invention, the treatment according to the invention comprises or corresponds to: i), the duration of the treatment or of at least one step of the treatment, ii) the initial temperature, iii) the cooling temperature, iv) the maintaining temperature, v) the minimum temperature, vi) the warming temperature, vii) the maximum temperature, viii) the final temperature, ix) the rate(s) at which the initial, cooling, minimum, maximum, warming, and/or final temperature(s) is/are reached, ix) the use of an equipment or substance to reach the initial, cooling, minimum, maximum, warming and/or final temperature, and/or x), the use of an equipment or substance to measure the temperature or ROS or NOS, preferentially of or produced by the body part or nanoparticle(s) during the treatment.

In some cases, the final temperature is the final temperature of the treatment, preferentially of the warming step.

In some cases, the maximum temperature can be the maximum temperature of the treatment or of at least one step of the treatment and preferentially be designated as $T_{max}$.

In some cases, the maximum temperature can be the maximum temperature of the warming step also in some cases corresponding to the final temperature.

In some other cases, the maximum temperature can be the maximum temperature of the cooling step also in some cases corresponding to the initial temperature.

In another embodiment of the invention, cryotherapy occurs or takes place in the presence of at least 1, 10, $10^3$, $10^5$, $10^{10}$, $10^{50}$ or $10^{100}$ nanoparticle(s) or mg of nanoparticle(s), preferentially comprised in the body part, preferentially per $cm^3$ of body part.

In another embodiment of the invention, the treatment according to the invention occurs or takes place in the presence of less than $10^{100}$, $10^{50}$, $10^{10}$, $10^5$, $10^3$, 10, 5, 2 or 1 nanoparticle(s) or mg of nanoparticle(s), preferentially comprised in the body part, preferentially per $cm^3$ of body part.

In one embodiment of the invention, the biggest volume of the body part is estimated by calculating the volume associated with the largest dimension(s), diameter(s) of the body part. In some cases, the biggest volume of the body part is the volume of the body part delineated by a surface or external surface of such volume that is the frontier between a unhealthy site such as a tumor or a tissue comprising bacteria, viruses and/or tumor cells and a healthy site such as healthy tissue or non-tumoral tissue or tissue not comprising bacteria, viruses and/or tumor cells.

Administration of Nanoparticle and/or Cryo-Probe

The cryotherapy treatment according to the invention is a treatment comprising the administration or at least one step or administration step during or in which the nanoparticle(s) and/or cryo-probe is/are administered to the body part. The administration of the nanoparticles and/or cryo-probe to/in the body part can correspond to the first step or administration step of the treatment.

In some cases, the administration or administration step comprises the administration of the segment or penetrating segment, preferentially belonging to the cryo-probe, to/in the body part.

In some other cases, the administration or administration step comprises the administration of cryogenic gas, liquid, or solid, preferentially expelled from or diffusing from the non-penetrating segment, preferentially belonging to the cryo-probe, to/in/towards the body part.

In one embodiment of the invention, the nanoparticles, cryo-probe, penetrating segment, and/or cryogenic gas, liquid, or solid, is/are administered to the body part only once.

In one embodiment of the invention, the nanoparticles, cryo-probe, penetrating segment, and/or cryogenic gas, liquid, or solid, is/are administered to/in the body part more than 2, 5, 10 or $10^3$ times.

In some embodiment, the administration of the nanoparticles to/in the body part is repeated several times when the nanoparticles leave the body part or are degraded in the body part during the treatment and/or the nanoparticles in the body part are not sufficiently efficient to destroy the body part or to reach the desired medical, therapeutic or diagnostic activity of the treatment.

In some embodiment, the nanoparticles, cryo-probe, penetrating segment, and/or cryogenic gas, liquid, or solid, is/are administered to/in the body part more than once preferentially when one administration is not sufficient to reach treatment efficacy or full treatment efficacy.

In one embodiment of the invention, the nanoparticles, cryo-probe, penetrating segment, and/or cryogenic gas, liquid, or solid, is/are administered to/in the body part less than $10^{10}$, $10^5$, $10^3$, 10, 5 or 2 time(s).

In some embodiment, the administration of the nanoparticles to/in the body part is repeated a limited number of times when the nanoparticles remain in the body part or are not degraded in the body part during the treatment.

In an embodiment of the invention, the nanoparticles, cryo-probe, penetrating segment, and/or cryogenic gas, liquid, or solid, is/are administered in the body part a limited number of times when such limited administrations are sufficiently efficient to destroy the body part or to reach the desired medical, therapeutic or diagnostic activity of the treatment.

In one embodiment of the invention, the nanoparticles, cryo-probe, penetrating segment, and/or cryogenic gas, liquid, or solid are administered to or in the body part when they are directly administered to the body part or when they are administered close to the body part, preferentially less than 1, $10^{-1}$, $10^{-2}$, $10^{-3}$, $10^{-4}$, $10^{-5}$, $10^{-6}$ or $10^{-9}$ m away from the body part. In this case, the nanoparticles, cryo-probe, penetrating segment, and/or cryogenic gas, liquid, or solid may not need to be transported or diffuse, for example in blood circulation, from the region or site where they are administered to the body part.

In another embodiment of the invention, the nanoparticles, cryo-probe, penetrating segment, and/or cryogenic gas, liquid, or solid are administered to or in the body part, when they are indirectly administered to the body part or when they are administered far from the body part, preferentially more than 1, $10^4$, $10^{-2}$, $10^{-3}$, $10^{-4}$, $10^{-5}$, $10^{-6}$ or $10^{-9}$ m away from the body part. In this case, the nanoparticles, cryo-probe, penetrating segment, and/or cryogenic gas, liquid, or solid may be transported or diffuse from the region or site where they are administered to the body part.

In still another embodiment of the invention, administering nanoparticles, cryo-probe, penetrating segment, and/or cryogenic gas, liquid, or solid to or in the body part comprises at least one of the steps of: i), localizing or having localized nanoparticles, cryo-probe, penetrating segment, and/or cryogenic gas, liquid, or solid in the body part, ii) having nanoparticles, cryo-probe, penetrating segment, and/ or cryogenic gas, liquid, or solid diffuse or be transported to the body part, iii) transport nanoparticles, cryo-probe, penetrating segment, and/or cryogenic gas, liquid, or solid to the body part, or iv) imaging nanoparticles, cryo-probe, penetrating segment, and/or cryogenic gas, liquid, or solid, preferentially to verify that nanoparticles, cryo-probe, penetrating segment, and/or cryogenic gas, liquid, or solid reach or are in the body part or that they are transported or diffusing towards the body part or that they are distributed or localized in the body part.

In another embodiment of the invention, the nanoparticles, cryo-probe, penetrating segment, and/or cryogenic gas, liquid, or solid are administered to or in the body part when they occupy more than $10^{-9}$, $10^{-7}$, $10^{-5}$, $10^{-3}$, 1, 10, 25, 50 or 75%, preferentially by mass or volume, of the body part, where this percentage can be the ratio between the volume of the region occupied by the nanoparticles, cryo-probe, penetrating segment, and/or cryogenic gas, liquid, or solid in the body part or nanoparticle region and the volume of the nanoparticles, cryo-probe, penetrating segment, and/or cryogenic gas, liquid, or solid. This occupation can correspond to that measured $10^{-5}$, $10^{-3}$, $10^{-1}$, 1, 10, $10^3$ or $10^5$ minute(s) following nanoparticles, cryo-probe, penetrating segment, and/or cryogenic gas, liquid, or solid administration.

In another embodiment of the invention, the nanoparticles, cryo-probe, penetrating segment, and/or cryogenic gas, liquid, or solid are administered to or in the body part following at least one of the following administration routes: local, enteral, gastrointestinal, parenteral, topical, oral, inhalation, intramuscular, subcutaneous, intra-tumor, in an organ, in a vein, in arteries, in blood, or in tissue.

In some cases, the cryogenic gas, liquid or solid can be the same as the refrigerant gas, liquid or solid.

In another embodiment of the invention, the nanoparticles are in suspension or in an assembly, where the concentration of the nanoparticle suspension or assembly is lower than $10^{10}$, $10^5$, $10^3$, 500, 200, 100, 50, 20, 10, 5, 2, 1, $10^{-1}$, $10^{-3}$ or $10^{-5}$ mg of nanoparticles or of at least one chemical element comprised in nanoparticles, preferentially metallic, per ml or cm$^3$ of suspension or assembly. In some embodiment, the concentration of the nanoparticle suspension or assembly is lower than the threshold concentration, above which the nanoparticles are not soluble or dispersible in suspension or in the medium of the suspension.

In some cases, the nanoparticles optionally in assembly are nanoparticles in powder, dried, soluble or dispersed form, preferentially in or outside or with or without the body part, preferably before, during or after nanoparticle administration to/in the body part.

In some embodiment, the nanoparticle concentration is sufficiently low to avoid side effects.

In another embodiment of the invention, the concentration of the nanoparticle suspension, preferentially of the administered nanoparticle suspension, is larger than $10^{-50}$, $10^{-30}$, $10^{-20}$, $10^{-10}$, $10^{-5}$, $10^{-1}$, 1, 5, 10, 100, 250, 500, $10^3$ or $10^5$ mg of nanoparticles or of at least one chemical element comprised in nanoparticles, preferentially metallic, per ml or cm$^3$ of suspension. In some embodiment, the nanoparticle concentration is sufficiently large to be efficient.

In another embodiment of the invention, the concentration of the nanoparticle suspension, preferentially of the administered nanoparticle suspension, is between $10^{-50}$ and $10^{50}$, $10^{-10}$ and $10^{10}$, $10^{-5}$ and $10^5$, $10^{-3}$ and $10^3$, or between $10^{-1}$ and $10^3$ mg of nanoparticles or of at least one chemical element comprised in nanoparticles, preferentially metallic, per ml or cm$^3$ of suspension or assembly.

In another embodiment of the invention, the nanoparticles are administered, preferentially in/to the body part, at a rate or speed that is larger than $10^{-100}$, $10^{-50}$, $10^{-20}$, $10^{-10}$, $10^{-5}$, $10^{-3}$, $10^{-1}$, 1, 5, 10, 50, 100 or $10^3$ mg of nanoparticles or of at least one chemical element comprised in nanoparticles, preferentially metallic, per second, preferentially per second of administration time. In some embodiment, a fast administration is necessary, for example when the administration needs to be carried out under anesthesia, preferentially local or global anesthesia, and the time of anesthesia needs to be short.

In some cases, the nanoparticles can be administered before, at the same time as, or after the cryo-probe.

In some cases, the administration of the cryo-probe to the body part is realized with a least one property in common with the administration of the nanoparticle(s) to the body part.

In another embodiment of the invention, the nanoparticles are administered, preferentially in/to the body part, at a rate or speed that is smaller than $10^{100}$, $10^{50}$, $10^{20}$, $10^{10}$, $10^5$, $10^3$, 10, 5, 1, $10^{-3}$ or $10^{-5}$ mg of nanoparticles or of at least one chemical element comprised in nanoparticles, preferentially metallic, per second, preferentially per second of administration time. In some embodiment, a slow administration is necessary, for example when the pressure in the body part is large pushing the nanoparticles outside of the body part following administration.

In some cases, the nanoparticles are administered to/in the body part at a lower rate than the cryo-probe.

In another embodiment of the invention, the nanoparticles are administered, preferentially in/to the body part, at a rate or speed that is between $10^{-100}$ and $10^{100}$, $10^{-50}$ and $10^{50}$, $10^{-20}$ and $10^{20}$, $10^{-10}$ and $10^{10}$, $10^{-5}$ and $10^5$, $10^{-5}$ and $10^3$, or between $10^{-3}$ and $10^2$ mg of nanoparticles or of at least one chemical element comprised in nanoparticles, preferentially metallic, per second, preferentially per second of administration time.

In one embodiment of the invention, the equipment or substance used for the administration of the nanoparticle, such as a syringe or catheter or medium in which the nanoparticles are suspended, is such that it enables reaching a sufficient nanoparticle concentration in the body part for the method or treatment according to the invention to be efficient.

Cryotherapy

In some cases, cryotherapy can be designated as or designates the method or the treatment according to the invention or the method or treatment designates cryotherapy.

In one embodiment, cryotherapy is not or is different from cryo-ablation or does not induce or produce ablation of the body part or does not decrease the temperature of the body part below 0, −5, −10, −20, −40, −50, −100, −150, −200 or −250° C., preferentially for more than 1, 10 or $10^3$ second(s), preferentially within more than $10^{-3}$, $10^{-1}$, 1, 5, 10, 50, 70, 80 or 90% in mass or volume of the body part.

In one embodiment of the invention, cryotherapy is a therapy or medical treatment comprising at least one step in or during which the temperature of the body part is decreased, preferentially by or using the cryo-system, preferentially from an initial temperature to a cooling or minimum or maintaining temperature. The decrease of the temperature of the body part, preferentially from an initial temperature to a cooling or minimum or maintaining temperature, can correspond to the second step or the cooling step of the treatment.

In one embodiment of the invention, the method or treatment according to the invention, also designated as cryotherapy, results in or is associated with a medical, cosmetic, therapeutic, or diagnostic effect or activity of the treatment, where such effect or activity can be the destruction, healing, cure, disappearance, attraction, movement, change in color or appearance, production, of compounds, substances, nanoparticles, preferentially occurring in the body part or nanoparticle region.

In one embodiment, the cryo-system cools down the body part, preferentially during a cooling step.

The step of cooling the body part comprising the nanoparticles, preferentially designated as step b), by decreasing the temperature of body part from an initial or maximum temperature of said body part down to a cooling or maintaining or minimum temperature of the body part, which is lower than the initial temperature, is designated as the cooling step.

In one embodiment of the invention, the cooling step is the cooling of the body part preferentially comprising the nanoparticles. In some embodiment, it can mean, be associated with, or consist in: i) cooling or decreasing the temperature of the body part from an initial temperature to a cooling or maintaining or minimum temperature, or ii) cooling or decreasing the temperature of the body part to a cooling or maintaining or minimum temperature. In some embodiment, cooling or decreasing the temperature of the body part from an initial temperature to a cooling or maintaining or minimum temperature can be expressed more simply without any loss in meaning as cooling or decreasing the temperature of the body part.

In one embodiment of the invention, at least one of the step(s) of the method, preferentially the cooling step, is a step at which a medical, cosmetic, diagnostic, or therapeutic effect or activity occurs.

In one embodiment of the invention, the cooling temperature reached during the treatment is the temperature at which a medical, cosmetic, diagnostic, or therapeutic effect or activity occurs.

In one embodiment of the invention, the temperature gradient, occurring during the cooling step and/or warming step is the temperature interval, preferentially estimated as a function of time or as a function of space or unit surface or volume of the body part, at which a medical, cosmetic, diagnostic, or therapeutic effect or activity occurs.

In some cases, the temperature gradient can be the variation of temperature over time and/or the variation of temperature between two different positions in the boy part.

In one embodiment of the invention, the medical, cosmetic, diagnostic, or therapeutic effect or activity is or is associated with a change in color or appearance of the body part or the destruction or damages of the pathological cells, or the healing, partly or fully, of the body part.

In one embodiment of the invention, the medical, cosmetic, diagnostic, or therapeutic effect or activity occurs, most preferably predominantly, at the cooling or warming or minimum or maximum temperature or during or at the end of the cooling or warming step, or within the temperature gradients of the cooling and/or warming step(s).

In one embodiment of the invention, the medical, cosmetic, diagnostic, or therapeutic effect or activity occurs, most preferably predominantly, at the maintaining temperature or at the beginning or during or at the end of the maintaining step. In some cases, the maintaining step can occur in or be due to the presence of at least one nanoparticle in the body part, preferentially a nanoparticle comprising at least one other atom, preferentially at least one other metallic atom, than iron.

In some cases, the maintaining step can be the step during which the temperature of the body part is maintained or does not vary by more than $10^{-20}$, $10^{-3}$, 1, 5, 10, 90, 99, 100 or $10^{20}$% where this percentage can be equal to $[T_{maxm}-T_{minm}]/T_{avm}$, where $T_{maxm}$, $T_{minm}$, and $T_{avm}$ are the maximum, minimum, and average temperatures of the maintaining step, respectively.

In some cases, the cooling step can be the step during which the temperature of the body part varies or decreases by more than $10^{-20}$, $10^{-3}$, 1, 5, 10, 90, 99 or 100% where this percentage can be equal to $[T_{maxc}-T_{minc}]/T_{avc}$, where $T_{maxc}$, $T_{minc}$, and $T_{avc}$ are the maximum, minimum, and average temperatures of the cooling step, respectively.

In some cases, the warming step can be the step during which the temperature of the body part varies or increases by more than $10^{-20}$, $10^{-3}$, 1, 5, 10, 90, 99 or 100% where this percentage can be equal to $[T_{maxw}-T_{minw}]/T_{avw}$, where $T_{maxw}$, $T_{minw}$, and $T_{avw}$ are the maximum, minimum, and average temperatures of the warming step, respectively.

In one embodiment of the invention, the medical, cosmetic, diagnostic, or therapeutic effect or activity does not occur preferentially predominantly at the maximum, initial and/or final temperature(s).

In one embodiment of the invention, the medical, cosmetic, diagnostic, or therapeutic effect or activity is more pronounced when the temperature is decreased from the initial or maximum temperature to the cooling or maintaining or minimum temperature during the cooling step and/or when the temperature is increased from the cooling or minimum or maintaining temperature to the final or maximum temperature during the warming step than when the temperature is maintained at the maintaining or cooling temperature during the maintaining step.

In one embodiment of the invention, the medical, cosmetic, diagnostic, or therapeutic effect or activity is more pronounced at the cooling or minimum temperature than at the initial or final or maximum temperature.

In one embodiment of the invention, the initial temperature, preferentially of the body part or nanoparticle, is the temperature occurring: i), before, during, or at the end of the administration step, or ii) at the beginning of the cooling step. The situations i) and ii) can correspond to temperatures, T, preferentially of the body part or nanoparticles, that have decreased by less than 100, 75, 50, 25, 10, 5, 2 or 1%, where this percentage can be $T/T_i$, or by less than $10^5$, $10^3$, 100, 10, 5, 2, 1 or $10^{-1}$° C. following at least one step of the method according to the invention.

In another embodiment of the invention, the initial temperature, preferentially of the body part or nanoparticles, is: i), the maximum temperature reached during the treatment or method according to the invention ii), the temperature reached when no equipment or substance or cryo-probe is used to adjust the temperature of the body part or before an equipment or substance or cryo-probe is used to adjust the temperature of the body part, or iii), the temperature reached when a thermal equilibrium of the body part is established with its surrounding environment or with the living organism or individual comprising the body part, preferentially in the absence of equipment or substance or cryo-probe used to adjust the temperature of the body part.

In some embodiment, the thermal equilibrium of the body part with its surrounding environment occurs when the temperature of the body part does not vary by more than $10^{-5}$, $10^{-3}$, $10^{-1}$, 1, 5, 10, $10^2$ or $10^3$° C., preferentially ° C. per second or ° C. per cm$^3$ of body part.

In one aspect, the invention relates to nanoparticle or cryo-system for use according to the invention, wherein the initial temperature and/or the final temperature is/are physiological temperature(s).

As used herein, physiological temperatures relate to normal body temperature, or temperature of a healthy individual. In some cases, the physiological temperature is the normothermia or euthermia temperature of the body part or of whole organism of an individual or of part of the individual.

In some embodiment, physiological temperatures are temperatures of a healthy individual, or of an individual with fever, or of an individual with a maximal body temperature of 43° C.

In some embodiment, the physiological temperature can be 37±6° C.

In some embodiment, physiological temperatures can be significantly larger than 37, 40, 45, 50, 60, 70, 80, 90 or 100° C., for example when the individual is treated by a method of hyperthermia or thermo-ablation or when the individual is different from a human, for example an extremophile that can live in conditions of high temperatures, preferentially larger than 100° C.

In some embodiment, physiological temperature can be significantly smaller than 37, 30, 20, 10, 5, 0, −10, −20, −50, −100° C., for example when the individual is suffering from hypothermia or when the individual is different from a human, for example an extremophile that can live in conditions of low temperatures, preferentially lower than 0° C.

In one embodiment, the initial temperature is the temperature or the corporal temperature of a healthy individual, most preferentially between 36° C. and 37.8° C. In some embodiment, the initial temperature can be lower than 36° C., preferentially below 30, 20 or 10° C. when the individual is in a state of hypothermia. In some other embodiment, the initial temperature can be above 37.8° C., preferentially above 38, 39, 40, 41° C. when the individual has fever. In still some other embodiment, the initial temperature can be above 38, 40, 43, 45, 50 or 55° C., for example when the individual is treated by hyperthermia such as whole-body hyperthermia. In still some other embodiment, the initial temperature is above 55, 60, 65, 70, 80, 90 or 100° C., for example when the individual is treated by thermo-ablation or high intensity focused ultrasound.

In some other embodiment, the cooling temperature, which can be designated as $T_c$, is the temperature of the body part or individual at the beginning, during or at the end of the cooling step. In some embodiment, the temperature at the end of the cooling step, $T_{ECS}$, has decreased by at least $10^{-1}$, 1, 5, 10, 25, 50, 75, 80, 90, 95 or 99% or by at least $10^{-5o}$, $10^{-10}$, $10^{-1}$, 1, 5 or 10° C. compared with the temperature at the beginning of the cooling step, $T_{BCS}$, where this percentage can be equal to $|T_{ECS}/T_{BCS}|$ or $|T_{ECS}-T_{BCS}|/|T_{BCS}|$, where the symbols | | designate the absolute value.

In some embodiment of the invention, $T_{BCS}$, is the temperature occurring at least $10^{-5o}$, $10^{-3}$, $10^{-1}$, 1, 5, 10, $10^2$ or $10^3$ second(s) following the administration step or following the use or switching on of the temperature adjuster or cryo-probe.

In some embodiment of the invention, $T_{BCS}$ is the temperature occurring at least $10^{-5o}$, $10^{-3}$, $10^{-1}$, 1, 5, 10, $10^2$ or $10^3$ second(s) before the beginning of the warming step or before the end of use or switching off of the temperature adjuster or cryo-probe.

In some embodiment of the invention, $T_{ECS}$ is separated from $T_{BCS}$ by a lapse of time of at least $10^{-5o}$, $10^{-3}$, $10^{-1}$, 1, 5, 10, $10^2$ or $10^3$ second(s).

In another embodiment of the invention, the cooling temperature is the minimum temperature reached during the treatment or during at least one step of the treatment.

In some cases, the minimum temperature can be the minimum temperature reached during at least one step of the method.

In another embodiment of the invention, the cooling temperature is a temperature that is lower than the initial temperature by a quantity or variation of temperature of the second step, $\Delta T_{2S}=|T_C-T_i|$, which is larger than 1, 2, 5, 10, 20, 50, 100 or 200° C.

In another embodiment of the invention, the cooling temperature is a temperature that is lower than the initial temperature by a quantity, factor or percentage $|T_C-T_i|/|T_i|$, and/or $|T_C|/|T_i|$, which is/are larger than $10^{-5}$, $10^{-3}$, $10^{-1}$, 0, 1, 5, 10, 25, 50, 75, 80, 90, 95, 99, 100, $10^3$ or $10^5$.

In some embodiment of the invention, a low value of the cooling temperature is desired when one wishes to form ice-balls or to limit the number of cycles of the method according to the invention.

In another embodiment of the invention, the cooling temperature is a temperature that is lower than the initial temperature by a quantity $\Delta T=|T_C-T_i|$, which is lower than $10^3$, 100, 50, 20, 10, 5, 2 or 1° C.

In another embodiment of the invention, the cooling temperature is a temperature that is lower than the initial temperature by a quantity, factor or percentage $|T_C-T_i|/|T_i|$ and/or $|TCl/|T_i|$, which is/are lower than $10^5$, $10^3$, 100, 99, 90, 75, 50, 20, 10, 0, $10^{-1}$, $10^{-3}$ or $10^{-5}$.

In some embodiment of the invention, a large value of the cooling temperature, preferentially above 0° C., is desired when one wishes to avoid the side effects associated with a too low cooling temperature such as those associated with the formation of ice-balls.

In another embodiment of the invention, the cooling temperature is a temperature that is lower than the initial temperature by a quantity or variation of temperature of the second step, $\Delta T_{2S}=|T_C-T_i|$, which is between $10^{-10}$ and $10^{10}$, $10^{-5}$ and $10^5$, $10^{-3}$ and $10^3$, or $10^{-1}$ and $10°$ C.

In another embodiment of the invention, the cooling temperature is a temperature that is lower than the initial temperature by a quantity, factor or percentage $\Delta T_{2S}/T_i=|T_C-T_i|/|T_i|$ and/or $|T_C/T_i|$, which is/are between $10^{-5o}$ and $10^{50}$, $10^{-10}$ and $10^{10}$, $10^{-5}$ and $10^5$, $10^{-3}$ and $10^3$, or $10^{-1}$ and 10.

In one embodiment of the invention, the initial temperature, cooling temperature, maintaining temperature, warming temperature, minimum temperature, maximum temperature, and/or final temperature is/are larger than −273, −150, −100, −50, −20, −10, −5, −2, −1, 0, 1, 5, 10, 20, 50, 70 or 100° C.

In another embodiment of the invention, the initial temperature, cooling temperature, maintaining temperature, warming temperature, minimum temperature, maximum temperature, and/or final temperature is/are lower than $10^3$, $10^2$, 70, 50, 20, 10, 5, 2 or 1° C. In still another embodiment of the invention, the initial temperature, cooling temperature, maintaining temperature, warming temperature, minimum temperature, maximum temperature, and/or final temperature is/are between −273 and $10^3$, −50 and 100, −20 and 20, −20 and 10, −10 and 10, −5 and 5, −2 and 5, −1 and 5, or between 0 and 5° C.

In still another embodiment of the invention, the difference between the cooling or maintaining or minimum temperature and initial or final or maximum temperature is lower than the difference in temperature between the maximum temperature at which an organism can live or at which an enzyme or protein or DNA strand can be non-denatured or non-destroyed or 100° C. and 0 degree.

In one embodiment of the invention, cryotherapy is a therapy or medical treatment comprising at least one step during or in which the temperature of the body part is maintained at the maintaining or cooling temperature, preferentially by the cryo-system. The step in or during which the body part is maintained at the maintaining or cooling temperature for a duration of time can correspond to the third step or maintaining step of the treatment according to the invention.

In some cases, the maintaining step can occur within the cooling step. In such situation, the temperature of the body part can first decrease, be maintained, and then decrease again. In such situation, the cooling step can be divided in two parts separated by the maintaining step. In some cases, the maintaining step can occur within the warming step. In such situation, the temperature of the body part can first increase, be maintained, and then increase again. In such situation, the warming step can be divided in two parts separated by the maintaining step.

In one embodiment of the invention, there is no lapse of time or duration during the method, preferentially during the maintaining step, which is preferentially longer than $10^{-5°}$, $10^{-20}$, $10^{-10}$, $10^{-5}$, $10^{-3}$, $10^{-1}$, 1, 5, 10, $10^3$ or $10^5$ second(s), during or in which the temperature varies by less than $10^{10}$, $10^5$, $10^3$, 100, 75, 50, 25, 10, 5, 2, 1 or $10^{-1°}$ C. or by less than 100, 75, 50, 25, 10, 5, 2, 1 or $10^{-1}$%, where this percentage can be equal to $|\Delta T/T_{min}|$ or $|\Delta T/T_{max}|$, where $\Delta T$, $T_{min}$ and $T_{max}$ are the temperature variation, minimum and maximum temperatures reached during this lapse of time or duration.

In one embodiment of the invention, the duration of the maintaining step is shorter than $10^{50}$, $10^{30}$, $10^{20}$, $10^{10}$, $10^5$, $10^3$, 100, 75, 50, 25, 10, 5, 2, 1, $10^{-1}$ or $10^{-3}$ second(s).

In one embodiment of the invention, the temperature of the body part is maintained at the maintaining or minimum or cooling temperature, preferentially by the cryo-system, when the temperature of the body part differs by less than 100, 90, 80, 70, 60, 50, 20, 10, 5, 1 or $10^{-1}$% from the maintaining or cooling or minimum temperature, where this percentage can be the absolute values of $(T_{BP}-T_{Ct})/T_{CT}$, $T_{CT}/T_{BP}$ or $T_{BP}/T_{CT}$, $(T_{BP}-T_{MT})/T_{MT}$, $T_{MT}/T_{BP}$ or $T_{BP}/T_{MT}$, $(T_{BP}-T_{minT})/T_{minT}$, $T_{minT}/T_{BP}$ or $T_{BP}/T_{minT}$ where $T_{BP}$, $T_{CT}$, $T_{MT}$, and $T_{minT}$ are the temperature of the body part, the cooling temperature, the maintaining temperature, and the minimum temperature, respectively.

In some cases, the maintaining temperature can be the cooling or warming or minimum or maximum temperature.

In one embodiment of the invention, one person or the cryo-system can prevent maintenance of the body part temperature at the cooling or maintaining or warming or minimum or maximum temperature by: i) stopping or switching off the temperature adjuster or cryo-probe, preferentially when or before the cooling or maintaining or warming or minimum or maximum temperature is reached, or ii) letting the body part warm up, for example by being exposed to blood, tissue, ambient air or a medium that is not maintained at the cooling or maintaining or warming or minimum or maximum temperature or below the cooling or maintaining or warming or minimum or maximum temperature.

In one embodiment of the invention, one person or the cryo-system can maintain the body part temperature at the cooling or maintaining or warming or minimum or maximum temperature by: i) using or switching on the temperature adjuster or cryo-probe, preferentially when or before the cooling or maintaining or warming or minimum or maximum temperature is reached, or ii) letting the nanoparticles maintain the temperature of the body part at a given value.

In one embodiment of the invention, cryotherapy is a therapy or medical treatment comprising at least one step during or in which the temperature of the body part is increased, preferentially from the cooling or maintaining or minimum temperature to a final or maximum temperature, preferentially by the cryo-system. The increase of the temperature of the body part, preferentially from the cooling temperature or maintaining or minimum temperature to a final temperature, can correspond to the fourth step or warming step of the treatment.

In some cases, cryotherapy comprises a step of warming the body part, preferentially by the cryo-system, also designated as step d). In some cases, the step d) of warming the body part preferentially comprising the nanoparticles by increasing the temperature of the body part from the cooling or maintaining or minimum temperature of the body part to a final or maximum temperature of the body part, which is above the cooling temperature or maintaining or minimum. Such step can be designated as the warming step and at least one of its temperature can be the warming temperature.

In one embodiment of the invention, the warming step consists in warming the body part comprising the nanoparticles by increasing the temperature of the body part from the cooling or maintaining or minimum temperature to the final or maximum temperature.

In one embodiment of the invention, the final temperature of the body part is the temperature measured or occurring at the end of the cryotherapy treatment or at the end of the method according to the invention or at the end of the warming step. In some cases, it can the maximum temperature of the whole treatment or of at least one step of the treatment, preferentially of the warming step.

In one embodiment of the invention, the medical, cosmetic, diagnostic, or therapeutic effect or activity occurs, most preferably predominantly, at the beginning, during or at the end of the warming step.

In some embodiment, the final temperature, which can be designated as $T_f$, is the temperature of the body part or individual at the end of the treatment. In some embodiment, the end of the treatment is reached: i) at the end of the warming step, ii) at least $10^{-5°}$, $10^{-20}$, $10^{-10}$, $10^{-5}$, $10^{-1}$, 1, 5, 10 or $10^3$ second(s) following the beginning of the treatment or the switching on or use of the temperature adjuster or cryo-probe, and/or iii) when or after the temperature of the body part is stabilized.

In one embodiment of the invention, the temperature of the body part is stabilized when the variation of temperature of the body part, $\Delta T$, within a lapse of time, $\Delta t$, which is preferentially longer than $10^{-5°}$, $10^{-20}$, $10^{-10}$, $10^{-5}$, $10^{-3}$, $10^{-1}$, 1, 5, 10, $10^3$ or $10^5$ second(s), is smaller than $10^{10}$, $10^5$, $10^3$, 100, 75, 50, 25, 10, 5, 2, 1 or $10^{-1°}$ C. or is smaller by a factor of at least 0, 0.5, 1, 1.1, 1.5, 2, 5, 10, $10^3$ or $10^5$ than the temperature variation of the cooling and/or warming step(s).

In some cases, the temperature of the body part is stabilized during the maintaining step.

In one embodiment, the final temperature $T_f$ has the same value as the initial temperature $T_i$ or differs from the initial temperature by less than:
  i) $10^{-5°}$, $10^{-10}$, $10^{-1}$, 0, 1, 5, 10, $10^3$, $10^5$, $10^{10}$, $10^{20}$ or $10^{50°}$ C., and/or
  ii) $10^{-5°}$, $10^{-10}$, $10^{-1}$, 1, 5, 10, 25, 50, 75, 90, 99 or 100%, where this percentage can be equal to $|T_f/T_i|$, $|T_f-T_i|/|T_i|$ or $|T_f-T_i|/|T_f|$.

In another embodiment of the invention, the final temperature, which is preferentially designated as $T_f$, is a temperature that is larger than the cooling or maintaining or minimum temperature by a quantity or variation of temperature of the fourth step, $\Delta T_{4S}=|T_f-T_C|$ or $|T_f-T_M|$, which is larger than $10^{-10}$, $10^{-1}$, 1, 2, 5, 10, 20, 50, 100 or 200° C.

In another embodiment of the invention, the final temperature is a temperature that is larger than the cooling or maintaining or minimum temperature by a quantity, factor or percentage $T_f/T_c$, $\Delta T_{4S}/T_c$, $|T_f/T_c|$, $T_f/T_M$, $\Delta T_{4S}/T_M$, $|T_f/T_M|$, $T_f/T_{min}$, $\Delta T_{4S}/T_{min}$, and/or $|T_f/T_{min}|$ which is/are larger than $10^{-5}$, $10^{-3}$, $10^{-1}$, 0, 1, 5, 10, 25, 50, 75, 80, 90, 95, 99, 100, $10^3$ or $10^5$.

In one embodiment of the invention, the final temperature is much above the cooling or maintaining or minimum temperature by: i) having a large temperature gradient during the warming step, ii) having a low cooling or minimum temperature, and/or iii) having a high final temperature, where the values i) to iii) preferentially enable reaching the desired medical or cosmetic or therapeutic or diagnostic activity of the treatment.

In another embodiment of the invention, the final temperature is a temperature that is larger than the cooling or maintaining or minimum temperature by a quantity or temperature variation $\Delta T_{4S}=|T_f-T_c|$ or $|T_f-T_M|$ or $|T_f-T_{min}|$, which is lower than $10^3$, 100, 50, 20, 10, 5, 2 or 1° C.

In another embodiment of the invention, the final temperature is a temperature that is larger than the cooling or maintaining or minimum temperature by a quantity, factor or percentage $\Delta T_{4S}/T_c$, $|T_f/T_c|$, $\Delta T_{4S}/T_M$, $|T_f/T_M|$, $\Delta T_{4S}/T_{min}$, and/or $|T_f/T_{min}|$, which is/are lower than $10^5$, $10^3$, 100, 99, 90, 75, 50, 20, 10, 0, $10^{-1}$, $10^{-3}$ or $10^{-5}$.

In one embodiment of the invention, the difference in temperature between the final or maximum temperature and the cooling or maintaining or minimum temperature is small when: i) the warming step is characterized by a small temperature gradient, ii) the number of cycles is large, preferentially within a short lapse of time, iii) the small temperature gradient is compensated by a large number of cycles, where the points i) to iii) preferentially enable reaching the desired medical or cosmetic or therapeutic or diagnostic activity of the treatment.

In another embodiment of the invention, the final temperature is a temperature that is larger than the cooling or maintaining or minimum temperature by a quantity $\Delta T_{4S}=|T_f-T_c|$ or $|T_f-T_M|$ or $|T_f-T_{min}|$, which is between $10^{-10}$ and $10^{10}$, $10^{-5}$ and $10^5$, $10^{-3}$ and $10^3$, or $10^{-1}$ and $10°$ C.

In another embodiment of the invention, the final temperature is a temperature that is larger than the cooling or maintaining or minimum temperature by a quantity, factor or percentage $|T_f-T_c|/|T_c|$, $|T_f/T_c|$, $|T_f-T_M|/T_M|$, $|T_f/T_M|$, $|T_f-T_{min}|/|T_{min}|$, and/or $|T_f/T_{min}|$, which is/are between $10^{-50}$ and $10^{50}$, between $10^{-10}$ and $10^{10}$, between $10^{-5}$ and $10^5$, between $10^{-3}$ and $10^3$, or between $10^{-1}$ and 10.

In one embodiment of the invention, the initial temperature is the temperature measured at the beginning of at least one step of the treatment, preferentially the cooling step.

In one embodiment of the invention, the cooling temperature is the temperature measured at the beginning, during, or at the end of the cooling step.

In one embodiment of the invention, the maintaining temperature is the temperature measured at the beginning, during, or at the end of the maintaining step.

In one embodiment of the invention, the warming temperature is the temperature measured at the beginning, during, or at the end of the warming step.

In another embodiment of the invention, the final temperature is the temperature measured at least one step of the treatment, preferentially at the end of the warming step.

In some cases, the temperature does not vary during the administration step or varies less than during the cooling or warming step.

In one embodiment of the invention, the assembly of at least two nanoparticles or the at least one nanoparticle is cooled down by the cryo-probe or by switching on the cryo-probe, where such mechanism preferentially involves the transfer of cold or the initiation or the activation of such transfer from the cryo-probe to the nanoparticle(s) or form the location of the cryo-probe to the location of the nanoparticle(s).

In one embodiment of the invention, the assembly of at least two nanoparticles or the at least one nanoparticle is warmed up by not using the cryo-probe or by switching off the cryo-probe, where such mechanism preferentially involves stopping the transfer of cold from the cryo-probe to the nanoparticle(s) or form the location of the cryo-probe to the location of the nanoparticle, where stopping the transfer of cold can mean that the transfer of cold is less important after than before the stopping of such transfer has been initiated.

Temperature

In one embodiment, the temperature is selected in the group consisting of: i) the initial temperature, ii) the final temperature, iii) the minimum temperature, iv) the maximum temperature, v) the cooling temperature, vi) the maintaining temperature, vii) the warming temperature, viii) the physiological temperature, viii) the temperature of the nanoparticle, ix) the temperature of the body part, x) the temperature of ice-ball, preferentially nanoparticle-ice-ball, xi) the temperature of ice-ball formation, preferentially nanoparticle-ice-ball formation, and xii) the temperature of the treatment or of at least one step of the treatment.

In some cases, the temperature can be larger than −273, −50, −200, −100, −50, −40, −20, −10, −5, 0, 5, 10, 15, 20, 50, 100, $10^3$, $10^5$ or $10^{10}$° C.

In some other cases, the temperature can be lower than $10^{20}$, $10^{10}$, $10^5$, $10^3$, $10^2$, 10, 5, 2, 1, 0, −5, −10, −20, −50, −100, −150, −200 or −250° C.

In still some other cases, the temperature can be between −273 and $10^{20}$, −273 and $10^3$, −273 and 100, −273 and 25, −200 and 25, −100 and 25, −50 and 25, −40 and 25, −20 and 20, −10 and 0, −273 and 0, or between −5 and 0° C.

In some cases, the initial and/or final temperature is/are the maximum temperature.

In some cases, the warming and/or cooling temperature is/are the minimum temperature, preferentially when they are measured at the end of the cooling step or at the beginning of the warming step.

In some cases, the minimum temperature is lower, preferentially by a factor of at least 0, 0.1, 0.5, 1, 1.1, 1.5, 2, 5, 10, $10^3$ or $10^5$, or by at least $10^{-10}$, $10^{-1}$, 0, 1, 5, 10, 20, 50 or 100° C., than the maximum temperature.

Radiation

In one embodiment of the invention, cryotherapy, the treatment, the method, the cryo-system, the nanoparticles, the cryo-probe according to any of the invention, do/does not involve or comprise the application of a radiation or do/does not apply a radiation, preferentially selected from the group consisting of: i) a magnetic field such as an alternating magnetic field or a magnetic field oscillating at more than one frequency, ii) a laser or a laser applied sequentially, and iii) an acoustic wave or ultrasound or an ultrasound or acoustic wave applied sequentially.

In one embodiment of the invention, cryotherapy, the treatment, the method, the cryo-system, the nanoparticles, the cryo-probe according to any of the invention, do/does not involve or comprise: i) a laser or the application of a laser as defined in patent EP19020331.5/U.S. Ser. No. 16/412,933 (EP/US Pat. Appl. Numb.) incorporated in reference or ii) nanoparticles or magnetosomes or cryo-system for use in a sequential laser radiation medical or biological or cosmetic treatment, wherein nanoparticles or magnetosomes are optionally administered to a body part of an individual and optionally:

In a first step, the magnetosomes are irradiated by a laser radiation at a first power, and In a second step, the magnetosomes are irradiated by a laser radiation of lower power than in the first step or no laser irradiation of the magnetosomes is performed, wherein the second step comprises cooling and/or non-dissociation of at least one compound from the magnetosomes, and optionally the sequence comprising the first step and the second step is repeated at least once.

In one embodiment of the invention, cryotherapy, the treatment, the method, the cryo-system, the nanoparticles, the cryo-probe according to any of the invention, do/does not involve or comprise: i) an ultrasound or acoustic wave or the application of an ultrasound or acoustic wave as defined in patent IB2018001460/WO2019106428/EP18827221.5/U.S. Ser. No. 16/486,574 incorporated by reference or ii) nanoparticles for use in an acoustic wave medical treatment of a body part of an individual, wherein the nanoparticles are optionally administered to the body part of the individual and optionally the acoustic wave is optionally applied on the body part sequentially, with a frequency optionally between 0.01 and 100 MHz, with either:

i. an intensity, power or power density that is optionally lower than $10^3$ Watt, or W per cm of body part, or W per $cm^2$ of body part, or W per $cm^3$ of body part, or W per cm of transducer, or W per $cm^2$ of transducer, or W per $cm^3$ of transducer; or ii. an energy or energy density that is optionally lower than $10^5$ W·sec per cm of body part, or W·sec per $cm^2$ of body part, or W·sec per $cm^3$ of body part, or W·sec per cm of transducer, or W·sec per $cm^2$ of transducer, or W·sec per $cm^3$ of transducer, wherein optionally the treatment comprises a heating step and the temperature increase of the heating step is optionally such that the maximum temperature reached during said heating step remains below 50° C., or wherein optionally the temperature increase of the body part or nanoparticle exposed to the acoustic waves is above the temperature of the body part before the application of the acoustic wave optionally by an amount between 0.1 and 30° C.

In one embodiment of the invention, a radiation is applied on the body part or nanoparticle, or the body part or nanoparticle is exposed to a radiation, preferentially during at least one step of the method, preferentially by the cryo-system, most preferentially during the warming step of the method.

In one embodiment of the invention, a radiation is not applied on the body part or nanoparticle, or the body part or nanoparticle is not exposed to a radiation, preferentially during at least one step of the method, preferentially by the cryo-system, most preferentially during the warming step of the method.

In some embodiment, the radiation can be an electromagnetic radiation, light, monochromatic or polychromatic, a laser, a magnetic field, preferentially an alternating magnetic field, acoustic wave, preferentially an infra-sound, an ultra-sound, a hyper sound, or a radiofrequency.

In some embodiment, the radiation can be thermal, and preferentially induce a temperature increase of the body part or nanoparticles, preferentially of more than $10^{-10}$, $10^{-5}$, $10^{-1}$, 1, 2, 5, 10, $10^3$, $10^5$ or $10^{10}$° C., preferentially per second or minute, preferentially per $cm^3$ of body part.

In some other embodiment, the radiation can be non-thermal, and preferentially not induce a temperature increase, or induce a temperature increase of less than $10^{10}$, $10^5$, $10^3$, 10, 5, 2, 1, $10^{-1}$ or $10^{-5}$° C., preferentially per second or minute, preferentially per $cm^3$ of body part.

In one embodiment of the invention, the cryo-system does not involve the application of a magnetic field, preferentially of an alternating magnetic field.

In another embodiment of the invention, the cryo-system involves the application of a magnetic field, preferentially of an alternating magnetic field.

In another embodiment of the invention, the cryo-system does not involve the application of a source of ice-destruction or of a radiation that destroys or can destroy ice.

In another embodiment of the invention, the cryo-system involves the application of a source of ice-destruction or of a radiation that destroys or can destroy ice.

In another embodiment of the invention, the cryo-system does not involve the application of a radiation.

In another embodiment of the invention, the cryo-system involves the application of a radiation.

According to the invention, the radiation can be waves, such as electromagnetic waves, sound or acoustic waves, or particle waves. The particles can have: i) a weight or mass in some cases, ii), do not have a weight or mass in some other cases, iii) a movement in some cases, or iv) not a movement in some other cases.

According to the invention, the radiation can be electromagnetic radiation, acoustic radiation forces, radiation forces, or radiation pressures, irradiation, preferentially of the body part.

Preferably, the radiation is selected from the group consisting of: i) a magnetic or electric field, ii) laser light, iii) light produced by a lamp, iv) light emitted at a single wavelength, v) light emitted at multiple wavelengths, vi) a ionizing radiation, vii) microwave, viii) radiofrequencies, and ix) acoustic wave.

In some cases, the radiation can be selected from the group consisting of: alpha, beta, gamma, X-ray, neutron, proton, electron, ion, neutrino, muon, meson, and photon particles or radiation.

Preferably, the radiation can also in some cases be selected from the group consisting of acoustic waves, infra-sounds, sounds, ultra-sounds, and hyper sounds.

The invention relates to the cryo-system for use according to the invention, wherein the second part has at least one property selected from the group consisting of:

i) The mass/volume of the associating or binding material is smaller than the mass/volume of at least one nanoparticle, ii) The associating/binding material is not an ice nucleation site, and iii) The at least one nanoparticle is an ice nucleation site.

In some cases, the binding and/or associating material differs from the nanoparticle by at least one property selected in the group consisting of: i) it is amorphous or not crystallized, ii) it is organic or carbonaceous, partly, predominantly, or fully, and iii) it does not comprise a majority or more than 50% in mass of metal or iron or iron oxide.

In some cases, the binding or associating material is a material whose function is to prevent the aggregation of the nanoparticle(s) and/or to enable the uniform distribution of the nanoparticle(s) and/or to arrange the nanoparticle(s) in chains and/or to coat the nanoparticle(s) and/or to align the crystallographic directions of at least two nanoparticle(s) in the same direction and/or to yield a geometric figure of the assembly of nanoparticles such as a line, a circle, sphere, rectangle, or square.

In some cases, the volume or mass of the binding or associating material is at least $10^{10}$, $10^5$, $10^3$, 100, 50, 20, 10, 5, 2 or 1 time(s) smaller than the volume or mass of the nanoparticles.

This can be useful when the cryo-system works by promoting the formation of ice and the binding or associating material is not an ice nucleation site.

In some cases, an ice nucleation site is a site or material at the surface of which ice can grow, preferentially leading to the formation of ice-balls, preferentially ice-balls of larger sizes than ice-balls formed in the absence of ice nucleation site or material.

In some cases, the associating or binding material is not an ice nucleation site when at least one ice-ball formed in the presence of such material is not larger or at least 2, 5, or 10 times larger or is smaller or is of similar size as/than the size at least one ice-ball formed in the absence of such material.

In some cases, the nanoparticle(s) and/or binding material or associating material is a cryo-protectant.

In some other cases, the nanoparticle(s) and/or binding material or associating material is not a cryo-protectant.

The invention also relates to a cryo-system for use according to the invention, wherein the assembly of at least two nanoparticles bound to each other or associated with each other via binding or associating material has an external surface, which is the sum or combination of the external surface of the at least two nanoparticles and of the external surface of the binding or associating material, where the external surface has at least one property selected from the group consisting of:
  i) The external surface of at least two nanoparticles is larger than the external surface of the binding or associating material,
  iii) The external surface of the at least two nanoparticles is suitable for ice nucleation or is an ice nucleation site,
  iv) The external surface of the associating or binding material is not suitable for ice nucleation or is not an ice nucleation site,
  iv) The external surface of one nanoparticle is separated from the external surface of another nanoparticle by more than 1 nm,
  v) It is not the external surface of at least one nanoparticle comprised in an aggregate or agglomerate of nanoparticles,
  vi) It is the external surface of a chain, ring, or segment, preferentially linear or curved, comprising at least two nanoparticles, and
  vii) It is exposed to or in contact with the body part.

In one embodiment of the invention, the nanoparticle and/or binding or associating material possess(es) an internal surface or volume and/or an external surface. In some cases, the internal surface or volume of the nanoparticle and/or binding or associating material is the surface or volume of the nanoparticle and/or binding or associating material that is not in contact with the body part. In some other cases, the external surface of the nanoparticle and/or binding or associating material is the surface of the nanoparticle and/or binding or associating material that is in contact with the body part.

The invention also relates to a cryo-system for use according to the invention, wherein the nanoparticle(s) has/have at least one property selected from the group consisting of:
  i) It is ferromagnetic or ferrimagnetic,
  ii) It is crystalline or is not amorphous or comprises more than 1 crystallographic plane,
  iii) Filled or non-hollow nanoparticles,
  iv) an absence of: a) ice inside the nanoparticles or b) the possibility of forming inside the nanoparticles or c) ice inside the nanoparticles for a temperature of the nanoparticles lower than 10° C.,
  v) a presence of: a) ice outside the nanoparticles or ii) the possibility of forming ice outside of the nanoparticles or c) ice outside the nanoparticles for a temperature of the nanoparticles lower than 10° C.,
  vi) Ice nucleation sites, preferentially intracellular ice nucleation sites,
  vii) Solid nanoparticles or solid nanoparticles with more than 50% of their chemical elements or atoms in a solid state,
  viii) Magnetosomes, and
  ix) Chemical analogues of magnetosomes.

In one embodiment of the invention, the ferromagnetic or ferrimagnetic behavior of the nanoparticles and/or the crystallinity of the nanoparticle(s) and/or the presence of at least one crystallographic plane in the nanoparticle(s) and/or the fact that nanoparticles are filled or not hollow favor(s) or promote(s) the nucleation of ice at the surface of nanoparticle(s).

In one embodiment of the invention, a filled or non-hollow nanoparticle is a nanoparticle that comprises at least 1, 10, 50, 70, 80, 90, 95 or 99% in mass or volume, preferentially of its core, in a solid state.

In one embodiment, the nanoparticles have or are characterized by an absence of ice inside them when ice does not or can't form inside them, for example when at least one crystallographic plane of the nanoparticle prevents the insertion of atoms of ice within the crystallographic structure of the nanoparticle. An absence of ice inside the nanoparticles can correspond to less than 100, 90, 80, 50, 20, 10, 5, 2, 1% in mass or volume of the nanoparticle(s) that is made of ice, where the nanoparticle(s) preferentially correspond(s) to the metallic or core part of the nanoparticle(s). An absence of ice at the surface of the nanoparticles can correspond to less than $10^{-40}$, $10^{-20}$, $10^{-10}$, $10^{-5}$, $10^{-3}$, $10^{-1}$, 1, 10, $10^3$ or $10^5$ nm, nm$^2$ or nm$^3$ of ice or ice-ball(s) inside the at least one nanoparticle(s).

In one embodiment, the nanoparticles have or are characterized by at least one property such as an absence of ice inside them in one of the following conditions: i) for a temperature of the nanoparticles, preferentially measured or observed, preferentially by microscopy, which is lower than 10, 5, 2, 1, 0, −5, −10, −20, −40 or −100° C., and ii) after or during the treatment according to the invention.

In one embodiment, the nanoparticles do not comprise ice inside them or inside their core or inside their crystallized core or do not comprise ice-balls inside them, preferentially of larger sizes than that nanoparticle sizes, preferentially below 10, 5, 0, or −5° C., where the presence/absence of ice can preferentially be observed for example by microscopy.

In one embodiment, the nanoparticles have or characterized by the presence of ice outside them when ice forms or can form outside them, for example when the surface or external surface of the nanoparticles favors the formation of ice or ice forms or is located at or on top of the nanoparticle. The presence of ice at the surface of the nanoparticles can correspond to more than $10^{-40}$, $10^{-20}$, $10^{-10}$, $10^{-5}$, $10^{-3}$, $10^{-1}$, 1, 10, $10^3$ or $10^5$ nm, $nm^2$ or $nm^3$ of ice or ice-ball(s) at the surface of at least one nanoparticle(s).

In one embodiment, the nanoparticles have or are characterized by at least one property such as the presence of ice inside them in one of the following conditions: i) for a temperature of the nanoparticles, preferentially measured or observed, preferentially by microscopy, which is lower than 10, 5, 2, 1, 0, −5, −10, −20, −40 or −100° C., and ii) after or during the treatment according to the invention.

In one embodiment of the invention, the binding or associating material comprises ice or ice-balls, preferentially located inside or outside the binding or associating material, preferentially ice or ice-ball of dimension, diameter, length, surface or volume larger than $10^{-40}$, $10^{-20}$, $10^{-10}$, $10^{-5}$, $10^{-3}$, $10^{-1}$, 1, 10, $10^3$ or $10^5$ nm, $nm^2$ or $nm^3$, preferentially per nm, $nm^2$, $nm^3$ or nano-gram of associating or binding material.

In one embodiment of the invention, the nanoparticle(s) preferentially without the associating or binding material, is/are ice nucleation sites, where an ice nucleation site is a site where ice or ice-ball forms preferentially with a volume or size that is larger than: i) the volume or size of ice or ice-balls formed in the absence of such site or nanoparticles preferentially by a factor of at least 0, 1, 5, 10 or $10^3$, and/or ii) $10^{-40}$, $10^{-20}$, $10^{-10}$, $10^{-5}$, $10^{-1}$, 1, 5, 10, $10^3$, $10^5$ or $10^{10}$ $nm^3$.

In some cases, the ice or ice-ball forms or is observed at temperature lower than 50, 37, 20, 10, 5, 2, 1, 0, −5, −10, −40 or −100° C.

In some other cases, the ice or ice-ball forms or is observed at temperature larger than −200, −100, −50, −20, −10, −5, −2, −1, 0, 2, 5 or 10° C.

In some cases, the ice or ice-ball can be intracellular or form inside the cell(s).

In some other cases, the ice or ice-ball can be extracellular or form outside the cell(s).

In some other cases, the nanoparticle(s) is/are solid nanoparticle(s), where solid nanoparticle(s) preferentially more than 1, 2, 5, 10 of their chemical elements or atoms, or more than 1, 10, 50, 70 or 90% of their chemical elements or atoms in a solid state or more than 1, 10, 50, 70 or 90% of their mass or volume in a solid state, where this property is preferentially observed or preferentially occurs at a temperature larger than −200, −100, −50, −20, −10, 0, 5, 10, 50 or 100° C.

In one aspect, the invention relates to nanoparticles or cryo-system for use according to the invention, wherein the nanoparticles are magnetosomes.

In one embodiment of the invention, the magnetosomes are nanoparticles synthesized by, comprised in, originating from, extracted from, or isolated from magnetotactic bacteria.

In one embodiment of the invention, magnetotactic bacteria are selected from the group consisting of: *Magnetospirillum magneticum* strain AMB-1, magnetotactic coccus strain MC-1, three facultative anaerobic vibrios strains MV-1, MV-2 and MV-4, the *Magnetospirillum magnetotacticum* strain MS-1, the *Magnetospirillum gryphiswaldense* strain MSR-1, a facultative anaerobic magnetotactic spirillum, *Magnetospirillum magneticum* strain MGT-1, an obligate anaerobe, *Desulfovibrio magneticus* RS-1, *Nitrospira*, *Nitrospira moscoviensis*, *Magnetobacterium bavaricum*, *Desulfovibrio magneticus* RS-1, *Desulfovibrio desulfuricans*, *Geobacter metallireducens*, Protobacteria, MMPS, MMP2, where MM designates magnetotactic many-celled prokaryote, magnetic cossus, MC-1, CS103, NKMCS, α-Protobacteria, *Rhodospirillum rubrum*, *Agrobacterium vitis*, *Magnetospirillum magnetotacticum* MS-1, *Magnetospirillum magneticum* AMB-1, *Magnetospirillum magneticum* MGT-1, *Magnetospirillum gryphiswaldense* MSR-1, marine magnetic *vibrio* MV-1, *Magnetospirillum gryphiswaldense* MSR-1, *Magnetospirillum magneticum* AMB-1, *Magnetospirillum magnetotacticum* MS-1, *Magnetospirillum magneticum* strain MGT-1, magnetotactic coccus strain MC-1, *Desulfovibrio magneticus* RS-1, anaerobic *vibrio* strains, MV-1, MV-2, and MV-4.

In one embodiment of the invention, magnetotactic bacteria belong to the classes of bacteria selected in the group consisting of: zetaproteobacteria, beta-proteobacteria, Gammaproteobacteria, Deltaproteobacteria, Epsilon-proteobacteria, Nitrospirae, OP3, and Alphaproteobacteria.

In one embodiment of the invention, a magnetotactic bacterium is defined as a bacterium that synthesizes or is able to synthesize magnetosomes, wherein these magnetosomes are preferentially characterized by at least one of the following properties: i) they are produced intracellularly, ii) they are magnetic, iii) they comprise a mineral, iv) their core is preferentially composed of a metallic oxide such as iron oxide, v) their core is surrounded by biological material such as lipids, proteins, endotoxins, which can preferentially be removed, vi) they are arranged in chains, vii) they can produce heat under the application of an alternating magnetic field of typical strength 1 to 50 mT of typical frequency 20 to 200 KHz.

In one embodiment of the invention, the magnetosomes possess one or several property(ies) in common with the nanoparticles such as at least one magnetic, size, composition, chain arrangement, charge, core, mineral, coating, or crystallinity property.

In one embodiment of the invention, magnetosomes comprise the mineral part synthesized by magnetotactic bacteria, i.e. preferentially the crystallized iron oxide produced by these bacteria. In this case, magnetosomes or magnetosome mineral parts preferentially do not comprise proteins, lipids, endotoxins, or biological materials comprising carbon or do not comprise more or comprise less than 0.1, 1, 10, 30, 50 or 75% or percent in mass of carbon, which is/are produced by these bacteria.

The invention also relates to nanoparticles or cryo-system for use, wherein nanoparticles are or are assimilated to chemical analogues of magnetosomes.

In some cases, chemical analogues of magnetosomes can be synthesized chemically and/or are not synthesized by magnetotactic bacteria.

In some cases, chemical analogues of magnetosomes possess at least 1, 2, 3, 4, 5, 6, 7, 8, 9, or 10 common property(ies) with the magnetosomes, where these common properties are preferentially a ferrimagnetic behavior, preferentially a coercivity larger that $10^{-5\circ}$, $10^{-10}$, $10^{-2}$, 1, 5, 10 or 100 Oe at a temperature preferentially larger than 0, 5, 10, 50, 100, 200, 300, 500 or 1000 K, a large size, preferentially a size larger than 1, 5, 10, 20, 50 or 70 nm, and/or a chain arrangement, preferentially an arrangement of more than 1, 2, 5 or 10 nanoparticles in chain.

In one embodiment of the invention, the nanoparticles or magnetosomes are purified to remove more than 10, 50 or 90 percent or percent in mass of endotoxins and/or other biological material such as proteins or lipids originating from the synthetizing living organism or magnetotactic bacteria. In some other cases, the nanoparticles or magnetosomes are purified to remove less than 100, 99.9, 99, 95 or 90 percent or percent in mass of endotoxins and/or other biological material. This purification step preferentially yields purified nanoparticles or magnetosomes. In some cases, this percentage can be equal to $(Q_{BP}-Q_{AP})/Q_{BP}$ or $Q_{AP}/Q_{BP}$, where $Q_{BP}$ and $Q_{AP}$ are the quantities of endotoxins, biological material, proteins, or lipids before and after the purification step, respectively.

In some cases, the purification step can consist in using a method or detergent(s) such as NaOH and/or KOH, which is/are preferentially mixed with the synthetizing living organism or magnetotactic bacteria or bacterial debris, preferentially to remove organic material or separate the organic material from the inorganic material comprised in the nanoparticles or magnetosomes and preferentially then be able to harvest the nanoparticle or magnetosome mineral, preferentially comprised in the nanoparticles or magnetosomes.

In some cases, the purified nanoparticles or magnetosomes are nanoparticle or magnetosome minerals.

The invention also relates to the cryo-system for use according to the invention, wherein the nanoparticle(s) possess(es) at least one property selected from the group consisting of:
i) It comprises more than 1 metallic atom or more than 1% in mass, number of atoms or volume of metallic atoms,
ii) It is composed of metal oxide, partly, in majority or fully,
iii) It comprises at least one atom of iron,
iv) It comprises at least one other metal than iron preferentially selected from the group consisting of: barium, zinc, and manganese,
v) It comprises at least one other metal than iron at a percentage in mass relatively to the mass of all metals comprised in the nanoparticle that is between $10^{-20}\%$ and 50%,
vi) It possesses a volumic mass and/or density larger than the volumic mass and/or density larger of water,
vii) It possesses a ratio between surface and volume that is larger than $10^{-10}$ nm,
viii) It has a specific heat capacity smaller than the specific heat capacity of the body part or matrix or medium in which it is comprised,
ix) It has a thermal conductivity larger than the thermal conductivity of the body part or matrix or medium in which it is comprised,
x) It has a enthalpy of fusion larger than the enthalpy of fusion of the body part or matrix or medium in which it is comprised,
xi) It has a viscosity larger than the viscosity of the body part or matric or medium in which it is comprised,
xii) It has a heat capacity, thermal conductivity and/or enthalpy of fusion that is/are lower at its surface than at its center, and
xiii) It has a size between 1 and 1000 nm.

In one embodiment of the invention, the at least one nanoparticle comprises more than 0, 1, 5, 10, $10^3$, $10^5$ or $10^{10}$ metallic atom(s) or more than 0, 1, 5, 10, 25, 50, 70, 80, 90, 95 or 99% in mass, number of atoms or volume of metallic atoms.

In one embodiment of the invention, the at least one nanoparticle comprises less than $10^{20}$, $10^{10}$, $10^5$, $10^3$, 10, 5, 2, 1 or 0 metallic atom(s) or less than 100, 99, 90, 85, 80, 70, 50, 30, 290, 10, 5, 2 or 1% in mass, number of atoms or volume of metallic atoms.

In one embodiment of the invention, the nanoparticle(s) has/have a metallic composition. In some cases, the metallic composition of the nanoparticles maintains the cold, preferentially locally, preferentially within the body part.

In one embodiment of the invention, the nanoparticle(s) comprise(s) at least 1, 2, 5, 10 or 20 other metal(s) than iron. In some cases, the presence of such other metal(s) has one of the following properties: i) it increases the capacity of the nanoparticle(s) to maintain the cold, preferentially locally, preferentially within the body part, ii) it reduces the toxicity and/or increases the efficacy of cryotherapy.

In one embodiment of the invention, the nanoparticle(s) comprise(s) at least one other metal than iron at a percentage in mass relatively to the mass of all metals in the nanoparticles that is larger than 0, $10^{-20}$, $10^{-10}$, $10^{-5}$, $10^{-1}$, 1, 5, 10, 20 or 50%.

In one embodiment of the invention, the nanoparticle(s) comprise(s) at least one other metal than iron at a percentage in mass relatively to the mass of all metals in the nanoparticles that is smaller than 100, 70, 50, 30, 20, 10, 5, 2 or 1%.

In one embodiment of the invention, the nanoparticle(s) comprise(s) at least one other metal than iron at a percentage in mass relatively to the mass of all metals in the nanoparticles that is between $10^{-20}\%$ and 50%, $10^{-1}$ and 20%, or $10^{-1}$ and 5%.

In one embodiment of the invention, the at least one nanoparticle possesses a volumic mass and/or density larger than the volumic mass and/or density larger of water.

In one embodiment of the invention, the at least one nanoparticle possesses a volumic mass or density that is larger than $10^{-20}$, $10^{-10}$, $10^{-5}$, $10^{-3}$, $10^{-1}$, 0, 1, 5 or 10 grams per cm$^3$ of nanoparticle or nanoparticle assembly.

In some cases, a large volumic mass or density of nanoparticles can favor the formation of ice at the surface of the nanoparticles, for example by preventing ice to collapse or fuse or transform into liquid water or by providing coordination sites preferentially at atomic or molecular level at the interface between the nanoparticle surface and ice.

In another embodiment of the invention, the at least one nanoparticle possess a volumic mass or density that is lower than $10^{20}$, $10^{10}$, $10^5$, $10^3$, 10, 5, 2, 1 or $10^{-1}$ gram per cm$^3$ of nanoparticle or nanoparticle assembly.

In some cases, a low volumic mass or density of nanoparticles can enable ice to form in-between the nanoparticles.

In one embodiment, the at least one nanoparticle possesses a ratio between its surface, preferentially external one, and its volume, that is larger than $10^{-50}$, $10^{-10}$, $10^{-5}$, $10^{-1}$, 0, 1, 5 or 10 nm. In some cases, a large surface/volume ratio favors the formation of ice at nanoparticle surface.

In one embodiment, the at least one nanoparticle possesses a ratio between its surface, preferentially external one, and its volume, that is smaller than $10^{50}$, $10^{10}$, $10^5$, $10^3$, 10, 5, 2, 1, 0, $10^{-1}$ or $10^{-3}$ nm. In some cases, a low surface/volume ratio can prevent the collapse of the nanoparticle(s), for example between a three dimensional to a two-dimensional structure.

In one embodiment of the invention, the at least one nanoparticle has a specific heat capacity or heat capacity or heating capacity larger than $10^{-10}$, $10^{-5}$, $10^{-1}$, 1, 5 or 10 J per K per gram of nanoparticle(s) or J per K per mol of nanoparticle(s) or J per K per cm$^3$ of nanoparticle(s).

In another embodiment of the invention, the at least one nanoparticle has a specific heat capacity or heat capacity or heating capacity smaller than $10^{10}$, $10^5$, 10, 5 or 1 J per K per gram of nanoparticle(s) or J per K per mol of nanoparticle(s) or J per K per cm$^3$ of nanoparticle(s).

In some cases, the heat capacity can be the isobaric mass heat capacity, isobaric molar heat capacity, the isochore molar heat capacity, the isobaric volumetric heat capacity, and/or the isochore atom-molar heat capacity.

In one embodiment of the invention, the at least one nanoparticle has a thermal conductivity larger than $10^{-20}$, $10^{-10}$, $10^{-5}$, $10^{-1}$, 0, 1, 5, 10, $10^2$, $10^3$, $10^5$ or $10^{10}$ W·m$^{-1}$·K$^{-1}$. In some cases, the nanoparticles have a large thermal conductivity due to their metallic composition, crystallinity and/or nano-metric size.

In another embodiment of the invention, the at least one nanoparticle has a thermal conductivity smaller than $10^{50}$, $10^{10}$, $10^5$, $10^3$, 10, 5, 1, $10^{-1}$ or $10^{-3}$ W·m$^{-1}$·K$^{-1}$. In some cases, the nanoparticles have a thermal conductivity that is not too large for example when they are degraded.

In one embodiment of the invention, the at least one nanoparticle has an enthalpy of fusion or latent heat of fusion or latent heat larger than the enthalpy of fusion or latent heat of fusion or latent heat of the body part or matrix or medium in which it is comprised.

In another embodiment of the invention, the at least one nanoparticle has an enthalpy of fusion or latent heat of fusion or latent heat that is larger than $10^{-5\circ}$, $10^{10}$, $10^{-5}$, $10^{-1}$, 0, 1, 2, 5, 10 or 10, $10^3$ or $10^5$ KJ per mol or gram of nanoparticles. In some cases, a large enthalpy of fusion of the nanoparticles is due to the metallic composition of the nanoparticles and can in some cases favor the formation of ice or prevent the melting of ice, preferentially at nanoparticle surface.

In another embodiment of the invention, the at least one nanoparticle has an enthalpy of fusion or latent heat of fusion or latent heat that is smaller than $10^{50}$, $10^{10}$, $10^5$, 10, 5, 2, 1, $10^{-1}$ or $10^{-5}$ KJ per mol or gram of nanoparticles. In some cases, a small enthalpy of fusion of the nanoparticles can be due to the degradation of the nanoparticle.

In one embodiment of the invention, the at least one nanoparticle has a viscosity that is larger than $10^{-50}$, $10^{-10}$, $10^{-5}$, $10^{-3}$, $10^{-1}$, 0, 1, 5, 10, $10^2$, $10^3$, $10^5$ or $10^{10}$ Pa·sec. In some cases, the nanoparticle(s) can have a large viscosity when they move or diffuse slowly in water or in the body part.

In another embodiment of the invention, the at least one nanoparticle has a viscosity smaller than $10^{50}$, $10^{10}$, $10^5$, $10^3$, 10, 5, 2, 1, $10^{-1}$, $10^{-3}$ or $10^{-5}$ Pa·sec. In some cases, the nanoparticle(s) can have a low viscosity when they move or diffuse rapidly in water or in the body part.

In another embodiment of the invention, the nanoparticle has a heat capacity that is larger at its surface than at its center.

In another embodiment of the invention, the nanoparticle has a thermal conductivity that is larger at its center than at its surface.

In one aspect, the invention relates to nanoparticles or cryo-system for use according to the invention, wherein the nanoparticles have a heating capacity with at least one property selected from the group consisting of:
i) the heating capacity is comprised between $10^{-20}$, $10^{40}$, $10^{-5}$, $10^{-1}$, 0, 1 or 10 and 0, 1, 5, 10, $10^5$ or $10^{10\circ}$ C. per second per mg of nanoparticle,
ii) the heating capacity is the difference between the heating rate of the body part comprising the nanoparticles and the heating rate of the body part without the nanoparticles, iii) the heating capacity is measured during the heating step,
iv) the heating capacity can be increased by applying a radiation or an external source of radiation such as an acoustic wave, laser, or magnetic field on the body part or nanoparticle,
iv) the heating capacity is smaller in the presence than in the absence of nanoparticles preferentially when no radiation is applied during the heating step,
v) when the heating capacity is decreased preferentially by the presence of nanoparticles preferentially in the absence of radiation application, the nanoparticles more efficiently destroy cells than in the absence of nanoparticles and absence of radiation application, and
vi) when the heating capacity is increased, the nanoparticles preferentially exposed to radiation more efficiently destroy cells preferentially compared with nanoparticles not exposed to radiation.

In one aspect, the invention relates to nanoparticles or cryo-system for use according to the invention, wherein the nanoparticles have a cooling capacity with at least one property selected from the group consisting of:
i) the cooling capacity is comprised between $10^{-20}$, $10^{-10}$, $10^{-5}$, $10^{-1}$, 0, 1 or 10 and 0, 1, 5, 10, $10^5$ or $10^{10\circ}$ C. per second per mg of nanoparticle,
ii) the cooling capacity is the difference between the cooling rate of the body part comprising the nanoparticles and the cooling rate of the body part without the nanoparticles, iii) the cooling capacity is measured during the cooling step,
iv) the cooling capacity can be increased by switching on or activating the cryo-probe,
iv) the cooling capacity is larger in the presence than in the absence of nanoparticles preferentially when the cryo-probe is activated,
v) when the cooling capacity is increased preferentially by the presence of nanoparticles preferentially by the activation of the cryo-probe, the nanoparticles more efficiently destroy cells than: a) in the absence of nanoparticles and absence of cryo-probe application or b) in the absence of nanoparticles and cryo-probe application, and
vi) when the cooling capacity is increased, the nanoparticles preferentially exposed to cryo-probe more efficiently destroy cells preferentially compared with nanoparticles not exposed to cryo-probe.

In one aspect, the invention relates to nanoparticles or cryo-system for use according to the invention, wherein the nanoparticles have a capacity to maintain the temperature of the body part at a temperature called the maintaining temperature with at least one property selected from the group consisting of:
i) the maintaining temperature is a temperature comprised between −200 and 100° C., −200 and 0, −100 and 10, −100 and 0, −40 and 10, −40 and 0, −20 and 0, or between −10 and −5° C., and
ii) the maintaining temperature varies by less than $10^{-3}$, 1, 10, 50, 90, 99 or 100% preferentially within a lapse of time smaller than $10^5$, $10^3$, 1, $10^{-1}$ or $10^{-3}$ minute(s), where this percentage is preferentially equal to $|(T_{min} - T_{max})/T_{av}|$ with $T_{min}$, $T_{max}$ and $T_{av}$ being preferentially the minimum, maximum, and average temperatures measured within this lapse of time.

In one embodiment of the invention, the nanoparticle heating capacity is the number of degrees Celsius gained by the nanoparticles, preferentially per second, preferentially per mg of nanoparticles, preferentially during at least one step of the method such as the heating step.

In some embodiment, the nanoparticle heating capacity is estimated without exposing the nanoparticles to a source of radiation, preferentially a source of radiation that produces heat.

In some embodiment, the nanoparticle heating capacity is estimated by exposing the nanoparticles to a radiation or source of radiation, preferentially a source of radiation that produces heat. Such conditions may increase the value of the heating capacity compared with the heating capacity measured in the absence of the application of a source of radiation.

In another embodiment of the invention, the heating capacity is the difference between the number of degrees Celsius gained by the body part comprising the nanoparticles and the number of degrees gained by the body part not comprising the nanoparticles. The number of degrees that is gained is preferentially estimated per second, preferentially per mg of nanoparticles, preferentially during the heating step.

In an embodiment of the invention, the nanoparticle heating capacity is lower than $10^{50}$, $10^{20}$, $10^{10}$, $10^5$, $10^3$, 10, 1, $10^{-1}$, $10^{-3}$ or $10^{-5}$° C., preferentially per second, preferentially per mg of nanoparticle.

In another embodiment of the invention, the nanoparticle heating capacity is larger than $10^{-50}$, $10^{-10}$, $10^{-5}$, $10^{-1}$, 1, 5, 10 or $10^{3}$° C., preferentially per second, preferentially per mg of nanoparticle.

In still another embodiment of the invention, the nanoparticle heating capacity is between $10^{-50}$ and $10^{50}$, $10^{-20}$ and $10^{20}$, $10^{-10}$ and $10^{10}$, or between $10^{-5}$ and $10^{5}$° C., preferentially per second, preferentially per mg of nanoparticle.

In still another embodiment of the invention, the nanoparticle heating capacity is the nanoparticle heating rate, preferentially of or during the warming step.

In another embodiment of the invention, the nanoparticle cooling capacity is the number of degrees Celsius lost by the nanoparticles, preferentially per second, preferentially per mg of nanoparticles, preferentially during the cooling step.

In some embodiment, the cooling capacity is estimated without exposing the nanoparticles to the substance or equipment or cryo-probe that enables to adjust the temperature, preferentially during the cooling step or maintaining step.

In some embodiment, the cooling capacity is estimated by exposing the nanoparticles to the temperature adjuster or cryo-probe, preferentially during the cooling or maintaining step. Such conditions may increase the value of the nanoparticle cooling capacity compared with the nanoparticle cooling capacity measured in the absence of the temperature adjuster or cryo-probe.

In one embodiment of the invention, the efficacy to treat and/or destroy a disease increases with increasing heating and/or cooling capacity of the nanoparticles.

In another embodiment of the invention, the cooling capacity is the difference, preferentially in absolute value, between the number of degrees lost by the body part comprising the nanoparticles and the number of degrees lost by the body part not comprising the nanoparticles. The number of degrees that is lost is preferentially estimated per second, preferentially per mg of nanoparticles, preferentially during the cooling step.

In an embodiment of the invention, the nanoparticle cooling capacity is lower than $10^{50}$, $10^{20}$, $10^{10}$, $10^5$, $10^3$, 10, 1, $10^{-1}$, $10^{-3}$ or $10^{-5}$° C., preferentially per second, preferentially per mg of nanoparticle.

In another embodiment of the invention, the nanoparticle cooling capacity is larger than $10^{-50}$, $10^{-10}$, $10^{-5}$, $10^{-1}$, 1, 5, 10 or $10^{3}$° C., preferentially per second, preferentially per mg of nanoparticle.

In still another embodiment of the invention, the nanoparticle cooling capacity is between $10^{-50}$ and $10^{50}$, $10^{-20}$ and $10^{20}$, $10^{-10}$ and $10^{10}$, or between $10^{-5}$ and $10^{5}$° C., preferentially per second, preferentially per mg of nanoparticle.

In another embodiment of the invention, the nanoparticle cooling capacity is the nanoparticle cooling rate, preferentially of or during the cooling step.

In some cases, the heating capacity is the same as the heat capacity.

In some cases, at least one property of the nanoparticle(s) or cryo-system is measured or observed at a temperature larger than −200, −100, −50, −20, −10, −5, 0, 5, 10 or 40° C.

In some other cases, at least one property of the nanoparticle(s) or cryo-system is measured or observed at a temperature smaller than $10^5$, $10^3$, 500, 200, 100, 50, 37, 20, 10, 5, 2, 1, 0, −5, −10, −20, −40, −100 or −200° C.

The cryo-system for use according to the invention, wherein the penetrating segment has at least one property selected from the group consisting of:
  i) it has at least one dimension smaller than 10 cm,
  ii) it has a length smaller than 10 cm,
  iii) it has a width smaller than 5 cm,
  iv) it has a ratio between its longest and smallest dimension that is larger than 2,
  v) it occupies less than 50%, 25%, 15%, 10%, 5% or 1% in volume of the body part,
  vi) it is smaller than at least ½oth, ⅕oth, ¹/₁₀₀th, ¹/₅₀₀th or ¹/₁₀₀₀th of the biggest volume of the body part,
  vii) it is biocompatible and/or biodegradable,
  viii) it is rigid, or has a shear modulus larger than 1 GPa, and
  ix) it is flexible, or has a shear modulus smaller than 1 GPa.

In one embodiment of the invention, the segment, preferentially the penetrating one, has at least one dimension, surface, volume, length, and/or width, preferentially comprised in the body part, which is smaller than $10^{10}$, $10^5$, $10^3$, 500, 100, 50, 10, 5, 2, 1, 0.5, $10^{-3}$, $10^{-5}$ or $10^{-10}$ cm or cm² or cm³. In some cases, a segment with a small dimension is desired to avoid creating pain in a patient and/or to be able to maintain the segment for a long period of time, preferentially longer than $10^{-1}$°, 1, 5, 10, 30, 60 or $10^3$ minute(s), in the body part, and/or to be able to reintroduce several times the segment in the body part.

In another embodiment of the invention, the segment, preferentially the penetrating one, has a ratio between its longest and smallest dimension that is larger than $10^{-10}$, $10^{-5}$, $10^{-1}$, 1, 2, 5, 10 or $10^3$.

In another embodiment of the invention, the segment, preferentially the penetrating one, has a ratio between its longest and smallest dimension that is smaller than $10^{10}$, $10^5$, 10, 5, 2, or 1.

In one embodiment, the dimension of the segment is the usual dimension or most commonly used dimension of the segment or the dimension of the segment indicated in the notice of the cryo-system.

In some cases, the segment can be the cryo-system or cryo-probe or part of the cryo-system or cryo-probe.

In one embodiment of the invention, the segment, preferentially the penetrating one, occupies less than 100%, 50%, 25%, 15%, 10%, 5% or 1% in volume or mass of the body part.

In another embodiment of the invention, the segment, preferentially the penetrating one, occupies more than $10^{-5}$%, 0%, 1, 10, 25% or 50% in volume or mass of the body part.

In one embodiment of the invention, the segment, preferentially the penetrating one, is smaller or has at least one dimension smaller than at least 1, $1/5^{th}$, $1/20^{th}$, $1/50^{th}$, $1/100^{th}$, $1/500^{th}$ or $1/1000^{th}$ of the biggest volume or dimension of the body part.

In one embodiment of the invention, the segment, preferentially the penetrating one, is larger or has at least one dimension larger than at least $1/100000^{th}$, $1/1000^{th}$, $1/10^{th}$, $1/5^{th}$, $1/2^{th}$, or 1 time of the biggest volume or dimension of the body part.

In one embodiment of the invention, the segment, preferentially the penetrating one, is biocompatible and/or biodegradable.

In some cases, the segment and/or nanoparticle is/are biocompatible when they can be introduced in the body part, preferentially without causing the death or a disease or fever or a heart shock of the individual.

In some cases, the segment and/or nanoparticle is/are biodegradable when they can be or are degraded by the individual, for example when the body part or some of its components such as lysosomes dissolve the segment and/or nanoparticle, preferentially following their use in the method or cryo-system according to the invention.

In some embodiment, the segment, preferentially the penetrating one, is rigid or does not get bent or does not get bent by more than 90, 45, 20, 10, 5, 2 or 1°, preferentially between before and after administration in the body part, or has a shear modulus larger than $10^{-50}$, $10^{-20}$, $10^{-5}$, $10^{-1}$, 0, 1, 5, 10 or 50 GPa. In some cases, a rigid segment can be useful for example to avoid that the segments move during the cryotherapy.

In some embodiment, the segment, preferentially the penetrating one, is flexible or gets bent or gets bent by more than $10^{-10}$, $10^{-1}$, 0, 1, 5, 10, 45° (degrees), preferentially between before and after administration in the body part, or has a shear modulus smaller than $10^{50}$, $10^{20}$, $10^5$, 10, 5, 2, 1, $10^{-1}$ or $10^{-3}$ GPa. In some cases, a flexible segment can be useful for example to avoid that the segments remain stuck within part of the body part during the cryotherapy.

The invention also relates to the cryo-system for use according to the invention, wherein the non-penetrating segment does not have a solid or immobile part in contact with the body part or is not in contact or in continuous contact with the body part.

In one embodiment of the invention, the non-penetrating segment does not have a solid or immobile part in contact with the body part when the non-penetrating segment is located at a distance of more than 1, 10, $10^3$ or $10^{10}$ nm from the body part or the surface of the body part or when the segment produces or expels a cryogenic liquid or gas that is or enters in contact with the body part.

The invention relates to the cryo-system for use according to the invention, wherein the cryogen source is selected from the group consisting of: i) a cryogenic gas, ii) a cryogenic liquid, and iii) a cryogenic fuel. In some cases, the cryogenic source can be a cryogenic solid.

The invention also relates to a cryo-system for use according to the invention, wherein the cryogen source is a cryogenic gas selected from the group consisting of: Helium-3, Helium, Hydrogen, Neon, Nitrogen, Air, Fluorine, Argon, Oxygen, and Methane.

The invention also relates to the cryo-system for use according to the invention, wherein the cryogen source has a boiling point or boiling temperature larger than 0, 1, 5, 10, 50, 100, 200 or 300 K.

In some other cases, the cryogen source can have a boiling temperature lower than $10^5$, $10^3$, 500, 200, 100, 50, 20, 10, 5, 2 or 1 K.

The invention also relates to the cryo-system for use according to the invention, wherein the cryogen source is in direct contact with said body part.

In some cases, the cryogen source is in direct contact with the body when it is expelled from the cryo-probe or segment to diffuse in the body part.

In some cases, the cryogen source is in direct contact with the body part when it is in the body part or is located at a distance from the body part of less than $10^{10}$, $10^5$, $10^3$, 10 or 1 nm.

In some other cases, the cryogen source is in indirect contact with the body part when the cryogen source is separated from the body part, preferentially by at least one part of the cryo-probe such as the segment, or when the distance between the cryogen source and the body part is larger than $10^4$, 1, 5, 10, $10^3$ or $10^5$ nm.

The invention relates to the cryo-system for use according to the invention in a method of treating a body part of an individual by cryotherapy comprising at least one of the following steps:

a) preferentially during a nanoparticle administration time, administering nanoparticles to a body part of an individual, a step preferentially designated as the nanoparticle administration step, b) preferentially during an exposure time, exposing the body part of the individual to the cryo-probe, a step preferentially designated as the exposure step, c) preferentially during a cooling time, cooling down the body part of the individual preferentially comprising nanoparticles by using the cryo-probe from an initial temperature to a cooling temperature of said body part, where the cooling and/or maintaining temperature is/are lower than the initial temperature, a step preferentially designated as the cooling step, d) preferentially during a warming time, warming up or letting warmed up the body part comprising the nanoparticles either by increasing the temperature of the body part from the cooling temperature of said body part to a final temperature of said body part or by letting the temperature of the body part increase from the cooling temperature of said body part to a final temperature of said body part, a step preferentially designated as the warming step, and e) optionally, preferentially during a maintaining time, maintaining or letting maintained the temperature of the body part preferentially comprising the nanoparticles at: i) the cooling temperature or ii) a maintaining temperature that is comprised between the cooling temperature and the initial or final temperature, a step preferentially designated as the maintaining step.

In one embodiment, the nanoparticle administration time is the duration of nanoparticle administration or duration of the nanoparticle administration step or $t_0$.

In one embodiment, the exposure time is the duration of exposure of the body part by the cro-probe, preferentially when the cryo-probe is switched on or activated, or duration of the exposure step or $t_0'$. In some cases, $t_0'$ can be divided between or include or be the sum of the time of administration of the cryo-probe in the body part and the time during which the cryo-probe is switched on or activated in the body part.

In one embodiment, the cooling time is the duration of cooling down the body part or duration of the cooling step or $t_1$.

In one embodiment, the warming time is the duration of warming up the body part or duration of warming step or $t_2$.

In one embodiment, the maintaining time is the duration of maintaining or letting maintained the temperature of the body part at the maintaining or cooling or minimum temperature or duration of the maintaining step or $t_3$.

In one aspect, the invention relates to nanoparticles or cryo-system for use according to the invention, wherein the succession of at least one of the administration step, the cooling step, the maintaining step, and the warming step is repeated more than 1, 2, 3, 5, 6, 10, or $10^3$ times, preferably more than 6 times, most preferably more than 3 times.

The invention relates to the cryo-system for use according to the invention, wherein the initial temperature and/or the final temperature and/or maximum temperature is/are physiological temperature(s).

The invention also relates to the nanoparticle(s) for use according to the invention, wherein the physiological temperature is a temperature selected from the group consisting of: i) the temperature of the body part before or after the body part is treated by the method or cryo-system according to the invention, ii) the temperature of an individual that does not suffer from fever, iii) a temperature comprised between 35 and 45° C., between 25 and 45° C. or between 10 and 100° C., iv) the temperature of an individual or of its body part or of its blood that is not above by more than 5° C. than the average temperature of this individual or of its blood or of its body part measured over the course of the life of this individual, and v) the temperature of an individual or of its body part or of its blood that is not below by more than 5° C. than the average temperature of this individual or of its blood or of its body part measured over the life of this individual.

In some cases, the physiological temperature can be the temperature of the body part or of a whole living organism or of at least one eukaryotic or prokaryotic cell.

In some cases, the physiological temperature can be larger than −200, −150, −100, 650, −40, −20, −10, −5, −2, −1, 0, 2, 5, 10, 50, 100, 150, 200, 400 or 500° C.

In some other cases, the physiological temperature can be a lower than $10^5$, $10^3$, 500, 200, 100, 50, 42, 41, 20, 10, 5 or 0° C.

The invention also relates to the cryo-system for use according to the invention, wherein the cooling temperature has at least one characteristic selected from the group consisting of:
  i) a difference $\Delta T_1$ between the initial and the cooling temperature preferentially lower than $10^5$, $10^3$, 100, 57 or 10° C., and
  ii) a difference $\Delta T_2$ between the final and the cooling temperature preferentially lower than $10^5$, $10^3$, 100, 57 or 10° C.

In one aspect, the invention relates to nanoparticle or cryo-system for use according to the invention, wherein the cooling temperature has at least one characteristic selected from the group consisting of:
  i) a difference $\Delta T_1$ between the initial and the cooling temperature preferentially lower than $10^5$, $10^3$, 100, 57 or 10° C.,
  and/or
  ii) a difference $\Delta T_2$ between the final and the cooling temperature preferentially lower than $10^5$, $10^3$, 100, 57 or 10° C.,
  and preferably wherein the difference(s) $\Delta T_1$ and/or $\Delta T_2$ decrease(s) when the nanoparticle concentration increases in the body part.

In one embodiment of the invention, the difference $\Delta T_1$ between the initial and the cooling temperature is lower than $10^{10}$, $10^5$, $10^3$, 100, 90, 80, 60, 57, 50, 40, 30 or 20° C., preferably lower than $10^3$ or 100, more preferably lower than 57° C.

In one embodiment of the invention, the difference $\Delta T_2$ between the final and the cooling temperature is lower than $10^{10}$, $10^5$, $10^3$, 100, 90, 80, 60, 57, 50, 40, 30 or 20° C., preferably lower than 103 or 100, more preferably lower than 57° C.

In one embodiment of the invention, small value(s) of $\Delta T_1$ and/or $\Delta T_2$ is/are reached or desired to carry out a large number of cycles and/or to avoid reaching the ice-ball temperature or too low temperatures that can result in side effects.

In another embodiment of the invention, the difference $\Delta T_1$ between the initial and the cooling or minimum temperature is larger than $10^{-5°}$, $10^{-10}$, $10^{-5}$, $10^{-1}$, 1, 5, 10, 20, 30, 50, 70, 80, 100 or 1000° C., preferably larger than 1 or 5° C., more preferably larger than 10° C.

In one embodiment of the invention, the difference $\Delta T_2$ between the final and the cooling or minimum temperature is larger than $10^{-5°}$, $10^{-10}$, $10^{-5}$, $10^{-1}$, 1, 5, 10, 20, 30, 50, 70, 80, 100 or 1000° C., preferably larger than 1 or 5° C., more preferably larger than 10° C.

In some embodiment of the invention, large value(s) of $\Delta T_1$ and/or $\Delta T_2$ is/are reached or desired to carry out a small number of cycles and/or to reach the ice-ball temperature or temperature below 0° C. that can preferentially increase the medical or cosmetic or therapeutic or diagnostic activity of the treatment.

In another embodiment of the invention, the difference $\Delta T_1$ between the initial and the cooling or minimum temperature is between $10^{-50}$ and $10^{50}$, $10^{-10}$ and $10^{10}$, $10^{-5}$ and $10^5$, $10^{-3}$ and $10^3$, $10^{-2}$ and $10^2$, $10^{-1}$ and 100, preferably between 1 and 70, more preferably between 2 and 50° C.

In one embodiment of the invention, the difference(s) $\Delta T_1$ and/or $\Delta T_2$ can be decreased by increasing the nanoparticle concentration in the body part. This can mean that by introducing nanoparticles in the body part, preferentially at a concentration larger than $10^{-5°}$, $10^{-10}$, $10^{-5}$, $10^{-3}$, $10^{-1}$, 1, 5, 10, $10^3$ or $10^5$ mg of nanoparticles per cm$^3$ of body part, the medical or cosmetic or therapeutic or diagnostic activity of the treatment can be reached by using value(s) of $\Delta T_1$ and/or $\Delta T_2$ that is/are at least 0, 0.5, 1, 1.1, 1.5, 2, 5, 10, $10^3$ or $10^5$ smaller than the value(s) of $\Delta T_1$ and/or $\Delta T_2$ reached in the absence of nanoparticles.

The invention also relates to the cryo-system for use according to the invention, wherein the steps of the methods are characterized by at least one of the following properties:
  i) step(s) a), b), c), d) and/or e) of the method according to the invention is or are repeated at least 1, 2, 3, 5, 10, 15, 20, 50, $10^2$, $10^3$ or $10^5$ times, and
  ii) step c) precedes step d).

In some other cases, at least one step a), b), c), d) or e) of the method is not repeated or is repeated less than $10^{10}$, $10^5$, $10^3$, 500, 100, 50, 20, 10, 5, 2 or 1 time(s).

In still some other cases, the at least one step a), b), c), d) or e) of the method is carried out in any order or in the following order: step a) after step b), c), d) or e); step b) after step a), c), d) or e); step c) after step a), b), d) or e); step d) after step a), b), c) or e), step e) after step a), b), c) or d).

The invention also relates to the cryo-system for use according to the invention, wherein the cooling or minimum temperature of the body part is at least 1.01, 1.1, 1.5, 2, 5, 10 or 100 lower when the body part is cooled down by the cryo-system than when it is cooled down by the cryo-probe alone without the nanoparticles, wherein this comparison is preferentially made by using the same operating conditions of the cryo-probe in both cases.

The invention also relates to the cryo-system for use according to the invention, wherein the cooling time $t_1$ and the warming time $t_2$ are characterized by at least one property selected in the group consisting of:
i) $t_1$ is at least $10^3$, 100, 50, 20, 10, 5, 2, 1.5 or 1.1 shorter than $t_2$,
i) $t_1$ is larger than $10^{-9}$, $10^{-6}$, $10^{-3}$, $10^{-1}$, 1, 5, 10 or 100 seconds,
ii) $t_2$ is larger than $10^{-9}$, $10^{-6}$, $10^{-3}$, $10^{-1}$, 1, 5, 10 or 100 seconds,
iii) $t_2-t_1$ is larger than $10^{-9}$, $10^{-6}$, $10^{-3}$, $10^{-1}$, 1, 5, 10 or 100 seconds,
iv) $t_1$ is similar in the presence and absence of nanoparticles, and
v) $t_2$ is longer in the presence than absence of nanoparticles.

In some cases, $t_1$ in the presence of nanoparticles is $t_1$ measured in the presence of more than $10^{-20}$, $10^{-5}$, $10^{-3}$, $10^{-1}$, 0, 1, 5, 10 or $10^3$ mg of nanoparticles per $cm^3$ of body part, also designated as $t_{11}$.

In some other cases, $t_1$ in the absence of nanoparticles is $t_1$ measured in the presence of less than $10^{20}$, $10^{10}$, $10^5$, 100, 10, 5, 2, 1, $10^{-3}$ or $10^{-6}$ mg of nanoparticles per $cm^3$ of body part, also designated as $t_{12}$.

In some cases, $t_1$ is similar in the presence and absence of nanoparticles when $t_{11}/t_{12}$ is between $10^{-3}$ and $10^3$ or between $10^{-2}$ and $10^2$ or between $10^{-1}$ and 10.

In some cases, $t_2$ in the presence of nanoparticles is $t_2$ measured in the presence of more than 0, $10^{-20}$, $10^{-5}$, $10^{-3}$, $10^{-1}$, 0, 1, 5, 10 or $10^3$ mg of nanoparticles per $cm^3$ of body part, also designated as $t_{21}$.

In some other cases, $t_2$ in the absence of nanoparticles is $t_2$ measured in the presence of less than $10^{20}$, $10^{10}$, $10^5$, 100, 10, 5, 2, 1, 0, $10^{-3}$ or $10^{-6}$ mg of nanoparticles per $cm^3$ of body part, also designated as $t_{22}$.

In some cases, $t_{21}$ is at least 0, 0.5, 1, 1.1, 1.2, 1.5, 2, 5, 10, $10^2$, $10^3$ or $10^5$ longer than $t_{22}$ or $t_{21}/t_{22}$ is larger than 1, 1.1, 1.5, 2, 5, 10 or $10^3$.

The invention also relates to the cryo-system for use according to the invention, wherein $t_1$ and $t_2$ are characterized by at least one property selected from the group consisting of:
i) $t_1$ is smaller than $10^{20}$, $10^9$, $10^6$, $10^3$, 1, 0.1, $10^{-2}$ or $10^{-3}$ seconds,
ii) $t_2$ is smaller than $10^{20}$, $10^9$, $10^6$, $10^3$, 1, 0.1, $10^{-2}$ or $10^{-3}$ seconds, and
iii) $t_2-t_1$ is smaller than $10^{20}$, $10^9$, $10^6$, $10^3$, 1, 0.1, $10^{-2}$ or $10^{-3}$ seconds.

In some cases, the cooling time $t_1$ is the duration of the cooling step.

In some cases, the warming time $t_2$ is the duration of the warming step.

In some cases, $t_0$, $t_0'$, $t_1$, $t_2$ and/or $t_3$ is/are shorter than $10^{50}$, $10^{20}$, $10^{10}$, $10^5$, $10^3$, $10^2$, 50, 20, 10, 5, 2, 1 or $10^{-3}$ second(s).

In some other cases, $t_0$, $t_0'$, $t_1$, $t_2$ and/or $t_3$ are longer than $10^{-50}$, $10^{-10}$, $10^{-5}$, $10^{-3}$, $10^{-1}$, 0, 1, 5, 10, $10^3$ or $10^5$ second(s).

In one aspect, the invention also relates to nanoparticle or cryo-system for use according to the invention, wherein:
i) Preferentially in step d) the warming time to reach the final or maximum temperature from the cooling or maintaining or maintaining temperature is increased with increasing nanoparticle concentration in the body part, and/or
ii) preferentially in step b) the cooling time to reach the cooling or minimum temperature from the initial or maintaining or maximum temperature is not predominantly dependent on nanoparticle concentration in the body part.

In another embodiment of the invention, the time to reach the final or maximum temperature from either the initial or cooling or maintaining or minimum temperature increases or is increased, preferentially by a factor of at least 0, 0.5, 1, 1.1, 2, 5, 10, $10^3$ or $10^5$, when the nanoparticle concentration in the body part is increased, preferentially by a factor of at least 0, 0.5, 1, 1.1, 2, 5, 10, $10^3$ or $10^5$.

In the experimental example, when PC3-Luc cells, which are prostate tumor cells, in the presence (or not) of 1 mg/mL of N-CMD are cooled down from RT (room temperature) to a cooling temperature of 10° C. or 0° C. and let warming up from 10° C. or 0° C. to RT, the duration of the warming step increases: i) for the cooling temperature of 0° C., from 311 seconds without N-CMD to 461 seconds with 1 mg/mL of N-CMD, ii) for the cooling temperature of 10° C., from 256 seconds without N-CMD to 393 seconds with 1 mg/mL of N-CMD. In some embodiment, the difference between the warming time of the cells with N-CMD and the warming time of the cells without N-CMD can be increased when the nanoparticle concentration is increased, the cooling temperature is decreased, and/or the final temperature is increased.

In some embodiment, the difference between the warming time of the cells with N-CMD and the warming time of the cells without N-CMD can be decreased when the nanoparticle concentration is decreased, the cooling temperature is increased, and/or the final temperature is decreased.

In another embodiment of the invention, the cooling time to reach the cooling or maintaining or minimum temperature from the initial or maximum temperature is not predominantly dependent on nanoparticle concentration in the body part. In some embodiment, when the nanoparticle concentration in the body part increases, preferentially by a factor of at least 0, 0.5, 1, 1.1, 1.5, 2, 5, 10 or $10^3$, or preferentially from less than $10^{10}$, $10^5$, $10^3$, 10, 5, 2 or 1 mg of nanoparticles per $cm^3$ of body part to more than $10^{-10}$, $10^{-5}$, $10^{-3}$, $10^{-1}$, 1, 5, 10, 100 or 500 mg of nanoparticles per $cm^3$ of body part, the cooling time varies by less 100, 50, 20, 10, 5, 2 or 1%. This can be the case when the temperature adjuster or cryo-probe is used during the cooling step to cool the body part.

In the experimental example, when PC3-Luc cells in the presence (or not) of 1 mg/mL of N-CMD are cooled down from RT (room temperature) to a cooling temperature of 10° C. or 0° C. and let warming up from 10° C. or 0° C. to RT, the duration of the cooling step remains similar for the cooling temperature of 0° C. and 10° C. with/without N-CMD at 25-45 seconds. The difference between 25 and 45 seconds can be due to the conditions of use of the temperature adjuster (URGO).

In one aspect, the invention relates to nanoparticle(s) or cryo-system for use according to the invention, wherein in step b) the temperature decreases from the initial or maintaining or maximum temperature to the cooling or minimum temperature in the cooling step according to at least one of:

i) a cooling rate in the range from $10^{-6\circ}$ C./sec to $10^{6\circ}$ C./sec, preferably $10^{-3\circ}$ C./sec to $10^{3\circ}$ C./sec, ii) a cooling rate with the nanoparticle(s) that differs by less than 10° C./sec from the cooling rate without the nanoparticles, iii) a cooling rate that does vary with varying nanoparticle concentration or vary by a factor in the range of less than $10^{-6\circ}$ C./sec to $10^{6\circ}$ C./sec, preferably less than $10^{-3\circ}$ C./sec to $10^{3\circ}$ C./sec, when the nanoparticle concentration increases, preferably either by a factor of at least 1.1 or from a concentration lower than 100 μg of nanoparticles per cm³ of body part to a concentration larger than 100 μg of nanoparticles per cm³ of body part, iv) a cooling time of between $10^{-6}$ and $10^{6}$ seconds, preferably of between $10^{-3}$ and $10^{3}$ seconds, v) a cooling rate that is smaller than the rate of increasing the temperature in the warming step d) by a factor in the range from $10^{-10}$ to $10^{5}$, preferably $10^{-5}$ to $10^{3}$, and vi) a cooling time shorter than the warming time in the warming step d) by a factor in the range of $10^{-6}$ to $10^{6}$, preferably $10^{-3}$ to $10^{3}$.

In one embodiment of the invention, the temperature, preferentially of the body part, is decreased or decreases from the initial or maximum temperature down to the cooling or minimum temperature or from the initial or maximum temperature to the maintaining temperature or from the maintaining temperature to the cooling or minimum temperature, preferentially in or during the cooling step, preferentially at a rate designated as the rate of temperature decrease or cooling rate.

In still another embodiment of the invention, the cooling rate is larger than $10^{-20}$, $10^{-10}$, $10^{-5}$, $10^{-3}$, $10^{-1}$, 1, 5, 10, $10^{3}$ or $10^{5\circ}$ C. (degree Celsius) per second or ° C. per minute, preferentially per cm³ of body part, preferentially per mg of nanoparticle.

In still another embodiment of the invention, the cooling rate is smaller than $10^{100}$, $10^{50}$, $10^{10}$, $10^{5}$, $10^{3}$, 10, 5, 2, 1, $10^{-1}$, $10^{-5}$ or $10^{-10\circ}$ C. per second or ° C. per minute, preferentially per cm³ of body part, preferentially per mg of nanoparticles.

In still another embodiment of the invention, the cooling rate is between $10^{-100}$ and $10^{100}$, $10^{-50}$ and $10^{20}$, $10^{-1}$ and $10^{5}$, or between 1 and 100° C. per second or ° C. per minute, preferentially per cm³ of body part, preferentially per mg of nanoparticles.

In the experimental example, when PC3-Luc cells in the presence (or not) of 1 mg/mL of N-CMD are cooled down from RT (room temperature) to a cooling temperature of 10° C. or 0° C. and let warming up from 10° C. or 0° C. to RT, the cooling rate is relatively similar for the cooling temperature of 0° C. and 10° C., with/without N-CMD, at 0.6 to 1° C./sec. The difference between 0.6° C./sec and 1° C./sec can be due to the conditions of use of the temperature adjuster (URGO). In some embodiment, the cooling rate can be larger if/when the temperature adjuster enables reaching the cooling temperature faster.

In some other embodiment, the cooling rate can be lower if/when the temperature adjuster enables reaching the cooling or minimum temperature more slowly.

In still another embodiment of the invention, the cooling rate is lower by a factor of at least 0, 1, 1.001, 1.1, 1.5, 2, 5 or 10, in the presence than in the absence of ice-ball(s).

In still another embodiment of the invention, the cooling rate is larger by a factor of at least 0, 1, 1.001, 1.1, 1.5, 2, 5 or 10, in the presence than in the absence of ice-ball(s).

In still another embodiment of the invention, the cooling rate is lower, preferentially by a factor of at least 0, 1, 1.001, 1.1, 1.5, 2, 5 or 10, in the presence than in the absence of nanoparticles.

In still another embodiment of the invention, the cooling rate is larger, preferentially by a factor of at least 0, 1, 1.001, 1.1, 1.5, 2, 5 or 10, in the presence than in the absence of nanoparticles.

In still another embodiment of the invention, the cooling rate is similar in the presence and absence of nanoparticles.

In still another embodiment of the invention, the cooling rate of the body part with nanoparticles differs by less than $10^{100}$, $10^{50}$, $10^{3}$, 10, $10^{-1}$, $10^{-3\circ}$ C./sec from the cooling rate of the body part without the nanoparticles.

In still another embodiment of the invention, the cooling rate of the body part with nanoparticles differs by more than $10^{-100}$, $10^{-50}$, $10^{-3}$, $10^{-1}$, 1, 10 or $10^{3\circ}$ C./sec from the cooling rate of the body part without the nanoparticles.

In still another embodiment of the invention, the cooling rate of the body part comprising the nanoparticle(s) varies by less than $10^{20}$, $10^{10}$, $10^{5}$, 10, 5, 2, 1, $10^{-3}$ or $10^{-5\circ}$ C./sec. when the nanoparticle concentration increases by a factor of at least 0, 0.5, 1, 1.1, 2, 5, 10 or $10^{3}$, or when the nanoparticle concentration increases from a concentration lower than $10^{3}$, $10^{2}$, 10, 1, $10^{-1}$, $10^{-3}$, $10^{-6}$ or $10^{-9}$ mg of nanoparticle per cm³ of body part to a concentration larger than $10^{-9}$, $10^{-6}$, $10^{-3}$, $10^{-1}$, 1 or 10 mg of nanoparticles per cm³ of body part.

In one embodiment of the invention, the temperature of the body part is decreased or decreases preferentially from the initial or maintaining or maximum temperature to the cooling or minimum temperature in or during the cooling step within a lapse of time designated as the duration of temperature decrease or cooling time.

In still another embodiment of the invention, the cooling time is longer than $10^{-100}$, $10^{-50}$, $10^{-10}$, $10^{-5}$, $10^{-3}$, $10^{-1}$, 1, 5, 10 or $10^{2}$ second(s).

In still another embodiment of the invention, the cooling time is shorter than $10^{100}$, $10^{50}$, $10^{10}$, $10^{5}$, $10^{3}$, 10, 5, 2, 1, $10^{-1}$ or $10^{-2}$ second(s).

In still another embodiment of the invention, the cooling time is between $10^{-100}$ and $10^{100}$, between $10^{-50}$ and $10^{50}$, between $10^{-10}$ and $10^{10}$, between $10^{-5}$ and $10^{5}$, between $10^{-3}$ and $10^{3}$, or between $10^{-3}$ and 10 seconds.

In one embodiment of the invention, the temperature is increased or increases from the cooling or minimum temperature to the final or maximum temperature or from the cooling or maintaining temperature to the maintaining temperature or from the maintaining temperature to the final or maximum temperature, preferentially in or during the warming step, at a rate designated as the rate of temperature increase or warming rate.

In one embodiment of the invention, the cooling rate is smaller than the warming rate, preferentially by: i) a factor of at least $10^{-50}$, $10^{-10}$, 0, 0.5, 1, 1.1, 1.5, 2, 5, 10, $10^{3}$ or $10^{5}$ or ii) more than $10^{-50}$, $10^{-10}$, $10^{-5}$, $10^{-1}$, 0, 0.5, 1, 1.1, 1.5, 2, 5, 10, $10^{3}$ or $10^{5\circ}$ C./sec.

In one embodiment of the invention, the cooling rate is smaller than the warming rate, preferentially by: i) a factor of less than $10^{10}$, $10^{5}$, 10, 5, 2, 1, 1.1, 1, 0.5, 0, $10^{-3}$ or $10^{-10}$ or ii) less than $10^{50}$, $10^{10}$, $10^{5}$, 10, 5, 2, 1.1, 1, 0.5, 0, $10^{-3}$ or $10^{-5\circ}$ C./sec.

In one embodiment of the invention, the cooling rate is smaller than the warming rate, preferentially by: i) a factor of between $10^{-100}$ and $10^{100}$, $10^{-10}$ and $10^{10}$, $10^{-5}$ and $10^{5}$, $10^{-3}$ and $10^{3}$, or between $10^{-1}$ and 10, or ii) between $10^{-100}$ and $10^{100}$, $10^{-10}$ and $10^{10}$, $10^{-5}$ and $10^{5}$, $10^{-3}$ and $10^{3}$, or between $10^{-1}$ and 10° C./sec.

In the experimental example, when PC3-Luc cells in the presence (or not) of 1 mg/mL of N-CMD are cooled down from RT (room temperature) to a cooling temperature of 10° C. or 0° C. and let warming up from 10° C. or 0° C. to RT, the rate of temperature increase or warming rate, RTI, is between 0.05 and 0.08° C./sec while the rate of temperature decrease or cooling rate, RTD, is between 0.6 and 1° C./sec. Therefore, the ratio RTD/RTI is between 7.5 and 20.

Smaller or larger values of this ratio may also be obtained by using other experimental conditions (different temperature adjuster, nanoparticle type or concentration, or another cell type).

In one embodiment of the invention, the temperature is increased or increases from the cooling or minimum temperature to the final or maximum temperature, preferentially in or during the warming step, within a lapse of time designated as the duration of the warming step or warming time.

In one embodiment of the invention, the cooling time is shorter than the warming time, preferentially by: i) a factor of at least $10^{-5\circ}$, $10^{-10}$, 0, 0.5, 1, 1.1, 1.5, 2, 5, 10, $10^3$ or $10^5$ or ii) more than $10^{-50}$, $10^{-10}$, 10–5, $10^{-1}$, 0, 0.5, 1, 1.1, 1.5, 2, 5, 10, $10^3$ or $10^5$ sec.

In one embodiment of the invention, the cooling time is shorter than the warming time, preferentially by: i) a factor of less than $10^{10}$, $10^5$, 10, 5, 2, 1, 1.1, 1, 0.5, 0, $10^{-3}$ or $10^{-10}$ or ii) less than $10^{50}$, $10^{10}$, $10^5$, 10, 5, 2, 1.1, 1, 0.5, 0, $10^{-3}$ or $10^{-5}$ sec.

In one embodiment of the invention, the cooling time is shorter than the warming time, preferentially by: i) a factor of between $10^{-100}$ and $10^{100}$, $10^{-10}$ and $10^{10}$, $10^{-5}$ and $10^5$, $10^{-3}$ and $10^3$, or between $10^{-1}$ and 10, or ii) between $10^{-100}$ and $10^{100}$, $10^{-10}$ and $10^{10}$, $10^{-5}$ and $10^5$, $10^{-3}$ and $10^3$, or between $10^{-1}$ and 10 sec.

In the experimental example, when PC3-Luc cells in the presence (or not) of 1 mg/mL of N-CMD are cooled down from RT (room temperature) to a cooling temperature of 10° C. or 0° C. and let warming up from 10° C. or 0° C. to RT, the time of temperature increase, $t_{TI}$, is between 256 and 469 seconds while the time of temperature decrease, $t_{TD}$, is between 12 and 46 sec. Therefore, the ratio $t_{TI}/t_{TD}$ is between 6 and 39.

In some embodiment, smaller values of the ratio $t_{TI}/t_{TD}$ and/or $R_{TD}/R_{TI}$ is/are reached when the temperature adjuster or cryo-probe cools down the body part at a slower rate and/or when the warming step is carried out in the presence of a larger quantity of nanoparticle, of radiation, or of a medium than enables to increase the rate of temperature increase in the warming step.

In some embodiment, larger values of the ratio $t_{TI}/t_{TD}$ and/or $R_{TD}/R_{TI}$ is/are reached when the temperature adjuster or cryo-probe cools down the body part at a faster rate and/or when the warming step is carried out in the presence of a lower quantity of nanoparticle, of radiation, or of a medium that enables to decrease the rate of temperature increase in the warming step.

In still another embodiment of the invention, the cooling time is shorter by a factor of at least 0, 0.5, 1, 1.001, 1.1, 1.5, 2, 5 or 10, in the presence than in the absence of ice-ball(s).

In still another embodiment of the invention, the cooling time is larger by a factor of at least 0, 0.5, 1, 1.001, 1.1, 1.5, 2, 5 or 10, in the presence than in the absence of ice-ball(s).

In one aspect, the invention relates to nanoparticles or cryo-system for use according to the invention, wherein the maintaining step is carried out according to at least one of:

i) a maintaining time that is shorter than the cooling time and/or warming time, preferably by a factor of at least 1.5, more preferably by a factor of at least 10, and ii) fluctuation of the temperature during the maintaining step c) that is smaller, preferably by a factor of at least 1.5, than $\Delta T_1$ and/or $\Delta T_2$ according to the invention.

In one embodiment of the invention, the step of maintaining the body part comprising the nanoparticles at the cooling temperature, preferentially for a duration of time of more than $10^{50}$, $10^{20}$, $10^3$, $10^2$, 10, 5, 2, 1, $10^{-1}$ or $10^{-3}$ seconds is designated as the maintaining step.

In one embodiment of the invention, the temperature is maintained at the maintaining or cooling temperature, preferentially in or during the maintaining step, within a lapse of time designated as the duration of the maintaining step or maintaining time.

In one embodiment of the invention, the maintaining time is shorter than $10^{20}$, $10^{10}$, $10^5$, $10^3$, 10, 5, 2, 1, 0, $10^{-1}$, $10^{-3}$ or $10^{-6}$ second(s).

In another embodiment of the invention, the maintaining time is longer than $10^{-50}$, $10^{-20}$, $10^{-6}$, $10^{-3}$, $10^{-1}$, 0, 1, 2, 5, 10, $10^3$, $10^5$ or $10^{10}$ second(s).

In still another embodiment of the invention, the maintaining time is between $10^{-5\circ}$ and $10^{50}$, $10^{-10}$ and $10^{10}$, $10^{-5}$ and $10^5$, $10^{-3}$ and $10^3$, or between $10^{-1}$ and $10^3$ seconds.

In the experimental example, the duration of the maintaining steps is less than 1 second for the short cycles and longer than 1 second for the long cycles. The maintaining time can be decreased by starting the warming step quicker after the cooling step. The maintaining time can be longer by using a temperature adjuster or cryo-probe that enables maintaining the temperature at the cooling temperature for a longer period of time.

In still another embodiment of the invention, the maintaining time is at least 0, 1, 1.001, 1.1, 2, 3, 5, 10, 15, 20, 50, $10^2$, $10^3$, $10^5$ or $10^{10}$ longer than the cooling time and/or than the warming time. In some cases, the duration of the maintaining step can be long when the temperature is maintained at the minimum or cooling temperature for a long period of time, notably when an equipment or cryo-probe is used to maintain the temperature of the body part at the minimum temperature for a long period of time.

In still another embodiment of the invention, it can be useful to maintain the temperature at the cooling temperature during a certain time, preferentially to be in similar conditions as a usual cryotherapy treatment that would be improved in terms of efficacy and/or reduction of side effects by the presence of nanoparticles.

In still another embodiment of the invention, the duration of the maintaining step is at least 0, 1, 1.001, 1.1, 2, 3, 5, 10, 15, 20, 50, $10^2$, $10^3$, $10^5$ or $10^{10}$ shorter than the duration of the cooling step and/or than the duration of the warming step. In some embodiment, the duration of the maintaining step can be short when the temperature is not maintained at the minimum or maintaining or cooling temperature for a long period of time, notably when an equipment or cryo-probe is not used to maintain the temperature at the minimum temperature for a long period of time. This method can be used when one desires making an important number of cycles, which can be more efficient than maintaining the temperature at the cooling or maintaining temperature. This method can also be easy to implement since it does not necessitate to measure the temperature during the treatment, but just to know the times or durations of the cooling and/or warming step(s).

In still another embodiment of the invention, the maintaining step is a step in or during which the temperature of the body part is maintained at the cooling or maintaining temperature, where the cooling or maintaining temperature is preferentially the temperature of the body part reached during the maintaining step.

In some other embodiment, the fluctuation of temperature in or during the maintaining step, preferentially designated as maintaining step temperature fluctuation, is estimated by the absolute value of $(T_{cool}-T_{min})/T_{min}$, $(T_{BP}-T_{min})/T_{min}$, $T_{BP}/T_{min}$, $T_{cool}/T_{min}$, $(T_M-T_{min})/T_{min}$ or $T_M/T_{min}$ where $T_{BP}$, $T_{cool}$, $T_M$ and $T_{min}$ are the temperature of the body part, the cooling temperature, the maintaining temperature and the minimum temperature, preferentially of or reached during the maintaining step.

In still some other embodiment, the fluctuation of the maintaining temperature is smaller than $10^{100}$, $10^{50}$, $10^{10}$, $10^5$, $10^3$, $10^2$, 50, 10, 5, 2, 1, 0.5, 0, $10^{-1}$, $10^{-3}$, $10^{-5}$ or $10^{-10}$%. In still some other embodiment, the fluctuation of the maintaining temperature is larger than $10^{-100}$, $10^{-50}$, $10^{-10}$, $10^{-5}$, $10^{-3}$, $10^{-1}$, 0, 1, 5, 10, $10^3$ or $10^5$%.

In still some other embodiment, the fluctuation of the maintaining temperature lies within the range from $10^{-20}$% to $10^{20}$%, $10^{-5}$% and $10^5$%, $10^{-3}$% to $10^3$%, or from $10^{-1}$% and 10%.

In some other embodiment, the fluctuation of the maintaining temperature is small or is smaller, preferentially by a factor of at least 0, 0.1, 0.5, 1, 1.1, 1.5, 2, 5, 10, $10^2$, $10^3$ or $10^5$, than the temperature gradient(s) of the cooling step and/or of the warming step, $\Delta T_1$ and/or $\Delta T_2$.

In the experimental examples, the temperature variation of the maintaining step is typically between 0° C. and 1° C. while the temperature variation of the cooling and/or warming step(s) is typically between 15 and 65° C.

In one aspect, the invention relates to nanoparticles or cryo-system for use according to the invention, wherein preferentially in step d) or warming step the temperature increases from the cooling temperature to the final temperature or from the cooling temperature to the maintaining temperature or from the maintaining temperature to the final temperature according to at least one of:
  i) a warming rate in the range of $10^{-6}$° C./sec to $10^{6}$° C./sec, preferably in the range of $10^{-3}$° C./sec to $10^{3}$° C./sec,
  ii) a warming rate with the nanoparticle(s) that differs or is larger by a factor of more than $10^{-3}$° C. from the warming rate without the nanoparticle(s),
  iii) a warming rate that is smaller than the cooling rate by a factor in the range from $10^{-10}$ to $10^5$, preferably $10^{-5}$ to $10^3$,
  iv) a warming time of between $10^{-6}$ and $10^6$ seconds, preferably of between $10^{-3}$ and $10^3$ seconds, and
  vi) a warming time longer than the cooling time by a factor in the range of $10^{-6}$ to $10^6$, preferably a factor in the range $10^{-3}$ to $10^3$.

In one embodiment of the invention, the temperature, preferentially of the body part, is increased or increases from the cooling or minimum temperature up to the final or maximum temperature or from the cooling or minimum temperature to the maintaining temperature or from the maintaining temperature to the final or maximum temperature, preferentially in or during the warming step, at a rate designated as the rate of temperature increase or warming rate.

In still another embodiment of the invention, the warming rate is larger than $10^{-20}$, $10^{-10}$, $10^{-5}$, $10^{-3}$, $10^{-1}$, 1, 5, 10, $10^3$ or $10^5$° C. (degree Celsius) per second or ° C. per minute, preferentially per cm$^3$ of body part, preferentially per mg of nanoparticle.

In still another embodiment of the invention, the warming rate is smaller than $10^{100}$, $10^{50}$, $10^{10}$, $10^5$, $10^3$, 10, 5, 2, 1, $10^{-1}$, $10^{-5}$ or $10^{-10}$° C. per second or ° C. per minute, preferentially per cm$^3$ of body part, preferentially per mg of nanoparticles.

In still another embodiment of the invention, the warming rate is between $10^{-100}$ and $10^{100}$, $10^{-50}$ and $10^{20}$, $10^{-3}$ and $10^3$, $10^{-1}$ and $10^5$, or between 1 and 100° C. per second or ° C. per minute, preferentially per cm$^3$ of body part, preferentially per mg of nanoparticles.

In still another embodiment of the invention, the warming rate is lower by a factor of at least 1.001, 1.1, 1.5, 2, 5 or 10, in the presence than in the absence of ice-ball(s).

In still another embodiment of the invention, the warming rate is larger by a factor of at least 1.001, 1.1, 1.5, 2, 5 or 10, in the presence than in the absence of ice-ball(s).

In still another embodiment of the invention, the warming rate is lower, preferably by a factor of at least 0, 1, 1.001, 1.1, 1.5, 2, 5 or 10, in the presence than in the absence of nanoparticles. In some cases, the presence of the nanoparticles in the body part can decrease the rate at which the temperature increases in the warming step, for example when nanoparticles capture or absorb the heat of the body part, preferentially without releasing it, or when nanoparticles act as isolating material.

In still another embodiment of the invention, the warming rate is larger, preferably by a factor of at least 0, 1, 1.001, 1.1, 1.5, 2, 5 or 10, in the presence than in the absence of nanoparticles. In some cases, the presence of the nanoparticles in the body part can increase the rate at which the temperature increases in the warming step, for example when the nanoparticles release heat during the warming step.

In still another embodiment of the invention, the warming rate is similar in the presence and absence of nanoparticles.

In still another embodiment of the invention, the rate of temperature increase of the body part with nanoparticles differs by less than $10^{100}$, $10^{50}$, $10^3$, 10, $10^{-1}$, or $10^{-3}$° C./sec from the rate at which the temperature of the body part without the nanoparticles increases from the cooling temperature to the final temperature.

In still another embodiment of the invention, the rate of temperature increase of the body part with nanoparticles differs by more than $10^{-100}$, $10^{-50}$, 10-3, $10^{-1}$, 1, 10 or $10^3$° C./sec from the rate at which the temperature of the body part without the nanoparticles increases from the cooling temperature to the final temperature.

In still another embodiment of the invention, the rate of temperature increase of the body part comprising the nanoparticle varies by more than $10^{20}$, $10^{10}$, $10^5$, 10, 5, 2, 1, $10^{-3}$ or $10^{-5}$° C./sec. when the nanoparticle concentration increases by a factor of at least 0, 0.5, 1, 1.1, 2, 5, 10 or $10^3$ or when the nanoparticle concentration increases from a concentration lower than $10^3$, $10^2$, 10, 1, $10^{-1}$, $10^{-3}$, $10^{-6}$ or $10^{-9}$ mg of nanoparticle per cm$^3$ of body part to a concentration larger than $10^{-9}$, $10^{-6}$, $10^{-3}$, $10^{-1}$, 1 or 10 mg of nanoparticles per cm$^3$ of body part.

In one embodiment of the invention, the temperature of the body part is increased or increases from the cooling or minimum temperature to the final or maximum temperature or from the cooling or minimum temperature to the maintaining temperature or from the maintaining temperature to the final or maximum temperature in or during the warming step within a lapse of time designated as the duration of temperature increase or warming time.

In still another embodiment of the invention, the warming time is longer than $10^{-100}$, $10^{-50}$, $10^{-10}$, $10^{-5}$, $10^{-3}$, $10^{-1}$, 1, 5, 10 or $10^2$ seconds.

In still another embodiment of the invention, the warming time is shorter than $10^{100}$, $10^{50}$, $10^{10}$, $10^5$, $10^3$, 10, 5, 2, 1, $10^{-1}$ or $10^{-2}$ seconds.

In still another embodiment of the invention, the warming time is between $10^{-100}$ and $10^{100}$, between $10^{-50}$ and $10^{50}$, between $10^{-10}$ and $10^{10}$, between $10^{-5}$ and $10^5$, between $10^{-3}$ and $10^3$, or between $10^{-3}$ and 10 seconds.

Experimentally, the parameters of the different treatments (initial, cooling, final temperatures as well as duration and rate of temperature decrease and temperature increase) are summarized in tables 1 to 6 for 1, 3, 6 cycles during which PC3-Luc cells alone or PC3-Luc cells mixed with 1 mg of nanoparticles (N-MCD) are cooled down during the cooling step and let warming up during the warming step. The cooling temperatures are either just above 0° C. (>0° C.) or just below 0° C. (<0° C.). We observed that the rate of temperature increase is usually smaller in the presence than in the absence of nanoparticle. Hence, the presence of nanoparticles enables: i) extending the duration of the warming step and/or ii) decreasing the rate of temperature increase of the warming step.

In one embodiment, in the absence of the application of a radiation that can heat the nanoparticles, such as a laser, acoustic wave, magnetic field, preferentially alternating magnetic field, the rate of temperature increase of the warming step is smaller, preferentially by a factor of at least 0, 0.5, 1, 1.5, 2, 5, 10, $10^3$ or $10^5$, in the presence than in the absence of the nanoparticle.

In one embodiment, in the presence of the application of a radiation that can heat the nanoparticles, such as a laser, acoustic wave, magnetic field, preferentially alternating magnetic field, the rate of temperature increase of the warming step is larger, preferentially by a factor of at least 0, 0.5, 1, 1.5, 2, 5, 10, $10^3$ or $10^5$, in the presence than in the absence of the nanoparticle.

In one embodiment of the invention, the warming rate is smaller than the cooling rate, preferentially by: i) a factor of at least $10^{-50}$, $10^{-10}$, 0, 0.5, 1, 1.1, 1.5, 2, 5, 10, $10^3$ or $10^5$ or ii) more than $10^{-50}$, $10^{-10}$, $10^{-5}$, $10^{-1}$, 0, 0.5, 1, 1.1, 1.5, 2, 5, 10, $10^3$ or $10^5$ ° C./sec. This may occur when no radiation is applied during the warming step and/or a substance or equipment or cryo-probe is used during the cooling step to adjust the temperature during this step.

In one embodiment of the invention, the warming rate is smaller than the cooling rate, preferentially by: i) a factor of less than $10^{10}$, $10^5$, 10, 5, 2, 1, 1.1, 1, 0.5, 0, $10^{-3}$ or $10^{-10}$ or ii) less than $10^{50}$, $10^{10}$, $10^5$, 10, 5, 2, 1.1, 1, 0.5, 0, $10^{-3}$ or $10^{-5}$ ° C./sec. This may occur when radiation is applied during the warming step and/or no substance or no equipment or no cryo-probe is used during the cooling step to adjust the temperature during this step.

In one embodiment of the invention, the warming rate is smaller than the cooling rate, preferentially by: i) a factor of between $10^{-100}$ and $10^{100}$, $10^{-10}$ and $10^{10}$, $10^{-5}$ and $10^5$, $10^{-3}$ and $10^3$, or between $10^{-1}$ and 10, or ii) between $10^{-100}$ and $10^{100}$, $10^{-10}$ and $10^{10}$, $10^{-5}$ and $10^5$, $10^{-3}$ and $10^3$, or between $10^{-1}$ and 10° C./sec.

In one embodiment of the invention, the warming time is longer than the cooling time, preferentially by: i) a factor of at least $10^{-5}$, $10^{-10}$, 0, 0.5, 1, 1.1, 1.5, 2, 5, 10, $10^3$ or $10^5$ or ii) more than $10^{-5}$, $10^{-10}$, $10^{-5}$, $10^{-1}$, 0, 0.5, 1, 1.1, 1.5, 2, 5, 10, $10^3$ or $10^5$ sec.

In one embodiment of the invention, the warming time is longer than the cooling time, preferentially by: i) a factor of less than $10^{10}$, $10^5$, 10, 5, 2, 1, 1.1, 1, 0.5, 0, $10^{-3}$ or $10^{-10}$ or ii) less than $10^{50}$, $10^{10}$, $10^5$, 10, 5, 2, 1.1, 1, 0.5, 0, $10^{-3}$ or $10^{-5}$ sec.

In one embodiment of the invention, the warming time is longer than the cooling time, preferentially by: i) a factor of between $10^{-100}$ and $10^{100}$, $10^{-10}$ and $10^{10}$, $10^{-5}$ and $10^5$, $10^{-3}$ and $10^3$, or between $10^{-1}$ and 10, or ii) between $10^{-100}$ and $10^{110}$, $10^{-10}$ and $10^{10}$, $10^{-5}$ and $10^5$, $10^{-3}$ and $10^3$, or between $10^{-1}$ and 10 sec.

In still another embodiment of the invention, the warming time is shorter by a factor of at least 0, 1, 1.001, 1.1, 1.5, 2, 5 or 10, in the presence than in the absence of ice-ball(s).

In still another embodiment of the invention, the warming time is larger by a factor of at least 0, 1, 1.001, 1.1, 1.5, 2, 5 or 10, in the presence than in the absence of ice-ball(s).

In one aspect, the invention relates to nanoparticle or cryo-system for use according to the invention, wherein the temperature is preferentially controlled or adjusted during the cooling step b) and/or the maintaining step c), whereas the temperature is preferentially not controlled or not adjusted during the warming step d), preferably wherein the temperature control or adjustment is preferentially carried out using an equipment or a substance or the temperature adjuster or the cryo-probe.

In some embodiment, the equipment or substance or cryo-probe used to adjust the temperature or temperature variation or temperature fluctuation or temperature gradient, preferentially designated as temperature adjuster or cryo-probe, does not belong to the living organism, body part, or their environment, preferentially before or without the treatment. In some cases, it is different from blood, or ambient air or tissue or organ or body part or cell.

In some embodiment, the temperature adjuster or cryo-probe is an equipment used during cryotherapy or cryosurgery such as a cryosurgery unit, more specifically a gynecological or oncological or medical or dermatology or neurosurgery cryosurgery unit.

In some embodiment, the temperature adjuster or cryo-probe or part of the cryo-probe is selected from the group consisting of: i) freezing liquid, ii), cryogenic gas, iii), $NO_2$ gas, iv), nitrous oxide gas, v), liquid nitrogen, and vi), dimethyl-ether gas.

In some embodiment, the temperature adjuster or cryo-probe is a liquid, a gas, or a solid.

In some embodiment, the temperature adjuster or cryo-probe is a metal, a rod, preferentially a metal rod or a piece of metal, preferentially connected to a unit that controls the heat of the rod or metal.

In some embodiment, the temperature adjuster or cryo-probe is an equipment that produces or generates radiation, preferentially a radiation that generates heat, such as electromagnetic radiation, light or laser radiation, a magnetic field, preferentially an alternating magnetic field, an acoustic wave, preferentially an ultrasound, or radiofrequency.

In some embodiment, the temperature adjuster or cryo-probe is not an equipment that produces or generates radiation.

In some embodiment of the invention, the temperature adjuster or cryo-probe maintains the temperature: i), in some embodiment below $10^{10}$, $10^5$, $10^3$, $10^2$, 10, 5, 2, 1, 0, −10, −20, −50, −100, −150 or −200° C., ii) in some other embodiment above −200, −150, −100, −50, −20, −10, 0, 2, 5, 10, 20, 50, $10^2$ or $10^3$ ° C., iii) in still some other embodiment between −200 and $10^3$, −100 and $10^3$, −50 and 100, or between −10 and 100° C. (degree Celsius). In some embodiment, the temperature is the temperature of the body part in thermal equilibrium with the temperature adjuster or cryo-probe, preferentially during at least one step of the method. In some other embodiment, the temperature is the temperature of the temperature adjuster or cryo-probe before it enters into contact with or diffuses heat towards the body part.

In one embodiment of the invention, when the temperature adjuster or cryo-probe is used during at least one step of the method, the initial, cooling, and/or final temperature(s) of treatment is/are reached, while when no temperature adjuster or no cryo-probe is used during at least one step of the method, the initial, cooling, and/or final temperature(s) of the treatment is/are not reached.

In one embodiment of the invention, the temperature adjuster or cryo-probe adjusts the temperature of the body part, preferentially comprising the nanoparticles, without modifying the temperature of the remaining part of the living organism, which does not comprise the body part, preferentially without modifying the temperature of the remaining part of the living organism which does not comprise the body part by more than $10^{-5°}$, $10^{-10}$, $10^{-3}$, $10^{-1}$, 1, 5, 10 or $10^{3°}$ C.

In one embodiment of the invention, the method uses or comprises an equipment or substance or cryo-probe that measures the temperature or the production of ROS or NOS or the release of at least one compound from the nanoparticle, preferentially designated as the sensor. In some embodiment, the sensor can be a thermometer, a thermocouple, an infrared camera. In some other embodiment, the sensor can be a fluorescent probe. The sensor can be used to adjust the temperature or quantity of ROS or NOS produced by the nanoparticles or to control the release of at least one compound from the nanoparticles, preferentially to specific values that are desired or targeted, preferentially values that yield an efficient treatment and/or minimal side effects and/or maximal benefit to risk ratio of the treatment.

In one embodiment of the invention, the method uses or comprises an equipment or substance or cryo-probe that images nanoparticle in the body part and/or that images the body part. Such equipment or substance or cryo-probe, also designated as imaging equipment, can be MRI (magnetic resonance imaging), a scanner, CT scanner, PET (positron emission tomography), biopsy, fluorescence, luminescence, absorption, histology, microscopy, transmission or scanning electron microscopy, X-ray, electron, neutron, particle, elemental particle, light diffusion or diffraction or scattering.

In one aspect, the invention also relates to the method or cryo-system according to the invention, wherein temperature is controlled during at least one of the cooling step, the maintaining step, and the warming step without using the temperature adjuster or cryo-probe.

In one embodiment of the invention, the cooling step occurs without using the temperature adjuster or cryo-probe to cool down the body part, for example when the living organism is entering a state of hypothermia that decreases the temperature of the body part.

In one embodiment of the invention, the warming step occurs without using the temperature adjuster or cryo-probe to warm up the body part, for example when the body part is left to warm up by being in contact with air or blood circulation without the need of using a temperature adjuster or cryo-probe that does not belong to the organism or body part.

In one aspect, the invention relates to nanoparticles or cryo-system for use according to the invention, wherein at least one of the cooling step, the maintaining step, and the warming step is carried out in the presence of:

i) a percentage of nanoparticles internalized in cells of the body part that is in a range from $10^{-10}$ to 90%, $10^{-3}$% to 90% or from $10^{-10}$ and 50 or from $10^{-5}$ and 20%, where this percentage is preferentially the ratio between the number or quantity of nanoparticles internalized in cells of the body part and the total number or quantity of nanoparticles comprised in the body part, and/or ii) a concentration of nanoparticles in the body part in the range from $10^{-9}$, $10^{-5}$, $10^{-3}$, 1 or 5 mg of nanoparticles per $cm^3$ of body part to $10^{-3}$, $10^{-1}$, 1, 5, 10, $10^3$, $10^6$ or $10^9$ mg of nanoparticles per $cm^3$ of body part or from $10^{-10}$ $10^{-5}$, $10^{-3}$, $10^{-1}$, 1 or 10 to 1, 10, $10^3$, $10^6$ or $10^{10}$ pg of nanoparticles per cell preferentially comprised in or originating from the body part.

In another embodiment of the invention, the cooling region is the volume, surface or length that is cooled down to the cooling temperature.

In some embodiment, the nanoparticle region can be smaller by a factor of at least 0, 1, 1.01, 1.1, 1.2, 1.5, 2, 5, 10, $10^3$ or $10^5$ than the cooling region.

In some other embodiment, the nanoparticle region can be larger by a factor of at least 0, 1, 1.01, 1.1, 1.2, 1.5, 2, 5, 10, $10^3$ or $10^5$ than the cooling region.

In another embodiment of the invention, at least one step of the method is carried out in the presence of a percentage of nanoparticles internalized in cells of the body part, which is larger than $10^{-5°}$, $10^{-20}$, $10^{-10}$, $10^{-5}$, $10^{-1}$, 0, 1, 5, 10, 50, 75, 80, 90 or 99% In another embodiment of the invention, at least one step of the method is carried out in the presence of a percentage of nanoparticles internalized in cells of the body part, which is lower than 100, 99, 90, 70, 50, 20, 10, 5, 2, 1, 10-1, $10^{-5}$ or $10^{-10}$%.

In another embodiment of the invention, at least one step of the method is carried out in the presence of a percentage of nanoparticles internalized in cells of the body part, which is in a range from $10^{-5°}$ to 100%, from $10^{-10}$ to 99%, from $10^{-5}$ to 95%, from $10^{-3}$ to 90%, or from $10^{-1}$ to 70%.

In the experimental example number 2, the percentage of N-CMD internalized in PC3-Luc cells is measured for PC3-Luc cells incubated in the presence of N-CMD for different concentrations of N-CMD (0, 62, 250 and 1000 μg/mL of N-CMD) and different incubation times (5 min, 30 min, 3 h, 6 h, 24 h, 96 h), where the percentage of internalized N-CMD is the ratio between the quantity of nanoparticles or N-CMD inside cells and the quantity of nanoparticles or N-CMD incubated with PC3-Luc cells or in the body part. The percentage of internalized N-CMD varies from 6% to 26% (FIG. 1(b)). This percentage increases with increasing N-CMD concentration and with increasing incubation time (FIG. 1(b)). In some embodiment, larger values of this percentage can be obtained, preferentially larger by a factor of at least 0, 0.5, 1, 1.5, 2, 5, 10 or $10^3$, by increasing the nanoparticle concentration or the incubation time, preferentially by a factor of at least 0, 0.5, 1, 1.5, 2, 5, 10 or $10^3$, or by using a different cell type, and/or by carrying out the internalization in the presence of a radiation. In some other embodiment, lower values of this percentage can be obtained, preferentially lower by a factor of at least 0, 0.5, 1, 1.5, 2, 5, 10 or $10^3$, by decreasing the nanoparticle concentration or the incubation time, preferentially by a factor of at least 0, 0.5, 1, 1.5, 2, 5, 10 or $10^3$, or by using a different cell type.

In one aspect, the invention relates to nanoparticles or cryo-system for use according to the invention, wherein at least one of the cooling step, the maintaining step, and the warming step is carried out when nanoparticles occupy a portion of the body part, which is preferentially smaller than the biggest volume of the body part or whole body part or is or represents between $10^{-10}$, $10^{-5}$, $10^{-1}$% and 1, 10, 50, 70% or 90% by mass or volume of the body part as a whole.

In some cases, the body part as a whole or the biggest volume of the body part can be the sum of the portion of the body part comprising the nanoparticles, also designated as portion of the body part, and the portion of the body part not comprising the nanoparticles, also designated as other portion of the body part.

In one embodiment of the invention, the cooling step, maintaining step, and/or warming step is/are carried out on nanoparticles occupying a portion of the body part, which is smaller than 99.9, 90, 80, 70, 60, 50, 30, 20, 10, 5, 2 or 1% by mass or volume of the body part as a whole.

In one embodiment of the invention, the cooling step, maintaining step, and/or warming step is/are carried out on nanoparticles occupying a portion of the body part, which is larger than $10^{-10}$, $10^{-5}$, 1, 2, 5, 10, 20, 30, 50, 60, 70, 80, 90 or 99% by mass or volume of the body part as a whole.

In one embodiment of the invention, the cooling step, maintaining step, and/or warming step is carried out on nanoparticles occupying a portion of the body part, which is smaller than 99.9, 90, 80, 70, 60, 50, 30, 20, 10, 5, 2 or 1% by mass or volume of the body part as a whole.

In one embodiment of the invention, the cooling step, maintaining step, and/or warming step is carried out on nanoparticles occupying a portion of the body part, which is larger than $10^{-10}$, $10^{-5}$, 1, 2, 5, 10, 20, 30, 50, 60, 70, 80, 90 or 99% by mass or volume of the body part as a whole.

In another embodiment of the invention, the cooling region is the volume, surface or length that is cooled down to the minimum temperature.

In some cases, the nanoparticle region can be smaller by a factor of at least 0, 1, 1.01, 1.1, 1.2, 1.5, 2, 5, 10, $10^3$ or $10^5$ than the cooling region.

In some other cases, the nanoparticle region can be larger by a factor of at least 0, 1, 1.01, 1.1, 1.2, 1.5, 2, 5, 10, $10^3$ or $10^5$ than the cooling region.

The invention also relates to the cryo-system for use according to the invention, wherein the nanoparticles have a capacity to maintain the body part at a cooling temperature, defined as $|T_{BPWNP}(\xi t) - T_{BPWONP}(\xi t)|$, which is larger than $10^{-5}$, $10^{-2}$, 0.1, 0.5, 1, 5 or 10° C., wherein:
  i) $T_{BPWNP}(\xi t)$ is the cooling temperature of the body part comprising the nanoparticle(s),
  ii) $T_{BPWONP}(\xi t)$ is the cooling temperature of the body part not comprising the nanoparticle(s),
  iii) $T_{BPWNP}(\xi t)$ and $T_{BPWONP}(\xi t)$ are measured a certain time t after the body part has been cooled down to the cooling temperature T with the cryo-probe, and
  iv) $|T_{BPWNP}(\xi t) - T_{BPUWONP}(t)|$ can estimate the capacity of the nanoparticle(s) to maintain the body part at a cooling temperature, i.e. the larger the value of $|T_{BPWNP}(\xi t) - T_{BPUWONP}(\xi t)|$ is the better the capacity of the cryo-system to maintain the temperature of the body part at the cooling temperature is.

The invention also relates to the cryo-system for use according to the invention, wherein $\xi t$ is larger than $10^{-3}$, $10^{-2}$, 1, 5, 10, 20, 50, $10^2$, $10^3$ or $10^5$ second(s).

The invention also relates to the cryo-system for use according to the invention, wherein $\xi t$ is smaller than $10^{10}$, $10^5$, $10^3$, $10^2$, 5, 1, $10^{-2}$, $10^{-3}$ or $10^{-5}$ second(s).

The invention also relates to the cryo-system for use according to the invention, wherein the cooling temperature, preferentially designated as $T_g$, is larger than −273° C., −250° C., −200° C., 100° C., −50° C., −40° C., −20° C., −10° C., −5° C., −3° C., −2° C., −1° C., 0, 2° C., 5° C., 10° C., 20° C., 30° C., 0K, 1K, 2K, 5K, 10K, 20K, 50K, 70K, 100K, 150K, 200K, 250K, 273K, 300K, 350K or 400K.

In some cases, the cooling temperature $T_g$ is smaller than $10^5$° C., $10^3$° C., 200° C., 100° C., 50° C., 40° C., 20° C., 10° C., 0, −5° C., −10° C., −15° C., −20° C., −30° C., −40° C., −50° C., −100° C., −200° C., 1000K, 500K, 200K, 100K, 50K, 40K, 20K, 10K, 5K, 3K, 2K, 1K or 0.1K.

The invention also relates to the cryo-system for use according to the invention, wherein the nanoparticles have a capacity to slow down the heating or warming up of the body part, defined as $|T_{BPWNP}(t_2) - T_{BPWONP}(t_1)|/(t_2 - t_1)$, which is larger than $10^{-5}$, $10^{-3}$, 0.5 or 5° C. per minute, wherein:
  i) $T_{BPWNP}(t_1)$ is the cooling temperature of the body part comprising the nanoparticle(s), measured a certain time $t_1$ after the body part has been cooled down to the cooling temperature T by the cryo-probe,
  ii) $T_{BPWNP}(t_2)$ is the cooling temperature of the body part comprising the nanoparticle(s), measured a certain time $t_2$ after the body part has been cooled down to the cooling temperature $T_g$ by the cryo-probe,
  iii) $t_2$ is different from $t_1$, and
  iv) $|T_{BPWNP}(t_2) - T_{BPWONP}(t_1)|/(t_2 - t_1)$ can estimate the capacity of the cryo-system to slow down the heating up or warming up of the body part, i.e. the larger the value of $|T_{BPWNP}(t_2) - T_{BPWONP}(t_1)|/(t_2 - t_1)$ is the better the capacity of the cryo-system to slow down the heating up or warming up of the body part is.

The invention also relates to the cryo-system for use according to the invention, wherein the nanoparticles have a capacity to slow down the heating or warming up of the body part, defined as:
  $[|T_{BPWONP}(t_2) - T_{BPWONP}(t_1)/(t_2 - t_1)] - [|T_{BPWNP}(t_2) - T_{BPWNP}(t_1)/(t_2 - t_1)]$, which is larger than $10^{-5}$, $10^{-3}$, $10^{-1}$, 0.5, 1, 5 or 10° C. per minute, wherein:
  i) $T_{BPWNP}(t_1)$ is the cooling temperature of the body part comprising the nanoparticle(s), measured a certain time $t_1$ after the body part has been cooled down to the cooling temperature $T_g$ by the cryo-probe,
  ii) $T_{BPWNP}(t_2)$ is the cooling temperature of the body part comprising the nanoparticle(s), measured a certain time $t_2$ after the body part has been cooled down to the cooling temperature T by the cryo-probe,
  iii) $T_{BPWONP}(t_1)$ is the cooling temperature of the body part not comprising the nanoparticle(s), measured a certain time $t_1$ after the body part has been cooled down to the cooling temperature $T_g$ by the cryo-probe,
  iv) $T_{BPWONP}(t_2)$ is the cooling temperature of the body part not comprising the nanoparticle(s), measured a certain time $t_2$ after the body part has been cooled down to the cooling temperature $T_g$ by the cryo-probe,
  v) $t_2$ is different from $t_1$, and
  vi) $[|T_{BPWONP}(t_2) - T_{BPWONP}(t_1)|/(t_2 - t_1)] - [|T_{BPWNP}(t_2) - T_{BPWNP}(t_1)|/(t_2 - t_1)]$ can estimate the capacity of the cryo-system to slow down the heating up or warming up of the body part, i.e. the larger the value of $[|T_{BPWONP}(t_2) - T_{BPWONP}(t_1)|/(t_2 - t_1)] - [|T_{BPWNP}(t_2) - T_{BPWNP}(t_1)|/(t_2 - t_1)]$ is the better the capacity of the cryo-system to slow down the heating up or warming up of the body part is.

The invention relates to the cryo-system for use according to the invention, wherein the cryo-system cools down the body part to the cooling temperature T in a cooling volume that is larger than either half of the whole body part or the cooling volume reached by the cryo-system without the nanoparticles.

The invention relates to the cryo-system for use according to the invention, wherein the cooling temperature T is larger than:
i) −200, −100, −70, −40, −20, −10, −5, −2, −1, 0, 2, 5, 10 or 20° C., or
ii) the cooling temperature reached without the nanoparticles.

The invention also relates to the cryo-system for use according to the invention, wherein the cryo-system cools down the body part at a rate that does not depend on concentration of the nanoparticle(s).

The invention also relates to the cryo-system for use according to the invention, wherein the cryo-system lets the body part warm up at a rate that decreases with increasing concentration of nanoparticle(s).

The invention also relates to the cryo-system for use according to the invention, where cryotherapy is a treatment that involves, consists in, or is combined with: i) destruction, detection, stimulation, or transformation of at least one pathological cell, ii) decrease in temperature of the body part of an individual, ii) heat therapy, iii) radiation therapy, iv) chemotherapy, v) surgery, and/or vi) immune-therapy.

The invention also relates to the cryo-system for use according to the invention, wherein cryotherapy is the treatment of a disease selected in the group consisting of: i) a disease associated with a proliferation of cells that is different from the cellular proliferation in a healthy individual, ii) a disease associated with the presence of pathological cells such as tumor or cancer cells in the body part or in the individual, iii) a disease associated with the presence of a pathological site, i.e. a site comprising pathological cells, in an individual or body part, iv) a disease or disorder or malfunction of the body part, v) a disease associated with the presence of radio-resistant or acoustic-resistant or laser-resistant or magnetic field resistant cells, vi) an infectious disease, vii) an auto-immune disease, viii) a neuropathology, ix) a cancer, x) a tumor, xi) a disease comprising or due to at least one cancer or tumor cell, xii) a cutaneous condition, xiii) an endocrine disease, xiv) an eye disease or disorder, xv) an intestinal disease, xvi) a communication disorder, xvii) a genetic disorder, xviii) a neurological disorder, xix) a voice disorder, xx) a vulvovaginal disorder, xxi) a liver disorder, xxii) a heart disorder, xxiii) a heating disorder, xxiv) a mood disorder, xxv) anemia, preferentially iron anemia, xxvi) a personality disorder, xxvii) aids, notably neuro-aids, xxviii) Parkinson, xxix) Alzheimer, xxx) bacterial and/or fungi infection or contamination, xxxi) blood disease due for example to an absence or lack of efficient coagulation, and xxxii) a disease due to a deficiency in immune function or an immune disease.

In one embodiment of the invention, the cryo-system is used to treat an individual in need thereof suffering from an infectious disease, and the body part of this individual preferentially comprises cells affected by the infectious disease.

In one aspect, the invention relates to nanoparticle or cryo-system for use according to the invention, wherein the individual in need thereof is suffering from an infectious disease, and the body part comprises cells affected by the infectious disease.

In one embodiment of the invention, the treatment or method according to the invention is the treatment of an infectious disease or the treatment of hypothermia.

In one embodiment, when the method is the treatment of hypothermia, it may not involve or comprise the cooling step. It can then consist in treating a body part of an individual, preferentially by non-predominant ice-ball cryotherapy, using the following steps:
a) administering nanoparticles to a body part of an individual;
and
b) Warming the body part comprising the nanoparticles by increasing the temperature of the body part from the cooling temperature of said body part to a final temperature of said body part that is above the cooling temperature, characterized in that said cooling temperature of the body part is preferentially the temperature reached by the body part or individual when it is in hypothermia.

In one embodiment of the invention, the temperature reached by the individual when it is in state of hypothermia is preferentially a temperature that is lower than 37° C. or the physiological temperature or lower than the temperature of the individual without or before being in hypothermia by at least 10-1, 1, 5, 10, 20, 50, 100 or 150° C.

In one embodiment of the invention, the method or cryo-system according to the invention enables to control, adjust, decrease or increase the rate at which the individual in hypothermia is warmed up, hence preferentially enabling to save the life of the individual.

In one embodiment of the invention the infectious disease is due to, originates from, or is associated with the presence in the body part of: i), bacteria, preferentially pathological bacteria, ii), viruses, iii), tumor cells or, iv), foreign biological material not belonging to the living organism or body part.

In one embodiment of the invention, the disease is selected from the group consisting of: a malfunction of the living organism or body part, a disease associated with a proliferation of cells that is different from the cellular proliferation in a healthy individual, a disease associated with the presence of pathological cells in the body part, a disease associated with the presence of a pathological site in an individual or body part, a disease or disorder or malfunction of the body part, a disease associated with the presence of radio-resistant or acoustic-resistant cells, an infectious disease, an auto-immune disease, a neuropathology, a cancer, a tumor, a disease comprising or due to at least one cancer or tumor cell, a cutaneous condition, an endocrine disease, an eye disease or disorder, an intestinal disease, a communication disorder, a genetic disorder, a neurological disorder, a voice disorder, a vulvovaginal disorder, a liver disorder, a heart disorder, a heating disorder, a mood disorder, anemia, preferentially iron anemia, and a personality disorder.

In one embodiment of the invention, the cancer or tumor is selected from the group consisting of: the cancer of an organ, cancer of blood, cancer of a system of a living organism, adrenal cancer, anal cancer, bile duct cancer, bladder cancer, bone cancer, brain cancer, breast cancer, cervical cancer, colon/rectum cancer, endometrial cancer, esophagus cancer, eye cancer, gallbladder cancer, heart cancer, kidney cancer, laryngeal and hypopharyngeal cancer, leukemia, liver cancer, lung cancer, nasal cavity and paranasal sinus cancer, nasopharyngeal cancer, neuroblastoma, non-Hodgkin lymphoma, oral cavity and oropharyngeal cancer, osteosarcoma cancer, ovarian cancer, pancreatic cancer, pancreatic penile cancer, prostate cancer, retinoblastoma, rhabdomyosarcoma, salivary gland cancer, sarcoma, skin cancer, small intestine cancer, stomach cancer, testicular cancer, thymus cancer, thyroid cancer, uterine cancer, uterine sarcoma cancer, vaginal cancer, vulvar cancer, waldenstrom macroglobulinemia wilms tumor, castleman disease ewing family of tumor, gastrointestinal carcinoid tumor, gastrointestinal stromal tumor, myelodysplastic syndrome pituitary tumor, and a cancerous disease such as gestational trophoblastic disease, Hodgkin disease, kaposi sarcoma, malignant mesothelioma, and multiple myeloma.

In one embodiment of the invention, the disorder or malfunction of the body part is associated with the malfunction of cells, which divide more rapidly or enter in an apoptotic or necrotic state for example, or with the malfunction of the immune system or immune cell(s).

In one embodiment of the invention, the method or cryo-system according to the invention is a method or cryo-system, which preferentially detects diagnoses, heals, or cures a disease such as one of those mentioned in the previous embodiments.

The invention also relates to the cryo-system for use according to the invention, where the cryo-stem is a kit or a combination of:
  i) a cryo-probe that is a medical device, an apparatus or an equipment, preferentially a medical, diagnostic, imaging, biological, or cosmetic apparatus or equipment
  and
  ii) at least one nanoparticle that is a composition, a drug or a medical device, preferentially a medical, diagnostic, imaging, biological, or cosmetic composition.

In some cases, the cryo-system can be designated as a system, apparatus, equipment, kit, designed to carry out cryo-therapy.

The invention also relates to the use of the nanoparticles in the cryo-system, as defined in the invention, to store or retain the cold or cold energy or cryogenic energy in a body part of an individual during a cryotherapy.

In some cases, the nanoparticle(s) can store more than $10^{-50}$, $10^{-20}$, $10^{-10}$, $10^{-5}$, $10^{-1}$, 0, 1, 5 or 10 J preferentially of energy or cold energy preferentially per mg of nanoparticle(s), In some cases, the nanoparticle(s) can store or retain the cold or cold energy when it can maintain the temperature of the body part at the cooling temperature or maintaining temperature, preferentially during more than $10^{-10}$, $10^{-1}$, 0, 1, 10 or $10^3$ second(s).

In some cases, the nanoparticle can store or retain the cold or cold energy or cryogenic energy during more than $10^{-1°}$, $10^{-1}$, 0, 1, 10 or $10^3$ second(s).

In some cases, the nanoparticle can store or retain the cold or cold energy or cryogenic energy during less than $10^{50}$, $10^{10}$, $10^5$, $10^2$, 10, 5, 2, 1 or $10^{-3}$ second(s).

In some cases, the nanoparticle can store or retain the cold or cold energy or cryogenic energy during the maintaining step.

In some cases, the temperature is maintained at the maintaining or cooling or minimum temperature when it does not vary, increase or decrease by more than 1, 5, 10, 50 or 100%, where this percentage can be equal to $\Delta T_\alpha/T_\alpha$, where $\Delta T_\alpha$ is the variation of temperature during the maintaining step and $T_\alpha$ is the maintaining temperature, where the maintaining temperature can in some cases be the cooling temperature.

The invention also relates to the use of the cryo-system according to the invention, wherein:
  i) a temperature gradient lower than 150° C.,
  or
  ii) a cooling or minimum temperature above −100° C., is reached in the body part.

In some cases, the temperature gradient is the difference in temperature between two different positions or locations in the body part.

In some cases, the two different positions or locations are separated by a distance of more than $10^{-50}$, $10^{-10}$, $10^{-1}$, 0, 1, 5 or 10 cm.

In some other cases, the two different positions or locations are separated by a distance of less $10^{50}$, $10^{10}$, $10^5$, $10^2$, 10, 5, 2, 1, $10^{-3}$ or $10^{-5}$ cm.

In some other cases, the temperature gradient is the temperature gradient reached or observed or measured in the body part.

In some other cases, the temperature gradient is lower than $10^5$, $10^3$, 150, 50, 20, 10, 5, 2, 1 or $10^{-3°}$ C., optionally as measured per cm or mm or cm$^2$ or mm$^2$ or cm$^3$ or mm$^3$ of body part.

In some other cases, the temperature gradient is larger than $10^{-10}$, $10^{-5}$, $10^{-1}$, 1, 5, 10 or $10^{3°}$ C. optionally as measured per cm or mm or cm$^2$ or mm$^2$ or cm$^3$ or mm$^3$ of body part.

In still some other cases, the temperature gradient is lower, preferentially by a factor of at least 0, 0.5, 1, 1.1, 1.5, 2, 5, 10 or $10^3$, in the presence of nanoparticles, preferentially in the presence of more than 0, $10^{-20}$, $10^{-10}$, $10^{-1}$, 1, 10 or 100 mg of nanoparticle(s) per cm$^3$ of body part, than in the absence of nanoparticles, preferentially in the absence of more than $10^5$, $10^3$, 100, 5, 2, 1 or 0 mg of nanoparticle(s) per cm$^3$ of body part, where the temperature gradient in the presence and absence of nanoparticles is preferentially measured in the same conditions except that the nanoparticle concentration in the body part is different in both cases and that the presence of nanoparticles can modify the temperature(s) and/or duration(s) of at least one step of the method.

The invention also relates to the use of the cryo-system according to the invention, wherein:
  i) more than $10^{-10}$, $10^{-5}$, $10^{-1}$, 1, 5, 10, 20, 50, 70, 80, 90 or 99% preferentially in mass or volume of the body part is cooled down, where this percentage can be the ratio $\beta_{CD}/(\beta_{NCD}+\beta_{CD})$ where $\beta CD$ is the mass or volume of the body part cooled down at the cooling or maintaining temperature and $\beta_{NCD}$ is the mass or volume of the part cooled down at a temperature that is different from the cooling or maintain temperature, preferentially by at least 0, $10^{-10}$, $10^{-1}$, 2, 5, 10, 20, 50, 100 or $10^{3°}$ C.,
  and/or
  ii) a larger volume, surface or length of the body part, preferentially by a factor of more than 0, 0.5, 1, 1.1, 1.5, 2, 5, 10 or $10^3$, is cooled down in the presence of nanoparticles, preferentially in the presence of more than 0, $10^{-20}$, $10^{-10}$, $10^{-1}$, 1, 10 or 100 mg of nanoparticles per cm$^3$ of body part, than in the absence of the nanoparticles, preferentially in the absence of more than $10^5$, $10^3$, 100, 5, 2, 1 or 0 mg of nanoparticles per cm$^3$ of body part, where the volume, surface or length of the body part in the presence and absence of nanoparticles is preferentially measured in the same conditions except that the nanoparticle concentration in the body part is different in both cases and that the presence of nanoparticles can modify the temperature(s) and/or duration(s) of at least one step of the method.

The invention also relates to the use of the cryo-system according to the invention, wherein:
i) less than $10^{10}$, $10^5$, 100, 99, 90, 80, 70, 50, 20, 10, 5, 2 or 1% preferentially in mass or volume of the body part is cooled down,
and/or
ii) a smaller volume, surface or length of the body part, preferentially by a factor of more than 0, 0.5, 1, 1.1, 1.5, 2, 5, 10 or $10^3$, is cooled down in the presence than absence of nanoparticles.

The situation of the above embodiment could occur when the nanoparticles are degraded or when they have lost their property to store or retain cold energy.

The invention also relates to the use of the cryo-system according to the invention, to cool down more than $10^{-10}$, $10^{-5}$, $10^{-3}$, $10^{-1}$, 0, 1, 5, 10, 20, 50, 70, 90 or 99% in mass or volume of the body part or to cool down a larger portion of the body part than that cooled down in the absence of nanoparticles.

The invention also relates to the use of the cryo-system according to the invention, wherein the second part has at least one property selected from the group consisting of:
i) The at least one nanoparticle is an ice nucleation site, and
ii) The size of the ice nucleation site of the at least two nanoparticles bound to each other or associated with each other via binding/associating material is larger, preferentially by a factor of at least 0, 0.5, 1, 5, 10 or $10^3$, than the size of the ice nucleation site of the at least two nanoparticles not bound to each other or not associated with each other via binding or associating material site.

In some cases, the ice nucleation site can be an ice-ball, preferentially when the nanoparticle(s) is cooled down at or below the threshold temperature, cooling temperature, or a temperature lower than 100, 50, 20, 10, 5, 2, 1, 0, −1, −2, −5, −10 or −50° C.

In some other cases, the ice nucleation site can be a nanoparticle-ice-ball or nanoparticle ice nucleation site, preferentially when the ice nucleation site or ice-ball comprises more than 1, 5, 10, $10^3$ or $10^5$ nanoparticle(s) preferentially per $cm^3$ of body part.

In some other cases, the size of the ice nucleation site is the length, diameter or volume of the ice nucleation site or ice-ball, preferentially measured when the temperature of the nucleation site is lower than 100, 50, 20, 10, 5, 2, 1, 0, −1, −2, −5, −10 or −50° C.

The invention also relates to the use of the cryo-system according to the invention, wherein the cryotherapy is a non-ice-ball cryotherapy or a nanoparticle-ice-ball cryotherapy, characterized in that:
i) The non-ice-ball cryotherapy is not a cryotherapy only comprising ice-balls not embedding or not comprising metallic or iron oxide nanoparticles, and
ii) The nanoparticle-ice-ball cryotherapy is a cryotherapy comprising ice-balls embedding or comprising metallic or iron oxide nanoparticles.

The invention also relates to the use of the nanoparticles in the cryo-system, as defined in the invention, to form a non-continuous piece of ice within the body part, where such non-continuous piece of ice is characterized by at least two ice-balls in the body part, for example surrounding the nanoparticle(s) or the cryo-probe, which are not connected or linked together by ice.

The invention also relates to the use of the nanoparticles according to the invention, wherein at least two ice-balls are formed during at least one step of the method according to the invention.

The invention also relates to the use of the nanoparticles in the cryo-system, as defined in the invention, to form ice-balls with at least one property selected from the group consisting of:
i) Ice-balls with a size that is larger than the size of at least one nanoparticle,
ii) Ice-balls that are intracellular, and
iii) A number of large ice-balls that is equal or smaller than the number of nanoparticles.

The invention relates to the use of the nanoparticles in the cryo-system, as defined in the invention, to slow down the speed at which the body part is heated or warmed up following the cooling of the body part by the cryo-system.

The invention also relates to the use of the nanoparticles preferentially in the cryo-system, as defined in the invention, to favor the formation of intracellular ice.

In one aspect of the invention, the invention relates to nanoparticles or the cryo-system for use in a method of treating a body part of an individual by cryotherapy comprising the following steps:
a) administering nanoparticles and/or cryo-probe to a body part of an individual;
b) cooling the body part comprising the nanoparticles and/or cryo-probe by decreasing the temperature of said body part from an initial temperature to a cooling temperature of said body part, which is lower than the initial temperature, preferentially using the cryo-probe, preferentially in or during the cooling step;
c1) optionally not maintaining or not having the body part comprising the nanoparticles and/or cryo-probe at the cooling temperature or at a temperature comprised between the cooling temperature and the initial or final temperature or at a temperature below 0° C. or at a temperature above −250, −100, −40 or −20° C., preferentially for a duration of time of more than 100 or $10^{10}$ seconds;
c2) optionally maintaining or having the body part comprising the nanoparticles and/or cryo-probe at the cooling temperature or at a temperature comprised between the cooling temperature and the initial or final temperature or at a temperature below 0° C. or at a temperature above −250, −100, −40 or −20° C., preferentially for duration of time between $10^{-10}$ and $10^{10}$ or between $10^{-5}$ and $10^3$ or between $10^{-3}$ and 100 seconds, preferentially during or in the maintaining step,
and
d) warming or let warming the body part comprising the nanoparticles and/or cryo-probe by increasing or let increasing the temperature of the body part from the cooling temperature of said body part to a final temperature of said body part that is above the cooling temperature,
preferentially characterized in that said cooling temperature of the body part is:
above the freezing temperature of the body part and/or above 5, 0, −5, −10, −20 or −40° C.;
and/or
above a threshold temperature, where the threshold temperature has at least one property selected from the group consisting of:
i) above the threshold temperature, the body part comprises a quantity of ice-balls smaller than the quantity of nanoparticles;

ii) above the threshold temperature, the volume occupied by ice-balls in the body part is smaller than the volume occupied by the nanoparticles in the body part;

iii) below the threshold temperature, the body part comprises a quantity of ice-balls larger than the quantity of nanoparticles;

iv) below the threshold temperature, the volume occupied by ice-balls in the body part is larger than the volume occupied by the nanoparticles in the body part; and v) below the threshold temperature, the size or diameter of at least one ice-ball is larger than the size or diameter of at least one nanoparticle.

Repetition/Duration of the Steps, Cycles, and Sessions of the Method

Surprisingly, the present inventors also discovered that a sequential cryotherapy according to the present invention further improved cellular destruction.

In one embodiment, the invention relates to nanoparticles or cryo-system for use according to the invention or to the method according to the invention, wherein the succession of steps of at least the cooling step and the warming step, preferably the cooling step, the maintaining step and the warming step is repeated more than once, preferably more than 2, 3, 5, 6, 10, or $10^3$ time(s), more preferably more than 6 times, even more preferably more than 3 times. In some embodiment, an important number of steps is carried out to reach the medical, cosmetic, therapeutic or cosmetic effect or activity of the treatment.

In one embodiment, the succession of steps is repeated less than $10^{10}$, $10^5$, $10^3$, 100, 75, 50, 20, 10, 5, or 2 times. In some embodiment, a limited number of steps is carried out to avoid side effects that can be associated with a too large number of steps.

In one embodiment, the succession of steps is repeated between 1 and $10^{50}$, 1 and $10^{10}$, 1 and $10^5$, 1 and $10^3$, 1 and $10^2$, 1 and 50, or between 1 and 20 times.

In one embodiment of the invention, a cycle comprises: i) the administration step, the cooling step, the maintaining step, and the warming step, ii) the cooling step, the maintaining step, and the warming step, and/or iii) the cooling step and the warming step.

In one aspect, the invention relates to nanoparticles or cryo-system for use according to the invention, wherein a cycle is repeated more than 1, 2, 3, 5, 6, 10, or $10^3$ times, preferably more than 6 times, most preferably more than 3 times.

In one embodiment of the invention, the administration step is carried out only once or a limited number of times, preferentially less than $10^5$, $10^3$, 100, 50, 20, 10, 5 or 2 times, preferentially to avoid side effects or difficulties associated with a large number of nanoparticle or cryo-probe administrations.

In one embodiment of the invention, the maintaining step is not carried out or the method does not comprise the maintaining step or the cryo-system is not used with a maintaining step or the maintaining step is carried out for a short period of time, preferentially shorter than $10^5$, $10^3$, 100, 50, 20, 10, 5, 2, 1 or $10^{-1}$ second(s), preferentially to avoid side effects due to a too long maintaining step.

In some cases, the method comprises at least one step of the method or the cryo-system is used with at least one step of the method according to the invention.

In some other cases, the method does not comprise at least one step of the method or the cryo-system is not used with at least one step of the method according to the invention.

In one embodiment, a cycle is repeated more than 1, 2, 3, 5, 6, 10, or $10^3$ times, preferably more than 6 times, most preferably more than 3 times.

In one embodiment, a cycle is repeated less than $10^{50}$, $10^{20}$, $10^{10}$, $10^5$, $10^3$, 100, 75, 50, 20, 10, 5 or 2 times, preferably less than $10^3$ times, most preferably less than 100 times.

In one embodiment, a cycle is repeated between 1 and $10^{50}$, 1 and $10^{20}$, 1 and $10^{10}$, 1 and $10^5$, 1 and $10^3$, or between 1 and 100 time(s).

In one embodiment of the invention, several cycles correspond to a session and a session preferably comprises more than 1, 2, 3, 5, 10, $10^2$, $10^3$, $10^5$ or $10^{10}$ cycles.

In another embodiment of the invention, a session comprises less than $10^{10}$, $10^5$, $10^3$, $10^2$, 10, 5, 3 or 2 cycles.

In still another embodiment of the invention, a session comprises between 1 and $10^{50}$, 1 and $10^{10}$, 1 and $10^3$, 1 and $10^2$, or between 1 and 50 cycles.

In still another embodiment of the invention, the duration of at least one step, the duration between two steps, the duration of at least one cycle, the duration between two cycles, the duration of at least one session, and/or the duration between two sessions is/are longer than $10^{-5 0}$, $10^{-10}$, $10^{-5}$, $10^{-1}$, 1, 5, 10 or 100 second(s).

In still another embodiment of the invention, the duration of at least one step, the duration between two steps, the duration of at least one cycle, the duration between two cycles, the duration of at least one session, and/or the duration between two sessions is/are shorter than $10^{100}$, $10^{50}$, $10^{20}$, $10^{10}$, $10^5$, $10^3$, $10^2$, 50, 20, 10, 5, 2 or 1 second(s).

In still another embodiment of the invention, the duration of at least one step, the duration between two steps, the duration of at least one cycle, the duration between two cycles, the duration of at least one session, and/or the duration between two sessions is between $10^{-50}$ and $10^{100}$, $10^{-10}$ and $10^{50}$, $10^{-5}$ and $10^{10}$, $10^{-3}$ and $10^5$, $10^{-1}$ and $10^3$, or between $10^{-1}$ and 100 seconds.

In still another embodiment, the duration of at least one cycle is longer than the duration of at least one step, or the duration of at least one session is longer than the duration of at least one cycle or of at least one step, preferentially by a factor of at least 0, 0.5, 1, 1.1, 1.5, 2, 5, 10, $10^2$, $10^3$, $10^5$ or $10^{10}$.

In still another embodiment, the duration separating two sessions is longer than the duration separating two steps and/or than the duration separating two cycles, preferentially by a factor of at least 0, 0.5, 1, 1.1, 1.5, 2, 5, 10, $10^2$, $10^3$, $10^5$ or $10^{10}$.

In still another embodiment, the duration separating two steps is shorter than the duration of at least one step, preferentially by a factor of at least 0, 0.5, 1, 1.1, 1.5, 2, 5, 10, $10^2$, $10^3$, $10^5$ or $10^{10}$.

In still another embodiment, the duration separating two cycles is shorter than the duration of at least one cycle, preferentially by a factor of at least 0, 0.5, 1, 1.1, 1.5, 2, 5, 10, $10^2$, $10^3$, $10^5$ or $10^{10}$.

Non-Predominant Ice-Ball/Nanoparticle-Ice-Ball Cryotherapy

In one embodiment of the invention, a non-predominant ice-ball cryotherapy is a cryo-therapy with ice-balls or leading to the formation of at least one ice-ball of: i) size that is larger in the presence than the absence of nanoparticle(s), ii) number that is different, smaller or larger, in the presence than absence of nanoparticle(s) and/or iii) geometry or crystallinity or shape that is different in the presence than absence of nanoparticle(s), where the differences between the properties observed in the presence and absence of nanoparticle(s) are preferentially measured under the same or similar cooling and/or warming conditions with and without nanoparticle(s).

In some cases, a non-predominant ice-ball cryotherapy or a non ice-ball cryotherapy is a cryotherapy in which or during which: i) at least one ice-ball embedding or comprising at least one nanoparticle, also called nanoparticle-ice-ball, forms and/or ii) at least one ice-ball not embedding or not comprising at least one nanoparticle, also called non-nanoparticle-ice-ball, does not form.

In some cases, ice balls can be nanoparticle-ice-balls and/or non-nanoparticle-ice-balls.

In some cases, a non-predominant ice-ball cryotherapy or a non ice-ball cryotherapy is a cryotherapy in which or during which the number and/or the size of nanoparticle-ice-balls is larger than the number and/or size of non-nanoparticle-ice-balls.

According to the present invention, the cooling temperature of the body part is:
- above the freezing temperature of the body part or above 5, 0 or −5° C., preferably above −5 or 0° C., more preferably above 0° C.;

and/or
- above a threshold temperature, where the threshold temperature has at least one property selected from the group consisting of:
  i) above the threshold temperature, the body part comprises a quantity of ice-balls smaller than the quantity of nanoparticles;
  ii) above the threshold temperature, the volume occupied by ice-balls in the body part is smaller than the volume occupied by the nanoparticles in the body part;
  iii) below the threshold temperature, the body part comprises a quantity of ice-balls larger than the quantity of nanoparticles;
  and
  iv) below the threshold temperature, the volume occupied by ice-ball in the body part is larger than the volume occupied by the nanoparticles in the body part.

Preferably, in order to avoid any ice-balls formation, the cooling temperature of the body part according to the present invention is above 0° C. which is the freezing point of water. However, depending on the body part of the individual, the type of individual treated (mammal, plant, bacteria . . . ) and due notably to the electrolyte content of the cells and extracellular fluid, the freezing point can be below 0° C. For instance, the skin surface reportedly freezes from −3.7 to −4.8° C.

As such, in one embodiment, the cooling temperature of the body part according to the present invention can be above 10, 5, 2, 1, 0, −5, −10, −20, −50 or −100° C., preferably above −40 or −5° C., most preferably above 0° C.

In one embodiment, the cooling or maintaining temperature of the body part according to the present invention is between 10 and −100° C., between 10 and −20° C., preferably between 10 and −10° C., more preferably between 5 and −5° C., even more preferably between 2 and −2° C., even more preferably between 1° C. and −1° C., even more preferably about 0° C. or 0° C.

In one embodiment, ice-balls are nanoparticles, preferentially surrounded by ice, that are cooled down below the initial or final or cooling or freezing temperature of the body part or below 0° C. or below the threshold temperature. In some cases, such ice-balls are nanoparticle-ice-balls.

In another embodiment, ice-balls are nanoparticles and additional substances such as water or biological material surrounding the nanoparticles that are cooled down below the cooling or freezing temperature of the body part or below 0° C. or below the threshold temperature. In some cases, such ice-balls are nanoparticle-ice-balls.

In another embodiment, the size of the at least one ice-ball, preferentially nanoparticle-ice-ball, is larger than the size of the at least one nanoparticle, preferentially of the nanoparticles not surrounded by ice, preferentially by: i) at least 0, 0.5, 1, 5, 10 or $10^3$ nm, or ii) by a factor of at least 0, 0.5, 1, 1.1, 1.5, 2, 5, 10, $10^3$ or $10^5$. This may be the case when ice-balls surround or comprise nanoparticles.

In another embodiment, the size of the at least one ice-ball, preferentially non-nanoparticle-ice-ball, is smaller than the size of the at least one nanoparticle, preferentially by: i) at least 0, 0.5, 1, 5, 10 or $10^3$ nm, or ii) by a factor of at least 0, 0.5, 1, 1.1, 1.5, 2, 5, 10, $10^3$ or $10^5$. This may be the case when ice-balls do not surround or do not comprise nanoparticles.

In another embodiment, below the threshold temperature, the body part comprises ice-balls with at least one property selected from the group consisting of:
  i) a quantity of ice-balls that is smaller than 1, 5, 10, $10^3$, $10^5$ or $10^{50}$ ice-ball(s) or ice-ball(s) per $cm^3$ of body part;
  ii) a quantity of ice-balls that is smaller than the quantity of nanoparticles, preferentially by: i) at least 0, 0.5, 1, 5, 10 or $10^3$ ice-ball(s), or ii) by a factor of at least 0, 0.5, 1, 1.1, 1.5, 2, 5, 10, $10^3$ or $10^5$;
  iii) a volume occupied by ice-balls in the body part that is smaller than $10^{10}$, $10^5$, $10^3$, 10, $10^{-1}$, $10^{-3}$, $10^{-6}$ or $10^{-9}$ $cm^3$, preferentially as measured per $cm^3$ of body part;
  iv) a volume occupied by ice-balls in the body part that is smaller than the volume occupied by the nanoparticles in the body part, preferentially by: i) at least 0, $10^{-5°}$, $10^{-20}$, $10^{-10}$, $10^{-3}$, 1, 5, 10 or $10^3$ $cm^3$, or ii) by a factor of at least 0, 0.5, 1, 1.1, 1.5, 2, 5, 10, $10^3$ or $10^5$;
  v) a size or diameter of at least one ice-ball that is smaller than $10^{50}$, $10^{10}$, $10^5$, $10^3$, 1, $10^{-3}$ or $10^{-5}$ nm;
  and
  vi) a size or diameter of at least one ice-ball that is smaller than the size of at least one nanoparticle, preferentially by: i) at least 0, $10^{-50}$, $10^{-20}$, $10^{-10}$, $10^{-3}$, 1, 5, 10, $10^3$ or $10^6$ nm, or ii) by a factor of at least 0, 0.5, 1, 1.1, 1.5, 2, 5, 10, $10^3$ or $10^5$.

In another embodiment, above the threshold temperature, the body part comprises ice-balls with at least one property selected from the group consisting of:
  i) a quantity of ice-balls that is larger than 1, 5, 10, $10^3$, $10^5$ or $10^{50}$ ice-ball(s) or ice-ball(s) per $cm^3$ of body part;
  ii) a quantity of ice-balls that is larger than the quantity of nanoparticles, preferentially by: i) at least 0, 0.5, 1, 5, 10 or $10^3$ ice-ball(s), or ii) by a factor of at least 0, 0.5, 1, 1.1, 1.5, 2, 5, 10, $10^3$ or $10^5$;
  iii) a volume occupied by ice-balls in the body part that is larger than $10^{-5°}$, $10^{-10}$, $10^{-5}$, $10^{-1}$, 1, 2, 5, 10, $10^3$ or $10^6$ $cm^3$, preferentially as measured per $cm^3$ of body part;
  iv) a volume occupied by ice-balls in the body part that is larger than the volume occupied by the nanoparticles in the body part, preferentially by: i) at least 0, $10^{-5°}$, $10^{-20}$, $10^{-10}$, $10^{-3}$, 1, 5, 10 or $10^3$ $cm^3$, or ii) by a factor of at least 0, 0.5, 1, 1.1, 1.5, 2, 5, 10, $10^3$ or $10^5$;

v) a size or diameter of at least one ice-ball that is larger than $10^{-3}$, 1, 5, 10, $10^3$, $10^5$ or $10^{50}$ nm; and vi) a size or diameter of at least one ice-ball that is larger than the size of at least one nanoparticle, preferentially by: i) at least 0, $10^{-50}$, $10^{-20}$, $10^{-10}$, $10^{-3}$, 1, 5, 10, $10^3$ or $10^6$ nm, or ii) by a factor of at least 0, 0.5, 1, 1.1, 1.5, 2, 5, 10, $10^3$ or $10^5$.

In one embodiment of the invention, temperatures above that threshold temperature do not result predominantly in ice-balls formations and temperatures below that threshold temperature result predominantly in ice-balls formations.

In some embodiment, temperatures above said threshold temperature do not result predominantly in ice-balls formations if ice-balls are present in less than 50, 20, 5, 2 or 1 percent, preferentially in mass or volume, of the body part.

In some embodiment, temperatures below said threshold temperature result predominantly in ice-balls formations if ice-balls are present in more than about 50, 70, 80, 90 percent or present in about 100 percent, preferentially in mass or volume, of the body part. In some cases, the threshold temperature can be the initial, final, maintaining, cooling or freezing temperature or the ice-ball temperature.

In some cases, the temperature can be measured during at least one step of the method or treatment according to the invention.

As used herein, the ice-ball temperature is the temperature below which iceball(s) form(s) in the body part. Preferentially, below the ice-ball temperature, iceball(s) is/are formed.

Preferentially, above the ice-ball temperature, iceball(s) is/are not formed.

In some embodiment of the invention, the ice-ball temperature is a threshold temperature that is such that:
above the ice-ball temperature, or more than $10^{-3}$, $10^{-1}$, 1, 5 or $10°$ C. above the ice-ball temperature, less than $10^{100}$, $10^{50}$, $10^{10}$, 10, 5, 2 or 1 ice-ball(s) or ice-ball(s) per $cm^3$ of body part, is/are formed,
and/or
below the ice-ball temperature, or more than $10^{-3}$, $10^{-1}$, 1, 5 or $10°$ C. below the ice-ball temperature, more than $10^{100}$, $10^{50}$, $10^{10}$, 10, 5, 2 or 1 ice-ball(s) or ice-ball(s) per $cm^3$ of body part, is/are formed.

In some other embodiment, ice-ball(s) represent(s) or is/are an assembly of or of more than 1, 2, 5, 10, $10^3$, $10^5$, $10^{10}$, $10^{20}$ or $10^{50}$ ice-ball(s).

In some other embodiment, ice-ball(s) represent(s) or is/are an assembly of or of less than $10^{50}$, $10^{20}$, $10^{10}$, $10^5$, $10^3$, 10, 5 or 2 ice-ball(s).

In some cases, the treatment or method according to the invention can be a non-predominant ice-ball cryotherapy. A non-predominant ice-ball cryotherapy relates to a cryotherapy resulting in no or a negligible amount of ice-balls.

In some embodiment of the invention, a non-predominant ice-ball cryotherapy designates a cryotherapy in which the time during which the temperature is below the ice-ball temperature is smaller than:
i) $10^{-50}$, $10^{-20}$, $10^{-10}$, $10^{-5}$, $10^{-1}$, 0, 1, 5, 10, $10^3$, $10^5$ or $10^{10}$ second(s),
and/or
ii) $10^{-5°}$, $10^{-2°}$, $10^{-1°}$, $10^{-5}$, $10^{-1}$, 0, 1, 5, 10, 25, 50, 75, 80, 90, 99, 99.9 or 100% of the duration of the whole method or of at least one step of the method according to the invention, where this percentage can be equal to $t_{BIBT}/t_M$ or $(t_M-t_{BIBT})/t_M$, where $t_{BIBT}$ is the time or duration during which the temperature is below the ice-ball temperature and $t_M$ is the time or duration of the whole method or of at least one step of the method according to the invention.

In some other embodiment of the invention, a non-predominant ice-ball cryotherapy designates a cryotherapy in which a minority of temperatures or less than 100, 50, 20, 10, 5, 2 or 1% of temperatures of at least one step of the method, preferentially resulting in or associated with the medial, cosmetic, diagnostic or therapeutic effect or activity of the treatment, is below the ice-ball temperature or is at least $10^{-5}$, $10^{-1}$, 0, 1, 10, $10^2$, $10^3$ or $10^{5°}$ C. below the ice-ball temperature.

In some other embodiment of the invention, a non-predominant ice-ball cryotherapy designates a cryotherapy in which: i) the quantity of ice-ball(s), preferentially per $cm^3$ of body part, is smaller than $10^{10}$, $10^5$, $10^3$, 100, 50, 10 or 1 and/or the size of at least one ice-ball is smaller than the size of the nanoparticle or than $10^{10}$, $10^5$, $10^3$, 100, 50, 20, 10, 5, 2, 1, $10^{-3}$, $10^{-5}$ or $10^{-10}$ nm.

In still some other embodiment of the invention, the treatment or method according to the invention is a non-ice-ball cryotherapy. A non-ice-ball cryotherapy relates to a cryotherapy resulting in no ice-balls or no ice-ball formation, where ice-balls are preferentially those of the size, crystallinity, geometry obtained in the absence of nanoparticle(s).

In some embodiment of the invention, a non-ice-ball cryotherapy designates a cryotherapy in which the temperature of the treatment or method according to the invention is above the ice-ball temperature during the whole method or treatment.

In an embodiment of the invention, the non-ice-ball cryotherapy or non-predominant ice-ball cryotherapy, is characterized in that nanoparticle and/or body part do/does not comprise or is/are not surrounded by or is/are not covered by or is/are not enveloped by or is/are not in contact with ice or at least one ice-ball, preferentially during at least one step of the method according to the invention.

In an embodiment of the invention, cryotherapy can be non-ice-ball cryotherapy or non-predominant ice-ball cryotherapy. It can be characterized in that ice forms around nanoparticle(s) or nanoparticle(s) are ice-nucleation sites, where ice-balls formed around nanoparticles can be designated as nanoparticle-ice-ball(s).

In one embodiment, ice-balls are mixture or assembly of ice-balls not comprising or embedding nanoparticles and nanoparticle-ice-balls comprising ice-balls embedding nanoparticles.

In some cases, cryotherapy can result in the formation of ice-balls or is efficient in the presence of ice-balls, preferentially in the presence of nanoparticle-ice-balls.

In some cases, the non-ice-ball cryotherapy or non-predominant ice-ball cryotherapy can correspond to or be designated as nanoparticle-ice-ball cryotherapy.

In some cases, the cryotherapy is a nanoparticle-ice-ball cryotherapy, where nanoparticles are preferentially ice nucleation sites.

In some other embodiment, the treatment, preferentially the non-ice-ball cryotherapy or non-predominant ice-ball cryotherapy, is characterized in that the at least one ice-ball is located at a distance of more than $10^{-2}$, $10^{-1}$, 1, 5, 10, $10^3$, $10^5$ or $10^9$ nm from the nanoparticle or body part.

In some other embodiment, the treatment, preferentially the non-ice-ball or non-predominant ice-ball cryotherapy, is characterized in that ice-balls are present in less than 50, 20, 5, 2 or 1 percent, preferentially in mass or volume, of the body part.

In one embodiment of the invention, the treatment, preferentially the non-ice-ball or non-predominant ice-ball cryotherapy, is characterized in that: i), it leads to the formation of a less than $10^{10}$, $10^5$, $10^3$, 10, 5, 2 or 1 ice-ball(s), preferentially not comprising or embedding nanoparticle(s), preferentially per $cm^3$ of body part, preferentially comprised in the body part, ii), the cooling temperature is above 0° C. or above the temperature at which ice-ball(s) start(s) to form, and/or iii) it leads to the destruction, healing, detection of at least one pathological cell or to the cure or healing of the body part without ice-ball formation.

As used herein, an ice-ball can be a ball of ice or a round-shaped volume of ice.

In some embodiment, an ice-ball can be characterized by at least one of the following properties: i), a size or dimension in at least one direction larger than $10^{-2}$, $10^{-1}$, 1, 5, 10, $10^3$, $10^6$ or $10^9$ nm or $nm^2$ or $nm^3$, ii) a size or dimension in at least one direction between $10^{-2}$ and $10^{50}$ nm or $nm^2$ or $nm^3$, $10^{-2}$ and $10^9$, $10^{-1}$ and $10^6$, or between 1 and $10^3$ nm or $nm^2$ or $nm^3$, iii) a size or dimension in at least one direction larger than the size or dimension in at least one direction of a nanoparticle by a factor of at least 1.0001, 1.1, 1.5, 2, 5 or 10, where this factor can be the ratio between the size of the ice-ball(s) and the size of the nanoparticle(s).

In some other embodiment, an ice-ball characterized by at least one of the following properties: i), a size or dimension in at least one direction smaller $10^{20}$, $10^{10}$, $10^5$, $10^2$, 10, 5, 2 or 1 nm or $nm^2$ or $nm^3$, ii) a size or dimension in at least one direction smaller than the size or dimension in at least one direction of a nanoparticle by a factor of at least 1.0001, 1.1, 1.5, 2, 5 or 10, where this factor can be the ratio between the size or dimension in at least one direction of the ice-ball and the size or dimension in at least one direction of the nanoparticle.

In one embodiment of the invention, an ice-ball is a macroscopic ice-ball. In some embodiment, a macroscopic ice-ball is an ice-ball with a size or dimension in at least one direction larger than $10^{-50}$, $10^{-10}$, $10^{-5}$, $10^{-1}$, 1, 5, 10 or $10^3$ nm, preferentially larger than 100 or $10^3$ nm, most preferably between 100 nm and 1 meter in size.

In still some other embodiment, a macroscopic ice-ball is an ice-ball with a size larger than: i), 1, 10, $10^2$, $10^3$, $10^5$, $10^9$ or $10^{10}$ nm, ii) 1, 5, 10, 20, 50, 70, 90 or 99% in mass or in volume of the body part, iii) an assembly of more than 1, 5, 10, $10^2$, $10^3$, $10^5$ or $10^{10}$ nanoparticle(s), or iv) the size of at least one ice-ball produced when the body part comprises at least one nanoparticle.

In another embodiment of the invention, an ice-ball is a nanoscopic ice-ball. In some embodiment, a nanoscopic ice-ball is an ice-ball with a size or dimension in at least one direction smaller than $10^{50}$, $10^{10}$, $10^5$, $10^3$, 10, 5, 2 or 1 nm, preferentially smaller than 100, 10 or 5 nm, most preferentially between 0.1 and 100 nm.

In still some other embodiment, a nanoscopic ice-ball is an ice-ball with a size smaller than: i) $10^{50}$, $10^{10}$, $10^5$, $10^3$, $10^2$, 10, 5, 2 or 1 nm, ii) 99, 90, 70, 50, 25, 20, 5 or 1% in mass or in volume of the body part, or iii) an assembly of more than 1, 5, 10, $10^2$, $10^3$, $10^5$ or $10^{10}$ nanoparticle(s).

In some embodiment, an ice-ball has at least one property in common with a macroscopic or nanoscopic ice-ball.

In some other embodiment, an ice-ball has at least one property that is different from that of a macroscopic or nanoscopic ice-ball.

In still some other embodiment, an ice-ball, preferentially nanoscopic, is an ice-ball that covers, surrounds, envelops, partly or fully, at least one nanoparticle or that is located at a distance of less than $10^{100}$, $10^{50}$, $10^{20}$, $10^{10}$, $10^5$, $10^3$, 10, 5, 2 or 1 nm from at least one nanoparticle.

In one embodiment of the invention, an ice-ball, preferentially a nanoscopic ice-ball, is an ice-ball that is comprised in a cell, a cell organelle, or the cell cytoplasm. In some embodiment, such ice-ball can lead to or be associated with a variation in at least one cell or body part property such as a variation of: i), size, volume, length, surface, thickness of a cell or body part, ii), cell membrane permeability. In some embodiment, such variation is observed under the microscope, preferentially by comparing the cell or body part property(ies) before and after the cryo-therapy treatment.

In some embodiment, an ice-ball is ice comprised inside a cell or intracellular ice, and can be designated as intracellular ice-ball.

In some other embodiment, an ice-ball is ice comprised outside a cell or extracellular ice, and can be designated as extracellular ice-ball.

In some cases, the intracellular ice-ball(s) can be smaller or less numerous than extracellular ice-ball(s).

In some other cases, the intracellular ice-ball(s) can be larger or more numerous than extracellular ice-ball(s).

In some other embodiment, intracellular and/or extracellular ice induce(s) the swelling or dilatation or elongation of cells or the increase in the size or volume of cells, preferentially by a factor of at least 1.001, 1.1, 1.5, 2, 5, 10, $10^3$ or $10^5$, between before and after ice formation.

In some other embodiment, intracellular and/or extracellular ice induce(s) the decrease in the size or volume of cells, preferentially by a factor of at least 1.001, 1.1, 1.5, 2, 5, 10, $10^3$ or $10^5$, between before and after ice formation.

In some other embodiment, the factor of decrease or increase of the volume of cells between before and after ice formation can be increased in the presence of nanoparticles, preferentially nanoparticles internalized in cells.

In some cases, cryotherapy according to the invention increases or favors nanoparticle cellular internalization.

In some cases, more than 1, 5, 10, $10^3$, $10^6$, $10^9$ or $10^{12}$ nanoparticle(s) or pg of nanoparticle(s) are internalized per cell, preferentially belonging to the body part, preferentially following the use of the method or treatment according to the invention.

In some cases, the number of nanoparticle(s) internalized per cell, preferentially belonging to the body part, increases by a factor of more than 0, 1, 1.1, 2, 5, 10 or $10^3$ between before and after the method or treatment according to the invention.

In still some other embodiment, the treatment is non-ice-ball cryotherapy or non-predominant ice-ball cryotherapy means that:
  i) the treatment does not comprise a step of cooling the body part to a minimum temperature that is below the ice-ball temperature,
  and/or
  ii) the majority of the treatment, or more than $10^{-100}$, $10^{-50}$, $10^{-10}$, $10^{-5}$, $10^{-3}$, $10^{-1}$, 1, 5, 10, 50, 90, 99 or 99.9% of the treatment or treatment step(s) or treatment duration is carried out above the ice-ball temperature, where this percentage can be $T_{AIBT}/T_{tot}$, where $T_{AIBT}$ is the lapse of time during which the temperatures is above the ice-ball temperature during the treatment and $T_{tot}$ is the total duration of the treatment.

In some cases, the minimum temperature can be the cooling or freezing or threshold temperature.

In one embodiment of the invention, the ice-ball temperature is a threshold temperature characterized in at least one of the following properties:

a) temperatures above the ice-ball temperature do not result in ice or ice-ball formation, while temperatures below the ice-ball temperature result in ice or ice-ball formation, b) temperatures above the ice-ball temperature are non-freezing temperatures, while temperatures below the ice-ball temperature are freezing temperatures, and c) the ice-ball temperature is lower than 20, 10, 5, 2, 1, 0, −5 or −10° C.

In still another embodiment of the invention, non-freezing temperatures are temperatures at which ice does not form.

In still some other embodiment of the invention, a non-ice-ball cryotherapy or a non-predominant ice-ball cryotherapy is a cryo-therapy that preferentially does not lead to the formation of at least one macroscopic ice-ball but can lead to the formation of at least one nanoscopic ice-ball or nanoparticle-ice-ball.

In still some other embodiment of the invention, a non-ice-ball cryotherapy or a non-predominant ice-ball cryotherapy is a cryo-therapy that does not lead to the formation of at least one nanoscopic ice-ball or nanoparticle-ice-ball but can lead to the formation of at least one macroscopic ice-ball.

In still some other embodiment of the invention, a non-ice-ball cryotherapy or a non-predominant ice-ball cryotherapy is a cryo-therapy that does not lead to the formation of at least one nanoscopic ice-ball or nanoparticle-ice-ball and that does not lead to the formation of at least one macroscopic ice-ball.

In still some other embodiment, an ice-ball comprises crystallized ice, where the presence of crystallized ice can in some embodiment be revealed by the presence of at least one crystallographic plane or ordered atomic arrangement, preferentially of ice, within the ice-ball.

In some embodiment, an ice-ball is intracellular, i.e. it preferentially forms or is inside cells, cell organelles, cell cytoplasm, or cell membrane.

In some other embodiment, an ice-ball is extracellular, i.e. it preferentially forms or is outside cells, cell organelles, cell cytoplasm, or cell membrane.

In some other embodiment of the invention, an ice-ball comprises or embeds at least 1, 5, 10, $10^3$, $10^5$, or $10^{10}$ nanoparticles. In this case, it can be designated as a nanoparticle-ice-ball.

In some embodiment, the size of the ice-ball comprising or embedding the nanoparticle(s), also designated as nanoparticle-ice-ball, can be at least 1.01, 1.1, 1.5, 2, 5, 10 or $10^3$ smaller than the size of the ice-ball not comprising or not embedding the nanoparticle(s), where such comparison can be made by creating ice-ball(s) in similar conditions in terms of cooling conditions with and without nanoparticle(s).

In some cases, nanoparticles favor the formation of small ice-balls, preferentially ice-balls that comprise a limited number of nanoparticles, preferentially a number of nanoparticle(s) smaller than $10^{50}$, $10^{10}$, $10^5$, $10^3$, 100, 10, 5, 2 or 1 ice-ball(s) that surround or coat at least one nanoparticle with a coating or layer or ice that has a thickness smaller than: i) the diameter of the nanoparticle and/or ii) $10^{50}$, $10^{20}$, $10^{10}$, $10^5$, $10^3$, 500, 100, 75, 50, 20, 10, 5, 2, 1 or $10^{-1}$ nm.

In some embodiment, the size of the ice-ball(s) comprising or embedding the nanoparticle(s), also designated as nanoparticle-ice-ball is at least 1.01, 1.1, 1.5, 2, 5, 10 or $10^3$ larger than the size of the ice-ball(s) not comprising or not embedding the nanoparticle(s), where such comparison can be made by creating ice-ball(s) in similar conditions in terms of cooling conditions with and without nanoparticle(s).

In some cases, nanoparticle(s) favor the formation of large ice-balls, preferentially ice-balls that comprise a large number of nanoparticles, preferentially a number of nanoparticle(s) larger than 1, 5, 10, 100, $10^3$, $10^5$ or $10^{10}$, or ice-ball(s) that surround or coat at least one nanoparticle with a coating or layer or ice that has a thickness larger than: i) the diameter of the nanoparticle and/or ii) $10^{-50}$, $10^{-20}$, $10^{-10}$, $10^{-5}$, $10^{-3}$, $10^{-1}$, 0, 1, 5, 10, 50 or 100 nm.

In still some other embodiment, non-predominant ice-ball or non-ice ball cryotherapy means that ice-ball(s) do/does not form during or in at least one step of the method or treatment according to the invention.

In still some other embodiment, non-predominant ice-ball or non-ice ball cryotherapy means that ice-ball(s) do/does not form within a lapse of time shorter than $10^3$, 10, 5, 2, 1, $10^{-5}$ or $10^{-10}$ year(s), hour(s), minute(s) or second(s), or between $10^{-10}$ and $10^3$ year(s), hour(s), minute(s) or second(s).

In still some other embodiment, non-predominant ice-ball or non-ice-ball cryotherapy means that ice-ball(s) do/does not form within a lapse of time longer than $10^{-10}$, $10^{-5}$, 1, 2, 5, 10 or $10^3$ year(s), hour(s), minute(s) or second(s).

In still some other embodiment, the non-predominant ice-ball cryotherapy or non-ice ball cryotherapy is characterized in that:

a) it is carried out at temperatures, preferentially initial, cooling, maintaining, and/or final temperature(s), larger than the ice-ball temperature, preferentially by at least $10^{-10}$, $10^{-5}$, $10^{-3}$, $10^{-1}$, 1, 5 or 10° C., and/or b) it results in the formation of less than $10^{50}$, $10^{20}$, $10^{10}$, $10^5$, $10^3$, 10, 5, 2 or 1 ice-ball(s).

In some other embodiment, the treatment, preferentially ice-ball cryotherapy is characterized in that:

i) it is carried out at temperatures, preferentially initial, cooling, and/or final temperature(s), lower than the ice-ball temperature, preferentially by at least $10^{-10}$, $10^{-5}$, $10^{-3}$, $10^{-1}$, 1, 5 or 10° C., and/or ii) it results in the formation of more than 1, 2, 5, 10, $10^3$, $10^5$, $10^{10}$ or $10^{50}$ ice-ball(s).

In another embodiment, the ice-ball temperature is such that when the temperature is decreased from a temperature above the ice-ball temperature, preferentially at least $10^{-20}$, $10^{-10}$, $10^{-5}$, $10^{-3}$, $10^{-1}$, 1, 5, 10 or 100° C. above the ice-ball temperature, and a temperature below the ice-ball temperature, preferentially at least $10^{-20}$, $10^{-10}$, $10^{-5}$, $10^{-3}$, $10^{-1}$, 1, 5, 10 or 100° C. below the ice-ball temperature, the number or size of ice-ball increases by a factor of at least 1, 1.1, 2, 5, 10, $10^3$ or $10^{10}$, where this factor can be $N_2/N_1$ or $S_2/S_1$, where $N_2$ and $N_1$ are the numbers of ice-balls below and above the ice-ball temperature, respectively, and $S_2$ and $S_1$ are the sizes of ice-balls below and above the ice-ball temperature, respectively.

In one embodiment of the invention, the invention relates to a method according to the invention comprising the following steps:

a) administering nanoparticles or cryo-probe to a medium, preferentially in the administration step;

b) cooling the medium comprising the nanoparticles and/or cryo-probe by decreasing the temperature of the medium from an initial temperature of said medium, to a cooling temperature of the medium, which is lower than the initial temperature, preferentially using the cryo-probe, preferentially in the cooling step;

c1) optionally not maintaining the medium comprising the nanoparticles at the cooling or maintaining temperature preferentially for a duration of time of more or less than 1, 10, 20, $10^2$, $10^3$ or $10^5$ seconds;

c2) optionally maintaining the medium comprising the nanoparticles at the cooling or maintaining temperature preferentially for a duration of time of more or less than 1, 10, 20, $10^2$, $10^3$ or $10^5$ seconds, preferentially during the maintaining step;

and d) warming the medium comprising the nanoparticles by increasing the temperature of the medium from the cooling temperature to a final temperature above the cooling temperature, preferentially during the warming step, preferentially characterized in that said cooling temperature of the medium is above the freezing temperature of the body part or above 5, 0, −5, −20, −40 or −100° C., preferably above −5 or 0° C., more preferably above 0° C.

In one embodiment of the invention, the medium is a body part or has at least one property in common with a body part.

In another embodiment of the invention, the medium is different from a body part or has at least one property that is different from a property of a body part.

In one embodiment, the medium comprises at least $10^{-5}$, $10^{-3}$, $10^{-1}$, 0, 1, 5, 10, 50, 70, 80, 90 or 99% in mass or volume of water or gel or matrix or oxygen or hydrogen or carbon or chemical element or carbonaceous material, and is preferably different from the body part, and is preferentially in a solid, liquid or gaseous state, and preferentially comprises the cryo-system.

In one embodiment of the invention, a medium that is different from a body part can be a medium that does not belong to, is not synthesized by, and/or does not originate from a living organism and/or individual. Such medium can be an assembly of substances or compounds, preferentially chemical ones, which is preferentially the environment of the nanoparticle.

In one embodiment of the invention, the environment of the nanoparticle(s) is a liquid, solid or at least 1, 10, $10^2$, $10^3$, $10^6$, $10^{10}$ or $10^{40}$ substance(s), preferentially one or more substance(s) different from the compound, which surround(s) or include(s) the nanoparticle over a distance measured from the center or the outer surface of the nanoparticle preferably lower than 1 m, 1 dm, 1 cm, 1 mm, 1 µm, 100 nm, or 10 nm.

In one embodiment of the invention, the environment of the nanoparticle(s) is a liquid, solid or at least 1, 10, $10^2$, $10^3$, $10^6$, $10^{10}$, or $10^{40}$ substance(s), preferentially one or more substance(s) different from the compound, which surround(s) or include(s) the nanoparticle over a distance measured from the center or the outer surface of the nanoparticle preferably larger than 1 m, 1 dm, 1 cm, 1 mm, 1 µm, 100 nm, or 10 nm.

In one embodiment of the invention, a substance of the environment of the nanoparticle according to the invention may be an atom, a molecule, a polymer, a chemical or biological substance, preferentially a substance different from the compound or nanoparticle, DNA, RNA, a protein, a lipid, an enzyme, or a nucleic or amino acid contained in this environment.

In one embodiment of the invention, the environment of the nanoparticle according to the invention may be a biological environment, that is to say an environment comprising at least one biological substance such as a cell, an organelle, DNA, RNA, a protein, a lipid, an amino acid, or a nucleic acid.

In an embodiment of the invention, the nanoparticles or cryo-system according to the invention is/are drugs, medical devices, cosmetic products, biological products, products used for research purposes, or products used to determine the properties of biological samples.

In one embodiment of the invention, the threshold, freezing, ice-ball, initial, cooling, and final temperatures are temperatures measured or occurring or reached in: i), the body part, or ii), an environment or region of the body part.

In some cases, the body part comprises the cryo-system.

In some other cases, the body part does not comprise the cryo-system.

In still some other cases, the cryo-system comprises or consists of the nanoparticle(s) and/or cryo-probe.

In another embodiment of the invention, the body part is the body part treated by the method or cryo-system according to the invention.

General Considerations

In still another embodiment of the invention, the property(ies) or features, preferentially of the nanoparticle(s) or cryo-system or method or treatment, described in each individual embodiment or section or sentence of this patent application can be combined to result in a combination of property(ies) or features, preferentially of the nanoparticle(s) or cryo-system or method or treatment.

In still another embodiment of the invention, when an entity such as the compound, substance, nanoparticle, cryo-system, radiation, has a property with a value of P1 that is higher, longer, or larger by a factor α than a property with a value of P2, it means that: P1=α·P2 (α preferentially larger than 1) or P1=α+P2 (α preferentially larger than 0).

In still another embodiment of the invention, when an entity such as the compound, substance, nanoparticle, cryo-system, radiation, has a property with a value of P1 that is lower, smaller, or shorter by a factor β than a property with a value of P2, it means that: P1=β·P2 (β is preferentially smaller than 1), P1=P2/β (β is preferentially larger than 1), P1=P2−β (β is preferentially larger than 0) or P1=β−P2.

In one aspect of the invention, the invention relates to magnetosomes for use in a method or cryo-system according to the invention comprising the following steps:

a) administering magnetosomes to a medium or body part;

b) cooling the medium or body part comprising the magnetosomes by decreasing the temperature of medium of body part from an initial temperature of said medium or body part, to a cooling temperature of the medium or body part, which is lower than the initial temperature;

c) optionally not maintaining the medium or body part comprising the magnetosomes at the cooling temperature for a duration of time of more than 100 seconds; and d) warming the medium or body part comprising the magnetosomes by increasing the temperature of the body part or medium from the cooling temperature to a final temperature above the cooling temperature.

The invention also relates to nanoparticle(s) or cryo-system for use in a method of treating a body part of an individual by sequential cryotherapy comprising the following steps:

a) administering nanoparticles to a body part of an individual;

b) cooling the body part comprising the nanoparticles by decreasing the temperature of the body part from an initial temperature to a cooling temperature of said body part, which is lower than the initial temperature;

c) optionally not maintaining the body part comprising the nanoparticles at the cooling temperature for a duration of time of more than 100 seconds;
and
d) warming the body part comprising the nanoparticles by increasing the temperature of the body part from the cooling temperature of said body part to a final temperature of said body part that is above the cooling temperature,
wherein the succession of steps of at least the cooling step and the warming step is repeated more than once, preferably more than 3 times.

The invention also relates to nanoparticle or cryo-system for use according to the invention, wherein the succession of the cooling step, the maintaining step and the warming step is repeated more than once, preferably more than 3 times.

The invention also relates to nanoparticle or cryo-system for use according to the invention, wherein said succession of steps is repeated between 1 and $10^{50}$, 1 and $10^{10}$, 1 and $10^5$, 1 and $10^3$, 1 and $10^2$, 1 and 50, or between 1 and 20 times.

The invention also relates to nanoparticle or cryo-system for use according to the invention, wherein said cooling temperature of the body part is:
above the freezing temperature or above 5, 0 or $-5°$ C., preferably above $-5$ or $0°$ C., more preferably above $0°$ C.;
and/or
above a threshold temperature, where the threshold temperature has at least one property selected from the group consisting of:
i) above the threshold temperature, the body part comprises a quantity of ice-balls smaller than the quantity of nanoparticles;
ii) above the threshold temperature, the volume occupied by ice-balls in the body part is smaller than the volume occupied by the nanoparticles in the body part;
iii) below the threshold temperature, the body part comprises a quantity of ice-balls larger than the quantity of nanoparticles;
iv) below the threshold temperature, the volume occupied by ice-ball in the body part is larger than the volume occupied by the nanoparticles in the body part;
and
v) below the threshold temperature, the size or diameter of at least one ice-ball is larger than the size or diameter of at least one nanoparticle.

The invention also relates to nanoparticle or cryo-system for use according to the invention, wherein the initial temperature and/or the final temperature is/are physiological temperature(s).

The invention also relates to nanoparticle or cryo-system for use according to the invention, wherein the cooling temperature has at least one characteristic selected from the group consisting of:
i) a difference $\Delta T_1$ between the initial and the cooling temperature lower than $57°$ C.,
and/or
ii) a difference $\Delta T_2$ between the final and the cooling temperature lower than $57°$ C., and preferably wherein the difference(s) $\Delta T_1$ and/or $\Delta T_2$ decrease(s) when the nanoparticle concentration increases in the body part.

The invention also relates to nanoparticle or cryo-system for use according to the invention, wherein:
in step d) the warming time to reach the final temperature from the cooling temperature is increased with increasing nanoparticle concentration in the body part,
and/or
in step b) the cooling time to reach the cooling temperature from the initial temperature is not predominantly dependent on nanoparticle concentration in the body part.

The invention also relates to the nanoparticle or cryo-system for use according to any of the preceding claims, wherein in step b) the temperature decreases from the initial temperature to the cooling temperature in the cooling step according to at least one of:
i) a cooling rate in the range from $10^{-6°}$ C./sec to $10^{6°}$ C./sec, preferably $10^{-3°}$ C./sec to $10^{3°}$ C./sec,
ii) a cooling rate with the nanoparticles that differs by less than $10°$ C./sec from the cooling rate without the nanoparticles,
iii) a cooling rate that does vary with varying nanoparticle concentration or vary by a factor in the range of less than $10^{-6°}$ C./sec to $10^{6°}$ C./sec, preferably less than $10^{-3°}$ C./sec to $10^{3°}$ C./sec, when the nanoparticle concentration increases, preferably either by a factor of at least 1.1 or from a concentration lower than 100 µg of nanoparticles per $cm^3$ of body part to a concentration larger than 100 µg of nanoparticles per $cm^3$ of body part,
iv) a cooling time of between $10^{-6}$ and $10^6$ seconds, preferably of between $10^{-3}$ and $10^3$ seconds,
v) a cooling rate that is smaller than the rate of increasing the temperature in the warming step d) by a factor in the range from $10^{-10}$ to $10^5$, preferably $10^{-5}$ to $10^3$,
and
vi) a cooling time shorter than the warming time in the warming step d) by a factor in the range of $10^{-6}$ to $10^6$, preferably $10^{-3}$ to $10^3$.

The invention also relates to nanoparticle or cryo-system for use according to the invention, wherein the maintaining step is carried out according to at least one of:
i) a maintaining time that is shorter than the cooling time and/or warming time, preferably by a factor of at least 1.5, more preferably by a factor of at least 10,
and
ii) fluctuation of the temperature during the maintaining step c) that is smaller, preferably by a factor of at least 1.5, than $\Delta T_1$ and/or $\Delta T_2$ according to the invention.

The invention also relates to nanoparticle or cryo-system for use according to the invention, wherein in step d) the temperature increases from the cooling temperature to the final temperature according to at least one of:
i) a warming rate in the range of $10^{-6°}$ C./sec to $10^{6°}$ C./sec, preferably in the range of $10^{-3°}$ C./sec to $10^{3°}$ C./sec,
ii) a warming rate with the nanoparticle(s) that differs by a factor of more than 1.1 from the warming rate without the nanoparticles,
iii) a warming rate that increases with increasing nanoparticle concentration by a factor in the range of $10^{-6°}$ C./sec to $10^{6°}$ C./sec, preferably $10^{-3°}$ C./sec to $10^{3°}$ C./sec,
iv) a warming rate that is smaller than the cooling rate by a factor in the range from $10^{-10}$ to $10^5$, preferably $10^{-5}$ to $10^3$,
v) a warming time of between $10^{-6}$ and $10^6$ seconds, preferably of between $10^{-3}$ and $10^3$ seconds,
and
vi) a warming time longer than the cooling time by a factor in the range of $10^{-6}$ to $10^6$, preferably a factor in the range $10^{-3}$ to $10^3$.

The invention also relates to nanoparticle or cryo-system for use according to the invention, wherein at least one of the cooling step, the maintaining step, and the warming step is carried out in the presence of:
i) a percentage of nanoparticles internalized in cells of the body part is in a range from $10^{-3}$% to 90%, and/or
ii) a concentration of nanoparticles in the body part is in the range from $10^{-9}$ to $10^{9}$ mg of nanoparticles per cm$^3$ of body part or from $10^{-5}$ to $10^{5}$ mg of nanoparticles per cell.

The invention also relates to nanoparticle or cryo-system for use according to the invention, wherein at least one of the cooling step, the maintaining step, and the warming step is carried out when nanoparticles occupy a portion of the body part, which is between $10^{-5}$% and 90% by mass or volume of the body part as a whole.

The invention also relates to nanoparticle or cryo-system for use according to the invention, wherein the individual in need thereof is suffering from an infectious disease, and the body part comprises cells affected by the infectious disease.

The invention also relates to nanoparticles or cryo-system for use according to the invention, wherein the nanoparticles are magnetosomes.

The invention also relates to a method comprising the following steps:
a) administering nanoparticles to a medium;
b) cooling the medium comprising the nanoparticles by decreasing the temperature of body part from an initial temperature of said medium, to a cooling temperature of the body part, which is lower than the initial temperature;
c) optionally not maintaining the medium comprising the nanoparticles at the cooling temperature for a duration of time of more than x seconds; and
d) warming the medium comprising the nanoparticles by increasing the temperature of the body part from the cooling temperature to a final temperature above the cooling temperature,
wherein the succession of steps of at least the cooling step, the maintaining step, and the warming step is repeated more than once, preferably more than 3 times.

The invention also relates to the use of the cryo-system according to the invention, to stimulate or activate the immune system.

In some cases, the immune system can comprise or be immune entities or substances such as immune cells, cytokines, and/or interleukins.

In some cases, the nanoparticles according to the invention can act as local reservoirs of cold or cold energy that preferentially creates a local perturbation, preferentially inside cells, that preferentially attract immune cells or immune entities, which preferentially attack or destroy pathological cells or the body part.

Preferably, the at least one nanoparticle is an immune attractant or at least one immune-attractant different from the nanoparticle(s) is bound or associated to the nanoparticle(s), preferentially releasably, and can be activated or released during one step of the method.

As intended herein an immune-attractant relates to a substance which attracts immune cells, optionally during at least one step of the method according to the invention.

The immune cells or immune entity(ies), which may preferentially be attracted by the immune-attractant according to the invention, may notably be selected from those belonging to the innate or adaptive immune system, in particular from the group consisting of an antigen presenting cell (APC), a basophil, a dendritic cell, an eosinophil, a granulocyte, a killing cell, a leukocyte, a lymphocyte, a macrophage, a mast cell, a natural killer, a neutrophil, a phagocyte, a B or T cell, such as a CD8+ T lymphocyte, a helper cell (Th1 or Th2), or a gamma delta T cell.

More preferably, the immune-attractant or immune entity is a pathological cell, an immune cell or part of an immune cell, an immune substance or part of an immune substance, where an immune substance can be one or more amino acids, an acid such as uric acid, an antigen, an antibody, a base such as NaOH, a cluster such as a cluster of differentiation, CpG, a complex such as a major histocompatibility complex, MHC, MHC-1, MHC-2, MHC-3, a cytokine, a cytoplasmic molecule such as HMGB1, DNA, preferentially bacterial DNA, an endotoxin, an enzyme, flagellin, glycan, glycol-conjugate, a ligand such as a ligand expressed at the surface of stressed cells, an interleukin, a lipid, a lipopolysaccharide (LPS), a lipoteichoic acid, a protein, a stress protein, a heat shock protein, a formylated protein, RNA, a pathogen-associated molecular pattern (PAMP), peptidoglycan, a receptor, such as a molecular pattern recognition receptor (PRR), a specific Toll-like receptor (TLR), a NOD-like receptor (NLR), a RIG-I-like receptor (RGR), or a C-type lectin receptor (CLR), a substance not belonging to the individual to be treated with the composition, an inactivated or attenuated microorganism, an inactivated toxic compound that leads to the appearance of the pathological cell, a biological substance, a subunit of protein, lipid, DNA, RNA, a substance produced by a plant, an animal, a bacterium, a fungus, a eukaryotic or prokaryotic cell, a polysaccharide, or a recombinant vector, a vaccine component or vaccine adjuvant, or an equivalently active substance to those listed above that is non-toxic such as MPLA, which is a non-toxic equivalent of LPS.

Preferably, the immune-attractant or immune entity is linked to the nanoparticle(s) by weak bonds, which can be hydrogen bonds or van der Waals interactions. Alternatively, the immune-attractant or immune entity may be linked to the nanoparticle(s) by strong bonds, which can be ionic or covalent bonds.

The invention also relates to a method or to the nanoparticle(s) or cryo-system for treating a body part of an individual by cryotherapy comprising a step of cooling with a cryo-system or at least one component of the cryo-system the body part of the individual from an initial temperature of the body part to a cooling temperature of the body part, which is lower than the initial temperature, wherein the cryo-system comprises two parts a) and b):
a) a first part, which is a cryo-probe having at least one property selected among i) and ii):
i) the cryo-probe is suitable for cooling down the body part internally or cooling down the body part from the inside of the body part, and the cryo-probe comprises a penetrating segment for penetrating the body part, wherein the penetrating segment has at least one property selected in the group consisting of: 1) the penetrating segment is in communication with a cryogen source, 2) the penetrating segment is smaller than at least 0, 1, 5, 10, 50% or ¹/₁₀th of the volume or dimension or diameter part of said body part, optionally of the largest volume or dimension or diameter or weight of said body part, or lighter or heavier than the weight of said body part, 3) the penetrating segment directly cools from the cryo-probe to the body part, and 4) the penetrating segment has at least one dimension or volume or diameter smaller than $10^5$, $10^3$, 100, 10, 5, 2 or 1 cm, and
ii) the cryo-probe is suitable for cooling down the body part externally or cooling down the body part from the outside of the body part, and the cryo-probe comprises a non-penetrating for not penetrating the body part, wherein the non-penetrating segment has at least one property selected in the group consisting of: 1) the non-penetrating segment is in communication with a cryogen source, 2) the non-penetrating segment is in contact or interaction with the external surface of the body part or with part of the external surface of the body part, and 3) the non-penetrating segment indirectly cools from the cryo-probe to the body part,
and
b) a second part, which is either:
i) an assembly of at least two nanoparticles, wherein the assembly comprises at least two nanoparticles bound to each other or associated with each other via binding/associating material,
or
ii) at least one nanoparticle comprising: α) iron and/or optionally at least one other metal or metalloid or semi-metal than iron and/or β) more than 1, 10, 30, 50 or 80% in mass or volume of iron or iron oxide or metal or metalloid or semi-metal or metal oxide, wherein the assembly of at least two nanoparticles or the at least one nanoparticle is to be cooled down by the cryo-probe,
wherein the cryotherapy preferentially involves:
i) at least 1, 5, 10, $10^3$, $10^5$ or $10^{10}$ ice-ball(s), preferentially per $cm^3$ of or mg or g body part, preferentially comprising at least 1, 5, 10, $10^3$, $10^5$ or $10^{10}$ nanoparticle(s), preferentially per $cm^3$ or mg or g of body part, or the formation of such ice-ball(s),
ii) at least 1, 5, 10, $10^3$, $10^5$ or $10^{10}$ piece(s) of ice, preferentially per $cm^3$ or mg or g of body part, preferentially comprising at least 1, 5, 10, $10^3$, $10^5$ or $10^{10}$ nanoparticle(s), preferentially per $cm^3$ or mg or g of body part, or the formation of such piece(s) of ice,
iii) at least 1, 5, 10, $10^3$, $10^5$ or $10^{10}$ nanoparticle(s), preferentially per $cm^3$ or mg or g of body part, preferentially without ice, preferentially without more than $10^{-50}$, $10^{-10}$, $10^{-5}$, $10^{-1}$, 1, 5, 10 g or mg of ice, preferentially per $cm^3$ or mg or g of body part, and/or
iv) at least 1, 5, 10, $10^3$, $10^5$ or $10^{10}$ nanoparticle(s), preferentially per $cm^3$ or mg or g of body part, preferentially without at least 1, 5, 10, $10^3$, $10^5$ or $10^{10}$ ice-ball(s) or piece(s) of ice, preferentially per $cm^3$ or mg or g of body part, or without the formation of such ice-ball(s) or piece(s) of ice.

In some cases, the penetrating segment can be larger or heavier than $10^{-3}$, $10^{-1}$, 0, 1, 5, 10, 50, 70, 80 or 90% of the volume or weight of body part.

In some cases, the penetrating segment can have at least one dimension or volume or diameter larger than $10^{-5}$, $10^{-3}$, $10^{-1}$, 1, 5 or 10 cm.

In one embodiment, the cryo-therapy comprises or involves: i) less than $10^{10}$, $10^5$, $10^2$, 50, 10, 5, 2, 1 or 0 ice-ball(s), preferentially per $cm^3$ of or mg or g body part, preferentially comprising at least 1, 5, 10, $10^3$, $10^5$ or $10^{10}$ nanoparticle(s), preferentially per $cm^3$ or mg or g of body part, or the formation of such ice-ball(s), or ii) less than $10^{10}$, $10^5$, $10^3$, 10, 5 or 1 piece(s) of ice, preferentially per $cm^3$ or mg or g of body part, preferentially comprising at least 1, 5, 10, $10^3$, $10^5$ or $10^{10}$ nanoparticle(s), or iii) less than $10^{10}$, $10^5$, $10^3$, $10^2$, 50, 20, 10, 5, 2, 1 or 0 nanoparticle(s), preferentially per $cm^3$ or mg or g of body part, preferentially without ice, preferentially without more than $10^{-50}$, $10^{-10}$, $10^{-5}$, $10^{-1}$, 1, 5, 10 g or mg of ice, preferentially per $cm^3$ or mg or g of body part, and/or iv) less than $10^{10}$, $10^5$, $10^3$, 50, 20, 10, 5, 2, 1 or 0 nanoparticle(s), preferentially per $cm^3$ or mg or g of body part, preferentially without at least 1, 5, 10, $10^3$, $10^5$ or $10^{10}$ ice-ball(s) or piece(s) of ice, preferentially per $cm^3$ or mg or g of body part, or without the formation of such ice-ball(s) or piece(s) of ice.

In one embodiment, at least one piece of ice or at least one ice ball or at least one nanoparticle ice-ball is larger than $10^{-5}$, $10^{-1}$, 1, 10, $10^3$, $10^5$ or $10^{10}$ nm or heavier than $10^{-10}$, $10^{-5}$, $10^{-1}$, 1, 10 or $10^3$ mg or g (gram) or kg.

In one embodiment, at least one piece of ice or at least one ice-ball or nanoparticle-ice-ball is smaller than $10^{20}$, $10^{10}$, $10^5$, $10^3$, 10, 5, 2, 1, $10^{-1}$ or $10^{-3}$ nm or lighter than $10^{10}$, $10^5$, $10^3$, 10, 5, 2, 1, $10^{-1}$, $10^{-3}$ or $10^{-5}$ mg or g (gram) or kg.

The invention also relates to the method or to the nanoparticle(s) or cryo-system according to the invention, wherein the cryo-system directly cools from the cryo-probe to the body part or to the at least one nanoparticle, preferentially when the cryo-system does not necessitate or does not use or does not comprise a thermal conductive material or when the cryo-system is not in contact or interaction with a thermal conductive material.

The invention also relates to the method or to the nanoparticle(s) or cryo-system according to the invention, wherein the cryo-system indirectly cools from the cryo-probe to the body part or to the at least one nanoparticle, preferentially when the cryo-system necessitates or uses or comprises or is in contact or interaction with a thermal conductive material.

The invention also relates to the method or nanoparticle(s) or cryo-system according to the invention, wherein the thermal conductive material has at least one property selected from the group consisting of:
i) the thermal conductive material is different from that constitutive of the cryo-probe/cryo-system and/or at least one component of the cryo-probe/cryo-system and/or body part and/or at least one nanoparticle,
ii) the thermal conductive material is between or sandwiched between the cryo-probe or cryo-system or at least one component of the cryo-probe or cryo-system and the body part or between the cryo-probe or cryo-system or at least one component of the cryo-probe or cryo-system and the at least one nanoparticle,
iii) the thermal conductive material is a part of the individual preferentially treated by the method, which is located between the body part such as a tumor, pathological site or body part to be treated and cryo-probe or cryo-system or at least one component of the cryo-probe or cryo-system, optionally it is a part or piece of the whole skin or organ or tissue or blood located between the body part such as a tumor, pathological site or body part to be treated and the cryo-probe/cryo-system or at least one component of the cryo-probe/cryo-system,
iv) the thermal conductive material is a gas, optionally a refrigerant gas,
v) the thermal conductive material is a liquid, optionally a refrigerant liquid,
vi) the thermal conductive material is a solid, optionally a refrigerant solid, vii) the thermal conductive material is a non-metallic material, viii) the thermal conductive material is an organic or carbonaceous material, and ix) the thermal conductive material has a thermal conductivity that is larger than the thermal conductivity of the body part or larger than $10^{-10}$, $10^{-8}$, $10^{-5}$, $10^{-1}$, 1, 5 or 10 W·m$^{-1}$·K$^{-1}$.

The invention also relates to the method or nanoparticle(s) or cryo-system according to the invention, wherein the cryo-probe is an apparatus or equipment that generates or produces a refrigerant gas or a refrigerant liquid or a refrigerant solid, wherein optionally the refrigerant gas, liquid, or solid is a gas, liquid, or solid that has a temperature that is below:

i) the temperature of the body part or the initial or final temperature, optionally by at least $10^{-5}$, $10^{-3}$, $10^{-1}$, 0.2, 0.5, 1, 5, 10, 20, 40, 50, 100, 200, 250, 300 or 500° C., or ii) 100, 50, 20, 10, 5, 2, 1, 0.1, 0, −2, −5, −10, −20, −50, −100, −150, −200, or −250° C., wherein optionally the temperature of the refrigerant gas or liquid or solid is measured or exists in the body part, wherein optionally the temperature of the refrigerant gas or liquid or solid is or corresponds to the temperature of the body part after the liquid or gas or solid has diffused inside or been inserted in the body part or has cooled down the body part, wherein optionally the refrigerant gas or liquid or solid is a gas or liquid or solid that has a temperature that is lower, optionally by at least a factor of at least 0, 0.5, 1, 1.1, 5, 10 or 100, than:

i) the temperature of the body part before or without the method or cryo-therapy, ii) the physiological temperature, iii) a temperature of the body part that is not decreased or cooled down by the cryo-probe, and/or iv) 100, 80, 50, 20, 10, 5, 2, 1, 0.5, 0.1, 0, −5, −10, −50, −100, −150, −200 or −250° C., wherein optionally the refrigerant gas or liquid or solid is selected in the group consisting of the following cooled or cold entities: i) a cooled or cold noble gas or liquid originating from such noble gas, ii) cooled or cold Argon gas, iii) cooled or cold Nitrogen gas, iv) cooled or cold Helium gas, v) cooled or cold metal, and v) cooled or cold semi-metal, wherein optionally a cooled or cold entity has a temperature lower than: 200, 100, 50, 20, 10, 5, 2, 1, 0, −5, −10, −50, −100, −200 or −250° C., wherein optionally at least one or two entity(ies) among the refrigerant gas, the refrigerant liquid, and the refrigerant solid has/have at least one property selected among: i) it/they exist(s) or coexist together, ii) it/they is/are comprised in, inside, at the surface of, or outside the cryo-probe/cryo-system or one of is component(s), iii) it/they is/are expelled from the cryo-probe/cryo-system or one of its component(s) or the surface, the inside, or the outside of the cryo-probe/cryo-system or one of its component(s), and iv) it/they is/are produced by the cryo-probe, wherein optionally at least one or two entity(ies) among the refrigerant gas, the refrigerant liquid, and the refrigerant solid is/are comprised in or diffuse(s) towards/in the cryo-system/cryo-probe or one of its component(s), the body part, the thermal conductive material and/or the nanoparticle(s).

In some other cases, the refrigerant gas, liquid, or solid is a gas, liquid, or solid that has a temperature that is above: i) the temperature of the body part or the cooling temperature, optionally by at least $10^{-5}$, $10^{-3}$, $10^{-1}$, 0.2, 0.5, 1, 5, 10, 20, 40, 50, 100, 200, 250, 300 or 500° C., or ii) −250, −200, −150, −100, −50, −20, −10, −5, −2, −1, 0, 1, 2, 5, 10, 20 or 50° C.

The invention also relates to the method or nanoparticle(s) or cryo-system according to the invention, wherein the cryo-probe or cryo-system or at least one component of the cryo-probe or cryo-system is an apparatus or equipment that cools down or decreases the temperature of the body part or of the at least one nanoparticle and has at least one property selected in the group consisting of:

i) the cryo-probe or cryo-system administers the at least one nanoparticle in the body part, optionally following at least one of the following manners or conditions: a) in some cases at a rate or speed smaller than $10^{10}$, $10^5$, $10^3$, 10 or $10^{-1}$ mg of nanoparticle(s) per minute or second of administration, b) in some other cases at a rate or speed larger than $10^{-10}$, $10^{-5}$, $10^{-1}$, 1, 5 or 10 mg of nanoparticle per minute or second of administration, c) in some cases within an injection volume that is larger than $10^{-5}$, $10^{-3}$, $10^{-1}$, 1, 5, 10, $10^3$ or $10^5$ μl of nanoparticle(s) or of the suspension comprising the nanoparticle(s), d) in some other cases within an injection volume that is smaller than $10^{10}$, $10^5$, $10^3$, 10, 5, 2, 1 or $10^{-1}$ μl of nanoparticle(s) or of the suspension comprising the nanoparticle(s), e) in some cases at a concentration that is larger than $10^{-10}$, $10^{-5}$, $10^{-1}$, 1, 5 or 10 mg of nanoparticle per liter, milliliter, microliter, gram, milligram or microgram of suspension or assembly of administered nanoparticle(s) or of body part, and f) in some other cases at a concentration that is smaller than $10^{50}$, $10^{10}$, $10^5$, 10, 5, 2, 1, $10^{-1}$, $10^{-5}$ or $10^{-10}$ mg of nanoparticle per liter, milliliter, microliter, gram, milligram or microgram of suspension or assembly of administered nanoparticle(s) or of body part, ii) the cryo-probe or cryo-system measures the temperature of the body part or of at least one nanoparticle, optionally of the whole body part, optionally the distribution of temperature within the whole body part, optionally the temperature at the location of the at least one nanoparticle, optionally the temperature gradient within the body part, optionally the temperature at a specific location of the body part, optionally a temperature at a distance from the cryo-probe/cryo-system or cryo-probe/cryo-system surface larger than 1 nm, optionally the temperature within more than $10^{-10}$, $10^{-3}$, $10^{-1}$, 1, 10, 50, 100, $10^3$, $10^6$ or $10^9$ percent in mass of body part or percent in volume of body part or percent in surface of body part or percent in length of body part or mm$^3$ of body part or cm$^3$ of body part, optionally a temperature measured with a resolution or sensitivity or precision that is larger than $10^{-5}$, $10^{-1}$, 1, 10 or $10^{3}$° C. as optionally measured per cm$^3$ or mm$^3$ of body part, iii) the cryo-probe or cryo-system either attracts the nanoparticle towards the body part or at least one component or part of the cryo-probe or the cryo-system or the cryo-probe or cryo-system maintains the nanoparticle(s) in the body part, optionally magnetically, optionally through the application of a magnetic field or magnetic field gradient, optionally through the application of a magnetic field of strength larger than B=$10^{-10}$, $10^{-6}$, $10^{-5}$, $10^{-3}$, $10^1$, 0, 1, 1, 5 or 10 Tesla (T), mT or μT applied in/on the body part or nanoparticle(s), optionally through the application of a magnetic field gradient of strength larger than ΔB=$10^{-10}$, $10^{-6}$, $10^{-5}$, $10^{-3}$, $10^{-1}$, 0, 1, 5 or 10 T, mT or μT per $m^3$ or $cm^3$, $mm^3$, g, mg, or μg of body part or nanoparticle(s), where ΔB is preferentially the variation of the magnetic field strength within a given unit volume of the body part, wherein the magnetic field or magnetic field gradient is optionally applied in a direction that is the opposite or different from that of the blood flow that optionally has a tendency to expel the nanoparticle(s) from the body part in the absence of such magnetic field, wherein optionally the magnetic field or magnetic field gradient is applied in a direction that is orientated towards at least one component of the cryo-probe such as the temperature adjuster or the temperature sensor, and iv) the cryo-probe or cryo-system images or visualizes the body part or the nanoparticle(s), optionally by echography, MRI, scanner, optical imaging, ultrasound imaging or magnetic particle imaging, optionally in some cases with a resolution that is sufficient to visualize the at least one nanoparticle, the body part, and/or to distinguish between the presence of the nanoparticle(s) and/or body part and/or to distinguish between the presence of a healthy cell or tissue and a pathological cell or tissue such as a tumor cell or tissue, wherein the at least one property mentioned above is optionally that conferred by at least one component of the cryo-probe or cryo-system, wherein optionally the cryo-probe or cryo-system comprises a first component that is a temperature adjuster that adjusts or decreases or maintains the temperature of the body part or of the at least one nanoparticle and at least one additional component selected in the group consisting of:

i) a second component that is an apparatus serving to administer nanoparticles such as a syringe or catheter or injection system, optionally comprising a pomp to control the injection rate, optionally adapted or modified compared with a usual syringe or catheter so that such apparatus can be inserted in the body part with the temperature adjuster or with at least one other component of the cryo-probe or cryo-system, ii) a third component that is a temperature sensor that measures the temperature of the body part or of the at least one nanoparticle, iii) a fourth component that attracts the at least one nanoparticle in the body part or maintains the nanoparticle in the body part, optionally by generating a magnetic field or magnetic field gradient optionally applied on the at least one nanoparticle, optionally within more than 1 second or within the whole treatment or part of the treatment or at least one step of the treatment, iv) a fifth component that images or visualizes the body part or nanoparticle(s), optionally selected in the group consisting of: an echographer, a scanner, a magnetic resonance imaging system, a magnetic particle imaging system, an optical imaging system, a photo-acoustic imaging system, and an ultrasound imaging system, and v) a sixth component that warms up or heats the body part or nanoparticle(s) or increases the temperature of the body part or nanoparticle(s), optionally during the warming step, where the sixth component is optionally a radiation, optionally a heating radiation, optionally a laser, a ultrasound, a magnetic field such as an alternating magnetic field, where the sixth component is optionally a heating apparatus or equipment, wherein optionally at least two different components of the cryo-probe or cryo-system are connected or communicating with each other, optionally through electric or electronic components, optionally through at least one software or computer, wherein optionally at least two different components are either comprised in the same unit, packaging, housing, case, carcass, hull, framework, frame, and/or skeleton, i.e. optionally the same system or computer or software controls these components, or in different units, packaging, housing, cases, carcasses, hulls, frameworks, frames, and/or skeleton, i.e. optionally different systems or computers or software control these components, wherein optionally two different components work or are switched on simultaneously, for example if the information or action given or provided by one component is needed for/by the other component to work, wherein optionally two different components work or are switched on one after the other, for example when two components can't be switched on or work simultaneously for example if such simultaneous action would prevent at least one component to work.

The invention also relates to the method or nanoparticle(s) or cryo-system according to the invention, wherein the cryo-system operates through a step in which a consign or instruction is given to at least one component of the cryo-probe or cryo-system, optionally by another component of the cryo-probe or cryo-system, or one component of the cryo-probe or cryo-system controls another component of the cryo-probe or cryo-system, wherein such step is optionally selected from the group consisting of:

i) setting or varying or increasing or controlling the temperature of the at least one component, preferentially of the temperature adjuster, at a desired temperature, optionally by the individual(s) using or operating the cryo-probe or cryo-system, optionally by or through the temperature sensor, optionally according to the following sequences in the following order or in a different order: 1) the temperature of the temperature adjuster is set at a desired temperature that the temperature adjuster should reach in the body part according to the choice made by the person operating or using the cryo-system, 2) the temperature adjuster is inserted in the body part or the temperature adjuster is positioned outside the body part in case a thermal conductive material is positioned between the body part and the temperature adjuster, 3) the temperature of the temperature adjuster varies towards the desired temperature, optionally from the initial temperature or a temperature close to the initial temperature to the cooling temperature or a temperature close to the cooling temperature, optionally inducing or resulting in the decrease of the temperature of the body part from the initial temperature to the cooling temperature, 4) the temperature sensor measures the temperature of the body part during at least one sequence, and 5) the temperature of the temperature adjuster stops varying or varies less when the desired or cooling temperature is reached, ii) adjusting or increasing or decreasing a magnetic field strength or a magnetic field gradient of the at least one component, preferentially the fourth component, to maintain the nanoparticles in the body part or to attract the nanoparticles towards the cryo-probe or a component of the cryo-probe or cryo-system, optionally after or based on the imaging of the body part or nanoparticles, where such imaging optionally enables determining if/where the nanoparticles are located in the body part, iii) adjusting at least one parameter of the nanoparticle administration of the at least one component, preferentially the second component, wherein the parameter of the nanoparticle administration is preferentially selected from the group consisting of: a) a location of nanoparticle administration, b) a speed of nanoparticle administration, and c) a concentration at which nanoparticles should be administered, optionally by the individual or medical personnel treating the individual receiving the treatment, optionally after or based on the imaging of the body part, where such imaging optionally enables determining the location of the body part to be treated and/or of the body part where nanoparticles should be administered, and iv) adjusting or increasing or decreasing at least one parameter of the at least one component, wherein the at least one component is preferentially for application of radiation, wherein the at least one component is preferentially the sixth component, and the at least one parameter is selected from the group consisting of: intensity, frequency, power, energy, and duration of application of the radiation, optionally in at least one of the following manners selected in the group consisting of: a) during the warming step, b) to heat up the body part or nanoparticle(s), c) within or during or for a time period that is controlled or adjusted by the radiation or the value of the at least one parameter of the radiation, d) from the cooling temperature to the final temperature, e) within less than 24 hours, f) more rapidly than without the use of such radiation, g) to reduce the overall time period of the treatment, h) to have the whole treatment duration being compatible with or similar to or smaller than the time during which anesthesia such as local or general anesthesia, optionally of the body part or individual, is carried out, and i) after or based on the measurement of the temperature of the body part by the temperature sensor, where the latter can under some circumstances estimate the time it takes for the body part to warm-up from the cooling temperature to the final temperature.

The invention also relates to the method or nanoparticles or cryo-system, wherein the second part in the cryo-system results in or is associated with at least one property, optionally measured or existing during at least one step of the method or part of one step of the method or less than 100, 50, 10, 5, 2 or 1% of the whole duration of the at least one step of the method, selected from the group consisting of:

i) a reduction in the temperature gradient in the body part compared with a cryo-therapy not using or not comprising or not involving nanoparticle(s), optionally by a factor of at least 0, 0.5, 1, 1.1, 1.5, 2, 5, 10 or 100, optionally by at least $10^{-3}$, $10^{-1}$, 0, 1 or $10°$ C. per $cm^3$ or $mm^3$ of body part and/or per second, optionally compared with a cryo-therapy not using or not comprising or not involving nanoparticle(s), ii) a temperature gradient smaller than the temperature gradient of the cryo-therapy not using, not comprising or not involving the nanoparticle(s), iii) a temperature gradient smaller than 0.1, 1, 10, 50, 100, 200 or $10^{3°}$ C. preferentially than a temperature gradient of cryo-therapy not involving nanoparticles, as optionally measured per $cm^3$ or $mm^3$ of body part and/or per second, whereas optionally the temperature gradient of the cryo-therapy not using or not comprising or not involving nanoparticle(s) is larger than 0.1, 1, 10, 50, 100, 200 or $10^{3°}$ C., as optionally measured per $cm^3$ or $mm^3$ of body part and/or per second, iii) an increase in the value of the minimum temperature that is reached during treatment or that is associated with the treatment compared with a minimum temperature that is reached during a cryotherapy or is associated with a cryotherapy not using, not comprising or not involving nanoparticle(s), optionally by a factor of at least 0, 0.5, 1, 1.1, 1.5, 2, 5, 10 or 100, optionally by at least $10^{-3}$, $10^{-1}$, 0, 1 or $10°$ C. per $cm^3$ or $mm^3$ of body part and/or per second, iv) a minimum temperature larger than −250, −200, −100, −50, −20, −10, −5, −2, −1, 0, 1, 2, 5 or $10°$ C., whereas optionally a minimum temperature of a cryo-therapy not using, not comprising, or not involving nanoparticle(s) is smaller than 50, 10, 5, 2, 1, 0, −1, −2, −5, −10, −20, −50, −100, −200 or $−250°$ C., v) a formation of at least one ice-ball comprising at least one nanoparticle, one ice-cooled nanoparticle, one ice-ball or a piece of ice embedding or surrounding or comprising at least one nanoparticle, whereas optionally a cryo-therapy not using, not comprising, or not involving nanoparticle(s) does not form at least one ice-ball comprising at least one nanoparticle, one ice-cooled nanoparticle, one ice-ball, or a piece of ice embedding or surrounding or comprising at least one nanoparticle, vi) an absence of formation of at least one ice-ball not embedding or not surrounding or not comprising at least one nanoparticle, whereas optionally a cryo-therapy not using, not comprising, or not involving nanoparticle(s) forms at least one ice-ball that does not comprise at least nanoparticle(s), vii) an increase in efficacy of destroying of a pathological cell at a given temperature, compared with a cryo-therapy not using or not comprising or not involving nanoparticle(s), or an increase in efficacy of at least one step of the method, viii) a decrease in the toxicity, side effects, or pain of the treatment, as optionally resulting from the use of higher cooling temperature, preferentially compared with a cryo-therapy not using or not comprising or not involving nanoparticle(s), and ix) the avoidance or suppression of anesthesia, optionally local or general anesthesia, optionally during the cooling or maintaining or warming step of the method, preferentially compared with a cryo-therapy not using or not comprising or not involving nanoparticle(s).

The invention also relates to the method or nanoparticles or cryo-system according to the invention, further comprising at least one of steps a) and b):

a) administering nanoparticle(s) to the body part, optionally before or while cooling the body part, and b) warming up or letting warm up or increasing the temperature of the body part or of the at least one nanoparticle, optionally either by increasing the temperature of the body part from the cooling temperature of said body part to a final temperature of said body part or optionally by letting the temperature of the body part increase from the cooling temperature of said body part to a final temperature of said body part, and at least one of the steps c) to i):

c) anesthetizing the body part or individual, optionally at least before or during part or the whole step of administering nanoparticle(s) to/in the body part, optionally in some cases anesthetizing locally the body part or region of the body part, optionally in some other cases anesthetizing generally the whole individual,
d) maintaining or letting maintained the temperature of the body part or of the at least one nanoparticle at: i) the cooling temperature or ii) the maintaining temperature that is optionally comprised between the cooling temperature and the initial or final temperature,
e) adjusting or decreasing or increasing or maintaining the temperature of the body part or of the at least one nanoparticle, optionally by using the temperature adjuster,
f) measuring the temperature of the body part or of the at least one nanoparticle, optionally by using a temperature sensor,
g) attracting the at least one nanoparticle in the body part, optionally by using the component of the cryo-probe that attracts the at least one nanoparticle towards the body part,
h) maintaining the at least one nanoparticle in the body part, optionally by using the component of the cryo-probe that maintains the at least one nanoparticle in the body part, optionally for more than $10^{-3}$ seconds,
i) imaging or visualizing the body part or the at least one nanoparticle, optionally by using a component of the cryo-probe selected in the group consisting of: an echographer, a scanner, a magnetic resonance imaging system, a magnetic particle imaging system, an optical imaging system, a photo-acoustic imaging system, and an ultrasound imaging system,
wherein optionally at least one step among a) to i) is carried out by using or switching on the cryo-probe or at least one component of the cryo-probe or cryo-system,
wherein optionally at least two different steps among a) to i) are carried out by using or switching on different components of the cryo-probe or by using differently the same component or different components of the cryo-probe, i.e. for example one component of the cryo-probe is switched on during one step and switched off during another step,
wherein optionally at least two different steps among a) to i) are carried out simultaneously or follow each other in any order,
wherein optionally at least one step, optionally step g) and/or h), is carried out by generating a magnetic field or magnetic field gradient optionally applied on the at least one nanoparticle, optionally during more than 1 second or during the whole treatment or during part of the treatment or during at least one step of the treatment or method.

The invention also relates to the method or nanoparticle(s) or cryo-system according to the invention, wherein the cryo-system or cryo-probe or at least one component of the cryo-system or cryo-probe enables:
i) to suppress or avoid or prevent: 1) step c), or 2) to use anesthesia such as local or general anesthesia, wherein optionally the suppression or avoidance or prevention of anesthesia is due to the fact that the cooling temperature reached during treatment is larger or above the temperature reached during a cryo-therapy treatment not using or not comprising or not involving nanoparticle(s), i.e. typically above −40° C., or is above −250, −200, −100, −50, −40, −20, −10, −5, −2 or 0° C., wherein optionally the suppression or avoidance or prevention of anesthesia occurs during at least one step of the method such as the cooling step, the warming step, and/or the maintaining step, optionally the suppression or avoidance or prevention of anesthesia does not occur during at least one step of the method such as the administration of the nanoparticle(s), wherein optionally the suppression or avoidance or prevention of anesthesia is that of general anesthesia and not of local anesthesia,
ii) to reduce a duration of anesthesia or strength, concentration or toxicity of products such as chemicals or gas used during anesthesia, preferentially compared with a cryo-therapy not using or not comprising or not involving nanoparticle(s),
iii) to reduce a duration of re-animation that can occur or be a necessary step following anesthesia, preferentially compared with a cryo-therapy not using or not comprising or not using nanoparticle(s),
iv) to reduce side effects, optionally associated with anesthesia, such as confusion, memory loss, dizziness, difficulty passing urine, bruising or soreness from the IV drip, nausea, vomiting, shivering, feeling cold, sore throat, feeling sick, allergic reaction, death, nerve blocks, discomfort, tingling sensation, weakness, twitching or weakened muscles, numbness, blurred or affected or reduced vision, dis-function or malfunction or damage of the body part, preferentially compared with a cryo-therapy not using or not comprising or not involving nanoparticle(s),
v) to suppress or prevent or avoid or reduce side effects or pain or diffusion of pathological cells or metastases resulting from a cryo-therapy treatment not using or not comprising or not involving nanoparticle(s), optionally due to low temperatures, typically below −40° C., which are reached during at least one step of such treatment without nanoparticle(s),
vi) to preserve or cryo-preserve or store or cryo-store at least one material selected from the group consisting of: biological material, body part, part of body part, biological part, enzyme, protein, DNA, RNA, tissue, organ, blood, biological fluid, cytoplasm, cell, and organelle, optionally for more than 0, $10^{-50}$, $10^{-10}$, $10^{-5}$, $10^{-1}$, 1, 5, 10, $10^3$ or $10^5$ second(s), wherein optionally such material is a healthy material, or does not comprise at least one virus, pathological bacterium or pathological/tumor cell,
vii) to destroy or damage or kill at least one material selected in group consisting of: biological material, body part, part of body part, biological part, enzyme, protein, DNA, RNA, tissue, organ, blood, biological fluid, cytoplasm, cell, and organelle, optionally for more than 0, $10^{-50}$, $10^{-10}$, $10^{-5}$, $10^{-1}$, 1, 5, 10, $10^3$ or $10^5$ second(s), wherein optionally such material is pathological or is a tumor or virus or pathological bacteria,
viii) to selectively destroy pathological material without destroying healthy material or without killing or inducing fever or side effects in or destroying/damaging an organ of the individual receiving the treatment,
and/or
ix) to enlarge and/or to modify the size of and/or to trigger the swelling of, optionally by a factor of at least 0, 1, 5, 10 or $10^3$, optionally by at least 0, $10^{-10}$, $10^{-5}$, $10^{-3}$, 1, 5, 10 or $10^3$ nm, at least one material selected inform the group consisting of: biological material, body part, part of body part, biological part, enzyme, protein, DNA, RNA, tissue, organ, blood, biological fluid, cytoplasm, cell, and organelle, optionally for more than 0, $10^{-50}$, $10^{-10}$, $10^{-5}$, $10^{-1}$, 1, 5, 10, $10^3$ or $10^5$ second(s).

The invention also relates to the method or cryo-system or nanoparticle according to the invention, wherein the initial temperature and/or a final temperature is/are physiological temperature(s), wherein the physiological temperature is a temperature selected from the group consisting of: i) a temperature of the body part before or after the body part is cooled, ii) the temperature of the individual who does not suffer from fever, iii) a temperature comprised between 25 and 45° C., iv) the temperature of the individual, or body part of the individual, or blood of the individual, which is not above by more than 5° C. than the average temperature of the individual, the body part of the individual, or the blood of the individual measured over the course of the life of the individual, and v) the temperature of the individual or body part of the individual or blood of the individual, which is not below by more than 5° C. than the average temperature of the individual, the body part, or the blood of the individual measured over the life of this individual.

The invention also relates to the method, nanoparticle, cryo-system, cryo-probe according to the invention, wherein the cooling temperature has at least one characteristic or property selected from the group consisting of:
i) a difference $\Delta T_1$ between the initial and the cooling temperature lower than $10^3$, 100, 57, 40, 30, 20, 10, 5, 2 or 1° C., and
ii) a difference $\Delta T_2$ between the final and the cooling temperature lower than $10^3$, 100, 57, 40, 30, 20, 10, 5, 2 or 1° C.

The invention also relates to the method, cryo-system, nanoparticle(s) or cryo-probe, wherein the at least one step of the method according to the invention, preferentially the cooling step, is repeated, optionally more than 2, 5, 10 or 20 times.

The invention also relates to the method, cryo-system, nanoparticle(s) or cryo-probe, wherein the at least one step of the method according to the invention, preferentially the cooling step, is not repeated or is repeated less than 1000, 100, 50, 20, 5 or 2 time(s).

The invention relates to the method according to the invention, wherein a given step of the method occurs or takes place before, during or after another step of the method that is different from the given step,
wherein optionally the cooling step occurs before the maintaining or warming step, or the cooling step is necessary for the maintaining or warming step to occur or for the method to be efficient or efficiently destroy or heal the individual or body part of the individual,
wherein optionally the nanoparticle administration step occurs before or during the cooling and/or maintaining and/or warming step, or the nanoparticle administration step is necessary for the cooling and/or maintaining and/or warming step(s) to be efficient or for at least one step of the method to be efficient or efficiently destroy or heal the body part of the individual,
wherein optionally the anesthetizing step occurs during the administration step, the cooling step, the maintaining step, and/or the warming step, or the anesthetizing step is necessary for the patient not to suffer from side effects or pain during at least one step of the method,
wherein optionally the adjusting step occurs during the cooling step, the maintaining step, and/or the warming step,
wherein optionally a duration of the adjusting step between the time point at which the temperature adjuster is set at a desired temperature that the body part should reach during the cooling step and the time point at which the body part decreases down to or reaches the cooling temperature is the duration of the cooling step,
wherein optionally a duration of the adjusting step between the time point at which the temperature adjuster is set at a desired temperature than the body part should reach during the maintaining step and the time point at which the body part maintains or keeps or has the maintaining temperature is the duration of the maintaining step,
wherein optionally a duration of the adjusting step between the time point at which the temperature adjuster is set at a desired temperature that the body part should reach during the warming step and the time point at which the body part increases up to or reaches the warming temperature is the duration of the warming step,
wherein optionally the step of measuring the temperature occurs before, during, or after the adjusting step, the cooling step, the maintaining step, and/or the warming step, or the step of measuring the temperature is used to adjust at least one parameter of the adjusting step, the cooling step, the maintaining step, and/or the warming step, where such parameter is optionally selected from the group consisting of: i) the cooling temperature, ii) the initial temperature, iii) the final temperature, iv) the rate at which the temperature increases during the warming step, v) the rate at which the temperature decreases during the cooling step, and vi) the temperature variation or fluctuation during the cooling, maintaining, and/or warming step(s),
wherein optionally the step of attracting the nanoparticles towards the body part or the step of maintaining the nanoparticles in the body part occurs before or during the cooling and/or maintaining and/or warming step, or the step of attracting the nanoparticles towards the body part or the step of maintaining the nanoparticles in the body part is necessary for the cooling and/or maintaining and/or warming step(s) to be efficient or for the method to be efficient or efficiently destroy or heal the body part of the individual,
wherein optionally without the step of attracting the nanoparticles towards the body part or the step of maintaining the nanoparticles in the body part, the concentration of nanoparticle(s) in the body part is insufficient for the treatment or method to be efficient,
wherein optionally the step of visualizing/imaging the body part and/or nanoparticle(s) is carried out before or during the nanoparticle administration step, optionally to determine the location where nanoparticles should be administered or are administered prior or during nanoparticle administration,
wherein optionally the step of visualizing/imaging the body part and/or nanoparticle(s) is carried out after the nanoparticle administration step, optionally to determine where nanoparticles are located after nanoparticle administration, optionally to determine if nanoparticles remain in the body part during the at least one step of the treatment,
wherein optionally the step of visualizing/imaging the body part and/or nanoparticle(s) is carried out before, during or after the cooling, maintaining, and/or maintaining step(s), optionally to determine is the treatment is efficient and/or results in side effects.

The invention also relates to the method according to the invention, wherein the step of cooling the body part is carried out during a cooling time $t_1$, wherein $t_1$ has at least one property selected from the group consisting of:
  i) $t_1$ is in some cases larger than $10^{-20}$, $10^{-6}$, $10^{-3}$, $10^{-1}$, 0, 1, 5, 10, $10^2$ or $10^5$ second(s) or minute(s),
  ii) $t_1$ is in some other cases shorter than 20 or 1 year, 24, 12 or 1 month, 30, 20, 10, 5, 2 or 1 day, 24, 12, 6, 3 or 1 hour, 60, 30, 20, 10, 5, 2 or 1 minute, 60, 30, 10, 5 or 1 second,
  and
  iii) $t_1$ is similar in the presence and absence of nanoparticle(s) or is not different by more than 1, 10, 50 or 80% or by a factor of more than 0, 1, 5, 10 or $10^5$ in the presence and absence of nanoparticle(s) or is not different by more than $10^{-1}$, 0, 1, 5, 10, $10^3$, $10^5$ or $10^{10}$ second(s) in the presence and absence of nanoparticle(s).

The invention also relates to the method, cryo-system, cryo-probe, nanoparticle(s), according to the invention, wherein at least one step of the method preferentially different from the cooling step, optionally the warming or maintaining step, is carried out during a time $t_2$, and $t_2$ has at least one property selected from the group consisting of:
  i) $t_2$ is in some cases longer than $t_1$, optionally by a factor of at least 0, 0.5, 1, 1.1, 5 or 10 or by at least $10^{-10}$, $10^{-5}$, $10^{-3}$, $10^{-1}$, 0, 1, 10 or 100 second(s),
  ii) $t_2$ is in some other cases shorter than $t_1$, optionally by a factor of at least 0, 0.5, 1, 1.1, 5 or 10 or by at least $10^{-10}$, $10^{-5}$, $10^{-3}$, $10^{-1}$, 0, 1, 10 or 100 second(s),
  iii) $t_2$ is in some cases longer than $10^{-20}$, $10^{-6}$, $10^{-3}$, $10^{-1}$, 0, 1, 5, 10, $10^2$ or $10^5$ second(s) or minute(s),
  iv) $t_2$ is in some other cases shorter than 20 or 1 year, 24, 12 or 1 month, 30, 20, 10, 5, 2 or 1 day, 24, 12, 6, 3 or 1 hour, 60, 30, 20, 10, 5, 2 or 1 minute, 60, 30, 10, 5 or 1 second,
  and
  v) $t_2$ is longer in the presence than absence of nanoparticles, optionally by more than 1, 10, 50 or 80% or by a factor of more than 0, 1, 5, 10 or $10^5$ or by more than $10^{-5}$, $10^{-1}$, 0, 1, 5, 10, $10^3$, $10^5$ or $10^{10}$ second(s).

In some cases, $t_2$ is the same as or similar than $t_1$ or do not differ from $t_1$ by more than $10^{-10}$, $10^{-5}$, $10^{-3}$, 0, 1, 5, 10, 100, $10^3$, $10^5$ or $10^{10}$ second(s) or minute(s).

The invention also relates to the method according to the invention, wherein the cooling temperature is larger than −200, −100, −50, −40, −30, −20, −10, −5, −2, −1, 0, 1, 2, 5 or 10° C.

In some cases, the cooling temperature can be lower than 200, 100, 50, 20, 10, 5, 2 or 1° C.

The invention also relates to the method according the invention, wherein the cryo-system, cryo-probe, at least one component of the cryo-system or cryo-probe, and/or at least one nanoparticle is, comprises, and/or produces: a) an apparatus, b) an equipment, c) a composition, d) a cosmetic composition, e) a chemical composition, f) a pharmaceutical composition, g) a biological composition, h) a suspension, i) a powder, j) a fluid, k) a ferro-fluid, l) a drug, m) a medical device, n) a product, and o) combinations thereof,
  wherein optionally any entity among a) to n) has a medical, diagnostic, and/or therapeutic purpose(s) or use(s),
  wherein optionally any entity among a) to n) is of class I, II, or III, or sub-class a, b, or c, or is an implant or is implantable or is not implantable or is activable or is not activable, preferentially by radiation.

The invention also relates to the method or cryo-system or cryo-probe or nanoparticle according to the invention, further comprising storing or maintaining the body part of the individual at the cooling temperature during a cryo-therapy, preferentially for more than $10^{-10}$, $10^{-5}$, $10^{-1}$, 0, 1, 5, 10 or 100 second(s), preferentially without changing or damaging or destroying or killing the body part or individual, preferentially enabling the preservation of the body part or individual, preferentially resulting in the destruction of the pathological site, tumor, pathological bacteria, or virus.

The invention also relates to the method or cryo-system or cryo-probe or nanoparticle(s) according to the invention, further comprising no storing or not maintaining the body part of the individual at the cooling temperature during a cryo-therapy, preferentially for more than $10^{-10}$, $10^{-5}$, $10^{-1}$, 0, 1, 5, 10 or 100 second(s).

The invention also relates to the method or cryo-system or cryo-probe or nanoparticle(s) according to the invention, wherein optionally a temperature gradient or temperature variation and/or a cooling temperature is/are reached in the body part and/or is/are associated with the temperature of the body part, optionally during the whole or part of the at least one step of the method, wherein the temperature gradient and/or cooling temperature has/have at least one property selected in the group consisting of:
  i) the temperature gradient is in some cases lower than $10^5$, $10^3$, 500, 150, 50, 10 or 1° C., optionally as measured per second or minute and/or per $cm^3$ or $mm^3$ of body part,
  ii) the temperature gradient is in some other cases larger than $10^{-10}$, $10^{-5}$, $10^{-3}$, $10^4$, 0, 1, 5, 10 or $10^{3}$° C., optionally as measured per second or minute and/or per $cm^3$ or $mm^3$ of body part,
  iii) the cooling temperature is in some cases above −200, −100, −50, −40, −20, −10, −5, −2, −1, 0, 1, 2, 5 or 10° C.,
  and
  iv) the cooling temperature is in some other cases below $10^3$, 500, 100, 50, 20, 10, 5, 2, 1, 0, −1, −5, −10, −20, −40, −50, −100 or −200° C.

The invention also method according to the invention, wherein the body part has a property selected from the group consisting of:
  i) more than $10^{-5}$, $10^{-3}$, 1, 20, 50, 80 or 90% of the mass or volume of the body part or more than $10^{-9}$, $10^{-6}$, $10^{-3}$, $10^{-1}$, 0, 1, 5, 10, 100 cm, $cm^2$, $cm^3$, mm, $mm^2$ or $mm^3$ of body part is cooled down, optionally by more than $10^{-5}$, $10^{-3}$, $10^{-1}$, 0, 1, 5 or $10^{3}$° C., optionally as measured below the initial or final temperature or above the cooling temperature, optionally as measured per second and/or per $mm^3$ or $cm^3$ of body part, optionally when the cryo-system enables the diffusion of cold or cold energy within a relatively large portion of the body part,
  ii) less than 100, 90, 80, 70, 50, 20, 10, 5, 2 or 1% of the mass or volume of the body part or less than $10^9$, $10^6$, $10^3$, 10, 5, 2, 1, $10^{-1}$, $10^{-3}$ or $10^{-6}$ cm, $cm^2$, $cm^3$, mm, $mm^2$ or $mm^3$ of body part is cooled down, optionally less than $10^5$, $10^3$, 500, 100, 80, 50, 40, 20, 10, 5, 2, 1 or $10^{-1}$° C., optionally as measured below the initial or final temperature or above the cooling temperature, optionally as measured per second and/or per $mm^3$ or $cm^3$ of body part, optionally when the cryo-system enables the diffusion of cold or cold energy within a relatively limited portion of the body part,
  iii) a larger volume, surface or length of the body part is cooled down in the presence than in the absence of nanoparticle(s), optionally an additional $10^{-5}$, $10^{-3}$, 1, 20, 50, 80 or 90% of the mass or volume of the body part or an additional $10^{-9}$, $10^{-6}$, $10^{-3}$, $10^{-1}$, 0, 1, 5, 10, 100 cm, cm$^2$, cm$^3$, mm, mm$^2$ or mm$^3$ of body part is cooled down in the presence than in the absence of nanoparticle(s), optionally when the nanoparticle(s) enable(s) the diffusion of cold or cold energy within a relatively large portion of the body part, which may occur when the nanoparticle(s) is/are homogenously distributed in the body part, iv) a smaller volume, surface or length of the body part is cooled down in the presence than in the absence of nanoparticle(s), optionally by $10^{-5}$, $10^{-3}$, 1, 20, 50, 80 or 90% of the mass or volume of the body part or by $10^{-9}$, $10^{-6}$, $10^{-3}$, $10^{-1}$, 0, 1, 5, 10, 100 cm, cm$^2$, cm$^3$, mm, mm$^2$ or mm$^3$ of body part, optionally when the nanoparticle(s) prevent(s) the diffusion of cold or cold energy within a relatively large portion of the body part, for example when nanoparticle(s) is/are aggregated and/or nanoparticle aggregate(s) is/are located near the cryo-probe or at least one component of the cryo-probe or cryo-system, wherein optionally the body part is the assembly of at least 1, 10, $10^3$, $10^5$ or $10^{10}$ pathological cell(s), pathological bacteria, and/or virus, or the region from which such assembly originate or is or has been located during or prior to the at least one step of the method.

The invention also relates to the method or cryo-system according to the invention, wherein the second part of the cryo-system has at least one property selected from the group consisting of:

i) the at least one nanoparticle is an ice nucleation site, wherein optionally the ice nucleation site forms an ice-ball or piece of ice surrounding at least one nanoparticle that is optionally larger than the ice-ball or piece of ice not surrounding the at least one nanoparticle and/or wherein optionally such formation occurs or is maintained at a higher temperature, optionally by more than $10^{-5}$, $10^{-3}$, $10^{-1}$, 0, 1, 2, 5, 10 or 100° C., than the temperature at which the ice-ball or piece of ice not surrounding the at least one nanoparticle exists or forms, and ii) a size of the ice nucleation site of the at least two nanoparticles bound to each other or associated with each other via binding/associating material is larger, optionally buy more than $10^{-3}$, $10^{-1}$, 0, 1, 5, 10 or 100 nm, than the size of the ice nucleation site of the at least two nanoparticles not bound to each other or not associated with each other via binding or associating material.

The invention also relates to the method or cryo-system or cryo-probe or nanoparticle(s) according to the invention, wherein the cryotherapy is a non-ice-ball cryotherapy, wherein the non-ice-ball cryotherapy has at least one property selected in the group consisting of:

i) the non-ice-ball cryotherapy does not use or comprise at least one ice-ball or one ice-ball embedding or comprising at least one metallic or iron oxide nanoparticle, optionally per m$^3$ or cm$^3$ or mm$^3$ of body part, ii) the non-ice-ball cryotherapy is carried out at, or reaches, a temperature that is either larger than the ice-ball temperature below which ice-balls form or start forming, or larger than −100, −50, −40, −20, −5, 0, or 5° C., wherein the ice-ball temperature is optionally the temperature below which ice-ball(s) form(s) or start(s) forming in the body part in the absence of nanoparticles.

The invention also relates to the method or cryo-system or cryo-probe or nanoparticle(s) according to the invention, wherein the cryotherapy is a nanoparticle-ice-ball cryotherapy, wherein the nanoparticle-ice-ball cryotherapy is a cryotherapy that uses or comprises at least one nanoparticle-ice-ball, wherein a nanoparticle-ice-ball is or comprises at least one ice-ball embedding or comprising at least one metallic or iron oxide nanoparticle, wherein optionally the nanoparticle-ice-ball cryotherapy is carried out at, reaches, or is associated with a temperature that is smaller than the nanoparticle-ice-ball temperature, wherein optionally the nanoparticle-ice-ball temperature is smaller than 50, 10, 5, 0, −2 or −5° C., wherein optionally the nanoparticle-ice-ball temperature is the temperature below which nanoparticle-ice-ball(s) form(s) or start(s) forming in the body part in the presence of nanoparticle(s).

The invention also relates to the method or cryo-system or cryo-probe or nanoparticle(s) according to the invention, wherein the at least one nanoparticle-ice-ball has at least one property selected from the group consisting of:

i) the at least one nanoparticle-ice-ball is larger than the at least one nanoparticle, optionally by a factor of at least 0, 0.1, 0.5, 1, 1.1, 1.5, 2, 5 or 10, optionally by at least 0, $10^{-6}$, $10^{-3}$, $10^{-1}$, 1 or 10 nm, ii) the at least one nanoparticle-ice-ball is larger than the at least one ice-ball, optionally by a factor of at least 0, 0.1, 0.5, 1, 1.1, 1.5, 2, 5 or 10, optionally by at least 0, $10^{-6}$, $10^{-3}$, $10^{-1}$, 1 or 10 nm, iii) there is a larger number of nanoparticle-ice-balls than a number of ice-balls used in the cryo-therapy, optionally by a factor of at least 0, 0.1, 0.5, 1, 1.1, 1.5, 2, 5 or 10, optionally by at least 0, 1, 2, 5 or 10, iv) the at least one nanoparticle-ice-ball is internalized in a cell, localized outside a cell, or in contact or interacting with biological material, whereas optionally at least one ice-ball does not have at least one property selected in the group consisting of: 1) it is internalized in a cell, 2) it is localized outside a cell, and 3) it is in contact or interaction with biological material, v) at least one nanoparticle-ice-ball is internalized in at least one cell whereas at least one ice-ball is localized outside at least one cell, vi) at least one nanoparticle-ice-ball leads to the swelling or enlargement or dilatation or cryo-preservation of at least one biological material or cell, optionally by a factor of at least 0, 0.1, 0.5, 1, 1.1, 1.5, 2, 5 or 10, optionally by at least 0, $10^{-6}$, $10^{-3}$, $10^{-1}$, 1 or 10 μm, optionally for more than $10^{-3}$, $10^{-1}$, 0, 1, 5, 10, $10^3$, $10^{10}$ or $10^{50}$ second(s), vii) the crystallinity of at least one nanoparticle-ice-ball is better than or increased compared with the crystallinity of at least one ice-ball or the number of crystallographic planes or ordered atom(s) in at least one nanoparticle-ice-ball is larger, optionally by a factor of at least 0, 0.1, 0.5, 1, 1.1, 1.5, 2, 5 or 10, optionally by at least 0, $10^{-6}$, $10^{-3}$, $10^{-1}$, 1 or 10 plane(s) or ordered atom(s), than the number of crystallographic planes or ordered atom(s) in at least one ice-ball, wherein optionally in some cases the size and/or number of the at least one nanoparticle-ice-ball is measured at a temperature where ice can form, optionally a temperature below 100, 50, 20, 10, 5, 2, 1, 0, −1 or −5° C.,
wherein optionally in some other cases the size and/or number of the at least one nanoparticle is measured at a temperature where ice can't form, optionally a temperature above −200, −100, −50, −40, −20, −10, −5, −2, −1, 0, 1 or 5° C.,
wherein optionally the size and/or number of the at least one ice-ball is measured at a temperature where ice can form, optionally a temperature below 100, 50, 20, 10, 5, 2, 1, 0, −1 or −5° C.

The invention also relates to the method or cryo-system or cryo-probe according to the invention, wherein the nanoparticle-ice-ball has at least one property selected from the group consisting of:
i) the nanoparticle-ice-ball exists at a larger temperature than the ice-ball, optionally by a factor of at least 0, 0.1, 0.5, 1, 1.1, 1.5, 2, 5 or 10, optionally by at least 0, $10^{-6}$, $10^{-3}$, $10^{-1}$, 1 or 10° C.,
and
ii) the nanoparticle-ice-ball transforms itself into the nanoparticle or melts within a lapse of time that is larger than the melting time of the ice-ball or ice, optionally by a factor of at least 0, 0.1, 0.5, 1, 1.1, 1.5, 2, 5 or 10, optionally by more than 0, $10^{-6}$, $10^{-3}$, $10^{-1}$, 1, 10, $10^3$ or $10^5$ second(s).

The invention also relates to the method or cryo-system or cryo-probe or nanoparticle(s) according to the invention, wherein the nanoparticle is an ice-cooled nanoparticle, wherein the ice-cooled nanoparticle has at least one property selected from the group consisting of:
i) the ice-cooled nanoparticle is a nanoparticle that is cooled down by ice, an ice-ball, and/or a nanoparticle-ice-ball, preferentially during the cooling step, optionally by decreasing the temperature of the nanoparticle below 100, 50, 10, 5, 2 1 or 0° C.,
ii) the ice-cooled nanoparticle is a nanoparticle that is or comprises or forms a nanoparticle-ice-ball, optionally at a temperature that is lower than 100, 50, 10, 5, 2 1 or 0° C.,
iii) the ice-cooled nanoparticle is a nanoparticle that comprises or forms or maintains ice in the body part at a temperature that is larger than −100, −50, −40, −20, −10, −5, −2, −1, 0, 1 or 5° C. or at a temperature that is larger than the temperature at which ice forms in the body part in the absence of the nanoparticle,
iv) the ice-cooled nanoparticle or the body part in which it is comprised has a temperature that increases at a smaller rate or smaller speed than the temperature of the at least one non-ice-cooled nanoparticle, optionally by a factor of at least 0, 0.1, 0.5, 1, 1.1, 1.5, 2, 5 or 10, optionally by at least 0, $10^{-6}$, $10^{-3}$, $10^{-1}$, 1 or 10° C. per second, optionally per unit volume or $cm^3$ of body part, optionally in some cases when the ice-cooled and/or non-ice cooled nanoparticle is/are exposed to radiation, optionally in some other cases when the ice-cooled and/or non-ice-cooled nanoparticle is/are not exposed to radiation,
v) the ice-cooled nanoparticle or the body part in which it is comprised has a temperature, which increases more slowly or at a smaller rate than the temperature of the body part not comprising the at least one ice-cooled nanoparticle, optionally by a factor of at least 0, 0.1, 0.5, 1, 1.1, 1.5, 2, 5 or 10, optionally by at least 0, $10^{-6}$, $10^{-3}$, $10^{-1}$, 1 or 10° C. per second, optionally per unit volume or $cm^3$ of body part, optionally when the nanoparticle(s) enable(s) keeping or maintaining the cold or cooling energy,
and
vi) the ice-cooled nanoparticle or the body part in which it is comprised has a temperature, which increases at a rate or speed smaller than $10^3$, 100, 50, 10, 5, 2 or 1° C. per second, optionally per $cm^3$ of body part.

The invention also relates to the method or cryo-system or cryo-probe or nanoparticle(s) according to the invention, wherein the cryotherapy stimulates or activates the immune system or at least one immune cell or immune entity of the individual, optionally to destroy at least one pathological/tumor cell or pathological bacteria or virus, optionally after nanoparticle administration and/or the cooling step, optionally due to the ice-cooled or cooled nanoparticle, optionally in the region where nanoparticle(s) and/or pathological/tumor cell or pathological bacteria or virus is/are located, optionally when the cooling temperature is above a certain threshold value, optionally when the cooling temperature is above −250, −200, −100, −50, −40, −20, −10, −5, −2, −1, 0, 1, 5 or 10° C. (degree Celsius),
wherein optionally the ice-cooled or cooled nanoparticle causes a local thermal perturbation,
wherein optionally the ice-cooled or cooled nanoparticle or the local thermal perturbation attracts or triggers the presence of at least one component of the immune system, optionally within the region or body part where nanoparticle(s) and/or pathological/tumor cell(s) and/or bacteria and/or virus is/are located,
wherein optionally the threshold temperature is such or is sufficiently high or large that it does not stop partly or fully the activity or metabolic activity or enzymatic activity of the body part or individual or of at least one component of the body part such as a cell, an enzyme, a protein comprised in the body part.

The invention will be further described by the following non-limiting figures and examples.

Example 1: Preparation of Magnetosomes Coated with Carboxy-Methyl Dextran (N-CMD)

Growth of MSR-1 magnetotactic bacteria. *Magnetospirillum gryphiswaldense* strain MSR-1 (DSM6361) was purchased from Deutsche Sammlung von Mikro-organismen and Zellkulturen (Brunswick, Germany). First, MSR-1 cells were deposited on a solid activated charcoal agar medium, containing 20 mM filtered iron citrate and 100 mM DTT (1,4-dithiothreitol) and incubated at 29° C. under microaerobic conditions for 7 days. Then, several black-brown colonies were collected from the solid agar medium and were cultivated and amplified at 29° C. under stirring. Cells were then introduced in a 35 L fermentation medium. Fermentation was carried out at 29-30° C. under agitation at 200 rpm for 5 days. During fermentation, the pH was maintained at 6.9 by adding an acidic feeding medium containing in 1 l of medium 118 ml of 85% lactic acid, 18 ml of 25% to 28% ammonia, 2.4 g of magnesium sulfate, 6 g of potassium phosphate, 0.2 ml of propylene glycol, 6 g of yeast extract and 7 ml of mineral elixir containing an iron source. The growth of magnetotactic bacteria was stimulated by bubbling oxygen in the growth medium. The temperature, agitation speed, pH, feeding pump flow and oxygen concentration were monitored and adjusted using an ez-Controller and BioXpert software from Applikon Biotechnology. After fermentation, MSR-1 cells were concentrated and washed in water using tangential flow filtration. To lyse the bacteria and obtain a suspension containing pyrogenic MC, concentrated MSR-1 cells were resuspended in 5 M NaOH, and heated at 60° C. for 2 hours. Then they were sonicated four times in the presence of a solution of PBS at 10 W for 20 s to remove all lysed bacterial cells that remain. This extraction step for isolating magnetosomes from MSR-1 cells was carried out about three times. The results were obtained from three replicates. MC then underwent the following four treatments: (i) they were re-suspended in a solution containing 1% Triton X-100 and 1% SDS and were then heated at 50° C. overnight; (ii) they were mixed in phenol at pH 8 and then heated at 60° C. for 2 hours in a 25 kHz sonicating bath (SB); (iii) they were re-suspended in chloroform and heated at 60° C. for 2 hours; and (iv) they were mixed with a 1M NaOH solution and heated at 60° C. for 1 hour in the SB, to remove all proteins and lipids. After bacterial lysis and each of the five treatments with detergents, magnetosomes were isolated from non-magnetic organic debris using a neodymium magnet. The supernatant was then removed and replaced by a detergent. Uncoated magnetosome minerals labeled N containing a low percentage of residual organic materials were thus obtained. They were autoclaved and stored at −80° C. The coating procedure was carried out under sterile conditions, using a sterile flow hood. To prepare the suspension of N-CMD, a solution containing 840 mg of carboxy-methyl dextran (CMD) powder dissolved in 12 ml of pyrogen-free water was first prepared. It was filtered with a polyether sulfone filter of 0.2 mm and its pH values was adjusted to 4.1. 1.5 ml of a suspension-CMD at 20 mg of iron per ml was then positioned against a neodymium magnet of remanence 1.3 T for 5 minutes. The supernatant was removed and replaced 6 ml of a CMD solution at 70 mg/ml. The mixture was then sonicated in the SB overnight at room temperature. After sonication, the suspension of coated magnetosome minerals was centrifuged at 13 000 g for 90 minutes, and the supernatant was removed and replaced by pure water. A neodymium magnet was then positioned against the tube containing the suspension of coated magnetosome minerals, and the supernatant was removed and replaced by pure water.

Example 2: Internalization of N-CMD in PC3-Luc Cells

Material and Methods: PC3-Luc cells were cultivated in was grown in high-glucose DMEM containing 10% fetal calf serum (FCS), 100 U/mL penicillin and 100 µg/mL at 37° C. in a 5% $CO_2$ atmosphere with 95% relative humidity until confluency. $5·10^5$ cells per mL were harvested. We introduced 500 µl containing $2.5\ 10^5$ cells in 12 wells (wells 1 to 12) and 500 µl of growth medium in 12 other wells (wells 13 to 24). Then, we left the 24 wells plate in an incubator for 24 hours at 37° C. in 5% $CO_2$ to let the cells adhere at the bottom of the wells. We then removed the growth medium. We added to the 12 wells containing the cells: i) 500 µl of growth medium (wells 1 to 3), ii) 500 µl of a suspension of N-CMD at 62·5 µg/ml (wells 4 to 6), iii) 500 µl of a suspension of N-CMD at 250 µg/ml (wells 7 to 9), iv), 500 µl of a suspension of N-CMD at 1 mg/ml (wells 10 to 12). We added to the 12 wells containing the growth medium without the cells: i) 500 µl of growth medium (wells 13 to 15), ii) 500 µl of a suspension of N-CMD at 62·5 µg/ml (wells 16 to 18), iii) 500 µl of a suspension of N-CMD at 250 µg/ml (wells 19 to 21), iv), 500 µl of a suspension of N-CMD at 1 mg/ml (wells 22 to 24). The magnetosomes incubated with the cells (wells 1 to 12) or the magnetosomes incubated with the growth medium alone (wells 13 to 24) were then incubated for different times of 5 minutes, 30 minutes, 3 hours, 6 hours, 24 hours, and 96 hours. The growth medium was removed from the different wells. 0.25% of trypsin EDTA was added to detach the cells from the bottom of the wells. For wells 1 to 12, the number of cells was counted using a cell counter for calculating the amount of internalized iron per cell. The content of the different wells was collected and centrifuged for 5 minutes at 1000 rpm and we harvested the growth medium with the magnetosomes originating from wells 13 to 24 or the cell pellets originating from wells 1 to 12. The magnetosomes originating from wells 13 to 24 and cell pellets originating from wells 1 to 12 were mixed with 12 N HCl overnight and then with 2% nitric acid for 48 hours to dissolve the magnetosomes into ionic iron. The amount of iron measured in samples originating from wells 13 to 24 was subtracted from the amount of iron measured in samples originating from wells 1 to 12. The ionic iron concentration was measured using an ICP-AES and we deduced the amount of iron originated from magnetosomes internalized per cell.

Results and Discussion:

For 62 µg/mL of N-CMD incubated with PC3-Luc cells, the quantity of iron coming from magnetosomes that is internalized in cells increases from 6 pg per cell at 5 minutes to 11 pg per cell at 3 hours and then decreases to 5 pg per cell at 96 h (FIG. 1(*a*)). At the same time the percentage of iron coming from the magnetosomes, which is internalized in PC3-cells increases from 7% at 5 minutes to 21% at 96 hours (FIG. 1(*b*)).

For 250 µg/mL of N-CMD incubated with PC3-Luc cells, the quantity of iron coming from magnetosomes that is internalized in cells increases from 31 pg per cell at 5 minutes to 56 pg per cell at 3 hours and then decreases to 45 pg per cell at 96 h (FIG. 1(*a*)). At the same time the percentage of iron coming from the magnetosomes, which is internalized in PC3-Luc cells increases from 9% at 5 minutes to 24% at 96 hours (FIG. 1(*b*)).

For 1000 µg/mL of N-CMD incubated with PC3-Luc cells, the quantity of iron coming from magnetosomes that is internalized in cells increases from 112 pg per cell at 5 minutes to 272 pg per cell at 3 hours and then decreases to 189 pg per cell at 96 h (FIG. 1(*a*)). At the same time the percentage of iron coming from the magnetosomes, which is internalized in PC3-cells increases from 8% at 5 minutes to 22% at 96 hours (FIG. 1(*b*)).

For the three studied concentrations, we observe an increase of the quantity of magnetosomes internalized per cell between 5 minutes and 3 hours of incubation, and then a decrease of this quantity per cell between 3 and 96 hours. The maximum quantity of magnetosomes internalized per cell is observed for an incubation time of 3 hours and for a magnetosome concentration of 1 mg/mL at 272 pg of iron per cell. When we considered the percentage of internalized magnetosomes, estimated as the ratio between the quantity of magnetosomes internalized in cells and the quantity of magnetosomes incubated with cells, we observed that the maximum percentage was reached at 96 hours, because the cell multiplication over time, and the number of cells that can internalize the magnetosomes is larger at this time.

Example 3: Cytotoxicity of PC3-Luc Cells Brought into Contact with Various Concentrations of N-CMD (0 mg/mL, 62 µg/mL, 250 µg/mL, 1000 µg/mL) During 3 Hours and Cooled Down to −10° C., and −0° C. Non Ice-Ball Cellular Death Highlighted in the Presence of Nanoparticles Note: In examples 3 to 5, the cells with/without the nanoparticles and/or the growth medium with/without the nanoparticles are let warming up during the warming step by being exposed to ambient air.

Material and method: 0.2 mL Eppendorf were used for this experiment. A hole was made through the cap of the Eppendorf to insert a thermocouple in the Eppendorf and measure the temperature inside. In each Eppendorf, we introduced 100 µl of cellular suspension containing 2·5 $10^5$ PC3-Luc cells. The tubes were centrifuged at 1000 rpm during 5 minutes. After that, we removed the growth medium and we added 100 µl of the different magnetosome suspensions containing 1000, 250, 62.5 µg/mL of N-CMD or 100 µl of growth medium. We incubated the cells with magnetosomes or growth medium (0 µg/mL) for 3 hours. As a whole, we used 48 Eppendorf (3 Eppendorf per condition) containing: i) 1000 µg/mL of N-CMD maintained at room temperature (tubes 1 to 3), cooled down to 10° C. (tubes 4 to 6), cooled down to 0° C. (tubes 7 to 9), ii) 250 µg/mL of N-CMD maintained at room temperature (tubes 13 to 15), cooled down to 10° C. (tubes 16 to 18), cooled down to 0° C. (tubes 19 to 21), iii), 62·5 µg/mL of N-CMD maintained at room temperature (tubes 25 to 27), cooled down to 10° C. (tubes 28 à 30), cooled down to 0° C. (tubes 31 to 33), iv) 0 µg/mL of N-CMD maintained at room temperature (tubes 37 to 39), cooled down to 10° C. (tubes 40 to 42), cooled down to 0° C. (tubes 43 to 45). Under laminar flow hood, we have exposed the Eppendorf tubes to a URGO product of reference 140111 that cools down the Eppendorf tubes by applying a spray of dimethyl ether on the Eppendorf tubes to decrease the temperature of the tubes from an initial temperature $T_i$, corresponding to room temperature (~28° C.), to a minimum temperature, $T_{min}$, of ~10° C. and ~0° C. This step occurred during a time $t_i$. We attempted to reach these temperatures. However, in some cases, there were a few degrees difference between the minimum temperature reached during the experiments and the minimum temperature that was targeted. Concerning the minimum temperature reached during the cycle that targeted 0 degree, it was always above 0 degree. After we reached the minimum temperature, we have let the Eppendorf tubes warming up from $T_{min}$ up to a final temperature, $T_f$, of equilibrium, which is close to room temperature (~28° C.), during a second step. This second step occurred during a time $t_f$. 48 hours later, we then measured with the MTT assay the cellular viability resulting from such treatment.

Results and Discussion:

We have observed that:
i) The duration of the cooling step does not strongly depend on nanoparticle concentration (between 0 mg/mL and 1 mg/mL of M-CMD) and minimal temperature (0 and 10 degrees). It is 22-47 seconds for the cooling step between RT and 0 degree for NP concentration between 0 mg/mL and 1 mg/mL and 13-32 seconds for the cooling step between RT and 10 degree for NP concentration between 0 mg/mL and 1 mg/mL.
ii) The rate at which the temperature is decreased during the cooling step (cooling rate) does not strongly depend on nanoparticle concentration (between 0 mg/mL and 1 mg/mL of M-CMD) and minimal temperature (0 and 10 degrees). It is 0.6-1.4° C. per second for the cooling step between RT and 0 degree for NP concentration between 0 mg/mL and 1 mg/mL and 0.6-1.7° C. per second for the cooling step between RT and 10 degree for NP concentration between 0 mg/mL and 1 mg/mL;
iii) By contrast to the duration of the cooling step, the duration of the warming step increases with increasing magnetosome concentration from 310 sec. at 0 mg/mL to 461 sec. at 1 mg/mL for the warming step from 0 degree to room temperature and from 256 sec. at 0 mg/mL to 396 sec. at 1 mg/mL for the warming step from 10 degree to room temperature;
iv) By contrast to the cooling rate, the warming rate decreases with increasing magnetosome concentration from 0.08° C. per sec for 0 mg/mL down to 0.06° C. per sec. for 1 mg/mL for the warming step between 0 degree and room temperature and from 0.07° C./sec for 0 mg/mL down to 0.05° C. per sec. for 1 mg/mL for the rewarming step between 10 degree and room temperature.
v) The duration of the warming step is longer than the duration of the cooling step and the warming rate is shorter than the cooling rate.

At 10 degrees, the percentage of living cells remains similar between 0 mg/mL (87±13%) and 1 mg/mL (77±2%) while at 0 degree, the percentage of living cells decreases from ~88±6% at 0 µg/mL of N-CMD to ~75±3% at 1 mg/mL. In this example, we have therefore shown that we could induce cellular death by decreasing the temperature of PC3-Luc cells in the presence of 1 mg/mL of N-MCD to a temperature that is just above 0° C. (degree Celsius).

Example 4: Cytotoxicity of PC3-Luc Cells Brought into Contact with 1 mg/mL of N-MCD During 3 Hours or Brought into Contact with Growth Medium without N-CMD During 3 Hours and Exposed to Two Different Types of Cooling Treatments with Short and Long Cycles For the short cycles, the cells with/without N-CMD are cooled down with URGO to a minimal temperature of 10° C., 5° C., 0° C., −5° C., −10° C., −20° C., and −40° C., and these assemblies are then let warming up from the minimal temperature to room temperature by being exposed to ambient air without using the URGO system.

For the long cycles, the cells with/without N-CMD are cooled down with URGO to a minimal temperature of 10° C., 5° C., 0° C., −5° C., −10° C., −20° C., and −40° C., the temperature of these assemblies is then maintained with URGO at the minimal temperature during 75-295 sec, and these assemblies are then let warming up from the minimal temperature to room temperature by being exposed to ambient air without using the URGO system.

Material and method: 0.2 mL Eppendorf were used for this experiment. A hole was made through the cap of the Eppendorf to insert a thermocouple in the Eppendorf and measure the temperature inside. In each Eppendorf, we introduced 100 µl of cellular suspension containing 2.5 $10^5$ PC3-Luc cells. The tubes were centrifuged at 1000 rpm during 5 minutes. After that, we removed the growth medium and we added 100 µl of the different magnetosome suspensions containing 1000 µg/mL of N-CMD or 100 µl of growth medium. We incubated the cells with magnetosomes or growth medium (0 µg/mL) for 3 hours. As a whole, we used 72 Eppendorf (3 Eppendorf per condition) containing: i) 1000 µg/mL of N-CMD maintained at room temperature (tubes 1 to 3), 0 µg/mL of N-CMD maintained at room temperature (tubes 4 to 6), 1000 µg/mL of N-CMD cooled down to ~10° C. with short cycle (tubes 4 to 6), 0 µg/mL of N-CMD cooled down to ~10° C. with short cycle (tube 7 to 9), 1000 µg/mL of N-CMD cooled down to ~10° C. with long cycle (tubes 10 to 12), 0 µg/mL of N-CMD cooled down to ~10° C. with short cycle (tube 13 to 15), 1000 µg/mL of N-CMD cooled down to ~5° C. with short cycle (tubes 13 to 15), 0 µg/mL of N-CMD cooled down to ~5° C. with short cycle (tube 16 to 18), 1000 µg/mL of N-CMD cooled down to ~5° C. with long cycle (tubes 19 to 21), 0 µg/mL of N-CMD cooled down to ~5° C. with long cycle (tube 22 to 23), 1000 µg/mL of N-CMD cooled down to ~0° C. with short cycle (tubes 22 to 24), 0 µg/mL of N-CMD cooled down to ~0° C. with short cycle (tube 22 to 24), 1000 µg/mL of N-CMD cooled down to ~0° C. with long cycle (tubes 22 to 24), 0 µg/mL of N-CMD cooled down to ~0° C. with long cycle (tube 22 to 24), 1000 µg/mL of N-CMD cooled down to ~−5° C. with short cycle (tubes 25 to 27), 0 µg/mL of N-CMD cooled down to ~−5° C. with short cycle (tube 28 to 30), 1000 µg/mL of N-CMD cooled down to ~−5° C. with long cycle (tubes 31 to 33), 0 µg/mL of N-CMD cooled down to ~−5° C. with short cycle (tube 34 to 36), 1000 µg/mL of N-CMD cooled down to ~−10° C. with short cycle (tubes 37 to 39), 0 µg/mL of N-CMD cooled down to ~−10° C. with short cycle (tube 40 to 42), 1000 µg/mL of N-CMD cooled down to ~−10° C. with long cycle (tubes 43 to 45), 0 µg/mL of N-CMD cooled down to ~−10° C. with short cycle (tube 46 to 48), 1000 µg/mL of N-CMD cooled down to ~−20° C. with short cycle (tubes 49 to 51), 0 µg/mL of N-CMD cooled down to ~−20° C. with short cycle (tube 52 to 54), 1000 µg/mL of N-CMD cooled down to ~−20° C. with long cycle (tubes 55 to 57), 0 µg/mL of N-CMD cooled down to −20° C. with short cycle (tube 58 to 60), 1000 µg/mL of N-CMD cooled down to ~−40° C. with short cycle (tubes 61 to 63), 0 µg/mL of N-CMD cooled down to ~−40° C. with short cycle (tube 64 to 66), 1000 µg/mL of N-CMD cooled down to ~−40° C. with long cycle (tubes 67 to 69), 0 µg/mL of N-CMD cooled down to ~−45° C. with short cycle (tube 70 to 72), For the treatments with the short cycles, we have exposed under laminar flow hood the Eppendorf tubes to a URGO product of reference 140111 that cools down the Eppendorf tubes by applying a spray of dimethyl ether on the Eppendorf tubes to decrease the temperature of the tubes from an initial temperature $T_i$, corresponding to room temperature (~25° C.), to a minimum temperature, $T_{min}$, of ~−10° C., ~5° C., ~0° C., ~−5° C., ~−10° C., ~−20° C., ~−40° C. However, in some cases, there were a few degrees difference between the temperature $T_{min}$ reached during the experiments and the attempted temperature. After we reached the minimum temperature, we have let the Eppendorf tubes warming up from $T_{min}$ up to a final temperature, $T_f$ of equilibrium, which is close to room temperature (~25° C.), during a second step. This second step occurred during a time $t_f$. Immediately after the treatment, cells were seeded in 96 well plate at a concentration of 2·10⁵ cells/mL. 48 hours later, we then measured with the MTT assay the cellular viability resulting from such treatment For the treatments with long cycles, we have exposed under laminar flow hood the Eppendorf tubes to a URGO product of reference 140111 that cools down the Eppendorf tubes by applying a spray of dimethyl ether on the Eppendorf tubes to decrease the temperature of the tubes from an initial temperature $T_i$, corresponding to room temperature (~25° C.), to a minimum temperature, $T_{min}$, of ~−10° C., ~5° C., ~0° C., ~−5° C., ~−10° C., ~−20° C. and ~−40° C. However, in some cases, there were a few degrees difference between the temperature $T_{min}$ reached during the experiments and the attempted minimum temperature. After we reached the minimum temperature, we have maintained the temperature of the assemblies of cells and magnetosomes to the minimum temperature during a lapse of time of 87-140 sec. we have then let the Eppendorf tubes warming up from $T_{min}$ up to a final temperature, $T_f$ of equilibrium, which is close to room temperature (~28° C.), during a second step. This second step occurred during a time $t_f$. Immediately after the treatment, cells were seeded in 96 well plate at a concentration of 2·10⁵ cells/mL. 48 hours later, we then measured with the MTT assay the cellular viability resulting from such treatment.

Results and Discussion:

We have observed that:

The duration of the warming step (200-650 sec) is longer than the duration of the cooling step (10-50 sec.) in the different tested conditions.

For the short cycles, a more important cellular death in the presence of 1 mg/mL of N-CMD than in the absence of N-CMD is observed at ~5° C., ~0° C., ~−5° C., ~−10° C., and ~−20° C. The value of A=% LC(1 mg)−% LC(0 mg), where % LC(1 mg) and % LC(0 mg) are the percentages of living cells in the presence and absence of N-CMD, respectively, is 10% for $T_{min}$=5° C., 26% for $T_{min}$=0° C., 24% for $T_{min}$=−5° C., 19% for $T_{min}$=−10° C., and 10% for $T_{min}$=−20° C. Interestingly, the value of A was the largest for $T_{min}$=0° C., indicating that decreasing the value of $T_{min}$ much below 0° C. does not increase the efficacy of cellular destruction induced by the presence of nanoparticles cooled down to $T_{min}$. This is counter intuitive since cryotherapy for tumor treatment is usually believed to increase in efficacy with decreasing temperature and is usually efficient at temperatures much below 0° C. (typically −40° C.).

For long cycles, a more important cellular death in the presence of 1 mg/mL of N-CMD than in the absence of N-CMD is observed at 5° C., 0° C., and −5° C. The value of A=% LC(1 mg)−% LC(0 mg), where % LC(1 mg) and % LC(0 mg) are the percentages of living cells in the presence and absence of N-CMD, respectively, is 10% for $T_{min}$=5° C., 23% for $T_{min}$=0° C., 33% for $T_{min}$=−5° C. For $T_{min}$=−10° C., $T_{min}$=−20° C., and $T_{min}$=−40° C., all cells were dead and A could not be estimated.

Comparing the values of A between long and short cycles, we have noted a series of interesting and counter intuitive behaviors:

A could be estimated for a narrower range of minimum temperatures in the case of long cycles (−5° C.<$T_{min}$<5° C.) than in the case of short cycles (−40° C.<$T_{min}$<5° C.).

The maximum value of A was larger for short cycles than for long cycles (26% at 0° C. for short cycles compared with 20% at −5° C. for long cycles).

The maximum value of A was observed at a higher temperature for short cycles than long cycles (0° C. for short cycles compared with −5° C. for long cycles).

One might have expected that the efficacy of tumor cell destruction would increase by increasing the duration of the step during which the temperature is maintained at the minimum temperature. In fact, the opposite behavior is observed. The strongest efficacy of cellular destruction is observed for the shortest duration of the maintaining step.

The effect of nanoparticles on cellular death can also be evaluated by measuring B=(% LC (0 mg/mL)−% LC (1 mg/mL)/% LC (0 mg/mL), which is plotted in FIG. 4 as a function of minimum temperatures. B is non-zero for a wider range of minimal temperatures for short cycles (−40° C.<$T_{min}$<10° C.) than for long cycles (−10° C.<$T_{min}$<10° C.). This is counter-intuitive since one might guess that when the minimal temperature is maintained for a longer period of time, the efficacy of cellular destruction due to the presence of nanoparticles increases.

In this example, we have therefore shown that the effect of nanoparticles on cellular death was more pronounced when the assemblies of cells and nanoparticles were cooled down to a minimum temperature without being maintained to this minimum temperature for more than 10 seconds than when they were cooled down to this minimum temperature and maintained at this minimum temperature for more than 60 seconds Example 5: Cytotoxicity of PC3-Luc Cells Brought into Contact with 1 mg/mL of N-MCD During 3 Hours or Brought into Contact with Growth Medium without N-CMD During 3 Hours and Exposed to Three Different Types of Cooling Treatments Consisting in 1 Cooling Cycle, 3 Cooling Cycles, and 6 Cooling Cycles Material and method: 0.2 mL Eppendorf were used for this experiment. A hole was made through the cap of the Eppendorf to insert a thermocouple in the Eppendorf and measure the temperature inside. In each Eppendorf, we introduced 100 µl of cellular suspension containing 2·5 $10^5$ PC3-Luc cells. The tubes were centrifuged at 1000 rpm during 5 minutes. After that, we removed the growth medium and we added 100 µl of the different magnetosome suspensions containing 1000 µg/mL of N-CMD or 100 µl of growth medium. We incubated the cells with magnetosomes or growth medium (0 µg/mL) for 3 hours.

We distinguish the above 0° C. ($T_{min}$>0° C.) cooling cycles for which the minimum temperatures are just above 0° C. from the below 0° C. ($T_{min}$<0° C.) cooling cycles for which the minimum temperatures are just below 0° C.

For the Just Above 0° C. ($T_{min}$>0° C.) Cycles, we have Carried Out 1 and 3 Cycles in the Following Manner:
- ia) 1 cycle during which the temperature of the cells is decreased from RT to $T_{min1}$~3° C. and the cells are then let to warm up from $T_{min1}$~3° C. to RT (tube 1 to 3, FIG. 5(a));
- ib) 1 cycle during which the temperature of the assembly of cells with 1 mg/mL of M-CMD is decreased from RT to $T_{min1}$~1° C. using the URGO system and the assembly is then let to warm up from $T_{min1}$~1° C. to RT (tube 4 to 6, FIG. 5(b));
- iia) 3 cycles during which the temperature of the cells is decreased from RT to $T_{min1}$ of 0.2° C. using the URGO system and the cells are then let to warm up from $T_{min1}$ of 0.2° C. to RT (first cycle), the temperature of the cells is decreased from RT to $T_{min2}$ of 1° C. with the URGO system and the cells are then let to warm up from $T_{min2}$ of 1° C. to RT (second cycle), the temperature of the cells is decreased from RT to $T_{min3}$ of 1° C. using the URGO system and the cells are then let to warm up from $T_{min3}$ of 1° C. to RT (third cycle) (tube 7 to 9, FIG. 5(c));
- iib) 3 cycles during which the temperature of the cells with 1 mg/mL of M-CMD is decreased from RT to $T_{min1}$ of 2° C. with the URGO system and the assembly are then let to warm up from $T_{min1}$ of 2° C. to RT (first cycle), the temperature of the assembly is decreased from RT to $T_{min2}$ of 1° C. with the URGO system and the assembly is let to warm up from $T_{min2}$ of 1° C. to RT (second cycle), the temperature of the assembly is decreased from RT to $T_{min3}$ of 2° C. with the URGO system and the assembly is then let to warm up from $T_{min3}$ of 2° C. to RT (third cycle) (tube 10 to 12, FIG. 5(d)), For the Just Above 0° C. ($T_{min}$>0° C.) Cycles, we have Carried Out 1 and 6 Cycles in the Following Manner:
- iiia) 1 cycle during which the temperature of the cells is decreased from RT to $T_{min1}$~2° C. and is the cells are then let to warm up from $T_{min1}$~2° C. to RT (tube 13 to 15, FIG. 8(a));
- iiib) 1 cycle during which the temperature of the assembly of cells with 1 mg/mL of M-CMD is decreased from RT to $T_{min1}$~2° C. using the URGO system and the assembly is then let to warm up from $T_{min1}$ 2° C. to RT (tube 16 to 18, FIG. 8(b));
- iva) 6 cycles during which the temperature of the cells is decreased from RT to $T_{min1}$ of ~4° C. using the URGO system and the cells are then let to warm up from $T_{min1}$ of ~4° C. to RT (first cycle), the temperature of the cells is decreased from RT to $T_{min2}$ of ~4° C. with the URGO system and the cells are then let to warm up from $T_{min2}$ of ~4° C. to RT (second cycle), the temperature of the cells is decreased from RT to $T_{min3}$ of ~4° C. using the URGO system and the cells are then let to warm up from $T_{min3}$ of ~4° C. to RT (third cycle), the temperature of the cells is decreased from RT to $T_{min4}$ of ~5° C. using the URGO system and the cells are then let to warm up from $T_{min4}$ of ~5° C. to RT (fourth cycle), the temperature of the cells is decreased from RT to $T_{min5}$ of ~4° C. with the URGO system and the cells are then let to warm up from $T_{min5}$ of ~4° C. to RT (fifth cycle), the temperature of the cells is decreased from RT to $T_{min6}$ of 4° C. using the URGO system and the cells are then let to warm up from $T_{min6}$ of ~4° C. to RT (sixth cycle) (tube 17 to 19, FIG. 8(c)),
- ivb) 6 cycles during which the temperature of the cells brought into contact with 1 mg/mL of N-CMD (assembly) is decreased from RT to $T_{min1}$ of ~3° C. using the URGO system and the assembly is then let to warm up from $T_{min1}$ of ~3° C. to RT (first cycle), the temperature of the assembly is decreased from RT of ~3° C. to $T_{min2}$ of ~3° C. with the URGO system and the assembly are then let to warm up from $T_{min2}$ of ~3° C. to RT (second cycle), the temperature of the assembly is decreased from RT to $T_{min3}$ of 4~° C. using the URGO system and the assembly is then let to warm up from $T_{min3}$ of ~4° C. to RT (third cycle), the temperature of the assembly is decreased from RT to $T_{min4}$ of ~3° C. using the URGO system and the assembly is then let to warm up from $T_{min4}$ of ~3° C. to RT (fourth cycle), the temperature of the assembly is decreased from RT to $T_{min5}$ of ~3° C. with the URGO system and the assembly is then let to warm up from $T_{min5}$ of ~3° C. to RT (fifth cycle), the temperature of the assembly is decreased from RT to $T_{min6}$ of ~3° C. using the URGO system and the assembly is then let to warm up from $T_{min6}$ of ~3° C. to RT (sixth cycle) (tube 20 to 22, FIG. 8(d)).

For the Just Below 0° C. ($T_{min}$<0° C.) Cycles, we have Carried Out 1 and 3 Cycles in the Following Manner:
- va) 1 cycle during which the temperature of the cells is decreased from RT to $T_{min1}$ of −2° C. and the cells are then let to warm up from $T_{min1}$ of −2° C. to RT (tube 17 to 19, FIG. 6(a));
- vb) 1 cycle during which the temperature of the assembly of cells with 1 mg/mL of M-CMD is decreased from RT to $T_{min1}$ of −2° C. using the URGO system and the assembly is then let to warm up from $T_{min1}$ of −2° C. to RT (tube 23 to 25, FIG. 6(b));
- via) 3 cycles during which the temperature of the cells is decreased from RT to $T_{min1}$ of −1° C. using the URGO system and the cells are then let to warm up from $T_{min1}$ of −1° C. to RT (first cycle), the temperature of the cells is decreased from RT to $T_{min2}$ of −2° C. with the URGO system and the cells are then let to warm up from $T_{min2}$ of −2° C. to RT (second cycle), the temperature of the cells is decreased from RT to $T_{min3}$ of −1° C. using the URGO system and the cells are then let to warm up from $T_{min3}$ of −1° C. to RT (third cycle) (tube 26 to 28, FIG. 6(c));

vib) 3 cycles during which the temperature of the cells with 1 mg/mL of M-CMD is decreased from RT to $T_{min1}$ of −1° C. with the URGO system and the assembly are then let to warm up from $T_{min1}$ of −1° C. to RT (first cycle), the temperature of the assembly is decreased from RT to $T_{min2}$ of −2° C. with the URGO system and the assembly is then let to warm up from $T_{min2}$ of −2° C. to RT (second cycle), the temperature of the assembly is decreased from RT to $T_{min3}$ of −1° C. with the URGO system and the assembly is then let to warm up from $T_{min3}$ of −1° C. to RT (third cycle) (tube 29 to 31, FIG. 6(d)).

For the Just Below 0° C. ($T_{min}<0°$ C.) Cycles, we have Carried Out 1 and 6 Cycles in the Following Manner:

viia) 1 cycle during which the temperature of the cells is decreased from RT to $T_{min1}$ of −2° C. and the cells are then let to warm up from $T_{min1}$ of −2° C. to RT (tube 32 to 34, FIG. 9(a));

viib) 1 cycle during which the temperature of the assembly of cells with 1 mg/mL of M-CMD is decreased from RT to $T_{min1}$ of −2° C. using the URGO system and the assembly is then let to warm up from $T_{min1}$ of −2° C. to RT (tube 35 to 36, FIG. 9(b));

viiia) 6 cycles during which the temperature of the cells is decreased from RT to $T_{min1}$ of −2° C. using the URGO system and the cells are then let to warm up from $T_{min1}$ of −2° C. to RT (first cycle), the temperature of the cells is decreased from RT to $T_{min2}$ of −1° C. with the URGO system and the cells are then let to warm up from $T_{min2}$ of −1° C. to RT (second cycle), the temperature of the cells is decreased from RT to $T_{min3}$ of −3° C. using the URGO system and the cells are then let to warm up from $T_{min3}$ of −3° C. to RT (third cycle), the temperature of the cells is decreased from RT to $T_{min4}$ of −1° C. using the URGO system and the cells are then let to warm up from $T_{min4}$ of −1° C. to RT (fourth cycle), the temperature of the cells is decreased from RT to $T_{min5}$ of 0° C. with the URGO system and the cells are then let to warm up from $T_{min5}$ of 0° C. to RT (fifth cycle), the temperature of the cells is decreased from RT to $T_{min6}$ of −1° C. using the URGO system and the cells are then let to warm up from $T_{min6}$ of −1° C. to RT (sixth cycle) (tube 37 to 39, FIG. 9(c));

viiib) 6 cycles during which the temperature of the cells brought into contact with 1 mg/mL of N-CMD (assembly) is decreased from RT to $T_{min1}$ of −3° C. using the URGO system and the assembly is then let to warm up from $T_{min1}$ of −3° C. to RT (first cycle), the temperature of the assembly is decreased from RT to $T_{min2}$ of −3° C. with the URGO system and the assembly are then let to warm up from $T_{min2}$ of −3° C. to RT (second cycle), the temperature of the assembly is decreased from RT to $T_{min3}$ of −3° C. using the URGO system and the assembly is then let to warm up from $T_{min3}$ of −3° C. to RT (third cycle), the temperature of the assembly is decreased from RT to $T_{min4}$ of −2° C. using the URGO system and the assembly is then let to warm up from $T_{min4}$ of −2° C. to RT (fourth cycle), the temperature of the assembly is decreased from RT to $T_{min5}$ of −1° C. with the URGO system and the assembly is then let to warm up from $T_{min5}$ of −1° C. to RT (fifth cycle), the temperature of the assembly is decreased from RT to $T_{min6}$ of −5° C. using the URGO system and the assembly is then let to warm up from $T_{min6}$ of −5° C. to RT (sixth cycle) (tube 40 to 42, FIG. 9(d)).

As a whole, we used 42 Eppendorf (3 Eppendorf per condition) containing the cells with 1000 µg/mL of N-CMD or the cells without N-CMD.

Results and Discussion:

The duration of the cooling step does not strongly depend on minimum temperature and the presence (or not) of N-CMD. In the different conditions, it is 20-65 sec.

By contrast, the duration of the warming step is longer in the presence of 1 mg/mL of N-CMD (540 sec in average for $T_{min}>0°$ C.) than in the absence of N-CMD (470 sec in average for $T_{min}>0°$ C.).

The cellular destruction is more pronounced for 6 than 1 cycle(s). This is true both for $T_{min}<0°$ C. and for $T_{min}>0°$ C. (FIGS. 7 and 10). It indicates that cellular death can be increased by increasing the number of cycles.

For $T_{min}>0°$ C., while for 3 cycles the percentage of living cells is similar in the presence and absence of nanoparticle (FIG. 7), for 6 cycles the percentage of living cells is lower in the presence than absence of nanoparticles (FIG. 10). It indicates that for $T_{min}>0°$ C., cellular toxicity can be induced by the presence of nanoparticles when the number of cycles is increased, preferentially above 3.

The value of B=(% LC (0 mg/mL)−% LC (1 mg/mL)/% LC (0 mg/mL) is larger for minimum temperatures just below 0° C. ($T_{min}<0°$ C.) than for minimum temperatures just above 0° C. ($T_{min}>0°$ C.) for the three types of cycles. For 1 cycle, B increases from 3% for $T_{min}>0°$ C. to 30% for $T_{min}<0°$ C. For three cycles, B increases from 10% for $T_{min}>0°$ C. to 53% for $T_{min}<0°$ C. For 6 cycles, B increases from 24% for $T_{min}>0°$ C. to 65% for $T_{min}<0°$ (FIG. 11).

The value of B=(% LC (0 mg/mL)−% LC (1 mg/mL)/% LC (0 mg/mL) increases with increasing number of cycles for the two minimum temperatures ($T_{min}>0°$ C. and $T_{min}<0°$ C.). B increases from 2% for one cycle to 15% for 6 cycles (for $T_{min}>0°$ C.), and from 31% for one cycle to 65% for 6 cycles (for $T_{min}<0°$ C.), FIG. 11.

We examine the variations of B between 1 and 3 cycles and between 1 and 6 cycles by estimating $C=B_{3cycle}/B_{1cycle}$ and $D=B_{6cycle}/B_{1cycle}$, where $B_{1cycle}$, $B_{3cycle}$, and $B_{6cycle}$ are the values of B estimated for 1 cycle, 3 cycles, and 6 cycles, respectively. The value of C increases from 1.75 for $T_{min}<0°$ C. to 3.06 for $T_{min}>0°$ C. while the value of D increases from 2·1 at $T_{min}<0°$ C. to 8.1 for $T_{min}>0°$ C. (FIG. 12).

This is counter-intuitive since one may have expected that carrying out cooling cycles below 0° C. would lead to a stronger increase in cellular destruction than carrying out cooling cycles above 0° C. The opposite behavior was observed. Carrying out cycles with $T_{min}$ below 0° C. increases less cellular death than carrying out cooling cycles with $T_{min}$ above 0° C.

Example 6

As shown in FIG. 15 that represents a possible variation of temperature during the various treatment steps, an optional maintaining step during which the temperature is maintained at Tm occurs during the cooling step, between the cooling step and the warming step, or during the warming step. In some cases, cryo-therapy is efficient or only efficient in the presence of at least one maintaining step. In some cases, the maintaining step is due to the presence of the nanoparticles in the body part or the nanoparticles are responsible for the maintaining step, preferentially nanoparticles comprising at least one atom of iron, most preferentially at least one atom of iron and another metallic atom than iron.

Tables

TABLE 1

Table 1: PC3-Luc cells alone (0 mg/mL) or PC3-Luc cells brought into contact with 1 mg/mL of N-CMD during 3 hours (1 mg/mL), which are firstly cooled down from $T_i$ to $T_{min}$ (>0° C.) during a time $t_d$ at a rate of temperature decrease, which are secondly let warming up from $T_{min}$ to $T_f$ during a time $t_m$ at a rate of temperature increase. Temperature data of PC3-Luc treated by Cryotherapy-1 cycle (>0° C.)

| Concentration of Magnetosomes | 0 mg/mL | 1 mg/mL |
|---|---|---|
| Targeted temperature (° C.) | >0° C. | |
| Initial temperature, $T_i$ (° C.) (cooling step) | 28.9 | 28 |
| Duration of temperature decrease, $t_d$ (s) (cooling step) | 31 | 26.5 |
| Minimal temperature, $T_{min}$ (° C.) (cooling step) | 1.99 | 1.75 |
| Rate of temperature decrease (° C./sec) (cooling step) | 0.87 | 0.99 |
| Duration of temperature increase $t_m$ (s) (warming step) | 464 | 617.5 |
| Final temperature, $T_f$ (° C.) (warming step) | 25.29 | 24 |
| Rate of temperature increase (° C./sec) (warming step) | 0.05 | 0.036 |
| Total duration of treatment, $T_t$ (sec) | 495 | 644 |

TABLE 2

Table 2: PC3-Luc cells alone (0 mg/mL) or PC3-Luc cells brought into contact with 1 mg/mL of N-CMD during 3 hours (1 mg/mL), which are firstly cooled down from $T_i$ to $T_{min}$ (<0° C.) during a time $t_d$ at a rate of temperature decrease, which are secondly let warming up from $T_{min}$ to $T_f$ during a time $t_m$ at a rate of temperature increase. Temperature data of PC3-Luc treated by Cryotherapy-1 cycle (<0° C.)

| Concentration of magnetosomes (mg/mL) | 0 mg/mL | 1 mg/mL |
|---|---|---|
| Targeted temperature (° C.) | <0° C. | |
| Initial temperature, $T_i$ (° C.) (cooling step) | 27.6 | 29.3 |
| Duration of temperature decrease, $t_d$ (s) (cooling step) | 41.5 | 34 |
| Minimal temperature, $T_{min}$ (° C.) (cooling step) | -2.33 | -2.33 |
| Rate of temperature decrease (° C./sec) (cooling step) | 0.72 | 0.93 |
| Duration of temperature increase $t_m$ (s) (warming step) | 706 | 829.5 |
| Final temperature, $T_f$ (° C.) (warming step) | 25.3 | 24 |
| Rate of temperature increase (° C./sec) (warming step) | 0.039 | 0.032 |
| Total duration of treatment, $T_t$ (sec) | 747.5 | 863.5 |

TABLE 3

PC3-Luc cells alone (0 mg/mL) or PC3-Luc cells brought into contact with 1 mg/mL of N-CMD during 3 hours (1 mg/mL), which are:

In a first cycle, firstly cooled down from $T_i$ to $T_{min}$ (>0° C.) during a time $t_d$ at a rate of temperature decrease, which are secondly let warming up from $T_{min}$ to $T_f$ during a time $t_m$ at a rate of temperature increase, In a second cycle, firstly cooled down from $T_i$ to $T_{min}$ (>0° C.) during a time $t_d$ at a rate of temperature decrease, which are secondly let warming up from $T_{min}$ to $T_f$ during a time $t_m$ at a rate of temperature increase, In a third cycle, firstly cooled down from $T_i$ to $T_{min}$ (>0° C.) during a time $t_d$ at a rate of temperature decrease, which are secondly let warming up from $T_{min}$ to $T_f$ during a time $t_m$ at a rate of temperature increase Temperature data of PC3-Luc treated by Cryotherapy-3 cycles (>0° C.)

| | Concentration of magnetosomes | | | | | |
|---|---|---|---|---|---|---|
| | 0 mg/mL | | | 1 mg/mL | | |
| | Freezing-thawing cycle | | | | | |
| | 1st cycle | 2nd cycle | 3rd cycle | 1st cycle | 2nd cycle | 3rd cycle |
| Targeted temperature (° C.) | >0° C. | | | >0° C. | | |
| Initial temperature, $T_i$ (° C.) (cooling step) | 29 | 24 | 24 | 27 | 29.5 | 20 |
| Duration of temperature decrease, $t_d$ (s) (cooling step) | 26.5 | 20 | 21 | 38 | 30 | 23 |
| Minimal temperature, $T_{min}$ (° C.) (cooling step) | 0.19 | 1.5 | 1 | 1.7 | 1.4 | 1.5 |
| Rate of temperature decrease (° C./sec) (cooling step) | 1.1 | 1.1 | 1.1 | 0.7 | 0.9 | 0.8 |
| Average rate of temperature decrease (° C./sec) | | 1.1 | | | 0.8 | |
| Duration of temperature increase $t_m$ (s) | 329 | 357 | 402.5 | 567.5 | 688.5 | 438 |
| Temp finale, $T_f$ (° C.) | 24 | 24 | 24 | 24 | 24 | 24 |
| Rate of temperature increase (° C./sec) | 0.07 | 0.06 | 0.06 | 0.04 | 0.03 | 0.05 |
| Average rate of temperature increase (° C./sec) | | 0.064 | | | 0.043 | |

TABLE 4

PC3-Luc cells alone (0 mg/mL) or PC3-Luc cells brought into contact with 1 mg/mL of N-CMD during 3 hours (1 mg/mL), which are:
In a first cycle, firstly cooled down from $T_i$ to $T_{min}$ (<0° C.) during a time $t_d$ at a rate of temperature decrease, which are secondly let warming up from $T_{min}$ to $T_f$ during a time $t_m$ at a rate of temperature increase,
In a second cycle, firstly cooled down from $T_i$ to $T_{min}$ (<0° C.) during a time $t_d$ at a rate of temperature decrease, which are secondly let warming up from $T_{min}$ to $T_f$ during a time $t_m$ at a rate of temperature increase,
In a third cycle, firstly cooled down from $T_i$ to $T_{min}$ (<0° C.) during a time $t_d$ at a rate of temperature decrease, which are secondly let warming up from $T_{min}$ to $T_f$ during a time $t_m$ at a rate of temperature increase.
Temperature data of PC3-Luc treated by Cryotherapy-3 cycles (<0° C.)

|  | Concentration of magnetosomes | | | | | |
| --- | --- | --- | --- | --- | --- | --- |
|  | 0 mg/mL | | | 1 mg/mL | | |
|  | Freezing-thawing cycle | | | | | |
|  | 1st cycle | 2nd cycle | 3rd cycle | 1st cycle | 2nd cycle | 3rd cycle |
| Targeted temperature (° C.) |  | <0° C. |  |  | <0° C. |  |
| Initial temperature, $T_i$ (° C.) (cooling step) | 27.02 | 25.2 | 25.53 | 29.02 | 25.97 | 25.88 |
| Duration of temperature decrease, $t_d$ (s) (cooling step) | 21.5 | 19.5 | 19.5 | 32.25 | 28 | 28 |
| Minimal temperature, $T_{min}$ (° C.) (cooling step) | −1.24 | −2.40 | −1.21 | −1.66 | −2.41 | −1.24 |
| Rate of temperature decrease (° C./sec) (cooling step) | 1.31 | 1.42 | 1.37 | 0.95 | 1.01 | 0.97 |
| Average rate of temperature decrease (° C./sec) (cooling step) |  | 1.37 |  |  | 0.98 |  |
| Duration of temperature increase $t_m$ (s) (warming step) | 469.5 | 457.5 | 426 | 589 | 537.5 | 445 |
| Temp finale, $T_f$ (° C.) (warming step) | 25.2 | 25.6 | 24 | 25.97 | 25.88 | 24.01 |
| Rate of temperature increase (° C./sec) | 0.06 | 0.06 | 0.06 | 0.05 | 0.05 | 0.06 |
| Average rate of temperature increase (° C./sec) |  | 0.059 |  |  | 0.052 |  |

TABLE 5

PC3-Luc cells alone (0 mg/mL) or PC3-Luc cells brought into contact with 1 mg/mL of N-CMD during 3 hours (1 mg/mL), which are:
In a first cycle, firstly cooled down from $T_i$ to $T_{min}$ (>0° C.) during a time $t_d$ at a rate of temperature decrease, which are secondly let warming up from $T_{min}$ to $T_f$ during a time $t_m$ at a rate of temperature increase,
In a second cycle, firstly cooled down from $T_i$ to $T_{min}$ (>0° C.) during a time $t_d$ at a rate of temperature decrease, which are secondly let warming up from $T_{min}$ to $T_f$ during a time $t_m$ at a rate of temperature increase,
In a third cycle, firstly cooled down from $T_i$ to $T_{min}$ (>0° C.) during a time $t_d$ at a rate of temperature decrease, which are secondly let warming up from $T_{min}$ to $T_f$ during a time $t_m$ at a rate of temperature increase.
In a fourth cycle, firstly cooled down from $T_i$ to $T_{min}$ (>0° C.) during a time $t_d$ at a rate of temperature decrease, which are secondly let warming up from $T_{min}$ to $T_f$ during a time $t_m$ at a rate of temperature increase,
In a fifth cycle, firstly cooled down from $T_i$ to $T_{min}$ (>0° C.) during a time $t_d$ at a rate of temperature decrease, which are secondly let warming up from $T_{min}$ to $T_f$ during a time $t_m$ at a rate of temperature increase,
In a sixth cycle, firstly cooled down from $T_i$ to $T_{min}$ (>0° C.) during a time $t_d$ at a rate of temperature decrease, which are secondly let warming up from $T_{min}$ to $T_f$ during a time $t_m$ at a rate of temperature increase.
Temperature data of PC3-Luc treated by Cryotherapy-6 cycles (>0° C.)

|  | Concentration of magnetosomes | | | | | | | | | | | |
| --- | --- | --- | --- | --- | --- | --- | --- | --- | --- | --- | --- | --- |
|  | 0 mg/mL | | | | | | 1 mg/mL | | | | | |
|  | Freezing-thawing cycle | | | | | | | | | | | |
|  | 1st cycle | 2nd cycle | 3rd cycle | 4th cycle | 5th cycle | 6th cycle | 1st cycle | 2nd cycle | 3rd cycle | 4th cycle | 5th cycle | 6th cycle |
| Targeted temperature (° C.) |  | >0° C. |  |  |  |  |  | >0° C. |  |  |  |  |
| Initial temperature, $T_i$ (° C.) (cooling step) | 26.1 | 24.4 | 24.2 | 24.3 | 24.3 | 24.3 | 26.4 | 25.6 | 24.5 | 23.9 | 24 | 24 |
| Duration of temperature decrease, $t_d$ (s) (cooling step) | 38 | 76 | 22.5 | 19 | 55 | 46 | 45 | 24 | 32.5 | 58.5 | 32 | 39 |

TABLE 5-continued

PC3-Luc cells alone (0 mg/mL) or PC3-Luc cells brought into contact with 1 mg/mL
of N-CMD during 3 hours (1 mg/mL), which are:
In a first cycle, firstly cooled down from $T_i$ to $T_{min}$ (>0° C.) during a time $t_d$ at a rate of
temperature decrease, which are secondly let warming up from $T_{min}$ to $T_f$ during a time $t_m$ at a
rate of temperature increase,
In a second cycle, firstly cooled down from $T_i$ to $T_{min}$ (>0° C.) during a time $t_d$ at a rate
of temperature decrease, which are secondly let warming up from $T_{min}$ to $T_f$ during a time $t_m$ at
a rate of temperature increase,
In a third cycle, firstly cooled down from $T_i$ to $T_{min}$ (>0° C.) during a time $t_d$ at a rate of
temperature decrease, which are secondly let warming up from $T_{min}$ to $T_f$ during a time $t_m$ at a
rate of temperature increase.
In a fourth cycle, firstly cooled down from $T_i$ to $T_{min}$ (>0° C.) during a time $t_d$ at a rate
of temperature decrease, which are secondly let warming up from $T_{min}$ to $T_f$ during a time $t_m$ at
a rate of temperature increase,
In a fifth cycle, firstly cooled down from $T_i$ to $T_{min}$ (>0° C.) during a time $t_d$ at a rate of
temperature decrease, which are secondly let warming up from $T_{min}$ to $T_f$ during a time $t_m$ at a
rate of temperature increase,
In a sixth cycle, firstly cooled down from $T_i$ to $T_{min}$ (>0° C.) during a time $t_d$ at a rate of
temperature decrease, which are secondly let warming up from $T_{min}$ to $T_f$ during a time $t_m$ at a
rate of temperature increase.
Temperature data of PC3-Luc treated by Cryotherapy-6 cycles (>0° C.)

| | Concentration of magnetosomes | | | | | | | | | | | |
| --- | --- | --- | --- | --- | --- | --- | --- | --- | --- | --- | --- | --- |
| | 0 mg/mL | | | | | | 1 mg/mL | | | | | |
| | Freezing-thawing cycle | | | | | | | | | | | |
| | 1st cycle | 2nd cycle | 3rd cycle | 4th cycle | 5th cycle | 6th cycle | 1st cycle | 2nd cycle | 3rd cycle | 4th cycle | 5th cycle | 6th cycle |
| Minimal temperature, $T_{min}$ (° C.) (cooling step) | 4.2 | 4 | 5.2 | 4.4 | 4.2 | 4 | 2.9 | 3.4 | 4.3 | 3.2 | 3.4 | 3.3 |
| Rate of temperature decrease (° C./sec) (cooling step) | 0.58 | 0.27 | 0.85 | 1.05 | 0.37 | 0.44 | 0.52 | 0.93 | 0.62 | 0.35 | 0.64 | 0.53 |
| Average rate of temperature decrease (° C./sec) (cooling step) | | | 0.59 | | | | | | 0.6 | | | |
| Duration of temperature increase $t_m$ (s) (warming step) | 352.5 | 358 | 338 | 298 | 251 | 269 | 432 | 370 | 312.5 | 309 | 354 | 340.5 |
| Final temperature $T_f$ (° C.) (warming step) | 24.4 | 24.2 | 24.3 | 24.3 | 24.35 | 24 | 25.6 | 24.5 | 23.9 | 24 | 24.1 | 24 |
| Rate of temperature increase (° C./sec) (warming step) | 0.06 | 0.06 | 0.06 | 0.07 | 0.08 | 0.07 | 0.05 | 0.06 | 0.06 | 0.07 | 0.06 | 0.06 |
| Average rate of temperature increase (° C./sec) (warming step) | | | 0.065 | | | | | | 0.06 | | | |

TABLE 6

PC3-Luc cells alone (0 mg/mL) or PC3-Luc cells brought into contact with 1 mg/mL
of N-CMD during 3 hours (1 mg/mL), which are:
In a first cycle, firstly cooled down from $T_i$ to $T_{min}$ (<0° C.) during a time $t_d$ at a rate of
temperature decrease, which are secondly let warming up from $T_{min}$ to $T_f$ during a time $t_m$ at a
rate of temperature increase,
In a second cycle, firstly cooled down from $T_i$ to $T_{min}$ (<0° C.) during a time $t_d$ at a rate
of temperature decrease, which are secondly let warming up from $T_{min}$ to $T_f$ during a time $t_m$ at
a rate of temperature increase,
In a third cycle, firstly cooled down from $T_i$ to $T_{min}$ (<0° C.) during a time $t_d$ at a rate of
temperature decrease, which are secondly let warming up from $T_{min}$ to $T_f$ during a time $t_m$ at a
rate of temperature increase.
In a fourth cycle, firstly cooled down from $T_i$ to $T_{min}$ (<0° C.) during a time $t_d$ at a rate
of temperature decrease, which are secondly let warming up from $T_{min}$ to $T_f$ during a time $t_m$ at
a rate of temperature increase,
In a fifth cycle, firstly cooled down from $T_i$ to $T_{min}$ (<0° C.) during a time $t_d$ at a rate of
temperature decrease, which are secondly let warming up from $T_{min}$ to $T_f$ during a time $t_m$ at a
rate of temperature increase,
In a sixth cycle, firstly cooled down from $T_i$ to $T_{min}$ (<0° C.) during a time $t_d$ at a rate of
temperature decrease, which are secondly let warming up from $T_{min}$ to $T_f$ during a time $t_m$ at a
rate of temperature increase.
Temperature data of PC3-Luc treated by Cryotherapy-6 cycles (<0° C.)

| | Concentration of magnetosomes | | | | | | | | | | | |
|---|---|---|---|---|---|---|---|---|---|---|---|---|
| | 0 mg/mL | | | | | | 1 mg/mL | | | | | |
| | Freezing-thawing cycle | | | | | | | | | | | |
| | 1st cycle | 2nd cycle | 3rd cycle | 4th cycle | 5th cycle | 6th cycle | 1st cycle | 2nd cycle | 3rd cycle | 4th cycle | 5th cycle | 6th cycle |
| Temperature (° C.) | <0° C. | | | | | | <0° C. | | | | | |
| Initial temperature, $T_i$ (° C.) (cooling step) | 27.51 | 24.9 | 25 | 24.76 | 24.4 | 24.86 | 27.2 | 24.5 | 24.7 | 24 | 23.8 | 24.1 |
| Duration of temperature decrease, $t_d$ (s) (cooling step) | 23.5 | 27 | 27 | 21 | 35 | 42 | 47 | 47 | 43 | 37 | 47 | 33 |
| Minimal temperature, $T_{min}$ (° C.) (cooling step) | −2.58 | −1.06 | −3.75 | −1.98 | −0.67 | −1.48 | −3.84 | −3.12 | −3.45 | −2.06 | −1.62 | −5.5 |
| Rate of temperature decrease (° C./sec) (cooling step) | 1.28 | 0.96 | 1.07 | 1.27 | 0.72 | 0.63 | 0.66 | 0.59 | 065 | 0.7 | 0.54 | 0.9 |
| Average rate of temperature decrease (° C./sec) (cooling step) | 0.99 | | | | | | 0.67 | | | | | |
| Duration of temperature increase $t_m$ (s) (warming step) | 640.5 | 844 | 761 | 837 | 603 | 349 | 939 | 959 | 1027 | 868 | 631 | 860 |
| Final temperature $T_f$ (° C.) (warming step) | 24.95 | 24.8 | 24.28 | 24.37 | 24.9 | 24 | 24.5 | 24.7 | 24.01 | 23.8 | 24.1 | 23.9 |
| Rate of temperature increase (° C./sec) (warming step) | 0.04 | 0.03 | 0.04 | 0.03 | 0.04 | 0.07 | 0.03 | 0.03 | 0.03 | 0.03 | 0.04 | 0.03 |
| Average rate of temperature increase (° C./sec) (warming step) | 0.043 | | | | | | 0.032 | | | | | |

The invention claimed is:

1. A cryo-system for treating at least one body part, said cryo-system comprising:
   a) a first part, which is a cryo-probe comprising at least one element selected from the group consisting of:
      i) at least one penetrating element for penetrating the at least one body part that is configured for cooling down the at least one body part internally or cooling down the at least one body part from the inside of the at least one body part, wherein the at least one of a penetrating element has at least one property selected from the group consisting of: 1) the at least one penetrating element is configured to be in communication with a cryogen source, 2) the at least one penetrating element is configured to be smaller than at least $\frac{1}{10}^{th}$ of a largest dimension of the at least one body part or configured to be lighter or heavier than a weight of the at least one body part, 3) the at least one penetrating element is configured to directly cool from the cryo-probe to the at least one body part, 4) the at least one penetrating element has at least one dimension smaller than 1 cm, and 5) the at least one penetrating element is configured for penetrating into the at least one body part,
      ii) at least one a non-penetrating element that is configured for cooling down the at least one body part externally or cooling down the at least one body part from the outside of the at least one body part, wherein the at least one non-penetrating element has at least one property selected from the group consisting of: 1) the at least one non-penetrating element is configured to be in communication with a cryogen source, 2) the non-penetrating element is configured to contact or to interact with an external surface of the at least one body part or with part of the external surface of the at least one body part, 3) the non-penetrating element is configured to indirectly cool from the cryo-probe to the at least one body part, and 4) the non-penetrating element segment is configured to not penetrate into the at least one body part, and
iii) a cryogen source that is configured for cooling down the at least one body part,
wherein at least one of the penetrating element, non-penetrating element or cryogen source is configured to expel, diffuse, or carry a gas or a liquid or solid towards or in the at least one body part,
and
b) a second part, which is either:
i) an assembly of at least two nanoparticles, wherein the assembly comprises at least two nanoparticles bound to each other or associated with each other via binding or associating material, or
ii) at least one nanoparticle comprising: α) iron and at least one other metal than iron and/or β) more than 50% in mass of iron or iron oxide,
wherein the cryo-probe of the first part is configured to cool down the second part such that the cryo-system provides at least one ice-ball or formation of at least one ice-ball, wherein the ice-ball comprises the assembly of at least two nanoparticles or the at least one nanoparticle;
wherein the cryo-system is configured to position a part or all of the first part and the second part in two different portions of the at least one body part, wherein the two different portions of at least one body part comprises at least one different site or cell selected from the group consisting of: one or more different healthy site(s), one or more different healthy cell(s), one or more different pathological site(s), and one or more different pathological cell(s); and
wherein the cryo-system is configured to operate with the conditions of:
i) a cooling temperature that is smaller than or equal to 5° C. and larger than or equal to −273° C., and
ii) a nanoparticle concentration that is between $10^{-5}$ and $10^5$ mg of a nanoparticle or nanoparticles per cm$^3$ of a nanoparticle suspension or between $10^{-5}$ and $10^5$ mg of a nanoparticle or nanoparticles per cm$^3$ of the body part.

2. The cryo-system according to claim 1, wherein the cryo-system is configured to directly cool from the cryo-probe to the at least one body part or to either the assembly of at least two nanoparticles or the at least one nanoparticle when the cryo-system does not comprise a thermal conductive material or when the cryo-system is not in contact or interaction with a thermal conductive material.

3. The cryo-system according to claim 1, wherein the cryo-system is configured to indirectly cool from the cryo-probe to the at least one body part or to either the assembly of at least two nanoparticles or the at least one nanoparticle of the second part when the cryo-system comprises or is in contact or interaction with a thermal conductive material.

4. The cryo-system according to claim 1, wherein the cryo-system either (a) comprises a thermal conductive material located between the cryo-probe and the assembly of at least two nanoparticles or at least one nanoparticle of the second part or the cryo-system or (b) is configured to contact or interact with a thermal conductive material located between the cryo-probe and the at least one body part to be treated, and
the thermal conductive material has at least one property selected from the group consisting of:
i) the thermal conductive material is different from that constitutive of the cryo-probe and/or the at least one body part for which the cryo-system is configured to treat and/or the assembly of at least two nanoparticles or at least one nanoparticle of the second part,
ii) the thermal conductive material is a gas,
iii) the thermal conductive material is a liquid,
iv) the thermal conductive material is solid,
v) the thermal conductive material is a non-metallic material,
vi) the thermal conductive material is an organic or carbonaceous material, and
vii) the thermal conductive material has a thermal conductivity that is larger than the thermal conductivity of the at least one body part or larger than $10^{-8}$ W·m$^{-1}$·K$^{-1}$.

5. The cryo-system according to claim 1, wherein the cryo-probe is an apparatus or equipment that is configured to generate or produce a refrigerant gas, a refrigerant liquid, or a refrigerant solid.

6. The cryo-system according to claim 1, wherein the cryo-probe or cryo-system is an apparatus or equipment configured to cool down the at least one body part to be treated or either the assembly of at least two nanoparticles or at least one nanoparticle of the second part, and the cryo-probe or cryo-stem has at least one property selected from the group consisting of:
i) the cryo-probe or cryo-system is configured to administer the assembly of at least two nanoparticles or the at least one nanoparticle in the at least one body part,
ii) the cryo-probe or cryo-system is configured to measure a temperature of the at least one body part or of either the assembly of at least two nanoparticles or the at least one nanoparticle,
iii) the cryo-probe or cryo-system is configured to either attract the assembly of at least two nanoparticles or the at least one nanoparticle towards the at least one body part or at least one component or part of the cryo-probe or the cryo-system or the cryo-probe or cryo-system is configured to maintain the assembly of at least two nanoparticles or the at least one nanoparticle in the at least one body part,
and
iv) the cryo-probe or cryo-system is configured to image or visualize the at least one body part or the assembly of at least two nanoparticles or the at least one nanoparticle.

7. The cryo-system according to claim 6, wherein the cryo-system is configured to operate through a consign or instruction given to at least one component of the cryo-probe or cryo-system, optionally by another component of the cryo-probe or cryo-system, or one component of the cryo-probe or cryo-system is configured to control another component of the cryo-probe or cryo-system,
wherein the consign or instruction is selected from the group consisting of:
i) setting or controlling the temperature of the at least one component at a desired temperature,
ii) adjusting a magnetic field strength or a magnetic field gradient of the at least one component to maintain the nanoparticles in the at least one body part or to attract the nanoparticles towards the cryo-probe or a component of the cryo-probe or cryo-system,
iii) adjusting at least one parameter of nanoparticle administration of the at least one component selected from the group consisting of a location of nanoparticle administration, a speed of nanoparticle administration, and a concentration at which nanoparticles should be administered, and iv) adjusting at least one parameter of the at least one component, wherein the at least one component is for application of radiation and the at least one parameter is selected from the group consisting of: intensity, frequency, power, energy, and duration of application of the radiation.

8. The cryo-system according to claim 1, wherein the second part in the cryo-system is configured to cause or to be associated with at least one property, selected from the group consisting of:
i) reducing a temperature gradient in the at least one body part compared with a cryo-therapy not involving the assembly of at least two nanoparticles or the at least one nanoparticle,
ii) reducing a temperature gradient compared with a temperature gradient achieved with the cryo-therapy not involving the assembly of at least two nanoparticles nor the at least one nanoparticle,
iii) obtaining a temperature gradient smaller than 0.1, 1, 10, 50, 100, 200 or $10^{3}$° C.,
iv) increasing a minimum temperature that is reached during treatment or that is associated with the treatment compared with a minimum temperature that is reached during a cryotherapy not involving the assembly of at least two nanoparticles nor the at least one nanoparticle,
v) obtaining a minimum temperature larger than −250, −200, −100, −50, −20, −10, −5, −2, −1, 0, 1, 2, 5 or 10° C.
vi) providing the at least one ice-ball comprising the assembly of at least two nanoparticles or the at least one nanoparticle,
vii) providing the formation of the at least one ice-ball comprising the assembly of at least two nanoparticles or the at least one nanoparticle,
viii) providing the at least one piece of ice comprising the assembly of at least two nanoparticles or the at least one nanoparticle,
ix) not providing at least one ice-ball comprising the assembly of at least two nanoparticles or the at least one nanoparticle when the cryo-therapy does not involve the assembly of at least two nanoparticles or the at least one nanoparticle,
X) providing the formation of the at least one ice-ball comprising the assembly of at least two nanoparticles or the at least one nanoparticle,
xi) providing the at least one piece of ice comprising the assembly of at least two nanoparticles or the at least one nanoparticle,
xii) increasing efficacy of destruction of a pathological cell at a given temperature, compared with a cryo-system not involving the assembly of at least two nanoparticles nor the at least one nanoparticle,
xiii) decreasing toxicity, side effects, or pain of a treatment by said cryo-system, compared with a cryo-system not involving the assembly of at least two nanoparticles nor the at least one nanoparticle, and
xiv) avoiding or suppressing anesthesia, optionally compared with a cryo-system not involving the assembly of at least two nanoparticles nor the at least one nanoparticle.

9. The cryo-system according to claim 1, wherein the at least one nanoparticles is at least two nanoparticles, and the at least two nanoparticles or the assembly of at least two nanoparticles of the second part of the cryo-system are bound to each other or associated with each other via an associating/binding material that has at least one property selected from the group consisting of:
i) the associating/binding material is a junction or material of junction between the at least two nanoparticles or the assembly of at least two nanoparticles,
ii) the associating/binding material separates the at least two nanoparticles or the assembly of at least two nanoparticles by less than 103 nm,
iii) a distance separating the at least two nanoparticles or the assembly of at least two nanoparticles is larger in the presence of the associating/binding material than in the absence of associating/binding material,
iv) the associating or binding material can form or be or transform into the at least one piece of ice or the at least one ice-ball,
v) the associating or binding material is such that in the presence of associating/binding material the at least two nanoparticles or the assembly of at least two nanoparticles are well-distributed, not aggregated, well dispersed, or homogenously distributed,
vi) the associating/binding material is a material that embeds or surrounds or coats the at least two nanoparticles or the assembly of at least two nanoparticles in such a way that the at least two nanoparticles are linked or bound to each other through the associating/binding material,
vii) the associating/binding material is destroyed during cryotherapy,
viii) the associating/binding material is preserved during cryotherapy,
ix) the associating/binding material is a coating on at least one nanoparticle of the at least two nanoparticles or of the assembly of at least two nanoparticles,
x) the associating or binding material comprises at least one compound able to establish interactions or bonds with metallic ions, $Fe^{2+}$ or $Fe^{3+}$ ions, hydroxyls OH—, oxides $O^{2-}$, crystalline defects or impurities of at least one nanoparticle of the at least two nanoparticles or of the assembly of at least two nanoparticles, which may be in or at the surface of the at least one nanoparticle of the at least two nanoparticles or of the assembly of at least two nanoparticles,
xi) the associating or binding material comprises at least one compound, atom, ion, or chemical function, wherein the compound, atom or ion embedded in the associating/binding material is able to establish interactions or bonds with the at least two nanoparticles or the assembly of at least two nanoparticles, a chemical function of at least one nanoparticle of the at least two nanoparticles or the assembly of at least two nanoparticles, an ion of at least one nanoparticle of the at least two nanoparticles or the assembly of at least two nanoparticles or a crystalline defect of the at least one nanoparticle of the at least two nanoparticles or the assembly of at least two nanoparticles,
xii) the associating or binding material is chosen from substances which yield better cooling properties of the at least two nanoparticles or the assembly of at least two nanoparticles in the presence than absence of associating or binding material,
xiii) the associating or binding material has a thickness of less than 1 μm,
xiv) the associating or binding material comprises carbon compounds or at least one compound selected from the group consisting of: a chelator, an amphipathic molecule, a polarized or charged polymer, a metal or silicon oxide, a metal or silicon hydroxide, an acid, an acidic, basic, oxidized, reduced, neutral, positively charged, negatively charged, derivative of these compounds, and combinations thereof, xv) the associating or binding material comprises at least one compound selected from the group consisting of: a polysaccharide, a fatty acid, a phospholipid, a polymer of amino acids, polymeric or non-polymeric silica, and an aliphatic amine polymer, of an acidic, basic, oxidized, reduced, neutral, positively charged, negatively charged derivative of these compounds, and combinations thereof, xvi) the associating or binding material comprises at least one function selected from the group consisting of phosphoric acids, carboxylic acids, sulfonic acids, esters, amides, ketones, alcohols, phenols, thiols, amines, ethers, sulfides, acid anhydrides, acyl halides, amidines, nitriles, hydroperoxides, imines, aldehydes, peroxides, of an acidic, basic, oxidized, reduced, neutral, positively charged, negatively charged derivative of these compounds, and combinations thereof, xvii) the associating/binding material is chosen from sterilizable substances, and xviii) the associating or binding material is or comprises a compound selected from the group consisting of: citric acid, oleic acid, polymethacrylic acid, poly(ethyleneoxide)-b-poly(methacrylic acid) acid, polyacrylic acid (PAA), polylactic acid, poly(ethylene oxide)-blockpoly(glutamic acid) acid, phosphonic acid, albumin, alendronate, alginate, gold, Au, $Al_2O_3$, Alginate, Aluminium hydroxide, Arabinogalactan, Bentonite, Carboxymethylcellulose, Cellulose, Chitosan, Cholseterol, Citrate, Dextran, Dimercaptosuccinic acid, Dopamine, DOPC, DTAP, DVB, Ethylcellulose, Erythrocyte, Ferrite, Folic acid, Gelatin, Human serum albumin, Liposome, MIPS, MnO, $Mn_3O_4$, Oleic acid, PEI, PEG, PEO-PGA, PLA, PLGA, a polymer, Phosphatidylcholine, Phosphorylcholine, Pluronic, Polyacrylamide, Polyacrylic acid PAA, Polyaniline, Polyethylene glycol with terminal carboxyl groups, Polypeptides, Poly(ethylene oxide), Poly(vinyl alcohol), Poly(N-isopropylacrylamide), Poly(vinylpyrrolidone), Poly(oligoethylene oxide), Poly(N,N-dimethyl ethylamino acrylate), Poly(imine), Poly(acrylic acid), Poly-D-L lactide, Polyalkylcyanoacrylate, Polymer (PAMAM, PDMAEMA, PPEGMA), PolyNIPAAM, Polyacrylic acid, Polydipyrrole/dicarbazole, Poly-L-lysine, Polymethylmethaacrylate, Polymersomes, a Polysaccharide selected from the group consisting of agarose, alginate, carregeenan, chitosan, dextran, haparin, gum arabic, pullulan, starch, and combinations thereof, Polystyrene, PVA, PVP, Silica, Silane, $SiO_2$, Sodium Oleate, Starch, Styrene-divinylbenzene, $TaO_x$, $ZrO_2$, derivatives thereof, and combinations thereof.

10. The cryo-system according to claim 1, wherein the at least one nanoparticle or each of the at least two nanoparticles of the assembly of the second part of the cryo-system has at least one property selected from the group consisting of:

i) the at least one nanoparticle or each of the at least two nanoparticles of the assembly comprises iron and at least one other metal or metalloid than iron, and/or more than 1% in mass of iron or iron oxide, ii) the at least one nanoparticle or each of the at least two nanoparticles of the assembly comprises iron and less than 100 other metals than iron, iii) the at least one nanoparticle or each of the at least two nanoparticles of the assembly is magnetic or gives rise to a magnetic response when subjected to a magnetic field, wherein the response is selected from the group consisting of: a non-zero magnetization or coercivity, a coercivity or magnetization that increases in strength with increasing magnetic field strength, a nanoparticle magnetic moment that gets coupled with the magnetic field, a nanoparticle movement, and combinations thereof, iv) the at least one nanoparticle or each of the at least two nanoparticles of the assembly is ferromagnetic, ferrimagnetic, paramagnetic, superparamagnetic or diamagnetic, v) the at least one nanoparticle or each of the at least two nanoparticles of the assembly is metallic, vi) the at least one nanoparticle or each of the at least two nanoparticles of the assembly is crystallized, vii) the at least one nanoparticle or each of the at least two nanoparticles of the assembly has a thermal conductivity in the range from $10^{-5}$ to $10^5$ W/mK, viii) the at least one nanoparticle or each of the at least two nanoparticles of the assembly has a concentration in the range from $10^{-5}$ to $10^5$ mg of nanoparticles per $cm^3$ of suspension or mg of nanoparticles per $cm^3$ of at least one body part, ix) the at least one nanoparticle or each of the at least two nanoparticles of the assembly is selected from the group consisting of: a nanosphere, a nanocapsule, a dendrimer, a carbon nanotube, a lipid/solid nanoparticle, a lipid or protein or DNA or RNA based nanoparticle, a nanoparticle with an inner aqueous environment surrounded by a layer, a multilayer nanoparticle, a polymeric nanoparticle, a quantum dot, a metallic nanoparticle, a polymeric micelle, polymeric nanoparticle, a carbon based nano-structure, a nanobubble, a nanosome, a noisome, a nanopore, a microbivore, a liposome, a virus, a herbal nanoparticle, an antibody, and a vesicle, x) the at least one nanoparticle or each of the at least two nanoparticles of the assembly comprises at least one metal different from iron selected from the group consisting of: Sodium, Magnesium, Aluminum, Potassium, Calcium, Scandium, Titanium, Chromium, Manganese, Zinc, Gallium, Strontium, Yttrium, Zirconium, Niobium, Molybdenum, Technetium, Indium, Cesium, Barium, Lanthanum, Cerium, Praseodymium, Neodymium, Samarium, Europium, Gadolinium, Terbium, Dysprosium, Holmium, Erbium, Thulium, Lutetium, Hafnium, Rhenium, and Tungstate, xi) the at least one nanoparticle or each of the at least two nanoparticles of the assembly comprises a core composed of a metallic oxide, xii) the at least one nanoparticle or each of the at least two nanoparticles of the assembly comprises a coating that surrounds the core to prevent aggregation, to enable the at least one nanoparticle administration in an organism or in the at least one body part, or stabilize the at least one nanoparticle core, xiii) the at least one nanoparticle or each of the at least two nanoparticles of the assembly has a coating thickness between 0.1 nm and 10 µm, xiv) the at least one nanoparticle or each of the at least two nanoparticles of the assembly has or leads to a coercivity larger than 0.01 Oe, xv) the at least one nanoparticle or each of the at least two nanoparticles of the assembly has or leads to a ratio between remnant and saturating magnetization larger than 0.01, xvi) the at least one nanoparticle or each of the at least two nanoparticles of the assembly has or leads to a saturating magnetization larger than 0.1 emu/g, xvii) the at least one nanoparticle or each of the at least two nanoparticles of the assembly has at least one magnetic property, xviii) the at least one nanoparticle or each of the at least two nanoparticles of the assembly has a size that is larger than 0.1 nm, xix) the at least one nanoparticle or each of the at least two nanoparticles of the assembly has a size smaller than $10^4$ nm, xx) the at least one nanoparticle or each of the at least two nanoparticles of the assembly is non-pyrogenic or apyrogenici, xxi) the at least one nanoparticle or each of the at least two nanoparticles of the assembly is synthesized by a synthetizing living organism, xxii) the at least one nanoparticle or each of the at least two nanoparticles of the assembly is synthesized chemically, xxiii) the at least one nanoparticle or each of the at least two nanoparticles of the assembly comprises less than 1% of organic or carbon material originating from the synthetizing living organism, xxiv) the at least one nanoparticle or each of the at least two nanoparticles of the assembly comprises more than 25% of mineral material originating from the synthetizing living organism, xxv) the at least one nanoparticle or each of the at least two nanoparticles of the assembly has a specific absorption rate (SAR) that is larger than 1 Watt per gram of nanoparticle, xxvi) the at least one nanoparticle or each of the at least two nanoparticles of the assembly has a size distribution that is lower than 1000 nm, xxvii) the at least one nanoparticle or each of the at least two nanoparticles of the assembly has a size distribution that is larger than 1 nm, xxviii) the at least one nanoparticle or each of the at least two nanoparticles of the assembly has a surface charge, which is higher than -200 mV, xxix) the at least one nanoparticle or each of the at least two nanoparticles of the assembly has a surface charge, which is lower than 100 mV, xxx) the at least one nanoparticle or each of the at least two nanoparticles of the assembly has a mass that is larger than $10^{-20}$ gram, xxxi) the at least one nanoparticle or each of the at least two nanoparticles of the assembly has a mass that is lower than $10^{20}$ gram, xxxii) the at least one nanoparticle or each of the at least two nanoparticles of the assembly is stable, and xxxiii) the at least one nanoparticle or each of the at least two nanoparticles of the assembly is at least two nanoparticles arranged in a chain.

11. The cryo-system according to claim 1, wherein the cryo-system is configured to:
  i) suppress or avoid or prevent the use local or general anesthesia,
  ii) reduce a duration of anesthesia or strength, concentration or toxicity of products used during anesthesia compared with a cryo-system not involving the at least one nanoparticle,
  iii) reduce a duration of re-animation following anesthesia compared with a cryo-system not involving the at least one nanoparticle,
  iv) reduce side effects, compared with a cryo-system not involving the at least one nanoparticle,
  v) suppress or prevent or avoid or reduce side effects or pain or diffusion of pathological cells or metastases resulting from a cryo-system not involving the at least one nanoparticle,
  vi) preserve or cryo-preserve or store or cryo-store at least one material selected from the group consisting of: biological material, the at least one body part, part of the at least one body part, biological part, enzyme, protein, DNA, RNA, tissue, organ, blood, biological fluid, cytoplasm, cell, and organelle,
  vii) destroy or damage or kill at least one material selected from the group consisting of: biological material, body part, part of body part, biological part, enzyme, protein, DNA, RNA, tissue, organ, blood, biological fluid, cytoplasm, cell, and organelle,
  and/or
  viii) enlarge and/or to modify a size of and/or to trigger swelling of, at least one material selected from the group consisting of: biological material, the at least one body part, part of the at least one body part, biological part, enzyme, protein, DNA, RNA, tissue, organ, blood, biological fluid, cytoplasm, cell, and organelle.

12. The cryo-system according claim 1, wherein the cryo-system, cryo-probe, at least one component of the cryo-probe, and/or at least one nanoparticle or each of the at least two nanoparticles of the assembly is, comprises, and/or is configured to produce: a) an apparatus, b) an equipment, c) a composition, d) a cosmetic composition, e) a chemical composition, f) a pharmaceutical composition, g) a biological composition, h) a suspension, i) a powder, j) a fluid, k) a ferro-fluid, l) a drug, m) a medical device, n) a product, and o) combinations thereof.

13. The cryo-system according to claim 1, wherein the cryo-system is configured to provide or to form the at least one ice-ball having the property that the at least one ice-ball embeds or comprises at least one nanoparticle of the assembly of at least two nanoparticles or the at least one nanoparticle so as to form at least one nanoparticle-ice-ball so as to be suitable for nanoparticle-ice-ball cryotherapy.

14. The cryo-system according to claim 13, wherein the cryo-system is configured to provide or to form the at least one nanoparticle-ice-ball, with at least one property selected from the group consisting of:
  i) the at least one nanoparticle-ice-ball is larger than the at least one nanoparticle or the assembly of the at least two nanoparticles,
  ii) the at least one nanoparticle-ice-ball is larger than an ice-ball without the least one nanoparticle or the assembly of the at least two nanoparticles,
  iii) a larger number of nanoparticle-ice-balls are formed by the cryo-system than a number of ice-balls without the least one nanoparticle or the assembly of the at least two nanoparticles, and
  iv) crystallinity of the at least one nanoparticle-ice-ball is better than or increased compared with crystallinity of an ice-ball without the least one nanoparticle or the assembly of the at least two nanoparticles or a number of crystallographic planes in at least one nanoparticle-ice-ball is larger than a number of crystallographic planes in an ice-ball without the least one nanoparticle of the second part least one nanoparticle.

15. The cryo-system according to claim 13, wherein the at least one nanoparticle-ice-ball has at least one property selected from the group consisting of:

i) the at least one nanoparticle-ice-ball exists at a higher temperature than an ice-ball without the least one nanoparticle or the assembly of the at least two nanoparticles,
and
ii) the at least one nanoparticle-ice-ball transforms itself into the least one nanoparticle or the assembly of the at least two nanoparticles or melts within a lapse of time that is larger than the melting time of an ice-ball without the least one nanoparticle, or the assembly of the at least two nanoparticles, or ice.

16. The cryo-system according to claim 1, wherein the at least one nanoparticle or each of the at least two nanoparticles of the assembly is an ice-cooled nanoparticle, wherein the ice-cooled nanoparticle has at least one property selected from the group consisting of:
   i) the ice-cooled nanoparticle is a nanoparticle that is cooled down by the at least one piece of ice, the at least one ice-ball, and/or the at least one nanoparticle-ice-ball formed by the at least one ice-ball,
   ii) the ice-cooled nanoparticle is a nanoparticle that, comprises the at least one nanoparticle-ice-ball or forms the at least one nanoparticle-ice-ball,
   iii) the ice-cooled nanoparticle is a nanoparticle configured to comprise or form or maintain ice in the at least one body part at a temperature that is larger than −100, −50, −40, −20, −10, −5, −2, −1, 0, 1 or 5° C. or at a temperature that is larger than the temperature at which ice forms in the at least one body part in the absence of the ice-cooled nanoparticle,
   iv) the ice-cooled nanoparticle increases temperature at a smaller rate or smaller speed than a temperature of a non-ice-cooled nanoparticle,
   and
   v) the ice-cooled nanoparticle has a temperature increase rate or speed smaller than $10^3$, 100, 50, 10, 5, 2 or 1° C. per second.

17. The cryo-system according claim 1, wherein the cryo-probe is configured to be switched on and off so as to respectively cool down and warm up the assembly of at least two nanoparticles or the at least one nanoparticle.

18. The cryo-system according to claim 1, wherein the cryogen source has at least one property selected from the group consisting of:
   i) the cryogen source is a cryogenic gas selected from the group consisting of: Helium-3, Helium, Hydrogen, Neon, Nitrogen, Air, Fluorine, Argon, Oxygen, and Methane,
   ii) the cryogen source is a cryogenic liquid,
   iii) the cryogen source is a cryogenic fuel,
   iv) the cryogen source is a cryogenic solid,
   v) the cryogen source has a boiling point or boiling temperature larger than 0 or 1 K,
   vi) the cryogen source has a boiling temperature lower than $10^5$, $10^3$ or 100 K,
   vii) the cryogen source is configured to be in direct contact with the at least one body part,
   and
   viii) the cryogen source is configured to be in indirect contact with the at least one body part.

19. The cryo-system according to claim 1, wherein the cryogen source is configured to be located in the at least one body part or configured to be located at a distance from the at least one body part of less than $10^{10}$ nm.

20. The cryo-system according to claim 1, wherein the cryogen source is separated from the at least one body part by at least one part of the cryo-probe or the distance between the cryogen source and the at least one body part is larger than $10^{-1}$ nm.

21. The cryo-system according to claim 1, which is or comprises fully or part of at least one system, apparatus, equipment, and/or kit.

22. The cryo-system according to claim 21, wherein the system, apparatus, equipment, and/or kit is selected among the first and/or second part(s).

23. The cryo-system according to claim 1, wherein at least one of the cryo-system, the cryo-probe, the first part of the cryo-system, or the second part of the cryo-system is i) a medical device, ii) an apparatus, iii) an equipment, or iv) a medical, a diagnostic, an imaging, a biological, or a cosmetic apparatus or equipment or part of said apparatus or equipment.

24. The cryo-system according to claim 1, wherein the at least one nanoparticle or each of the at least two nanoparticles of the assembly is a composition, optionally selected from the group consisting of a medical composition, diagnostic composition, imaging composition, biological composition, and cosmetic composition; or the at least one nanoparticle or each of the at least two nanoparticles of the assembly is a drug or a medical device.

25. The cryo-system according to claim 1, wherein the cryo-system is configured to cool the at least one body part of the individual from an initial temperature of the at least one body part to a cooling temperature that is lower than the initial temperature.

26. The cryo-system according to claim 1, wherein the assembly of at least two nanoparticles are in powder, dried, soluble or dispersed form.

27. The cryo-system according to claim 1, wherein the at least one ice-ball or a component of the at least one ice-ball according to claim 1 has at least one property selected from the group consisting of:
   1) a nanoparticle is an ice-ball nucleation site,
   2) the at least one ice-ball is larger than a nanoparticle,
   3) the at least one ice-ball is an intracellular ice-ball,
   4) a quantity of the at least one ice-ball is equal or smaller to a quantity of nanoparticles,
   5) a quantity or volume of the at least one ice-ball in the at least one body part is smaller than a quantity of nanoparticles in the at least one body part or volume that nanoparticles occupy in the at least one body part above a threshold temperature,
   6) a quantity or volume or size or diameter of the at least one ice-ball in the at least one body part is larger than the quantity of nanoparticles in the at least one body part or volume that nanoparticles occupy in the at least one body part or diameters or sizes of nanoparticles below a threshold temperature,
   7) the at least one ice-ball has a size that is larger in the presence than the absence of nanoparticle(s),
   8) a number of the at least one ice-ball is smaller or larger in the presence than absence of nanoparticle(s),
   9) the at least one ice-ball has a geometry or crystallinity or shape that is different in the presence than absence of nanoparticle(s),
   10) the at least one ice-ball embeds or comprises at least one nanoparticle of the assembly of at least two nanoparticles or the at least one nanoparticle so as to form at least one nanoparticle-ice-ball,
   11) the at least one ice-ball does not embed or does not comprise a nanoparticle so as to form at least one non-nanoparticle-ice-ball, 12) the at least one ice-ball has a size larger than 1 nm or nm² or nm³,
13) the at least one ice-ball has a size smaller than 1020 nm or nm² or nm³,
14) the at least one ice-ball comprises ice inside a cell so as to form an intracellular ice-ball,
15) the at least one ice-ball comprises ice outside a cell so as to form an extracellular ice-ball, and
16) the at least one ice-ball is a piece of ice that has the shape, geometry, or appearance of a ball.

28. The cryo-system according to claim 1, wherein the at least one piece of ice has at least one of the following properties selected from the group consisting of:
1) the at least one piece of ice comprises the assembly of at least two nanoparticles or the at least one nanoparticle of the second part,
2) formation of at least one piece of ice comprising the assembly of at least two nanoparticles or the at least one nanoparticle of the second part,
3) the at least one piece of ice comprises a nanoparticle that is an ice nucleation site,
4) the at least one piece of ice comprises a non-continuous piece of ice,
5) the at least one piece of ice comprises nanoparticles favoring the formation of intracellular ice,
6) the at least one piece of ice has a size that is larger than 1 nm,
7) the at least one piece of ice is heavier than $10^{-10}$ mg,
8) the at least one piece of ice is smaller than 1020 nm,
9) the at least one piece of ice is lighter than 1010 Kg,
10) the at least one piece of ice embeds or surrounds or comprises at least one nanoparticle of the assembly of at least two nanoparticles or the at least one nanoparticle, and
11) the at least one piece of ice does not surround a nanoparticle.

29. A cryo-system for treating at least one body part comprising at least one pathological site and at least one healthy site, said cryo-system comprising:
  a) a first part, which is a cryo-probe comprising at least one element selected from the group consisting of:
    i) at least one penetrating element for penetrating a part of or all of the at least one body part that is configured for cooling down the part of or all of the at least one body part internally or cooling down the part of or all of the at least one body part from the inside of the part of or all of the at least one body part, wherein the at least one of a penetrating element has at least one property selected from the group consisting of: 1) the at least one penetrating element is configured to be in communication with a cryogen source, 2) the at least one penetrating element is configured to be smaller than at least $\frac{1}{10}^{th}$ of a largest dimension of the part of or all of the at least one body part or configured to be lighter or heavier than a weight of the part of or all of the at least one body part, 3) the at least one penetrating element is configured to directly cool from the cryo-probe to the part of or all of the at least one body part, 4) the at least one penetrating element has at least one dimension smaller than 1 cm, and 5) the at least one penetrating element is configured for penetrating into the part of or all of the at least one body part,
    ii) at least one non-penetrating element that is configured for cooling down a part of or all of the at least one body part externally or cooling down the part of or all of the at least one body part from the outside of the part of or all of the at least one body part, wherein the at least one non-penetrating element has at least one property selected from the group consisting of: 1) the at least one non-penetrating element is configured to be in communication with a cryogen source, 2) the non-penetrating element is configured to contact or to interact with an external surface of the part of or all of the at least one body part or with part of the external surface of the part of or all of the at least one body part, 3) the non-penetrating element is configured to indirectly cool from the cryo-probe to the part of or all of the at least one body part, and 4) the non-penetrating element is configured to not penetrate into the part of or all of the at least one body part,
    and
    iii) a cryogen source that is configured for cooling down a part of or all of the at least one body part,
    wherein at least one of the penetrating element, non-penetrating element or cryogen source is configured to expel, diffuse, or carry a gas or a liquid or solid towards or in the part of or all of the at least one body part,
  b) a second part, which is either:
    i) an assembly of at least two nanoparticles, wherein the assembly comprises at least two nanoparticles bound to each other or associated with each other via binding or associating material, or
    ii) at least one nanoparticle comprising: α) iron and at least one other metal than iron and/or β) more than 50% in mass of iron or iron oxide,
  c) a third part which is a heating apparatus or equipment for heating a part of or all of the at least one body part or the second part or increasing a temperature of the part of or all of the at least one body part or the second part, the third part comprising or emitting a radiation selected from group consisting of: a heating radiation, a laser, a ultrasound, a magnetic field, and an alternating magnetic field;
  wherein the third part is configured to heat the second part;
  wherein the cryo-probe of the first part is configured to cool down a healthy site of the part of or all of the at least one body part, optionally surrounding a pathological site of the part of the at least one body part, such that the cryo-system provides the assembly of at least two nanoparticles or the at least one nanoparticle of the second part without an ice-ball or without the formation of at least one ice-ball,
  wherein the cryo-system is configured to position the first part in a healthy site of the part of the at least one body part and second part in a pathological site of the part of the at least one body part,
  wherein the cryo-system is configured to operate with the conditions of:
  i) a cooling temperature that is less than physiological temperature, and
  ii) a nanoparticle concentration that is between $10^{-5}$ and $10^5$ mg of a nanoparticle or nanoparticles per cm³ of a nanoparticle suspension or between $10^{-5}$ and $10^5$ mg of a nanoparticle or nanoparticles per cm³ of the part of or all of the at least one body part.

* * * * *